(12) United States Patent
Laing

(10) Patent No.: US 11,401,307 B2
(45) Date of Patent: *Aug. 2, 2022

(54) GLYCOSYLATED ANALOGUES OF FLAVIVIRUS E PROTEINS AND THEIR USE IN DIAGNOSTIC METHODS

(71) Applicant: Excivion Limited (LTD), Cambridge (GB)

(72) Inventor: Peter Laing, Cambridge (GB)

(73) Assignee: Excivion LTD, Huntingdon (GB)

( * ) Notice: Subject to any disclaimer, the term of this patent is extended or adjusted under 35 U.S.C. 154(b) by 27 days.

This patent is subject to a terminal disclaimer.

(21) Appl. No.: 16/615,788

(22) PCT Filed: May 22, 2018

(86) PCT No.: PCT/EP2018/063422
§ 371 (c)(1),
(2) Date: Nov. 21, 2019

(87) PCT Pub. No.: WO2018/215495
PCT Pub. Date: Nov. 29, 2018

(65) Prior Publication Data
US 2020/0215180 A1    Jul. 9, 2020

Related U.S. Application Data

(63) Continuation-in-part of application No. PCT/US2017/033882, filed on May 22, 2017.

(30) Foreign Application Priority Data

Nov. 22, 2017    (GB) ...................................... 1719423

(51) Int. Cl.
*C07K 14/18*        (2006.01)
*A61P 31/14*        (2006.01)
(Continued)

(52) U.S. Cl.
CPC .......... *C07K 14/1825* (2013.01); *A61K 39/12* (2013.01); *A61P 31/14* (2018.01);
(Continued)

(58) Field of Classification Search
None
See application file for complete search history.

(56) References Cited

U.S. PATENT DOCUMENTS

2019/0300580 A1* 10/2019 Laing ................... C07K 14/005

FOREIGN PATENT DOCUMENTS

EP            0640619 A1    3/1995
WO      2016012800 A1    1/2016

OTHER PUBLICATIONS

Alaniz, AJ, et al., Spatial quantification of the world population potentially exposed to Zika virus, Int J Epidemiol, Jun. 1, 2017;46(3):1-10.

(Continued)

*Primary Examiner* — Michelle S Horning
(74) *Attorney, Agent, or Firm* — Koren Anderson

(57) ABSTRACT

The invention relates to isolated recombinant analogues of flavivirus E-proteins comprising an analogue of a flavivirus E-protein fusion loop, wherein the analogue of the flavivirus E-protein fusion loop comprises at least one glycosylation site for an N-linked glycan that is not present in a natural flavivirus E-protein fusion loop sequence, wherein the at least one glycosylation site is an N-linked glycosylation sequon (Asn-X-Ser/Thr) and the Asn (N) residue of the sequon occupies any of positions 98-110 (DRGWGNGCGLFGK) of the natural flavivirus E-protein fusion loop amino acid sequence, wherein X is any amino acid residue except proline and Ser/Thr denotes a serine or threonine residue for use in an in vitro method for specific (Continued)

detection of anti-flavivirus antibody, diagnosis of flavivirus infection and/or to investigate exposure to flavivirus.

20 Claims, 42 Drawing Sheets

Specification includes a Sequence Listing.

(51) Int. Cl.
    *A61K 39/12*     (2006.01)
    *G01N 33/569*     (2006.01)
    *C07K 14/005*     (2006.01)
    *A61K 39/00*     (2006.01)

(52) U.S. Cl.
    CPC ..... *C07K 14/005* (2013.01); *G01N 33/56983* (2013.01); *A61K 2039/5254* (2013.01); *A61K 2039/5258* (2013.01); *A61K 2039/53* (2013.01); *C12N 2770/24122* (2013.01); *C12N 2770/24134* (2013.01); *G01N 2333/185* (2013.01)

(56) References Cited

OTHER PUBLICATIONS

Balmaseda, A, et al., Antibody-based assay discriminates Zika virus infection from other flaviviruses, Proc Natl Acad Sci USA, Aug. 1, 2017;114(31):8384-8389.
Beltramello, M., et al., The human immune response to Dengue virus is dominated by highly cross-reactive antibodies endowed with neutralizing and enhancing activity, Cell Host & Microbe, Sep. 16, 2010;8(3):271-283.
Bournazos, S., et al, Signaling by Antibodies: Recent Progress, Annual Review of Immunology, 2017;35:285-311.
Chang, HH., et al., Systematic analysis of protein identity between Zika virus and other arthropod-borne viruses, Bull World Health Organ, Jul. 1, 2017;95(7):517-525.
Dalziel, M., el al. Emerging Principles for the Therapeutic Exploitation of Glycosylation, Science, Jan. 2014;343 (6166):1235681.
Davis C. W., et al., The Location of Asparagine-linked Glycans on West Nile Virions Controls Their Interactions with CD209 (Dendritic Cell-specific ICAM-3 Grabbing Nonintegrin), J Biol Chem, Dec. 2006;281(48):37183-37194.
Dejnirattisai, W., et al., A new class of highly potent, broadly neutralizing antibodies isolated from 10 viremic patients infected with dengue virus, Nature Immunology, 2014;16(2):170-177.
Dejnirattisai, W., et al., Dengue virus sero-cross-reactivity drives antibody-dependent enhancement of infectionwith Zika virus, Nature Immunology, 2016;17(9):1102-1108.
Elliott, S., et al., Enhancement of therapeutic protein in vivo activities through glycoengineering, Nature Biotechnology, 2003;21(4):414-421.
Ferguson, NM., et al.. Benefits and risks of the Sanofi-Pasteur dengue vaccine: Modeling optimal deployment, Science, Sep. 2, 2016;353(6303):1033-1036.
Flasche, S., et al., The Long-Term Safety, Public Health Impact, and Cost-Effectiveness of Routine Vaccination with a Recombinant, Live-Attenuated Dengue Vaccine (Dengvaxia): A Model Comparison Study, PLoS Med, Nov. 29, 2016;13(11):e1002181.
Frietze, K. M., et al, Engineering virus-like particles as vaccine platforms, Current Opinion in Virology, 2016;18:44-49.
Guzman, MG, et al., Secondary infection as a risk factor for dengue hemorrhagic fever/dengue shock syndrome: an historical perspective and role of antibody-dependent enhancement of infection, Arch Virol, Jul. 2013;158(7):1445-59.
Hadinegoro, S. R., et al., Efficacy and Long-Term Safety of a Dengue Vaccine in Regions of Endemic Disease, The New England Journal of Medicine, Sep. 2015;373(13):1195-1206.

Halstead, S. B., et al, Original antigenic sin in dengue, The American Journal of Tropical Medicine and Hygiene, Jan. 1983;32(1):154-156.
Halstead, SB, Achieving safe, effective, and durable Zika virus vaccines: lessons from dengue, Lancet Infect Dis, Nov. 2017;17(11):e378-e382.
Halstead, SB, Biologic Evidence Required for Zika Disease Enhancement by Dengue Antibodies, Emerg Infect Dis, Apr. 2017;23(4):569-573.
Halstead, SB., Dengue Antibody-Dependent Enhancement: Knowns and Unknowns, Microbiol Spectr. Dec. 2014;2(6):1-18.
Hanley, K. A., The Double-Edged Sword: How Evolution Can Make or Break a Live-Attenuated Virus Vaccine, Evolution: Education and Outreach, 2011;4(4):635-643.
Hofer, U., Viral Pathogenesis: Tracing the steps of Zika virus, Nat Rev Microbiol. Jul. 2016;14(7):401.
Houghton-Trivino, N., et al., Dengue-yellow fever sera cross-reactivity; challenges for diagnosis, Rev Salud Publica (Bogota), Mar.-May 2008;10(2):299-307.
Katzelnick, LC, et al., Antibody-dependent enhancement of severe dengue disease in humans, Science, Nov. 17, 2017;358(6365):929-932.
Kostyuchenko, V. A., et al., Structure of the thermally stable Zika virus, Nature, 2016,553:425-428.
Lai, CY, et al., Antibodies to envelope glycoprotein of dengue virus during the natural course of infection are predominantly cross-reactive and recognize epitopes containing highly conserved residues at the fusion loop of domain II, J Virol, Jul. 2008,82(13):6631-43.
Laing, P., et al., The "co-delivery" approach to liposomal vaccines: application to the development of influenza-A and hepatitis-B vaccine candidates, Journal of Liposome Research, 2006;16(3):229-235.
Laing, P., Luminescent visualization of antigens on blots, J Immunol Methods. Sep. 27, 1986;92(2):161-5.
Larocca, R., et al., Vaccine protection against Zika virus from Brazil, Nature, Aug. 25, 2016;536(7617):474-478.
Ling, Y, et al., Yellow Fever in a Worker Returning to China from Angola, Mar. 2016, Emerg Infect Dis, Jul. 2016;22(7):1317-8.
Lucey, D., et al., Congenital Zika Syndrome in 2017, JAMA. Apr. 4, 2017;317(13):1368-1369.
Medina, MT, et al., New spectrum of the neurologic consequences of Zika, J Neurol Sci. Dec. 15, 2017;383:214-215.
Mir, D., et al., Phylodynamics of Yellow Fever Virus in the Americas: new insights into the origin of the 2017 Brazilian butbreak, Sci Rep. Aug. 7, 2017;7(1):7385.
Paul, L.M., et al., Dengue virus antibodies enhance Zika virus infection, Clinical & Translational Immunology, 2016;5:e117.
Priyamvada, I., et al., Human antibody responses after dengue virus infection are highly cross-reactive to Zika virus, Proc Natl Acad Sci USA Jul. 12, 2016;113(28):7852-7.
Ramsauer, K., et al, Immunogenicity, safety, and tolerability of a recombinant measles-virus-based chikungunya vaccine: a randomised, double-blind, placebo-controlled, active-comparator, first-in-man trial, The Lancet, Infectious Diseases, 2015;15(5):519-527.
Roby J. A., et al., West Nile Virus Genome with Glycosylated Envelope Protein and Deletion of Alpha Helices 1, 2, and 4 in the Capsid Protein Is Noninfectious and Efficiently Secretes Subviral Particles, J Virol, Dec. 2013;87(23):13063-13069.
Roby, J. A., et al., Increased expression of capsid protein in trans enhances production 10 of single-round infectious particles by West Nile virus DNA vaccine candidate, J Gen Virol, Oct. 2014;95:2176-2191.
Russell, P. K., The Zika Pandemic—A Perfect Storm?, PLoS Neglected Tropical Diseases, 2016;10(3).
Sariol, CA, et al., A Tale of Two Viruses: Does Heterologous Flavivirus Immunity Enhance Zika Disease?, Trends Microbiol. Mar. 2018;26(3):186-190.
Screaton,G, et al., New insights into the immunopathology and control of dengue virus infection, Nat Rev Immunol. Dec. 2015;15(12):745-59.

(56) References Cited

OTHER PUBLICATIONS

Sen, P, et al., New insight into the surface denaturation of proteins: electronic sum frequency generation study of cytochrome c at water interfaces, J Phys Chem B. Oct. 30, 2008;112(43):13473-5.
Sirohi, D., et al, The 3.8 A resolution cryo-EM structure of Zika virus, Science, 2016;352(6284):467-470.
Smith, DR, Waiting in the wings: The potential of mosquito transmitted flaviviruses to emerge, Crit Rev Microbiol. Aug. 2017;43(4):405-422.
Stiasny K et al., Cryptic Properties of a Cluster of Dominant Flavivirus Cross-Reactive Antigenic Sites, J Virol, 2006;80(19):9557-68.
Tregoning J. S., et al, Using Plasmids as DNA Vaccines for Infectious Diseases. Microbiology Spectrum, 2014;2(6):1-16.
Tretyakova, I., et al., Plasmid DNA initiates replication of yellow fever vaccine in vitro and elicits virus-specificimmune response in mice, Virology, 2014;468-470:28-35.
Willis, E, et al., Characterization of Zika virus binding and enhancement potential of a large panel of flavivirus murine monoclonal antibodies, Virology. Aug. 2017;508:1-6.

* cited by examiner

Fig. 1

Western blot of wild type (left of each pair) and hyperglycosylated forms of dengue and Zika E-protein exodomains, +2 = plus two additional glycans, +1 = plus one additional glycan Purified hyperglycosylated E-protein exodomains from the four dengue virus strains and Zika MR$_2$|CIGISNR$_9$|DFVEGVSGGSWVDIVLEHGSCVTTMAK$_{36}$|NK$_{38}$|PTLDFELIK$_{47}$|TEAK$_{51}$|
T1   T2              T3                           T4    T5             T6

Site 1 ↓

QPATLR$_{57}$|K$_{58}$|YCIEAK$_{64}$|LTN$_{67}$TTTESR$_{73}$|CPTQGEPSLNEEQDK$_{88}$|R$_{89}$|FVCK$_{93}$|HSMVDR$_{99}$|
T7        T8      T9          T10                T11                T12    T13     T14

Site 2 ↓   Site 3 ↓

GN$_{101}$GSGCGLN$_{108}$GSGGIVTCAMFTCK$_{122}$|K$_{123}$|NMEGK$_{128}$|VVQPENLEYTIVITPHSGEEH
                    T15                            T16    T17              T18

Site 4 ↓

AVGN$_{153}$DTGK$_{157}$|HGK$_{160}$|EIK$_{163}$|ITPQSSITEAELTGYGTVTMECSPR$_{188}$|TGLDFNEMVLLQM
T18            T19      T20        T21                            T22

ENK$_{204}$|AWLVHR$_{210}$|QWFLDLPLPWLPGADTQGSNWIQK$_{234}$|ETLVTFK$_{241}$|NPHAK$_{246}$|K$_{247}$|
T22       T23           T24                         T25            T26         T27

QDVVVLGSQEGAMHTALTGATEIQMSSGNLLFTGHLK$_{284}$|CR$_{286}$|LR$_{288}$|MDK$_{291}$|LQLK$_{295}$|
                 T28                          T29     T30       T31      T32

GMSYSMCTGK$_{305}$|FK$_{307}$|VVK$_{310}$|EIAETQHGTIVIR$_{323}$|VQYEGDGSPCK$_{334}$|IPFEIMDLEK$_{344}$|
      T33           T34      T35          T36                T37                T38

R$_{345}$|HVLGR$_{350}$|LITVNPIVTEK$_{361}$|DSPVNIEAEPPFGDSYIIIGVEPGQLK$_{388}$|LNWFK$_{393}$|K$_{394}$|
T39    T40         T41                  T42                            T43         T44

GSSGGGSHHHHHH$_{407}$
     T45

Fig. 3c

IR$_2$|CIGVSNR$_9$|DFVEGMSGGTWVDVVLEHGGCVTVMAQDK$_{38}$|PTVDIELVTTTVSNMAEVR$_{57}$|
T1    T2                         T3                      T4

[Site 1 ↓]

SYCYEASISDMASDSR$_{73}$|CPTQGEAYLDK$_{84}$|QSDTQYVCK$_{93}$|R$_{94}$|TLVDR$_{99}$|N$_{100}$HTNGCGLFG
      T5                 T6          T7     T8    T9      T10

[Site 2 ↓]

K$_{110}$|GSLVTCAK$_{118}$|FACSK$_{123}$|K$_{124}$|MTGK$_{128}$|SIQPENLEYR$_{138}$|IMLSVHGSQHSGMIVN$_{154}$DTGH
T10    T11      T12    T13  T14     T15           T16

ETDENR$_{164}$|AK$_{166}$|VEITPNSPR$_{175}$|AEATLGGFGSLGLDCEPR$_{193}$|TGLDFSDLYYLTMNNK$_{209}$|
T16    T17    T18        T19            T20

HWLVHK$_{215}$|EWFHDIPLPWHAGADTGTPHWNNK$_{239}$|EALVEFK$_{246}$|DAHAK$_{251}$|R$_{252}$|QTVVVLGS
  T21               T22             T23     T24  T25  T26

QEGAVHTALAGALEAEMDGAK$_{281}$|GR$_{283}$|LSSGHLK$_{290}$|CR$_{292}$|LK$_{294}$|MDK$_{297}$|LR$_{299}$|LK$_{301}$|
T26                T27   T28   T29 T30 T31 T32 T33

GVSYSLCTAAFTFTK$_{316}$|IPAETLHGTVTVEVQYAGTDGPCK$_{340}$|VPAQMAVDMQTLTPVGR$_{357}$|
    T34                 T35              T36

LITANPVITESTENSK$_{373}$|MMLELDPPFGDSYIVIGVGEK$_{394}$|K$_{395}$|ITHHWHR$_{402}$|SGSTGGSGGS
     T37                T38        T39    T40       T41

GGSHHHHHH$_{421}$
T41

Fig. 3d

IR$_2$CIGVSNR$_9$DFVEGMSGGTWVDVVLEHGGCVTVMAQDK$_{38}$|PTVDIELVTTTVSNMAEVR$_{57}$
                    L1                               L2

⬇ Site 1

SYCYEASISDMASDSR$_{73}$CPTQGEAYLDK$_{84}$|QSDTQYVCK$_{93}$|R$_{94}$TLVDR$_{99}$N$_{100}$HTNGCGLFG
      L2                           L3                L4

⬇ Site 2

K$_{110}$|GSLVTCAK$_{118}$|FACSK$_{123}$|K$_{124}$|MTGK$_{128}$|SIQPENLEYR$_{138}$IMLSVHGSQHSGMIVN$_{154}$DTGH
L4     L5       L6     L7    L8                L9

ETDENR$_{164}$AK$_{166}$|VEITPNSPR$_{175}$AEATLGGFGSLGLDCEPR$_{193}$TGLDFSDLYYLTMNNK$_{209}$|
L9                                L10

HWLVHK$_{215}$|EWFHDIPLPWHAGADTGTPHWNNK$_{239}$|EALVEFK$_{246}$|DAHAK$_{251}$|R$_{252}$QTVVVLGS
   L10              L11               L12     L13    L14

QEGAVHTALAGALEAEMDGAK$_{281}$|GR$_{283}$LSSGHLK$_{290}$|CR$_{292}$LK$_{294}$|MDK$_{297}$|LR$_{299}$LK$_{301}$|
L14                           L15      L16    L17    L18

GVSYSLCTAAFTFTK$_{316}$|IPAETLHGTVTVEVQYAGTDGPCK$_{340}$|VPAQMAVDMQTLTPVGR$_{357}$
    L19                       L20                L21

LITANPVITESTENSK$_{373}$|MMLELDPPFGDSYIVIGVGEK$_{394}$|K$_{395}$|ITHHWHR$_{402}$SGSTGGSGGS
L21                      L22           L23        L24

GGSHHHHHH$_{421}$
L24

Sample Group 1-5: Dose-response curves against DENV

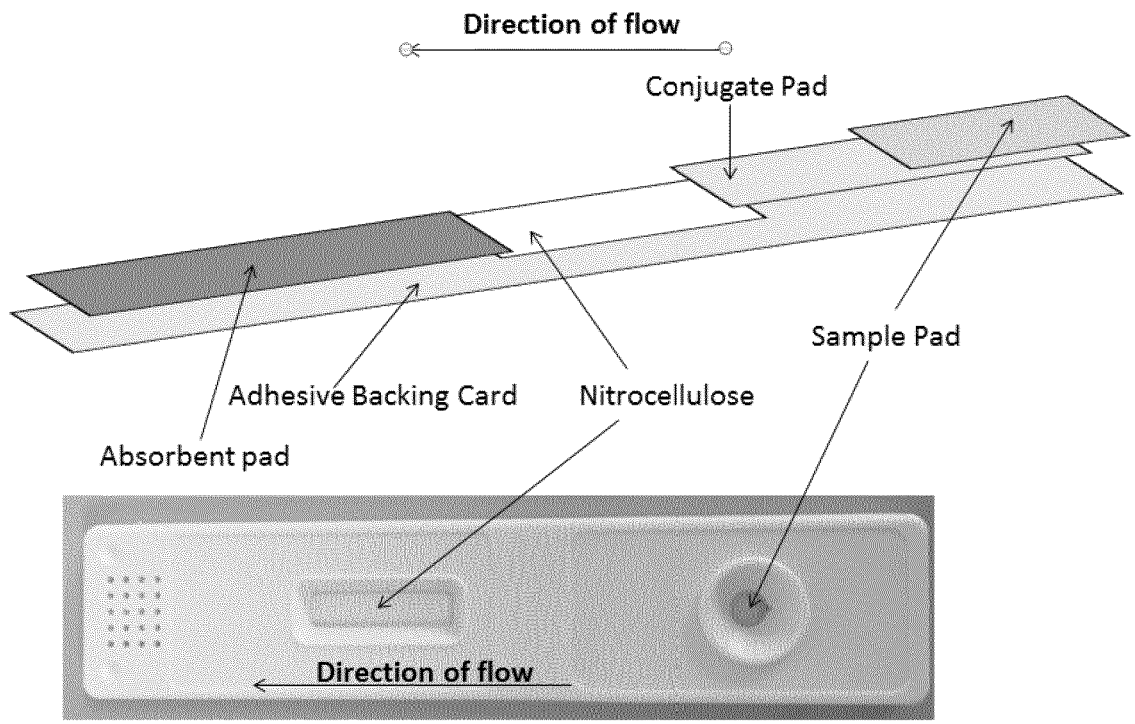
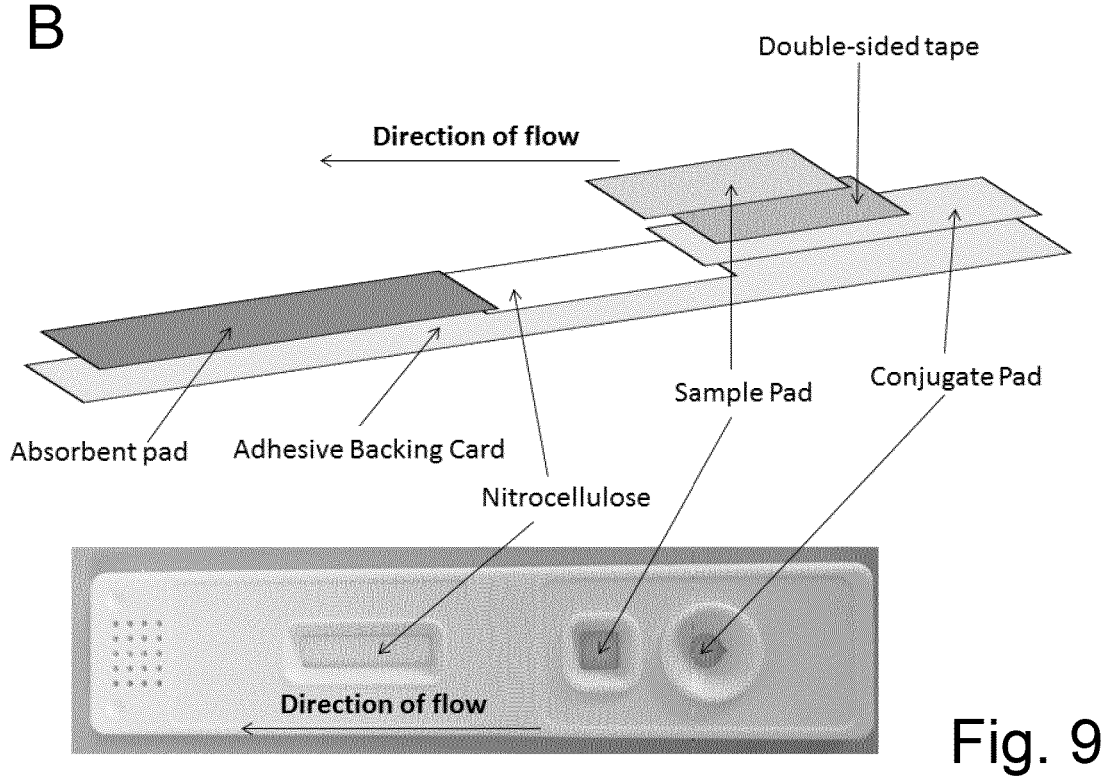
Fig. 9

A
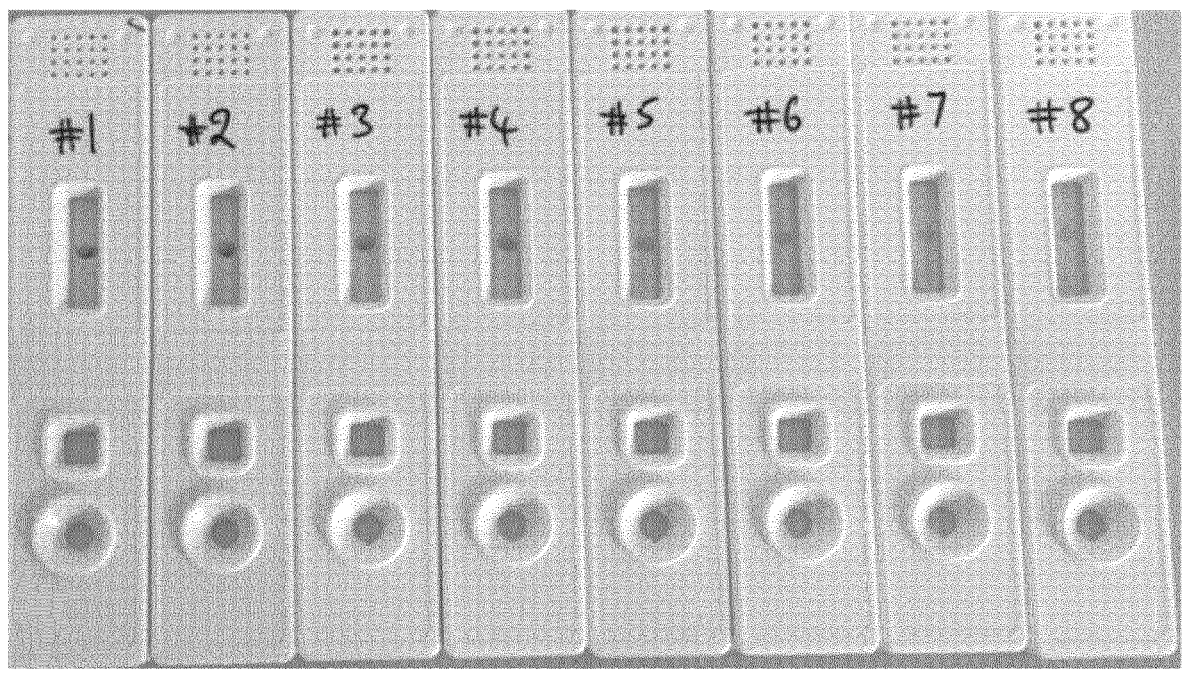
B
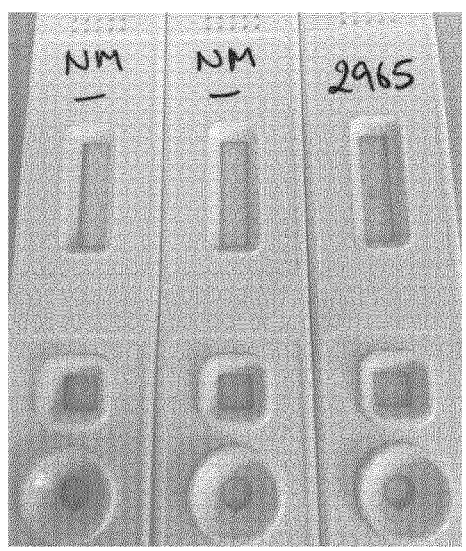
Fig. 10

A
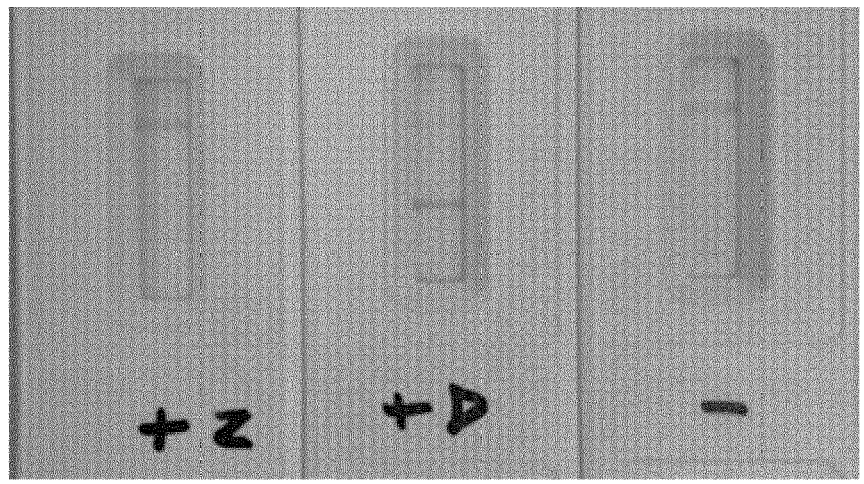
B
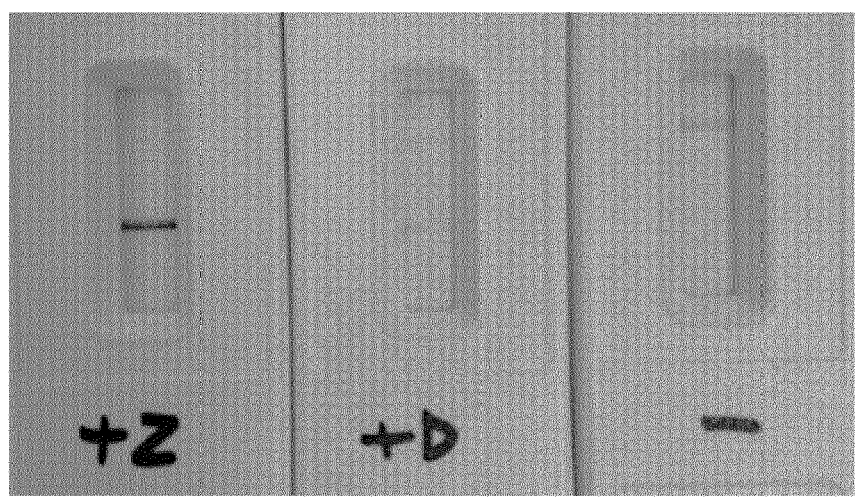
C
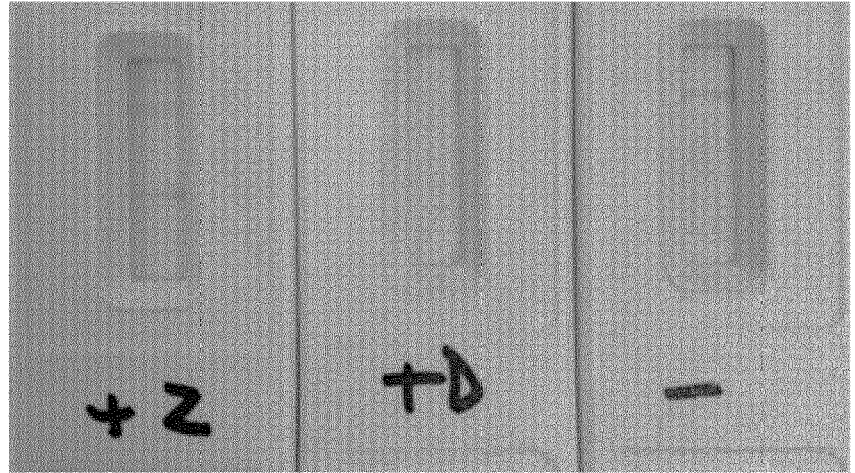
Fig. 14

A
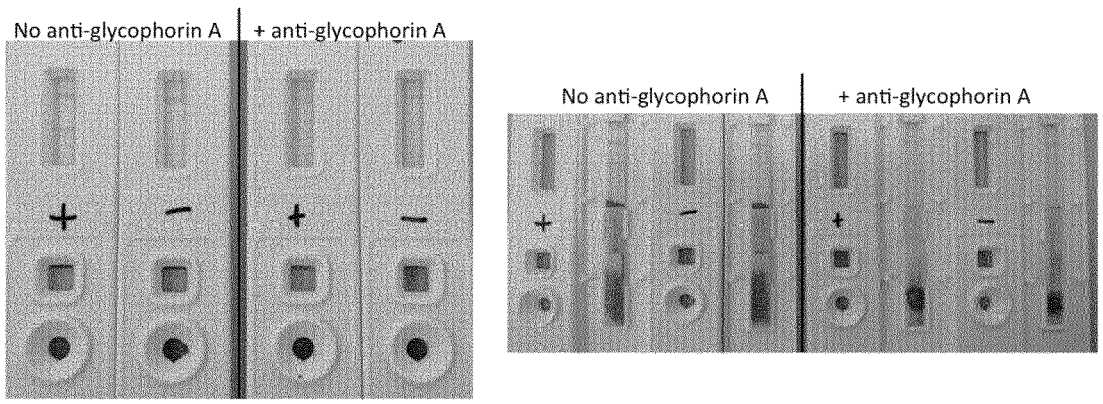
B
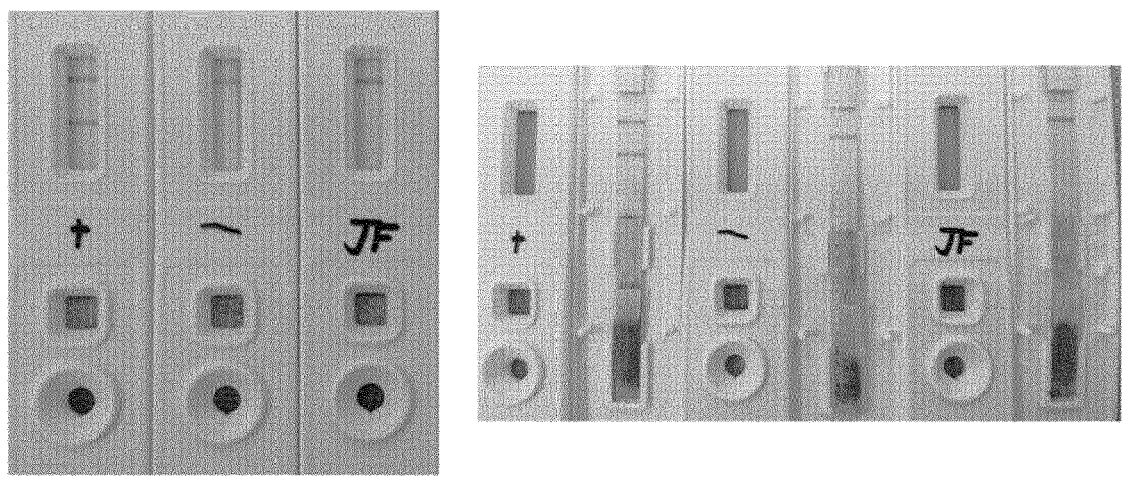
C
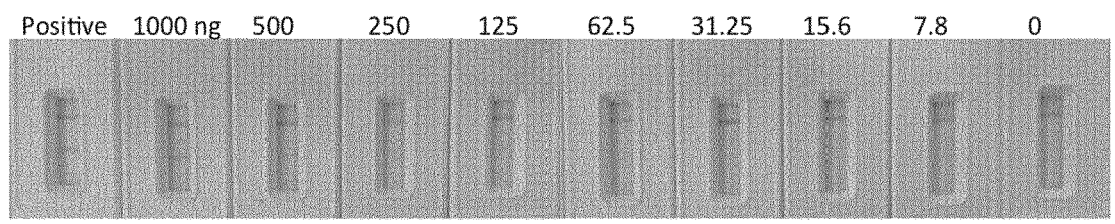
D
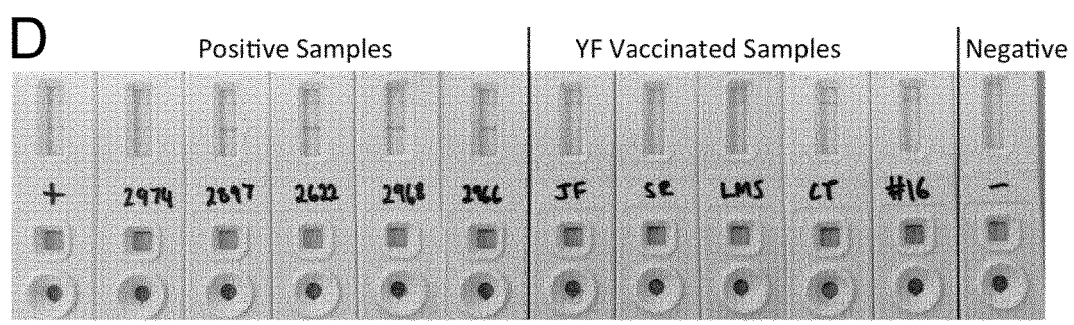
Fig. 15

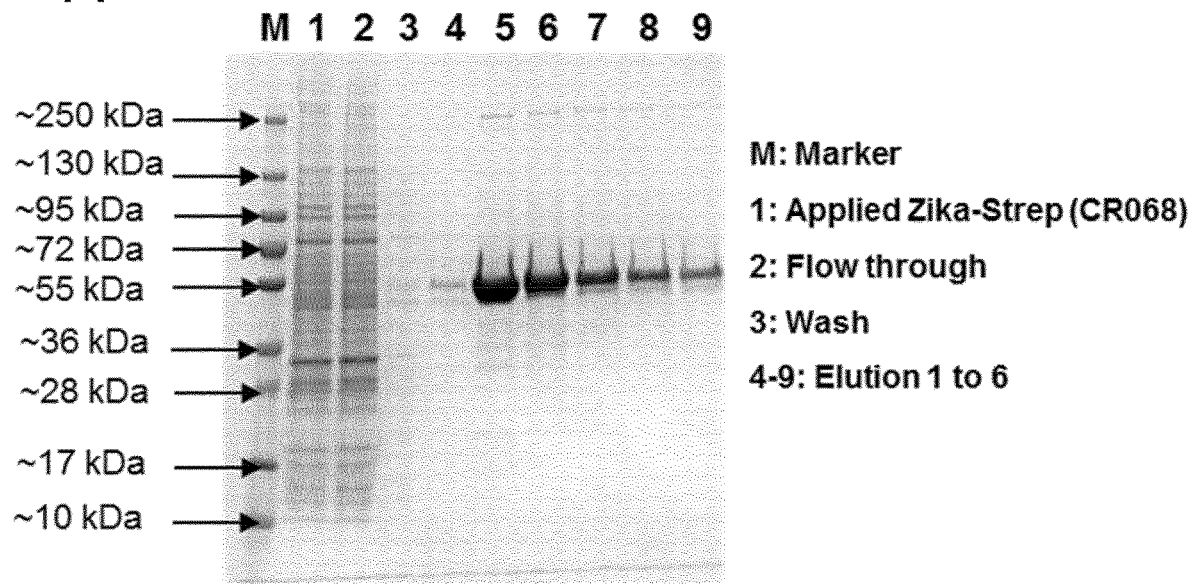
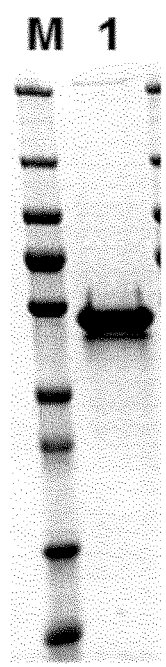
Fig. 16

A

| Sample No. | SD Duo Result (historic data) | | | Prototype Excivion Dengue and Zika Antibody Detection Lateral Flow Tests | Sample No. | SD Duo Result (historic data) | | | Prototype Excivion Dengue and Zika Antibody Detection Lateral Flow Tests |
|---|---|---|---|---|---|---|---|---|---|
| | IgG | IgM | NS1 | T (IgG) | | IgG | IgM | NS1 | T (IgG) |
| 1 | 1+ | 3+ | 0 | 2+ | 33 | 0 | 1W | 3+ | 0 |
| 2 | 0 | 0 | 2+ | 0 | 34 | 1W | 0 | 0 | 4+ |
| 3 | 0 | 2+ | 0 | 0 | 36 | 2+ | 0 | 0 | 4+ |
| 4 | 0 | 2+ | 1+ | 0 | 38 | 1+ | 1+ | 0 | 4+ |
| 5 | 0 | 2+ | 0 | 1W | 40 | 1+ | 0 | 0 | 4+ |
| 6 | 0 | 0 | 1W | 0 | 47 | 1+ | 0 | 1+ | 1W |
| 7 | 0 | 2+ | 3+ | 0 | 55 | 1W | 0 | 0 | 4+ |
| 8 | 0 | 0 | 2+ | 0 | 57 | 1W | 1+ | 0 | 4+ |
| 9 | 2+ | 1W | 0 | 4+ | 58 | 1+ | 2+ | 0 | 4+ |
| 11 | 0 | 0 | 3+ | 1W | 60 | 1+ | 0 | 0 | 4+ |
| 14 | 1+ | 1+ | 0 | 4+ | 61 | 1W | 0 | 1W | 4+ |
| 15 | 1W | 0 | 0 | 4+ | 62 | 1+ | 0 | 0 | 4+ |
| 16 | 0 | 3+ | 2+ | 0 | 64 | 1+ | 1W | 0 | 4+ |
| 20 | 1+ | 0 | 1+ | 4+ | 67 | 1W | 1W | 3+ | 3+ |
| 23 | 1W | 0 | 3+ | 4+ | 75 | 1W | 0 | 2+ | 2+ |
| 24 | 1W | 0 | 2+ | 4+ | 76 | 1W | 0 | 4+ | 4+ |
| 25 | 2+ | 1W | 0 | 4+ | 110 | 2+ | 0 | 0 | 4+ |
| 27 | 1W | 0 | 0 | 4+ | 117 | 4+ | 0 | 0 | 4+ |
| 28 | 1+ | 0 | 0 | 4+ | 119 | 1W | 1+ | 0 | 4+ |
| 29 | 1W | 0 | 0 | 4+ | 145 | 1W | 1W | 4+ | 1W |
| 30 | 1+ | 0 | 0 | 4+ | 152 | 2+ | 2+ | 0 | 4+ |
| 31 | 1+ | 0 | 0 | 4+ | 153 | 1W | 1W | 0 | 4+ |
| 32 | 0 | 1W | 1W | 4+ | 154 | 1W | 0 | 0 | 4+ |
| | | | | | 155 | 1+ | 1+ | 1W | 2+ |

B

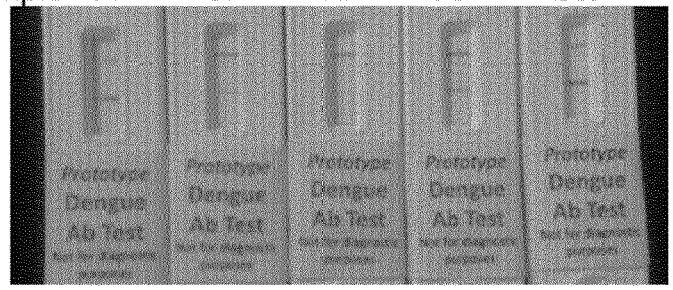

Sample   64    67    75    76    110

Score    4+    3+    2+    4+    4+

Fig. 17

E
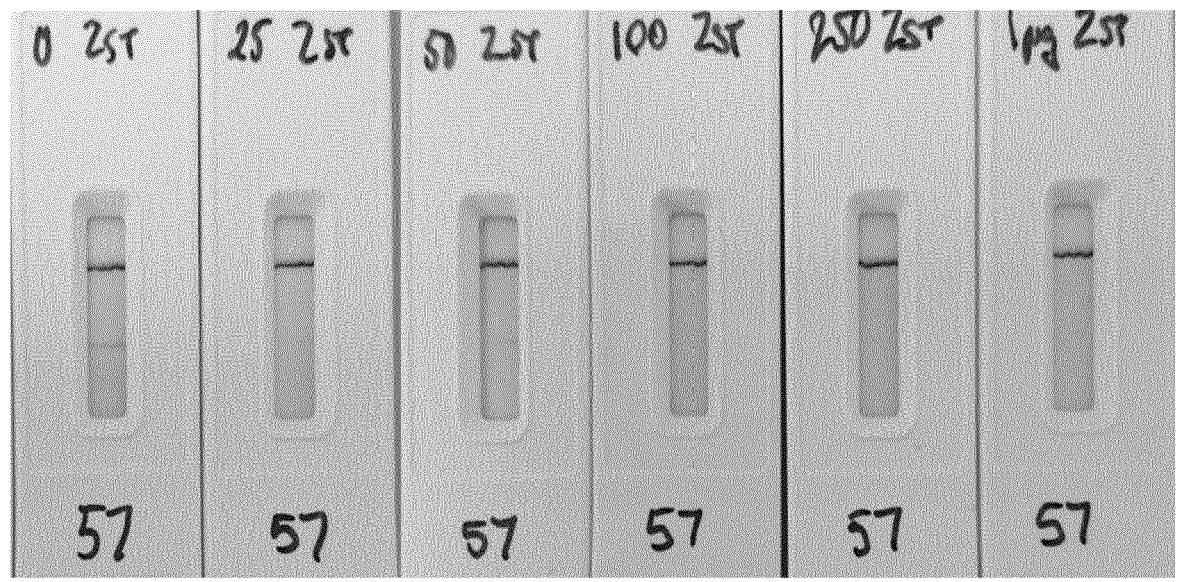
F
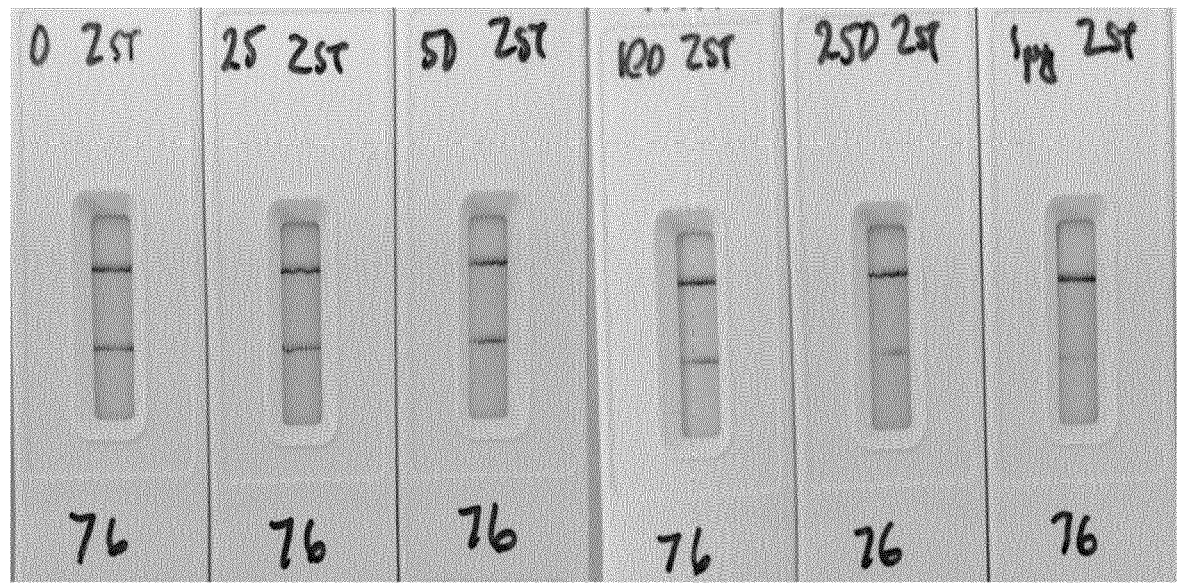
Fig. 19 (continued)

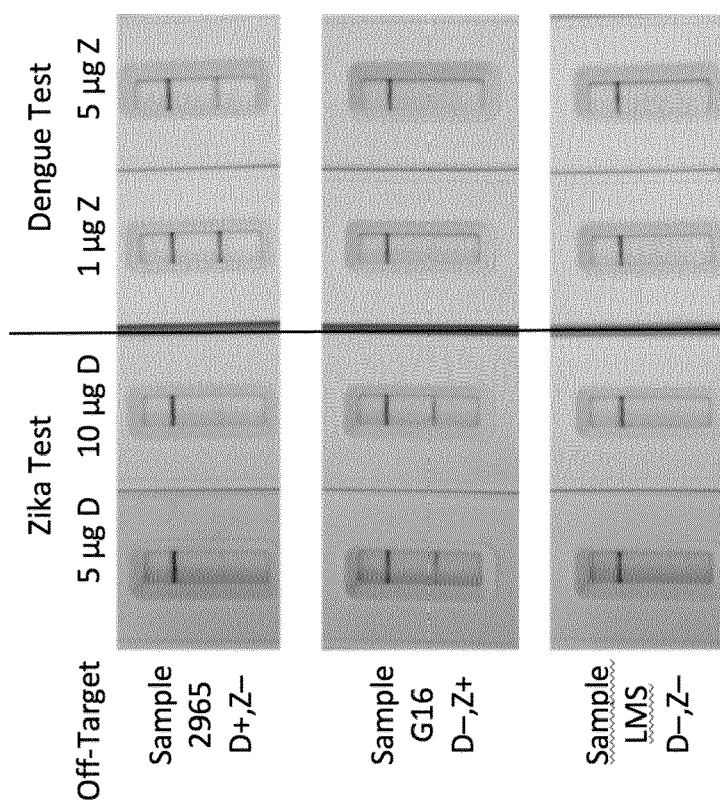
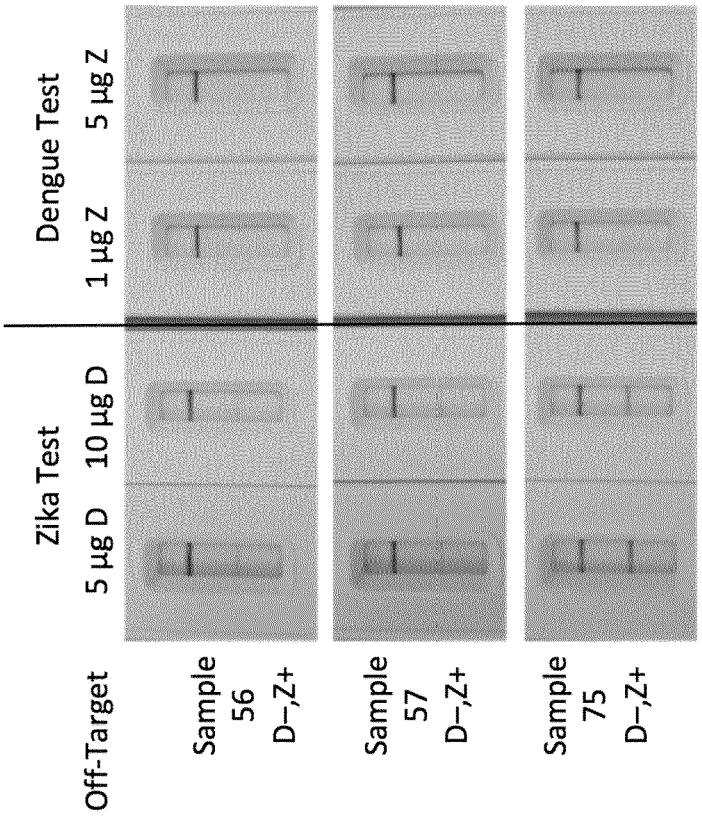
Fig. 19 (continued)

A
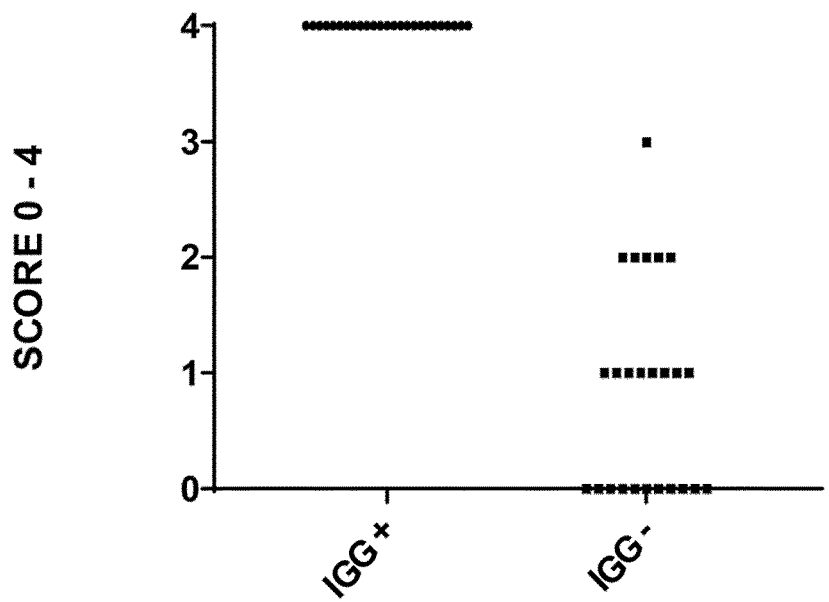
B
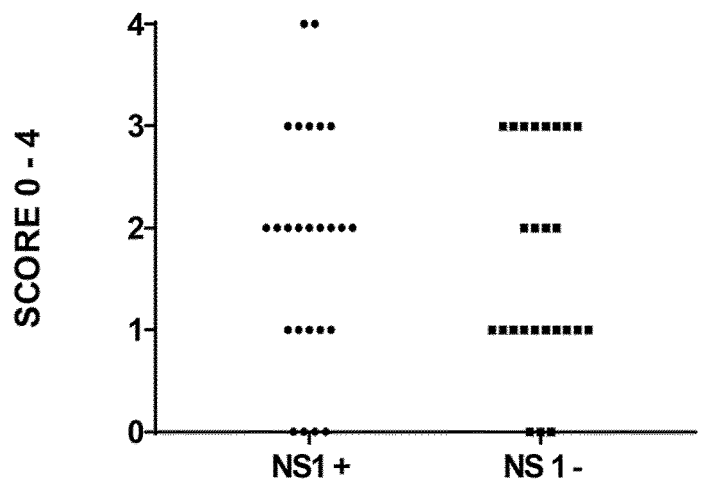
Fig. 21

B

| Sample number | Days between symptoms and 1st Sample | Score 0-4 ZIKV | Sample number | Days between symptoms and 2nd Sample | Score 0-4 ZIKV |
|---|---|---|---|---|---|
| 1044 A | 2 | 0 | 1044 B | 23 | 3 |
| 1624 A | 2 | 0 | 1624 B | 15 | 4 |
| 3334 A | 3 | 0 | 3334 B | 24 | 3 |
| 1867 A | 4 | 4 | 1867 B | 15 | 4 |
| 1474 A | 3 | 3 | 1474 B | 10 | 3 |
| 1552 A | 3 | 2 | 1552 B | 17 | 4 |
| 1637 A | 3 | 1 | 1637 B | 12 | 4 |
| 4456 A | 2 | 1 | 4456 B | 9 | 3 |
| 3045 A | 4 | 0 | 3045 C | 53 | 3 |
| 2471 A | 2 | 2 | 2471 B | 9 | 4 |
| 3532 A | 3 | 1 | 3532 B | 18 | 3 |
| 1681 A | 3 | 1 | 1681 B | 10 | 4 |

Fig. 22 (continued)

GLYCOSYLATED ANALOGUES OF FLAVIVIRUS E PROTEINS AND THEIR USE IN DIAGNOSTIC METHODS

TECHNICAL FIELD

The invention relates diagnostic systems comprising protein variants of the wild-type E proteins of Flaviviruses (e.g., a dengue or Zika virus) for use in diagnosis of Flavivirus infection as well as to compositions, tests devices, kits, kit-of-parts, methods and uses relating thereto, in particular for specific detection of Flavivirus antibody, diagnosis of Flavivirus infection and investigation of exposure to Flavivirus.

BACKGROUND ART

The Flaviviridae are a family of positive, single-stranded, enveloped RNA viruses. They are found in arthropods, (primarily ticks and mosquitoes), and can infect humans. Members of this family belong to a single genus, Flavivirus, and cause widespread morbidity and mortality throughout the world. Some of the mosquito-transmitted viruses include: Dengue Fever, Zika virus, Yellow Fever, Japanese encephalitis and West Nile viruses. Other Flaviviruses are transmitted by ticks and are responsible of encephalitis and hemorrhagic diseases: Tick-borne Encephalitis (TBE), Kyasanur Forest Disease (KFD) and Alkhurma disease, and Omsk hemorrhagic fever.

Flaviviruses are small spherical virions encoding ten viral proteins: three structural (capsid, precursor membrane/membrane, and envelope (E)) and seven nonstructural proteins. The E protein has important roles in viral attachment to cells, fusion with endosomal compartments, and modulating host immune responses. The ectodomain of the virus E protein folds into three structurally distinct domains (DI, DII, and DIII) forming head-to-tail homodimers on the surface of the virion. DI is the central domain that organizes the entire E protein structure. DII is formed from two extended loops projecting from DI and lies in a pocket at the DI and DIII interface of the adjacent E protein in the dimer. At the distal end of DII is a glycine-rich, hydrophobic sequence called the fusion loop, which encompasses residues 98-110, and is highly conserved among flaviviruses. This region has been implicated in the pH-dependent type II fusion event; during this process it becomes exposed and reoriented outward, making it available for membrane contact. DIII forms a seven-stranded Ig-like fold, is the most membrane distal domain in the mature virion, and has been suggested to be involved in receptor binding. A stem region links the ectodomain to a two-helix C-terminal transmembrane anchor that is important for virion assembly and fusion.

Dengue disease is a mosquito-borne viral infection caused by dengue virus (DENV), one of the most important human pathogens worldwide. The infection produces a systemic disease with a broad spectrum of outcomes, ranging from non-symptomatic/mild febrile illness (Dengue Fever, DF) to severe plasma leakage and haemorrhagic manifestations (Dengue Haemorrhagic Fever, DHF) that can further evolve into potentially fatal conditions (Dengue Shock Syndrome, DSS). DENV is spread by *Aedes* spp. mosquitoes and is widely distributed throughout the tropical and subtropical regions of the world. About 3 billion people, in over 100 countries, are estimated to be at risk of infection, with over 300 million infections, 500,000 episodes of DHF manifestations and 20,000 deaths reported each year. The spread and impact of Dengue disease has led the World Health Organization to classify it as the "most important mosquito-borne viral disease in the world".

Four different serotypes of dengue viruses (DENV1, DENV2, DENV3 and DENV4) have been identified to date; each serotype is pathogenic in humans. Infection with any one serotype induces lifelong immunity against that specific serotype, with only transient cross-protection against the three other serotypes. Severe manifestations of dengue infection are associated with secondary infections involving different viral serotypes; this happens through a mechanism known as antibody-dependent enhancement of infection (ADE). In ADE, recognition of viral particles by cross-reacting, but weakly or non-neutralising antibodies, leads to an increased Fc receptor-mediated uptake of immature or incompletely neutralised viruses by monocytes, macrophages and dendritic cells (the primary targets of dengue virus infections in humans) resulting in increased infectivity and deterioration of the patient's clinical condition. ADE is a critical consideration in dengue vaccine development, because an immunogen that does not elicit fully-neutralising antibodies to all four serotypes may contribute to disease, rather than prevent infection. Given the lack of efficient treatment against the infection and the risk to human health, there is a need to develop an efficient vaccine that provides a protective response without the potential to cause antibody-dependent enhancement.

One dengue vaccine has been licensed, Dengvaxia® (CYD-TDV), developed by Sanofi Pasteur. Approximately five additional dengue vaccine candidates are in clinical development, with two candidates (developed by NIH/Butantan and Takeda) which entered Phase III clinical trials in 2016.

In clinical trials, the Dengvaxia® vaccine was found to increase risk of hospitalization due to dengue haemorrhagic fever (the very disease it is meant to prevent) in young children (<5 years). As a result, Dengvaxia® vaccine has a limited license, i.e., only for persons of 9 years of age and above. Given the antigenic cross-reactivity of Zika and dengue, there is concern that vaccination with Dengvaxia® vaccine and other dengue vaccines under development may promote ADE of Zika virus, increasing the incidence of Guillain-Barré syndrome in adults and microcephaly in infants, and that vaccines in development against Zika may likewise increase risk of dengue haemorrhagic fever, as does Dengvaxia in some subjects.

Zika virus is a mosquito-borne flavivirus that was first identified in Uganda in 1947 in monkeys, it was later identified in humans in 1952 in Uganda and the United Republic of Tanzania. Outbreaks of Zika virus disease have been recorded in Africa, the Americas, Asia and the Pacific. From the 1960s to 1980s, human infections were found across Africa and Asia, typically accompanied by mild illness. The symptoms are similar to infections such as dengue, and include fever, skin rashes, conjunctivitis, muscle and joint pain, malaise, and headache. These symptoms are usually mild and last for 2-7 days. However, Zika virus infection may cause complications in some subjects. Zika virus infection during pregnancy has been recognised as a cause of congenital brain abnormalities, including microcephaly. Zika virus is a trigger of Guillain-Barré syndrome. Links between Zika virus and a range of neurological disorders are being investigated.

Sanofi reported in 2016 its collaboration with the Walter Reed Army Institute of Research (WRAIR) in the United States and Fiocruz public health center in Brazil to develop a Zika vaccine and reported in 2016 that immunization with a plasmid DNA vaccine or a purified inactivated virus vaccine provided complete protection in susceptible mice against challenge with a strain of Zika virus involved in an outbreak in northeast Brazil (Larocca et al., 2016 Nature 536, 474-478 (25 Aug. 2016)

However, plasmid DNA vaccination in man requires 'gene gun' or similar technology (e.g., electroporation) for delivery and this approach is not considered to provide a global solution to the problems of dengue and Zika. Also, both the DNA vaccine and inactivated virus vaccine approaches in development contain dengue-Zika cross-reactive epitopes implicated in the causation of ADE.

After infection, or vaccination, the body's immune system produces neutralizing antibodies that bind to the surface proteins of a virus to block infection. Antibody-dependent enhancement (ADE) occurs when antibodies elicited by one virus can bind to, but do not block (neutralise) the infection of a similar virus.

ADE is most commonly observed for dengue virus. The 4 known serotypes of dengue virus have distinct, but related surface proteins. Infection with a first dengue virus serotype typically results in mild, or no, symptoms in the infected subject. If the subject is infected subsequently with a second dengue serotype, the immune system will produce antibodies to the first serotype that bind to the second serotype of virus, but will not always block infection and which have the potential to cause ADE. As a result there is antibody-mediated uptake of virus into cells that dengue virus does not normally infect (i.e., cells having receptors for the 'tail' or Fc region of the antibody). This can result in a more severe form of disease such as dengue hemorrhagic fever or dengue shock syndrome. Only young infants develop dengue haemorrhagic fever upon a first exposure to dengue, as a result of transplacentally transmitted maternal anti-dengue antibodies. As such, antibodies are equal partners with virus in (severe) disease causation in adults and infants alike.

Dengue virus antibodies not only promote ADE of other dengue virus serotypes, but also enhance Zika virus infection. Dejnirattisai et al., (2016) Nature Immunology 17, 1102-1108. "Dengue virus sero-cross-reactivity drives antibody-dependent enhancement of infection with Zika virus". Dejnirattisai et al. tested the effect of dengue neutralizing antibodies or serum from dengue virus patients on Zika virus in cell culture. In the absence of antibody, Zika virus poorly infected the cells, but when Zika virus was incubated with dengue serum or neutralizing antibodies, Zika virus robustly infected these cells, indicating the operation of ADE. The physiological relevance of this finding requires confirmation in epidemiological studies, but these findings pose an obvious risk for current vaccine approaches. To date no satisfactory solution to this problem has been conceived or advocated.

While vaccines in this field may transpire to have net benefit on a population basis, on an individual basis the picture is different. In some subjects, tragically, preventing one disease may increase the severity or risk of mortality from another. Paul L M et al. Clinical & Translational Immunology (2016) 5, e117 "Dengue virus antibodies enhance Zika virus infection" have reported that:

"For decades, human infections with Zika virus (ZIKV), a mosquito-transmitted Flavivirus, were sporadic, associated with mild disease, and went underreported since symptoms were similar to other acute febrile diseases. Recent reports of severe disease associated with ZIKV have greatly heightened awareness. It is anticipated that ZIKV will continue to spread in the Americas and globally where competent *Aedes* mosquito vectors are found. Dengue virus (DENV), the most common mosquito-transmitted human flavivirus, is both well-established and the source of outbreaks in areas of recent ZIKV introduction. DENV and ZIKV are closely related, resulting in substantial antigenic overlap. Through antibody-dependent enhancement (ADE), anti-DENV antibodies can enhance the infectivity of DENV for certain classes of immune cells, causing increased viral production that correlates with severe disease outcomes. Similarly, ZIKV has been shown to undergo ADE in response to antibodies generated by other flaviviruses. We tested the neutralizing and enhancing potential of well-characterized broadly neutralizing human anti-DENV monoclonal antibodies (HMAbs) and human DENV immune sera against ZIKV using neutralization and ADE assays. We show that anti-DENV HMAbs, cross-react, do not neutralize, and greatly enhance ZIKV infection in vitro. DENV immune sera had varying degrees of neutralization against ZIKV and similarly enhanced ZIKV infection. Our results suggest that pre-existing DENV immunity may enhance ZIKV infection in vivo and may lead to increased disease severity. Understanding the interplay between ZIKV and DENV will be critical in informing public health responses and will be particularly valuable for ZIKV and DENV vaccine design and implementation strategies."

Dengue virus antibodies can promote ADE of Zika virus. Zika virus antibodies can promote ADE of dengue virus. Thus, immunization against Zika virus could increase the incidence of dengue hemorrhagic fever or dengue shock syndrome, or foster the development of these conditions in individuals that would not otherwise have developed them, but for immunisation. Given the interval between infections, which can be several years, it will be years before post-marketing surveillance studies are able to inform if, and to what extent, new vaccines predispose to severe dengue disease (haemorrhagic fever, shock syndrome) or severe Zika sequelae, such as Guillain-Barré syndrome or microcephaly.

Accordingly, there is a clear need for vaccine approaches that are designed purposefully to avoid the problem of antibody-dependent enhancement.

WO2016012800 discloses identification and characterisation of cross-reactive neutralising antibodies obtained from patients infected with dengue virus. The acute human antibody response was found to be focused on two major epitopes; a known epitope on the fusion loop (FL FLE), and a second epitope, said to be novel, which was found on intact virions or dimers of envelope protein and which encompassed areas of domains I, II and III. Antibodies reactive with the second epitope, the Envelope Dimer Epitope, or EDE, were reported to fully neutralise virus made in both insect and primary human cells in the low picomolar range. A subunit vaccine comprising a stabilized soluble protein E dimer was therefore proposed as a dengue vaccine. WO2016012800 discloses that a dengue virus envelope glycoprotein E ectodomain (sE; soluble envelope polypeptide/glycoprotein) refers to the 1-395 amino acid fragment of the envelope glycoprotein E of the dengue virus serotypes 1, 2 and 4, and to the 1-393 amino acid fragment of the envelope glycoprotein E of the dengue virus serotype 3. WO2016012800 described the EDE as a stabilised dimer of sE, selected from DENV-1 sE, DENV-2 sE, DENV-3 sE, DENV-4 sE and mutant sE thereof having at least one mutation (substitution) selected among H27F, H27W, L107C, F108C, H244F, H244W, S255C, A259C, T/S262C, T/A265C, L278F, L292F, L294N, A313C (S313C in DEN3) and T315C, which mutations are considered to contribute to increased stability in the dimer configuration. It is disclosed that mutant sE thereof may further comprise at least one mutation (substitution) selected from Q227N, E174N and D329N; preferably all three mutations Q227N, E174N and D329N, which mutations are said to mask non-appropriate immunogenic regions and allow the stabilized recombinant sE dimer of the invention to preferentially elicit neutralizing antibodies directed to all four dengue virus serotypes.

The sE dimer mutations described are said not to interfere with immunogenicity but to provide a higher dimer affinity, by including cysteine mutations at the dimer contacts to provide stabilization by cross-links, and/or by introduction of new glycosylation sites to allow chemical cross-linking between adjacent sugars on the dimer by click chemistry, and/or by substitution of at least one amino acid residue in the amino acid sequence of at least one sE monomer with at least one bulky side chain amino acid to allow forming cavities at the dimer interface or in domain 1 (D1)/domain 3 (D3) linker of each monomer.

WO2016012800 discloses that the envelope protein may be engineered such that an improved EDE is generated, an EDE which is incapable of being recognised or raising anti-fusion loop (anti-FL) antibodies was considered to be an improved EDE. It is disclosed that such improvement may be accomplished by one or more mutations, deletions or insertions in the envelope protein, by generating a hybrid protein wherein the specific epitope (without any antigens which would raise anti-FL antibodies) is fused to a scaffold protein, or by engineering the envelope protein by modifying the internal surface of the dimer (projecting to the inside of the virus) with sugars to make it less immunogenic by adding N or O linked glycan sequences.

Roby et al., (2013, 2014) describe an approach to development of a vaccine candidates for West Nile virus by introduction of large internal deletions within the capsid (C) gene of flavivirus genomes to generate replication-competent RNAs that are unable to be packaged into virions, yet maintain secretion of highly immunogenic subviral particles (SVPs) without generating infectious virus. Such pseudoinfectious C-deleted vaccines are able to replicate and secrete large amounts of non-infectious immunogenic subviral particles (SVPs) from transfected cells and thus are said to offer the combined benefit of the safety of noninfectious inactivated or subunit vaccines with the robust immune response generated by the replication of live vaccines.

Roby et al., (2013) generated a construct, pKUNdC/C (KUNdC18-100/CMV-C), with C-deleted CMV-promoter driven cDNA of West Nile virus Kunjin (KUNV) in which alpha helices 1, 2, and 4 were removed in two separate segments and the hydrophilic alpha helix 3 was maintained. In pKUNdC/C C-deleted WNV cDNA was placed under the control of one copy of the cytomegalovirus (CMV) promoter and the C gene was placed under the control of a second copy of the CMV promoter in the same plasmid DNA. The conservation of the larger cytosolic moiety (alpha helix 3) led to a significant improvement in SVP secretion compared to that of constructs with deletions of all alpha helices of C and dC44-59. Additional improvements to SVP secretion were also observed upon the incorporation of an Asn-linked glycosylation motif at N154 of the E protein, a feature of many circulating strains of WNV and recent isolates of KUNV, corresponding to an NYS motif at amino acids 154 to 156 of the E protein. pKUNdC/C was shown to generate single-round infectious particles (SRIPs) capable of delivering self-replicating C-deleted RNA producing SVPs to surrounding cells. However, the amounts of both SRIPs and SVPs produced from pKUNdC/C DNA were relatively low.

Roby et al., (2014) reported production of a second generation constructs with C-deleted cDNA of West Nile virus Kunjin (KUNV) in which the CMV promoter was replaced by a more powerful elongation factor EF1a promoter and different forms of C were used to attempt to increase SRIP production by optimizing trans-C expression. A construct containing an elongation factor EF1a promoter encoding an extended form of C was demonstrated to produce the highest titres of SRIPs and was immunogenic in mice. SRIP and SVP titres were further improved via incorporation of the N154 glycosylation motif in the envelope protein (corresponding to an NYS motif at amino acids 154 to 156 of the E protein) which enhanced secretion of SVPs.

Davis et al., (2014) investigated the ability of West Nile virus (WNV) to infect CD209-expressing cells. Mammalian cell-derived West Nile virus preferentially infects cells expressing the C-type lectin CD209L but not cells expressing CD209; by contrast, Dengue virus (DENV) infection is enhanced in cells expressing either attachment factor. DENV and WNV virions have very similar structures. Their surfaces consist of a regular array of 180 envelope (E) protein subunits arranged in an icosahedral lattice (36). The small membrane (M) protein, generated following furin-mediated processing of pre-membrane protein (prM), is also present on the virion surface but is mostly buried in the viral membrane. The major structural differences between DENV and WNV virions stem from the number and location of N-linked glycosylation sites in the DENV viral E proteins. Most DENV isolates contain glycosylation sites at residues 67 and 153, although the site at 153 may not always be utilized; WNV E proteins only contain an N-linked glycan at asparagine 154, although this is absent in many virus strains. The presence of N-glycosylation on the WNV E protein has been linked in some studies to increased neuro-invasiveness in mice and to altered cellular tropism in vitro. Davis et al. introduced a glycosylation site at position 67 into West Nile virus E. Reporter virus particles pseudotyped with this E protein infected cells using either CD209 or CD209L. Glycosylation sites were introduced at several other positions. The WNV strain NY99 prM-E expression plasmid pCBWN and a derivative of this plasmid lacking the N-linked glycosylation site at E protein residue 154 (NY99-N154Q) were used as templates for the introduction of novel N-linked glycosylation sites into the WNV E protein by site-directed mutagenesis. The following amino acid changes were introduced into NY99-N154Q: (i) Ala-54 to Thr (A54T) adds an N-linked glycosylation site at Asn-52; (ii) D67N adds a site at Asn-67; (iii) K84T adds a site at Asn-82; (iv) A173N and P174G (AP173NG) add a site at Asn-173; (v) Glu-182 to NGS (E182NGS) adds a site at Asn-182 by mutating Glu-182 to Asn and inserting two amino acids (Gly-Ser) to complete the sequon; (vi) S230N and V232T (STV230NTT) add a site at Asn-230; (vii) V279T adds a site at Asn-277; (viii) T301N and G303S (TYG301NYS) add a site at Asn-301; (ix) T330N adds a site at Asn-330; (x) K370T adds a site at Asn-368; (xi) G389N and Q391T (GEQ389NET) add a site at Asn-389. All sites allowed CD209L mediated infection, but only a subset promoted CD209 use. As seen for other viruses, mannose-rich glycans on West Nile virus were required for its interactions with CD209, however, mannose-rich glycans were not required for CD209L mediated infection. Complex glycans, particularly N-acetylglucosamine-terminated structures, were able to mediate reporter virus particle interactions with CD209L. Davis et al. proposed that that CD209L recognizes glycosylated flaviviruses with broad specificity, whereas CD209 is selective for flaviviruses bearing mannose-rich glycans and thus that the location of the N-linked glycosylation sites on a virion determines the types of glycans incorporated, thus controlling viral tropism for CD209-expressing cells.

The Zika epidemic is a global problem with profound consequences for nations and families that will take decades to unfold, with an estimated 2.3 billion people at high or very high risk of infection (Alaniz, Bacigalupo, & Cattan, 2017). While Zika is asymptomatic in 80% of cases, it can give rise to serious conditions such as Guillain-Barre' syndrome and acute disseminated encephalomyelitis in adults (Medina & Medina-Montoya, 2017), as well as microcephaly and other abnormalities of infants born to women infected during pregnancy (i.e., the Zika congenital syndrome ZCS (Lucey, Cummins, & Sholts, 2017)). While there is an urgent need for a new vaccine against Zika, there is a similar urgency and an ongoing need to accurately monitor, map and contain outbreaks of Zika—which is difficult to distinguish, in terms of its clinical presentation and symptoms, from various other infections—particularly dengue. While an ongoing infection with Zika, dengue or other flaviviruses can be accurately diagnosed by measurement of virus by reverse-transcriptase quantitative PCR, or similar methodologies that detect the viral genome in body fluids (plasma, serum, urine), the viraemic phase of these diseases is typically short, in the case of Zika lasting only a few days (Hofer, 2016), and can easily be missed. Also, nucleic-acid based tests using PCR or similar methodology are relatively expensive and not well-suited to deployment in resource-limited countries where epidemics may initiate undetected, hampering the targeted deployment vector-control measures to control mosquito populations. For these reasons there is a particular need for serological tests (which measure antibodies), that can determine if a person has been infected with Zika (or dengue), particularly serological tests, such as point-of-care tests, that can be executed without the need for centralised laboratory facilities.

In addition to the value of serodiagnostics in support of vector control campaigns for both Zika and dengue, there are additional needs for reliable serodiagnostics relating to the safe use of vaccines and the rapid mapping of ongoing Zika outbreaks for the effective and appropriate deployment of new vaccines in clinical trials, and once licensed. However, there is a problem in distinguishing, reliably, between Zika and other flavivirus infections based on existing serodiagnostic tests which are particularly prone to false positives due to antibody cross-reactivity. Thus, Zika is closely related to dengue (another flavivirus infection, spread by the same mosquito species), having about 50% sequence identity with dengue and a remarkably similar 3D structure, juxtaposition and topography of the immunogenic envelope proteins of the virion surface (Sirohi et al., 2016), explaining the high degree of antibody cross-reactivity between these viruses (Chang et al., 2017) (Priyamvada et al., n.d.) (Dejnirattisai et al., 2016).

By virtue of its cross-reactivity with dengue, Zika is part of a complex ecosystem of virus interactions where infection of a human subject with one flavivirus can give rise to antibodies that influence the course of other flavivirus infections both positively and negatively (Halstead, 2014). This phenomenon is well-established for dengue infection, where a second episode of infection (necessarily, with a different serotype of dengue) may give rise to severe disease (including dengue shock syndrome and dengue haemorrhagic fever) (Guzman, Alvarez, & Halstead, 2013). Dengue virus is responsible for 390 million infections annually, and is capable of causing life-threatening 'severe dengue' including haemorrhagic fever and shock syndrome. According to the WHO, "An estimated 500 000 people with severe dengue require hospitalization each year, and about 2.5% of those affected die.". The mechanism of severe dengue upon secondary infection, though long suspected, has recently been formally demonstrated to be attributable to antibody-dependent enhancement (ADE) of disease (Katzelnick et al., 2017). Likewise dengue vaccination, with the recently licensed DengVaxia™ vaccine can also have this undesirable effect in dengue naïve subjects, predisposing them to severe dengue by in effect acting as a silent primary infection (Ferguson et al., 2016; Flasche et al., 2016; Hadinegoro et al., 2015). In order to minimise the risk of priming for severe dengue, the dengue vaccine is licensed only for persons 9 years of age and above, and in territories with high endemicity for dengue. Clearly, however, these measures cannot be expected to eliminate the risk entirely (Halstead, 2017a), such that a serological diagnostic test capable of reliably distinguishing prior dengue exposure from prior Zika exposure could allow safer deployment of the DengVaxia vaccine and potentially other flavivirus vaccines in development.

Due to the cross-reactivity of Zika with dengue, and the phenomenon of antibody-dependent enhancement, it is rationally anticipated that Zika infection, and potentially also Zika vaccination (when vaccines become available), will prime dengue-naïve subjects for severe dengue (Russell, 2016; Screaton, Mongkolsapaya, Yacoub, & Roberts, 2015; Willis & Hensley, 2017); and (conversely) it is anticipated that antibodies generated by dengue infection or vaccination will likewise be capable of ADE of Zika infection (Dejnirattisai et al., 2016; Paul et al., 2016; Screaton et al., 2015), as would be predicted by Zika's notional status as a fifth serotype of dengue. Although these concerns await formal confirmation in human epidemiological studies (Halstead, 2017b; 2017a) (Sariol, Nogueira, & Vasilakis, 2017), as did (until recently) the role of antibody dependent enhancement in causation of severe dengue (Katzelnick et al., 2017), there are substantial grounds for concern.

A reliable point-of-care diagnostic could be applied to travellers from non-dengue endemic countries to dengue-endemic countries allowing them to be vaccinated safely, without risk of predisposing them to severe dengue, extending the utility of the DengVaxia vaccine (and likely other dengue and Zika vaccines that will be licensed) to traveller populations, who are predominantly dengue naïve. The consequences of prior Zika virus infection for the DengVaxia vaccine have not yet been established, but it may reasonably be expected to have an influence, positively or negatively, on the safety and efficacy of vaccination with the DengVaxia vaccine, and other vaccines that may be licensed for dengue.

Vaccine resources are often in short supply, serodiagnostics, especially point of care diagnostics, have the potential to allow targeted distribution to outbreak areas. Also, such diagnostics can be used to inform both the effectiveness and safety of development/deployment of novel vaccines. For example antibodies (resulting from prior infections with related viruses) already present in the blood of patients experiencing Zika virus infection may influence the course of the disease or the result of Zika vaccination (e.g. whether the naturally-encountered Zika virus crosses the placenta and damages the foetus, or whether live-attenuated vaccine strains might do the same thing). Current diagnostic practice is not adequate to properly enable the intelligent deployment of vaccines because it is based in central diagnostic labs that require the transport of blood samples from diverse, sometimes remote, areas of endemic countries, which is expensive and inefficient, and which may not be possible in many instances due to lack of the necessary refrigerated transport infrastructure.

What is needed to enable effective monitoring and safe development of Zika and dengue vaccines is a cheap 'point-of-care' diagnostic test that can distinguish reliably between them, i.e., a test that can be run without the need for clean water, electricity or equipment—e.g., like a do-it-yourself (DIY) pregnancy test, that can be operated in the home or in a Doctor's surgery or hospital clinic. Such test will help define which subjects are eligible to receive Zika vaccination (e.g., futile to immunise a Zika immune subject), maximising the safety and effectiveness of its deployment. It will also help define whether a subject has responded adequately to the vaccine (i.e. reached a 'to be determined' protective level of Zika-specific or dengue-specific antibodies, e.g., by detecting neutralising antibodies) or whether they may require a further dose (a factor that may vary in differing endemic territories, depending on prior exposure to related viruses).

To date, the 'gold standard' with respect to specificity for the serodiagnosis of dengue, Zika and other flaviviruses is the PRNT test (plaque reduction neutralisation test), wherein, in a laboratory centre, susceptible cells are infected in the presence of various concentrations of a test serum and a 50% inhibition value reported. However, this test is prone to false positives even with diverse flaviviruses. Thus Houghton-Trivino et al. found that 16/20 dengue infected subjects had high yellow fever neutralisation titres which were not attributable to yellow fever vaccination or infection ("Dengue-yellow fever sera cross-reactivity; challenges for diagnosis.—PubMed—NCBI," 2017). Serodiagnostic tests will face increasing challenges of cross-reactivity as new flavivirus pandemics emerge in the future (Smith, 2016), as did Zika recently, unexpectedly. Notably, there is particular concern at the time of writing about resurgent yellow fever in Brazil and Africa (Mir et al., 2017), and further concern about the introduction of yellow fever to China from Africa (Ling et al., 2016). The presence of yellow fever epidemics will further complicate serodiagnosis using tests that do not accurately distinguish between yellow fever and other flaviviruses.

Specific diagnosis of Flavivirus infections using current serological testing is complicated by the cross-reactivity between antibodies against other clinically-relevant flaviviruses. Cross-reactivity is particularly problematic in areas where different flaviviruses co-circulate or in populations that have been immunized with vaccines to Flaviviruses. The majority of cross-reactive antibodies are raised against the immunodominant flavivirus envelope (E) protein target a conserved epitope in the fusion loop at the distal end of domain II.

There is a need for a diagnostic approach that can differentiate between closely-related Flaviviruses, to assess if an individual is seronegative and thus has not been exposed to dengue or Zika, or if an individual is seropositive and has been exposed to Zika and/or dengue and for those who are seropositive, to distinguish to which of Zika and/or the four dengue serotypes the individual has been exposed. There is a need for a diagnostic approach that can be used to select subjects for immunization, or assess seroconversion to determine if immunization has raised a protective immune response against dengue or Zika. There is thus a need for diagnostic approaches that enable interrogation of the immune response to distinguish antibodies against the dengue virus serotypes and against Zika virus.

STATEMENT OF INVENTION

The invention provides:

1. An isolated recombinant analogue of a flavivirus E-protein comprising an analogue of a flavivirus E-protein fusion loop, wherein the analogue of the flavivirus E-protein fusion loop comprises at least one glycosylation site for an N-linked glycan that is not present in a natural flavivirus E-protein fusion loop sequence, wherein the at least one glycosylation site is an N-linked glycosylation sequon (Asn-X-Ser/Thr) and the Asn (N) residue of the sequon occupies any of positions 98-110 (DRGWGNGCGLFGK) of the natural flavivirus E-protein fusion loop amino acid sequence, wherein X is any amino acid residue except proline and Ser/Thr denotes a serine or threonine residue, for use in an in vitro method for diagnosis of flavivirus infection and/or to investigate exposure to flavivirus.

2. An isolated recombinant analogue of a flavivirus E-protein according to clause 1, wherein the analogue of the flavivirus E-protein fusion loop comprises two glycosylation sites that are not present in a natural flavivirus E-protein fusion loop.

3. An isolated recombinant analogue of a flavivirus E-protein of any preceding clause which is glycosylated with a glycan at one or at both of the introduced glycosylation sites in the analogue of the flavivirus E-protein fusion loop.

4. An isolated recombinant analogue of a flavivirus E-protein of clause 2 or clause 3 wherein the glycan is an N-linked glycan.

5. An isolated recombinant analogue of a flavivirus E-protein of any one of the preceding clauses, comprising an N-linked glycosylation sequon (Asn-X-Ser/Thr) such that an Asn (N) residue of the sequon occupies any of positions 98-101 and/or 106-110.

6. An isolated recombinant analogue of a flavivirus E-protein of any one of the preceding clauses, wherein X is any of the following 13 amino acid residues Gly, His, Asn, Gln, Tyr, Val, Ala, Met, Ile, Lys, Arg, Thr or Ser.

7. An isolated recombinant analogue of a flavivirus E-protein of any one of the preceding clauses, wherein the flavivirus E-protein is a dengue virus E-protein and the Asn (N) residue of a sequon occupies position 101, 108 or both 101 and 108 of the amino acid sequence of the flavivirus E-protein fusion loop or the flavivirus E-protein is a Zika E-protein and the Asn (N) residue of a sequon occupies position 100 of the amino acid sequence of the flavivirus E-protein fusion loop.

8. An isolated recombinant analogue of a flavivirus E-protein of any one of the preceding clauses, wherein the flavivirus is a dengue virus and the amino acid sequence of the analogue flavivirus E-protein fusion loop 98-110 is selected from: DRGNGSGCGLNGS, DRGNGSGCGLFGK and DRGWGNGCGLNGS.

9. An isolated recombinant analogue of a flavivirus E-protein of any one of the preceding clauses, wherein the flavivirus is a Zika virus and the amino acid sequence of the analogue flavivirus E-protein fusion loop 98-110 is DRNHTNGCGLFGK.

10. An isolated recombinant analogue of a flavivirus E-protein of any one of the preceding clauses which is the product of expression of a recombinant nucleic acid sequence in a host cell capable of post-translational glycosylation.

11. An isolated recombinant analogue of a flavivirus E-protein of any one of the preceding clauses, which is the product of expression of a recombinant nucleic acid sequence in a host cell capable of glycosylation with an N-linked glycan.

12. An isolated recombinant analogue of a flavivirus E-protein of clause 10 or clause 11, wherein the host is a mammalian cell or insect cell.

13. An isolated recombinant analogue of a flavivirus E-protein of any one of clauses 10 to 12, wherein the host is a HEK cell line or a Tni cell line.

14. A diagnostic test or test kit comprising an isolated recombinant analogue of a flavivirus E-protein of any one of clauses 1 to 13 and a reagent capable of detecting an immunological (antigen-antibody) complex which contains said isolated analogue or binding molecule.

15. A diagnostic test or test kit according to clause 14, further comprising one or more control standards and/or a specimen diluent and/or washing buffer.

16. A diagnostic test or test kit according to clause 14 or 15, wherein said analogue and/or binding molecule is immobilized on a solid support.

17. A diagnostic test or test kit according to any one of clauses 14 to 16, wherein the solid support is a microplate well.

18. A diagnostic test or test kit according to any one of clauses 14 to 17, wherein an immunological complex which contains said isolated analogue or binding molecule is detected by ELISA.

19. A diagnostic test or test kit according to any one of clauses 14 to 18, wherein said immunological complex which contains said isolated analogue or binding molecule is detected by lateral flow.

20. A diagnostic test or test kit according to any one of clauses 14 to 19, wherein said test or kit comprises a test device comprising a lateral flow test strip comprising:
a sample pad for application of a liquid sample.
a conjugate pad comprising a detector conjugate for conjugation of anti-flavivirus antibody in the liquid sample,
a capture strip (e.g. nitrocellulose strip) comprising a capture means to capture the detector conjugate-anti-flavivirus antibody complex
and
an absorbent pad,
the pads and capture strip being arranged to permit capillary flow communication with each other.

21. A diagnostic test or test kit according to clause 20, wherein the sample pad comprises a red blood cell arresting agent, e.g. an anti-glycophorin antibody.

22. A diagnostic test or test kit according to clause 20 or clause 21 wherein the detector conjugate is a coloured particle (e.g. colloidal gold) conjugated to an anti-human antibody (e.g. anti-human IgG or anti-human IgM antibody) and the capture means for capture of the detector conjugate-anti-flavivirus antibody complex is an antigen comprising a recombinant analogue of a flavivirus E-protein of any one of clauses 1 to 13.

23. A diagnostic test or test kit according to any one of clause 20 to 22, wherein the antigen is attached directly to the capture strip or indirectly via a tag system whereby an anti-tag reagent on the capture strip binds the tagged antigen.

24. A diagnostic test or test kit according to clause 20 or clause 21, wherein the detector conjugate is a coloured particle (e.g. colloidal gold) conjugated to an antigen comprising a recombinant analogue of a flavivirus E-protein of any one of clauses 1 to 13 and the capture means for capture of the detector conjugate-anti-flavivirus antibody complex is an anti-human Ig antibody (e.g. anti-human IgG antibody or anti-human IgM antibody).

25. A diagnostic test or test kit according to clause 24, wherein the anti-human Ig antibody is attached directly to the capture strip or indirectly via tag system whereby an anti-tag reagent on the capture strip binds to the tagged antibody.

26. A diagnostic test or test kit according to clause 23 or 25, wherein the tag system is a His tag system, a FLAG tag system or a Streptavidin tag system.

27. A diagnostic test or test kit according to any one of clauses 20 to 26 wherein the liquid sample is a biological sample 28. A diagnostic test or test kit according to one of clauses 20 to clause 27, wherein the liquid sample is a biological sample selected from blood, plasma, serum, saliva and CSF.

29. A diagnostic test or test kit according to any one of clauses 20 to 28, wherein lateral flow test strip is housed within a casing, said casing having a window for visual inspection of the test result wherein during use the accumulation of colored particles produces a color indicative of the presence of an anti-flavivirus antibody in the liquid sample, said casing comprising a first port for application of the liquid sample or liquid sample and diluent, optionally comprising a second port (preferably more distal from the window than the first port) for application of the diluent.

30. A method for detection of a flavivirus antibody in a sample comprising use of a diagnostic test or test kit according to any one of clauses 14 to 29.

31. A diagnostic test, kit, test device or method substantially as described herein with reference to the description, drawings and/or clauses 1 to 30 above and to the claims.

The invention employs an isolated recombinant analogue of a flavivirus E-protein fusion loop comprising at least one glycosylation site for an N-linked glycan that is not present in a natural flavivirus E-protein fusion loop sequence, wherein the at least one glycosylation site is an N-linked glycosylation sequon (Asn-X-Ser/Thr) and the Asn (N) residue of the sequon may occupy any of positions 98-110 (SEQ ID NO: 1 DRGWGNGCGLFGK) of the natural flavivirus E-protein fusion loop amino acid sequence, wherein X is any amino acid residue except proline and Ser/Thr denotes a serine or threonine residue.

An isolated recombinant analogue of a flavivirus E-protein fusion loop may comprise two glycosylation sites that are not present in a natural flavivirus E-protein fusion loop sequence.

The invention employs an isolated recombinant analogue of a flavivirus E-protein comprising an analogue of a flavivirus E-protein fusion loop of the invention. In some embodiments the only modifications to the sequence of the isolated recombinant analogue of a flavivirus E-protein are the modifications in the fusion loop to introduce N-linked glycosylation sequon(s) (Asn-X-Ser/Thr), in other embodiments one or more further modifications may be introduced in flavivirus E-protein at residues outside the fusion loop.

An analogue of the having at least one glycan attached thereto is preferred. Preferably the at least one glycan is an N-linked glycan. Preferably the analogue is the product of expression of a recombinant nucleic acid sequence. At least one glycan may be present at one or more native glycosylation sites in the flavivirus E-protein outside the flavivirus E-protein fusion loop.

An analogue employed in the invention, may comprise an N-linked glycosylation sequon (Asn-X-Ser/Thr) such that an Asn (N) residue of the sequon occupies any of positions 98-101 and/or 106-110.

Preferably, X is any of the following 13 amino acid residues Gly, His, Asn, Gln, Tyr, Val, Ala, Met, Ile, Lys, Arg, Thr or Ser.

In preferred analogues for use in the invention, the flavivirus E-protein is a dengue virus E-protein and the Asn (N) residue of a sequon occupies position 101, 108 or both 101 and 108 of the amino-acid sequence of the analogue flavivirus E-protein fusion loop or the flavivirus E-protein is a Zika E-protein and the Asn (N) residue of a sequon occupies position 100 of the amino acid sequence of the analogue flavivirus E-protein fusion loop.

In a preferred analogues for use in the invention, the flavivirus is a dengue virus and the amino acid sequence of the analogue flavivirus E-protein fusion loop 98-110 is selected from: SEQ ID NO: 2 DRGNGSGCGLNGS, SEQ ID NO: 3 DRGNGSGCGLFGK and SEQ ID NO: 4 DRGWGNGCGLNGS.

In another preferred analogue for use in the invention, the flavivirus is a Zika virus and the amino acid sequence of the analogue flavivirus E-protein fusion loop 98-110 is SEQ ID NO: 5 DRNHTNGCGLFGK.

An isolated recombinant DNA or RNA sequence comprising a sequence encoding an analogue of a flavivirus E-protein fusion loop for use according to the invention.

An isolated recombinant DNA sequence may be a plasmid or a linear DNA-based vaccine. An isolated recombinant DNA sequence of the invention may encode an analogue of a flavivirus E-protein according to the invention under control of a mammalian promoter.

A host cell comprising a DNA or RNA sequence according to the invention may be an eukaryotic host cell comprising a DNA sequence according to the invention or a plasmid.

Preferably, a host cell is capable of expressing an analogue for use in the invention. Further preferably, a host cell is capable of expressing and glycosylating an analogue for use in the invention.

A method of making an analogue for use in the invention may comprise culturing a host cell according to the disclosure in conditions suitable for expression of the analogue and isolating the analogue.

Further provided is a composition comprising an analogue for use in the invention and a diluent.

A composition may comprise one or more flavivirus analogues of the invention selected from an analogue of DEN-1, an analogue of DEN-2, an analogue of DEN-3, an analogue of DEN-4 and an analogue of Zika.

A composition may comprise four dengue analogues of the invention representing each of the four dengue virus serotypes DEN-1 DEN-2 DEN-3 and DEN-4.

A composition may comprise a zika virus analogue of the invention.

A composition may comprise four dengue analogues of the invention representing each of the four dengue serotypes DEN-1 DEN-2 DEN-3 and DEN-4 and a zika virus analogue of the invention.

The disclosure also provides a binding molecule capable of binding specifically to an analogue described herein. The binding molecule may be an antibody or a fragment thereof, a domain antibody, a protein scaffold, or an aptamer, provided that it is capable of binding specifically to an analogue described herein.

In preferred embodiments the flavivirus infection is a dengue virus infection or a Zika virus infection.

The disclosure provides vaccine approaches that are designed purposefully to avoid the problem of antibody-dependent enhancement, the vaccine approaches employ an analogue, composition, binding molecule or diagnostic test of the invention in an in vitro method for diagnosis of flavivirus infection and/or to investigate exposure to flavivirus, to determine if a subject proposed for immunisation is naïve to Dengue and/or Zika infection and/or has been exposed to dengue and/or Zika infection, thereby to inform the decision to immunise against dengue and/or Zika if the subject is naïve to dengue and/or Zika infection, or not to immunise if prior exposure to dengue and/or Zika is detected.

The invention provides an analogue, composition or binding molecule of the invention for use as a diagnostic.

The invention provides a diagnostic kit comprising an analogue, composition or binding molecule of the invention and a reagent capable of detecting an immunological (antigen-antibody) complex which contains said isolated analogue or binding molecule.

A diagnostic test kit in accordance with the invention may further comprise one or more control standards and/or a specimen diluent and/or washing buffer.

In a diagnostic test kit of the invention, the analogue and/or binding molecule specific thereto of the invention may be immobilized on a solid support. The solid support may be a microplate well. In a diagnostic test kit according to the invention, an immunological complex which contains said isolated analogue or binding molecule may be detected by ELISA or by lateral flow.

The invention provides diagnostic approaches that can differentiate between closely-related Flaviviruses, to assess if an individual is seronegative and thus has not been exposed to dengue or Zika, or if an individual is seropositive and has been exposed to Zika and/or dengue and for those who are seropositive, to distinguish to which of Zika and/or Dengue the individual has been exposed, in some aspects it will be distinguished to which of the four dengue serotypes the individual has been exposed. The invention provides diagnostic approaches that can be used to select subjects for immunization, or assess seroconversion to determine if immunization has raised a protective immune response against dengue or Zika. The invention provides diagnostic approaches that enable interrogation of the immune response to distinguish antibodies against the dengue virus serotypes and against Zika virus.

As described herein, we have developed and exemplified (in ELISA and lateral flow studies) the concept that diagnostics for Zika and dengue (and other flaviviruses) can be improved by creating antigens of enhanced type-specificity and serotype-specificity by cloaking the immunodominant fusion loop of the envelope protein with a glycan (these hyperglycosylated exodomain antigens are termed 'HX', in order to denote the presence of one or more additional glycans in the fusion loop). The fusion loop of dengue virus represents a 14-residue sequence element, comprising just a small percentage of the envelope protein surface, yet is the target of 55% of antibodies following a primary infection (Dejnirattisai et al., 2014) and >90% of antibodies following a secondary infection with dengue (Beltramello et al., 2010; Lai et al., 2008) (detailed figures for Zika are not yet available). Moreover, as explained above, the fusion loop sequence is 100% conserved across all four dengue serotypes, Zika, yellow fever, West Nile and Japanese encephalitis viruses, such that antibodies against the fusion loop are highly cross-reactive, not just between dengue and Zika but across these other more-distantly related viruses also. We have demonstrated herein that our approach of cloaking the fusion loop preserves the antigenic structure of Zika and dengue viral proteins, retaining conformational and neutralising epitopes while abolishing fusion loop reactivity (which, stereotypically, is dominated by the surface-exposed hydrophobic residues of the fusion loop). The glycan(s) that we have introduced into the fusion loop of the dengue and Zika envelope proteins transform the natural topography of this structure in a more profound way than amino acid replacements alone are capable of, supplanting a strongly hydrophobic surface patch (a contiguous surface formed of the hydrophobic side chains) with large branched hydrophilic glycan structures orthogonal to the path of the polypeptide chain. As shown herein, these modifications rigorously prevent recognition by fusion loop antibodies. In ELISA tests we found that the cloaked antigens have equal sensitivity (to wild-type equivalent antigens) for the detection of antibodies against multiple non-fusion-loop epitopes. Moreover we demonstrated that wild-type post-Zika macaque and tamarin sera strongly recognize the (uncloaked) fusion loop of wild-type dengue-2 and dengue-4 exodomain antigens, demonstrating that the fusion loop is likewise an immunodominant element of the Zika virus, in the course of natural infection (at least in the case of these non-human primate species), and a major cause of off-target recognition by antibodies in convalescent sera. However, there was no off-target reactivity of convalescent Zika primate sera with HX versions of the dengue envelope antigens. Furthermore, as expected, the HX Zika antigen was strongly recognized by primate Zika convalescent sera. These observations demonstrated the superior diagnostic sensitivity and specificity of HX antigens in ELISA tests, compared to wild-type antigen. We describe the translation of the advantages of these novel HX proteins to a lateral flow 'pregnancy-test-like' format for point-of-care diagnostic use.

DETAILED DESCRIPTION OF THE INVENTION

The invention is be described with reference to various embodiments of different aspects of the invention. It is appreciated that certain features of the invention, which are, for clarity, described in the context of separate embodiments, may also be provided in combination in one or more embodiments or in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

The invention uses modified Flavivirus nucleic acid and protein sequences in which the natural (native, wild-type) E-protein fusion loop epitope, known to be associated with generation of flavivirus cross-reactive, infection-enhancing antibodies has been modified to comprise one or more (e.g., 2) glycosylation sites for glycosylation of the protein with an N-linked glycan that is not normally present on the native fusion loop epitope. Such modification alters the fusion loop amino acid sequence and the presence of a glycan further disguises the epitope. Thus the modified Flavivirus nucleic acid and protein sequences of are designed to generate a protective response without concomitant generation of flavivirus cross-reactive infection-enhancing antibodies, thereby intending to avoid the problems of antibody-dependent enhancement observed with existing vaccine approaches. The modified Flavivirus nucleic acid and protein sequences are also designed for diagnostic use, either as antigens for detection of a specific Flavivirus or to generate binding molecules such as antibodies for detection of a specific Flavivirus.

By antibody we include the meaning of a substantially intact antibody molecule, as well as a chimeric antibody, humanised antibody (wherein at least one amino acid is mutated relative to a non-human antibody, for example a naturally occurring non-human antibody or antibody assembled from non-human antibody sequences), single chain antibody, bi-specific antibody, antibody heavy chain, antibody light chain, homo-dimer or heterodimer of antibody heavy and/or light chains, and antigen binding portions and derivatives of the same.

A binding molecule of the invention is preferably an antibody or antigen binding portion thereof. An antibody may be a full antibody with Fc, or antigen binding portion thereof. The antigen binding portion may be a Fv fragment; a Fab-like fragment (e.g. a Fab fragment, a Fab' fragment, a F(ab)2 fragment, Fv or scFv fragments); or a domain antibody. The antigen binding portion may be derived from the linear amino acid sequence present in an intact antibody, or may comprise a set of non-consecutive amino acids, optionally interspersed with other amino acids, for example may comprise particular amino acids that are required for contact with an epitope, but may for example not comprise the amino acids required for the framework of a native antibody, which, in some cases, may be replaced by a heterologous scaffold protein, for example. An antibody according to the present invention is obtainable by a method comprising a step of immunizing a mammal, such as a human, a monkey, a rabbit or a mouse; and/or by an in vitro method, for example comprising a phage display selection step, as will be well known to those skilled in the art.

The term antibody also includes all classes of antibodies, including IgG, IgA, IgM, IdD and IgE. The term antibody also includes variants, fusions and derivatives of any defined antibodies and antigen binding portions thereof.

By neutralise we mean reduce the ability of the virus to infect previously uninfected cells. The person skilled in the art will be well aware of suitable techniques to monitor viral neutralising ability.

Methods for manipulation of nucleic acid sequences to introduce sequence changes as described herein are well known in the art.

TABLE 1

Alignment of amino acids 98-110 of a group of wild-type sequences of flaviviruses and recombinant analogue sequences of the invention.

| | | |
|---|---|---|
| 1 | ZIKV_H/PF/2013 | DRGWGNGCGLFGK (SEQ ID NO: 1) |
| 2 | ZIKV_MR766 | DRGWGNGCGLFGK (SEQ ID NO: 1) |
| 3 | DENV_1_SG/07K3640DK1/2008 | DRGWGNGCGLFGK (SEQ ID NO: 1) |
| 4 | DENV_2_16681 | DRGWGNGCGLFGK (SEQ ID NO: 1) |
| 5 | DENV_3_SG/05K863DK1/2005 | DRGWGNGCGLFGK (SEQ ID NO: 1) |
| 6 | DENV_4_SG/06K2270DK1/2005 | DRGWGNGCGLFGK (SEQ ID NO: 1) |
| 7 | WNV_NY99 | DRGWGNGCGLFGK (SEQ ID NO: 1) |
| 8 | JEV_SA14 | DRGWGNGCGLFGK (SEQ ID NO: 1) |
| 9 | YFV_Asibi | DRGWGNGCGLFGK (SEQ ID NO: 1) |
| 10 | pCRO21 (dengue-1 HX) | DRGNGSGCGLNGS (SEQ ID NO: 2) |
| 11 | pCRO22 (dengue-2 HX) | DRGNGSGCGLNGS (SEQ ID NO: 2) |
| 12 | pCRO23 (dengue-3 HX) | DRGNGSGCGLNGS (SEQ ID NO: 2) |
| 13 | pCRO24 (dengue-4 HX) | DRGNGSGCGLNGS (SEQ ID NO: 2) |
| 14 | pCRO28 (Zika HX) | DRNHTNGCGLFGK (SEQ ID NO: 5) |
| 15 | pCRO26 (dengue-1 HX) | DRGNGSGCGLFGK (SEQ ID NO: 3) |
| 16 | pCRO27 (dengue-1 HX) | DRGWGNGCGLNGS (SEQ ID NO: 4) |
| 17 | pCRO25 (Zika) | DRGNGSGCGLNGS (SEQ ID NO: 2) |
| 18 | pCRO29 (Zika) | DRGWGNGCGNHTK (SEQ ID NO: 6) |
| 19 | pCRO30 (Zika) | DRGNGSGCGLFGK (SEQ ID NO: 3) |
| 20 | pCRO31 (Zika) | DRGWGNGCGLNGS (SEQ ID NO: 4) |

The fusion loop DRGWGNGCGLFGK (defined as residues 98-110, SEQ ID NO: 1) in the wild type sequences (rows 1 to 9) is shown in bold. The residues changed to make the N-linked glycosylation sequons in the modified analogue HX sequences are shown in bold in rows 10-20 The constructs pCRO21-24, 26, and 28 expressed well and were selected for further investigation. In the case of dengue E-proteins, 4 residues were changed to make two glycosylation sites (pCRO21-24). In the case of Zika E-protein, 3 residues were changed to make one glycosylation site (pCRO28).

The constructs pCRO25, 29, 30 and 31 did not express well in the expression system chosen, thus in some contexts the recombinant analogue sequences of the invention do not comprise the following sequences:

pCRO25 (SEQ ID NO: 7)
CKRTLVDRGNGSGCGLNGSGSLVTCAKFA pCRO29 (SEQ ID NO: 8)
CKRTLVDRGWGNGCGNHTKGSLVTCAKFA pCRO30 (SEQ ID NO: 9)
CKRTLVDRGNGSGCGLFGKGSLVTCAKFA pCRO31 (SEQ ID NO: 10)
CKRTLVDRGWGNGCGLNGSGSLVTCAKFA.

In an analogue of the invention, the N-linked glycosylation sequon (Asn-X-Ser/Thr) may be present such that an Asn (N) residue of the sequon occupies any of positions 98-101 and/or 106-110. That is, the N residue may occupy position a position selected from 98, 99, 100, and 101 and/or a position selected from 106, 107, 108, 109 and 110.

Preferably, in an analogue of the invention, X is any of the following 13 amino acid residues Gly, His, Asn, Gln, Tyr, Val, Ala, Met, Ile, Lys, Arg, Thr or Ser, with Gly or His being particularly preferred. In specific embodiments of the invention described herein for dengue viruses it is preferred that X is Gly and for Zika is preferred that X is His.

In preferred analogues of the invention, the flavivirus E-protein is a dengue virus E-protein and the Asn (N) residue of a sequon occupies position 101, 108 or both 101 and 108 of the amino-acid sequence of the analogue flavivirus E-protein fusion loop or the flavivirus E-protein is a Zika E-protein and the Asn (N) residue of a sequon occupies position 100 of the amino acid sequence of the analogue flavivirus E-protein fusion loop.

In a preferred analogue of the invention, the flavivirus is a dengue virus and the amino acid sequence of the analogue flavivirus E-protein fusion loop 98-110 is selected from: DRGNGSGCGLNGS (SEQ ID NO: 2), DRGNGSGCGLFGK (SEQ ID NO: 3) and DRGWGNGCGLNGS (SEQ ID NO: 4).

In another preferred analogue of the invention, the flavivirus is a Zika virus and the amino acid sequence of the analogue flavivirus E-protein fusion loop 98-110 is DRNHTNGCGLFGK (SEQ ID NO: 5).

The nucleic acid sequence encoding recombinant analogue E-protein fusion loop protein or encoding recombinant analogue E-protein comprising such fusion loop protein can be generally be expressed following the functional and operable insertion of the DNA sequence into an expression vector containing control sequences and secretory signal sequences.

A suitable promoter for expression of nucleic acid sequences of the invention is CMV for expression in mammalian cells.

Host cells that may be employed in accordance with the invention include the mammalian HEK and CHO cell lines, insect cells such as Tni and *Drosophila* S2; yeasts and non-mycelial fungi cells. The host may be genetically engineered to produce therapeutic glycoproteins with human-like N-linked glycans.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, Molecular Cloning: A Laboratory Manual, Second Edition (1989), Oligonucleotide Synthesis (M. J. Gait Ed., 1984), Animal Cell Culture (R. I. Freshhey, Ed., 1987), the series Methods in Enzymology (Academic Press, Inc.); Gene Transfer Vectors for Mammalian Cells (J. M. Miller and M. P. Calos eds. 1987), Handbook of Experimental Immunology, (D. M. Weir and C. C. Blackwell, Eds.), Current Protocols in Molecular Biology (F. M. Ausubel, R. Brent, R. E. Kingston, D. D. Moore, J. G. Siedman, J. A. Smith, and K. Struhl, eds., 1987), and Current Protocols in Immunology (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

Standard three and one-letter terminology is used for amino acid residues.

As used herein, the term "recombinant" refers to the use of genetic engineering methods (cloning, amplification) to produce an analogue, or a binding molecule such as an antibody or an antibody fragment of the present invention.

The principal problem of dengue vaccine development, wherein the use of vaccines runs the risk (in a finite number of cases) of giving rise to 'antibody dependent enhancement' of dengue infection, making the illness worse rather than preventing it. Enhancement is a feature of natural infection (where antibodies sent to neutralize the virus are subverted to gain access to human myeloid cells), usually upon encounter with a second 'serotype' of virus, resulting in more severe symptoms (Halstead, Rojanasuphot, & Sangkawibha, 1983). Vaccination, while for the most part conferring protection, is also liable on some occasions to predispose a recipient to severe dengue, including dengue haemorrhagic fever (DHF), upon first exposure to a wild dengue virus: i.e., 'iatrogenic' cases of severe dengue or DHF, which would not have occurred but for the vaccine. Furthermore, existing vaccine approaches also have the potential to create a population of vaccinated individuals who develop severe iatrogenic dengue, at some interval after the vaccine (or vaccine course) has been administered (e.g. a decade). This is because, as immunity to dengue wanes, protective antibodies reach a concentration where they 'enhance' rather than prevent infection. Also, the rate of decay of 'immunological memory' (where the immune system recalls encounter with a wild virus or vaccine dose) is not synchronous for the four serotypes of the vaccine, such that immunity to each serotype (at the antibody and memory level) of dengue is lost at different times, successively increasing the risk of severe disease. This gradual failure of immune memory likewise creates a new population of individuals who are now predisposed to severe dengue (when bitten by an infected mosquito), instead of protected, as a result of previous vaccination. While current vaccines against dengue (licensed and in development) may meanwhile prove to be of substantial 'net' benefit to public health, improved safety is still desirable in order to avoid cases of vaccine-induced dengue (i.e., iatrogenically-caused severe dengue). The likely role of natural dengue infection in paving the way for pandemic Zika infection has been elaborated recently by Philip K Russell of the Sabin Vaccine Institute (Russell, 2016). While no systematic investigation has been conducted that would determine the risk of dengue vaccination predisposing to Zika virus infection or of dengue vaccination giving rise to Zika infections of enhanced severity, it is a logical extension of Russell's observations to expect such cases. Likewise although dengue-vaccine-induced predisposition to severe dengue has not yet been reported or investigated 'as such', in a recent three-year follow-up study of the Sanofi-Pasteur vaccine there was an increased rate of hospitalisation in children less than nine years of age (Hadinegoro et al., 2015) which could be explained by vaccine-induced enhancement of susceptibility to severe dengue. These new epidemiological developments, and laboratory data (below) indicate that there is a significant risk that vaccines (unless designed to avoid enhancement) will cause, in some instances, enhancement of disease: i.e. dengue vaccination will result in cases of severe dengue that would not otherwise have happened. It is also possible that dengue vaccines could facilitate the spread of Zika virus infection if used on a population-wide basis. The legitimacy of this concern is supported additionally by in vitro experimental data which demonstrates that dengue virus antibodies enhance the infection of human myeloid cells by Zika virus (Paul et al., 2016). Furthermore, it follows that a stand-alone Zika vaccine could give rise to similar antibodies that would (conversely) enhance dengue infection giving rise to cases of severe iatrogenic dengue, by generating anti-Zika antibodies that cross-react with dengue virus, and that facilitate dengue infection. For the purposes of this application, while not wishing to be bound by any particular hypothesis, Zika virus is accorded the status of a 'fifth dengue serotype'. This is because dengue infection (and dengue vaccines) have the potential to facilitate the spread of Zika by generating infection-enhancing antibodies which also react with Zika virus facilitating its infection of bodily cells.

Since the advent of Zika as a pandemic phenomenon, its rapid global spread apparently facilitated by dengue-infection (Russell, 2016), the problem of vaccination (i.e. how to make a vaccine that does not, in some cases, worsen disease) has become more complicated. A new vaccine design is required in order to avoid homologous enhancement (whereby a dengue vaccine would facilitate, in some cases, dengue infection) and cross-enhancement (whereby a dengue vaccine would facilitate, in some cases, Zika infection); and moreover, whereby a Zika vaccine would facilitate, in some cases, dengue infection. Conventional approaches to the antibody enhancement problem, which involve such stratagems as combining all four serotypes of dengue in a single vaccine (Sanofi-Pasteur) or, for example, a subunit approach using N-terminal regions of the E-proteins of dengue (Merck) have recognized the antibody enhancement problem but have not provided a comprehensive solution appropriate to the Zika-pandemic situation. The most advanced dengue vaccine (the licensed Sanofi-Pasteur live attenuated tetravalent dengue vaccine), fails to deal with Zika, and from the epidemiological and in vitro observations above may be capable of promoting cases of Zika virus infection by cross-enhancement (even while having a net benefit community-wide by dint of herd immunity).

It is important to recognize that the distinction between enhancing epitopes and protective epitopes of flaviviruses is not 'binary' in character. Generally speaking, almost all anti-dengue-E antibodies (for example) have the potential to be both neutralising and infection-enhancing, the latter property emerging at lower antibody concentrations (Dejnirattisai et al., 2014), e.g. as immunity to a vaccine or an exposure wanes. Moreover, Dejnirattisai et. al. also found that antibodies against the fusion loop of the dengue E-protein (which comprise about half of all antibodies generated convalescently) are markedly worse than antibodies against other sites on the E-protein in terms of their propensity for antibody-dependent enhancement of infection.

The present disclosure provides a diagnostic test that may help to mitigate the issues of antibody-dependent enhancement and cross-enhancement, by detecting and distinguishing prior Zika and dengue virus infections to allow the intelligent and safe development and deployment of Zika and dengue vaccines.

Tests of the invention may be 'serologically' based (measuring antibodies) so as to determine whether a person had previously had Zika or dengue infection, because the infection and vaccination history of a subject is an important determinant of how they will respond to new vaccines recently licensed (i.e. Dengvaxia) and in development (Zika vaccines), and may determine a subject's susceptibility to adverse responses to vaccination against dengue and Zika, such as predisposition to dengue haemorrhagic fever and dengue shock syndrome.

Diagnostic tests of the invention can be used to identify prior Zika or dengue infection by detecting antibodies in a fingerprick blood sample.

Diagnostic tests of the invention may be provided as a lateral flow device for detection of antibodies against Zika and dengue viruses, or a pair of lateral flow devices for measuring antibodies against Zika and dengue viruses, respectively. The tests of the invention will help define which subjects are best-suited to receive Zika vaccination, maximising the safety and effectiveness of Zika vaccine deployment. The tests also detect virus-neutralising antibodies and will also help define whether a subject has responded adequately to the vaccine (i.e. reached a 'to be determined' protective level of Zika-specific antibodies) or whether they may require a further dose (a factor that may vary in differing endemic territories, depending on prior exposure to related viruses). Also, since the near-withdrawal of Dengvaxia (which is no longer permitted for use in persons not previously infected with dengue virus), the new test, once licensed, will allow safer deployment of Dengvaxia (and future dengue vaccines), markedly reducing the risk of 'priming' for haemorrhagic fever by (inadvertent) vaccination of dengue-naïve subjects.

The diagnostic of the invention can be used to distinguish Zika and dengue viruses to allow the intelligent and safe development and deployment of Zika and dengue vaccines. The test can be 'serologically' based (measuring antibodies) so as to determine whether a person had previously had Zika or dengue infection, because the infection and vaccination history of a subject is an important determinant of how they will respond to new vaccines recently licensed (i.e. Dengvaxia) and in development (Zika vaccines), and may determine a subject's susceptibility to adverse responses to vaccination against dengue and Zika, such as predisposition to dengue haemorrhagic fever and dengue shock syndrome. While other tests are available that are quite specific (eg. PCR), the disadvantage of these tests is that they only work during the very brief active phase of the infection (about seven days) which is easily missed, and PCR tests are not adequate to inform risk of adverse reactions to vaccination because dengue and Zika infections are frequently asymptomatic, and would not (in the ordinary course of events) be sampled for PCR.

There is an urgency to accurately monitor, map and contain outbreaks of Zika, which, while mostly asymptomatic, is easily confused, symptom-wise, and in antibody-based tests, with various other infections. The diagnostic test of the invention will enable these new vaccines to be used most effectively. Thus, once vaccines become available against Zika, it will be important to deploy precious vaccine resources appropriately in the field in resource-limited countries, making sure the vaccine is deployed to 'current' outbreak-areas as a priority, as the geographic prevalence is dynamic and changes over time. This will save health-care costs on unnecessary use of vaccine. In this way the diagnostic tests of the invention can play an important role in monitoring Zika activity and distinguishing it from dengue and other clinically similar infections.

Also, the diagnostic tests of the invention can be used to monitor the effectiveness and safety of development/deployment of novel vaccines and to understand the risks of vaccine development against this 'new' virus (i.e., Zika virus), which is only one of a group of related co-endemic viruses, including dengue, West Nile, Japanese encephalitis and yellow fever viruses (depending on the territory).

It is becoming increasingly apparent that antibodies resulting from prior infections (or vaccinations) with related viruses, especially dengue, already present in the blood of patients experiencing Zika virus infection, may influence the course of Zika disease and its complications. Zika infection has been implicated as a causative factor, via foetal infection, of microcephaly in neonates, as well as Guillain-Barré syndrome in adults). Likewise, antibodies generated during Zika infection or as a consequence of Zika vaccination may have analogous pathological consequences to those elicited by dengue infection and vaccination. For example, such antibodies may determine whether naturally-encountered Zika virus crosses the placenta and damages the foetus, and antibodies generated by Zika vaccination may influence the occurrence of haemorrhagic fever upon first or second encounter with dengue. Increasingly, in the case of dengue, antibodies are seen as essential co-factors in severe disease causation, as important as the viruses themselves. In the case of Zika this may also transpire to be the case. That Zika infection (or vaccination) may prime for dengue haemorrhagic fever is already strongly indicated by in vitro experiments with human cells and by animal in vivo experiments. The extent to which Zika antibodies may be a problem in man will take years of epidemiological research to unravel, and this will require tests of improved sensitivity and specificity—such as the tests of the invention.

Current diagnostic practice is not adequate to properly inform the intelligent deployment of vaccines because it is based in central diagnostic labs that require the transport of blood samples from diverse, sometimes remote, areas of endemic countries, which is expensive and inefficient, and which may not be possible in many instances due to lack of the necessary refrigerated transport infrastructure. Also, central and point-of-care serological tests developed for dengue in the pre-Zika era (ie. the only currently licensed tests) are confounded by Zika cross-reactivity with error-rates of 50% or more, making these tests of limited use in distinguishing Zika from dengue.

We have therefore developed a 'point-of-care' diagnostic test of the invention, i.e., a test that can be run without the need for clean water, electricity or equipment, that can be operated in the home or in a vaccination clinic, that can distinguish prior Zika or dengue infection with improved reliability over existing point-of-care tests (and improved relative to existing central laboratory-based tests). The test may comprise a test for Zika and or a test for and dengue, these may be provided individually as test devices or as part of a single diagnostic test device. The device(s) may be lateral flow device(s). In a preferred embodiment the test comprises a pair of lateral flow devices—one each for Zika and dengue. The diagnostic tests of the invention are enabled by the design of antigens engineered to render the immunodominant site of the viral envelope proteins 'invisible' to antibodies by the strategic planting of glycans in the fusion loop of the E protein, which is a small, highly conserved (100% conserved) site, recognized by the majority of antibodies that are generated in the course of dengue and Zika infections.

The diagnostic tests are based on recombinant analogues of Zika and dengue envelope (E) protein fusion loops into which one or more glycosylation sites have been introduced. The present invention uses E-proteins with at least one an additional glycan planted in the fusion loop, by virtue of engineering an additional, novel, glycosylation site into the nucleotide and amino acid sequence of recombinantly expressed E-proteins. The 'cloaking' effect of the glycan prevents cross-reactive (ADE-enhancing) antibodies binding to the fusion loop site, while leaving other sites that bind to neutralising antibodies available for binding to enable specific detection of neutralising antibodies (and thus evidence of prior virus exposure).

The E-protein of Zika virus is highly homologous in terms of its amino acid sequence and three-dimensional structure, to that of the dengue virus E-proteins. The recent cryo-EM 3.8 Angstrom structure of the Zika virion E-protein clearly identifies (by analogy) the Zika E-protein fusion loop location (Kostyuchenko et al., 2016; Sirohi et al., 2016). Indeed Sirohi et. al. catalogue the remarkable degree of homology among diverse flaviviruses with respect to the fusion loop sequence "DRGWGNGCGLFGK" (residues 98-110), which is perfectly preserved among diverse virus isolates of Zika, the four dengue serotypes, West-Nile, Japanese encephalitis and yellow fever viruses (see supplementary figure S2 of Sirohi). There are notable differences between dengue and Zika E-proteins, such as a five amino acid insert in the Zika E-protein, and the fact that Zika has a single N-linked glycan rather than two per monomer Methods for introducing additional glycosylation sites into proteins by site directed mutagenesis are well known in the art. In particular the creation of Aranesp (darbepoetin alfa), a modified form of the natural hormone erythropoietin, is a good example (Elliott ("EP0640619A1," 2010), (Elliott et al., 2003). It is important in making suitable genetic constructs to ensure that the leader sequence of the protein is incorporated into recombinant plasmid or other vector DNA sequences, in order to direct the nascent polypeptide chain into the endoplasmic reticulum of the host cell, allowing glycosylation and to facilitate protein folding. Various eukaryotic cell systems are suitable for recombinant production—such as Chinese hamster ovary cells (CHO), as well as yeast (e.g., *Pichia pastoris*) and other vector systems such as baculovirus (which has the added advantage of equipping the viral protein immunogen with an insect glycan, as per the inoculum form of the flavivirus). However, prokaryotic systems such as those based on *E. coli* are not generally suitable, because they do not have the cellular apparatus required to effect glycosylation of proteins. In the case of Aranesp, the molecule has two additional N-linked glycosylation sites, strategically placed to avoid hindrance of interaction of the glycoengineered molecule with the erythropoietin receptor. The purpose of glycoengineering the earlier erythropoietin-based product in this way was to improve the longevity of the molecule in circulation by increasing its size giving rise to a product that can be administered once instead of thrice weekly (Elliott et al., 2003).

In studies (by others) with human monoclonal antibodies isolated from patients previously exposed to dengue infection, 100% of (monoclonal) antibodies isolated in the first month of a Zika infection were found to be cross-reactive with dengue. Meanwhile, the need for an IgG-based assay for Zika was asserted by the observation that previously dengue infected subjects (90-95% of the population in Rio, for example), may bypass altogether a Zika-IgM response (the usual indicator of recent infection) launching instead an anamnestic 'boost' response of cross-reactive IgG antibodies, that gradually mature to include Zika-specific antibodies. Because Zika is asymptomatic in 80% of cases, measurement of IgG antibodies is the only way to obtain an accurate estimate of the burden of infection in society (IgM antibodies, when produced, being too transient for the purpose). The Zika IgG test of the invention will be instrumental in the management of patients presenting late, after an asymptomatic infection, with neurological complications or with congenital malformations to see if these phenomena indicate the effect of a prior Zika virus infection.

BRIEF DESCRIPTION OF DRAWINGS

The invention will now be described with reference to the accompanying drawing in which:

FIG. 1. Design of vaccine immunogens of the invention, to avoid generation of cross-reactive fusion loop antibodies and the elicitation or stimulation of infection-enhancing antibodies.

FIG. 1 'A' shows the effect of vaccination with a flavivirus vaccine, such as a live attenuated vaccine known in the art comprising the four dengue serotypes DEN-1, DEN-2, DEN-3 and DEN-4. Attenuated vaccine virions are shown as round structures with the E-protein moiety stem projecting therefrom, the fusion loop is depicted as a small spur on the stem of the virion E-protein moiety; antibodies are depicted as Y-shaped molecules, infection-enhancing antibodies are shown in solid black whereas neutralising antibodies are shown in white outlined in black, 'B' illustrates a vaccine immunogen design of the invention. The novel immunogen contains an E-protein wherein the fusion loop sequence has been substituted to include a glycosylation site for attachment of a glycan (depicted as a crescent attached to the fusion loop spur, to generate neutralising antibodies against the E-proteins of the vaccine without generating infection-enhancing antibodies. 'C' shows how infection-enhancing antibodies against the fusion loop of the E-proteins, when bound to the E-protein of a wild-type flavivirus virion, are able to engage with high affinity the Fc-gamma-receptor-IIa (depicted as a white rectangle outlined in black), facilitating infection of myeloid cells that carry the Fc-gamma receptor IIa. 'D' represents occasional failure of a vaccine to elicit a protective level of antibody response in some subjects (e.g., the immunosuppressed). While not protected against dengue, such immunocompromised subjects (immunized with the vaccine of the present disclosure) are at least not predisposed to dengue by the novel vaccine because they have not mounted an antibody response against the fusion loop. This may be contrasted to a vaccine of conventional design containing an uncloaked fusion loop, where a subject might then be predisposed to severe dengue infection by the conventional vaccine having elicited sub-neutralising concentrations of fusion-loop antibody.

FIG. 2. Recombinant expression of glycoengineered forms of dengue and Zika exodomain proteins.

FIG. 3. Characterisation of glycans present on the glycoengineered dengue 2 and Zika exodomain proteins and degree of occupancy of sequence-programmed N-linked-glycosylation-sites

FIG. 3c shows dengue-2 tryptic cleavage sites and peptide fragments.

FIG. 3d shows Zika tryptic cleavage sites and peptide fragments.

FIG. 3e shows Zika Endo-Lys-C cleavage sites and peptide fragments.

The x-axis shows the number of days after immunisation and the y-axis shows the IgG antibody titre. Three doses were given on days 0, 14 and 21. Dosages are indicated in Table 9. Antibody responses were measured in individual mice against all five antigens as wild-type VLPs on the ELISA solid phase as indicted: top row left Den 1 VLP antigen, top row right Den 2 VLP antigen, middle row left Den 3 VLP antigen, middle row right Den 4 VLP antigen, bottom row left Zika VLP antigen. Immunogens (as distinct from antigens uses for assay above) were Penta-DNA (a combination of each of the Den1-4 and Zika DNAs of the invention) shown as an open circle, Penta-Prot (a combination of each of the Den1-4 and Zika proteins of the invention) is shown as an filled square, Monovalent Zika is shown as a filled triangle, Penta VLP (a combination of each of the Den1-4 and Zika VLPs of the invention) is shown as a filled inverted triangle. PBS control is shown as an open inverted triangle.

FIG. 5. Avoidance of recognition of the glycoengineered proteins by fusion loop antibodies and retention of neutralizing epitopes.

Figure 4:
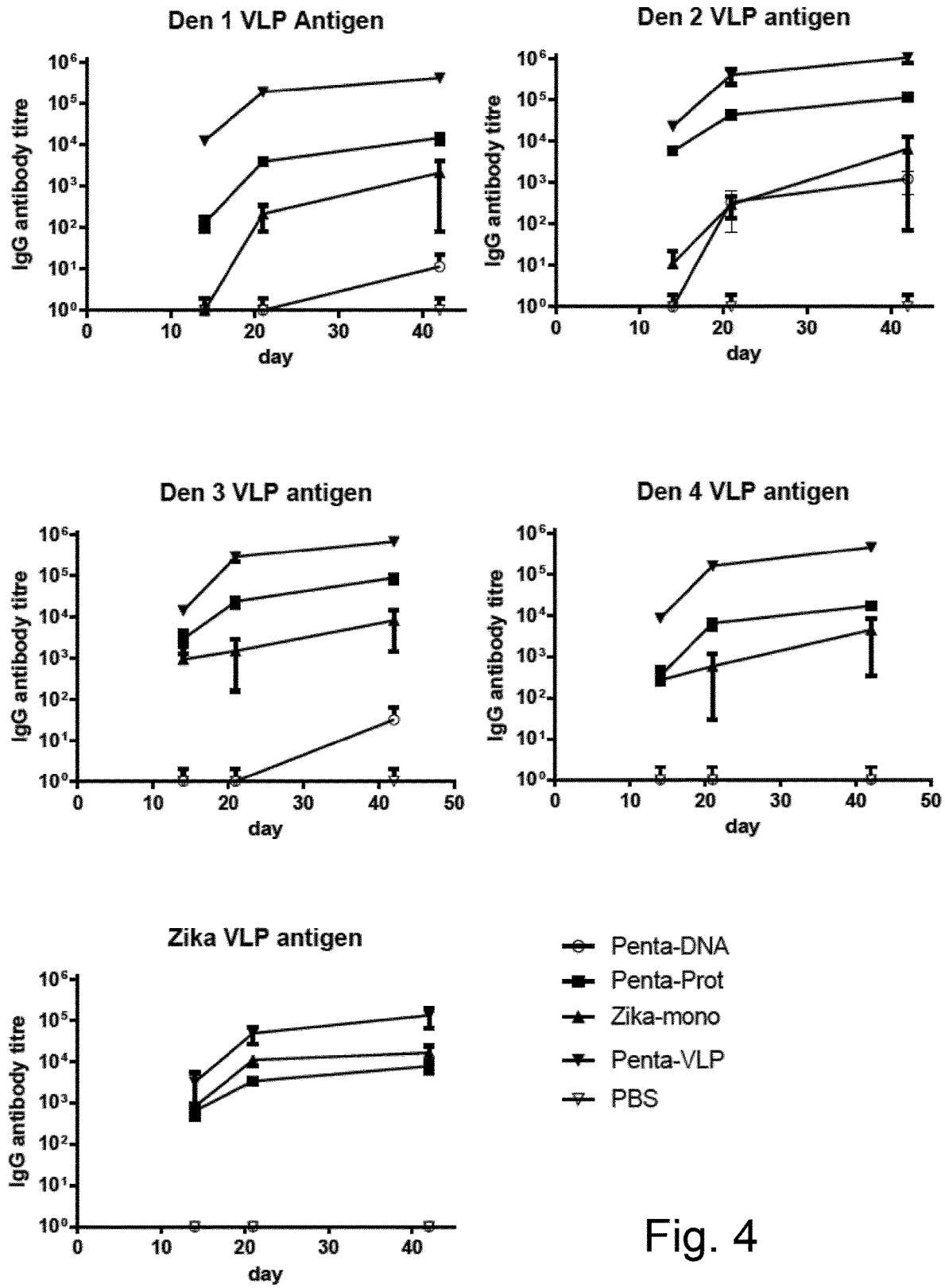
FIG. 4. Immunogenicity of select glycoengineered dengue proteins 1, 2, 3 and 4 and Zika in mice measured by direct ELISA.

In order to further characterize the hyperglycosylated antigens of the present disclosure, comparing them to wild-type equivalent antigens, an ELISA assay was established to measure antibody binding to diverse wild-type and recombinant exodomains (as distinct from the VLP antigens of FIG. 4). Unlike the ELISA used in FIG. 4, which used only wild-type VLPs as antigens this assay used only exodomain-type antigens (recombinant wild-type and recombinant hyperglycosylated forms 'HX' of the invention). In order to ensure the same orientation of each of these materially diverse (non-glycosylated bacterial, insect-glycosylated and human-glycosylated) species, they were anchored to the solid phase by a rabbit anti-His-tag monoclonal antibody, recognizing their C-terminal His tags. Coated plates were blocked and exposed to a constant concentration of the various His-tagged proteins in a 'post-coating' step and were then probed with monoclonal antibodies at various concentrations (FIG. 5a, for 4G2) or at a constant concentration (FIG. 5b,c). Various dengue and Zika antigens and probe antibodies were tested in FIG. 5b,c, including a human polyclonal anti-Zika convalescent serum sample. Probe antibodies were followed by incubation with a rabbit anti-mouse IgG Fc-horseradish peroxidase (or rabbit-anti-human IgG Fc-horseradish peroxidase) conjugate (as appropriate) and tetramethylbenzidine substrate. A mouse monoclonal anti-human-CD4 antibody served as a control for the mouse monoclonal antibodies.

Figure 5A:
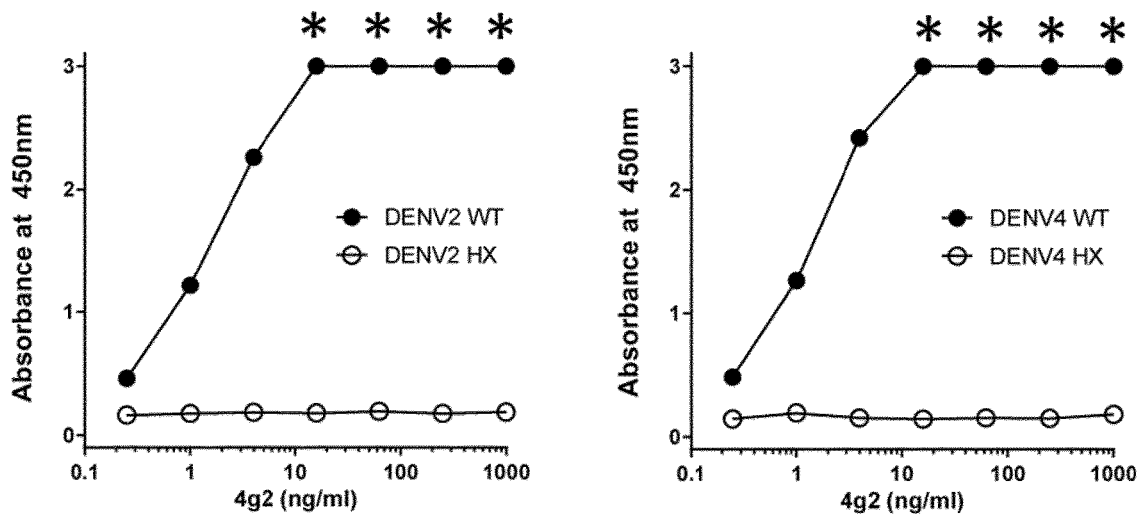
Figure 5B:
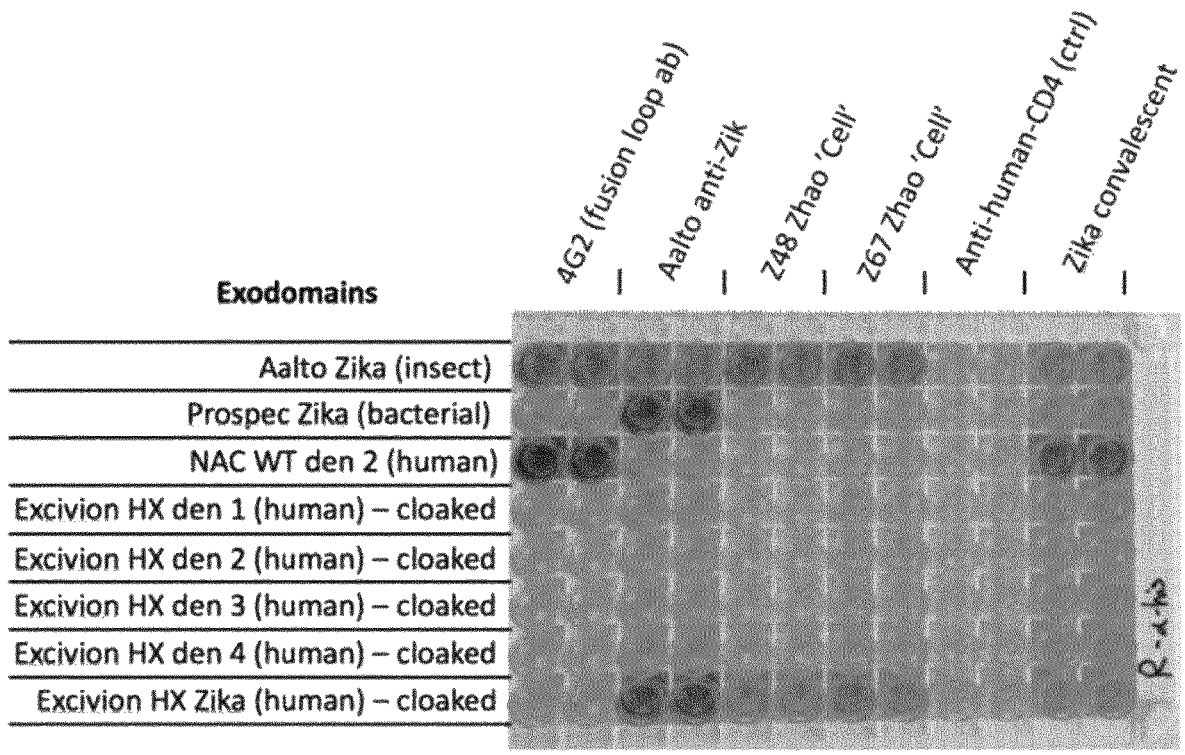

FIG. 5a represents fusion-loop antibody 4G2 (x-axis, ng/ml), which was raised against dengue-2 serotype but is highly cross-reactive among flaviviruses, binding to solid phase wild-type dengue serotype-2 or dengue serotype-4 wild type exodomain antigens, or their hyperglycosylated counterparts containing two additional programmed sequons in the fusion loop ('HX' for hyperglycosylated exodomain). (Asterisks denote absorbance values higher than the read-capability of the ELISA reader), Y Axis shows absorbance at 450 nm. Points are mean of duplicate determinations.

FIG. 5b is a photograph of an ELISA plate result of the present assay design, wherein various exodomains were screened for binding to antibodies, including a set of murine monoclonal antibodies, (left to right columns 1 and 2: 4G2 (cross-reative fusion-loop antibody), columns 3 and 4: Aalto Bioreagents anti-Zika antibody AZ1176-0302156-Lot3889; columns 5 and 6: Z48 anti-Zika antibody, wells 7 and 8: Z67 anti-Zika antibody (these are described as ZV48 and ZV67 Zika-neutralizing antibodies by Zhao et al, Cell 2016 and were obtained from The Native Antigen Company ZV67=MAB12125 and ZV48=MAB12124), wells 9 and 10: anti-human-CD4 control Millipore 024-10D6.B3 2322501; wells 11 and 12: Zika human convalescent serum). Exodomains (all having His-6 C-terminal tag) were as follows (top to bottom): 'Aalto insect'=Sf9 insect-cell produced wild-type recombinant Zika exodomain from Aalto Bioreagents, Dublin, Ireland; Prospec Zika=bacterially produced recombinant wild-type exodomain from Prospec, Israel; NAC WT den-2=HEK293-produced human wild-type dengue-2 exodomain (based on residues 280-675 of NCBI ACA48859.1 followed by a glycine-serine linker of 7 or 8 amino acids in length followed by the His6 tag); 'Excivion HX den-1 (human) cloaked' represents the expressed product of plasmid pCRO21 from HEK 293 cells having two N-glycosylation sequons programmed into the fusion loop; likewise for Excivion HX den-2 through den-4, representing plasmids pCRO22, pCRO23 and pCRO24 respectively. 'Excivion HX Zika human (cloaked)' represents the protein product of plasmid pCRO28 expressed in HEK293 cells, having a single glycosylation programmed into the fusion loop.

Figure 5C:
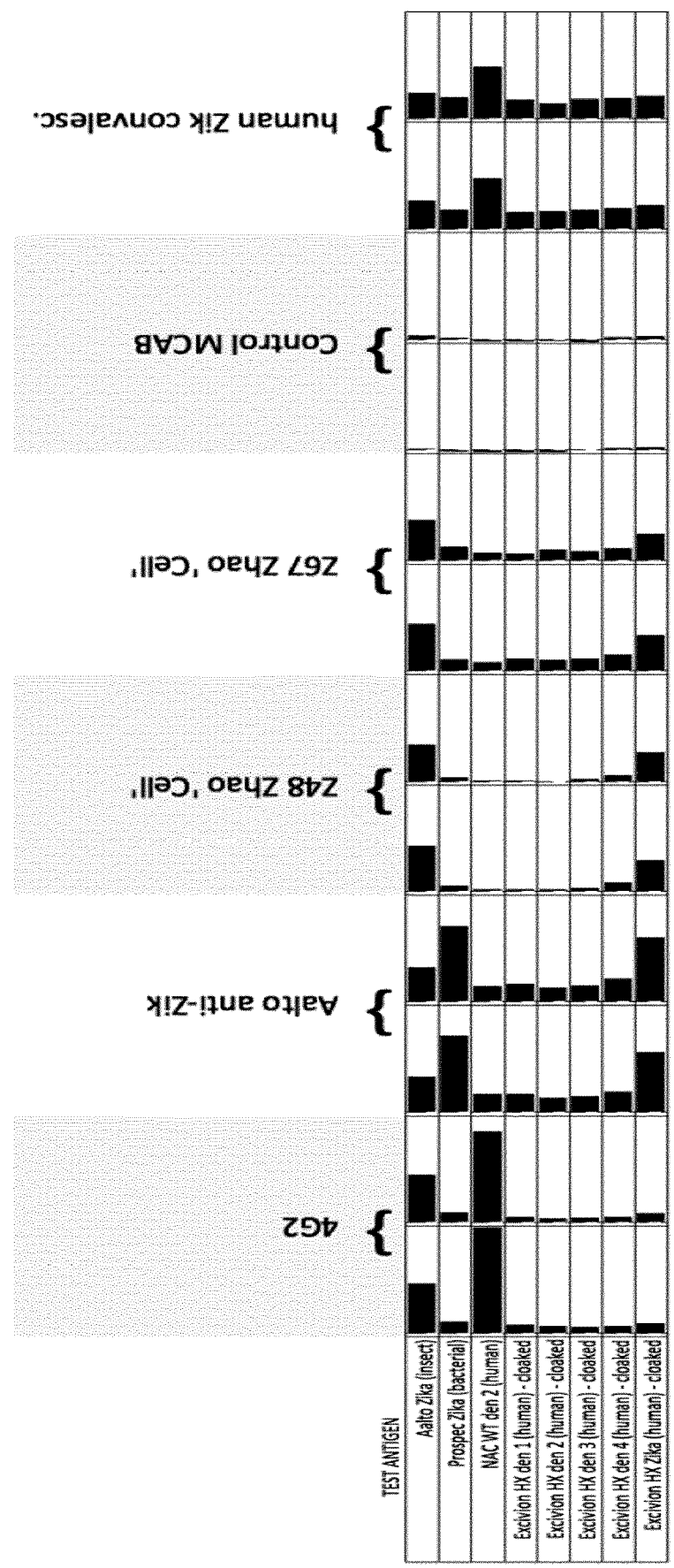

FIG. 5c shows the absorbance values represented as Excel data bars as % values of the maximum absorbance (which was 3.0 absorbance units), demonstrating the quality of replicates (duplicates). FIG. 5c is a graphical representation of the data in FIG. 5b and has the same layout as FIG. 5b.

Figure 5D:
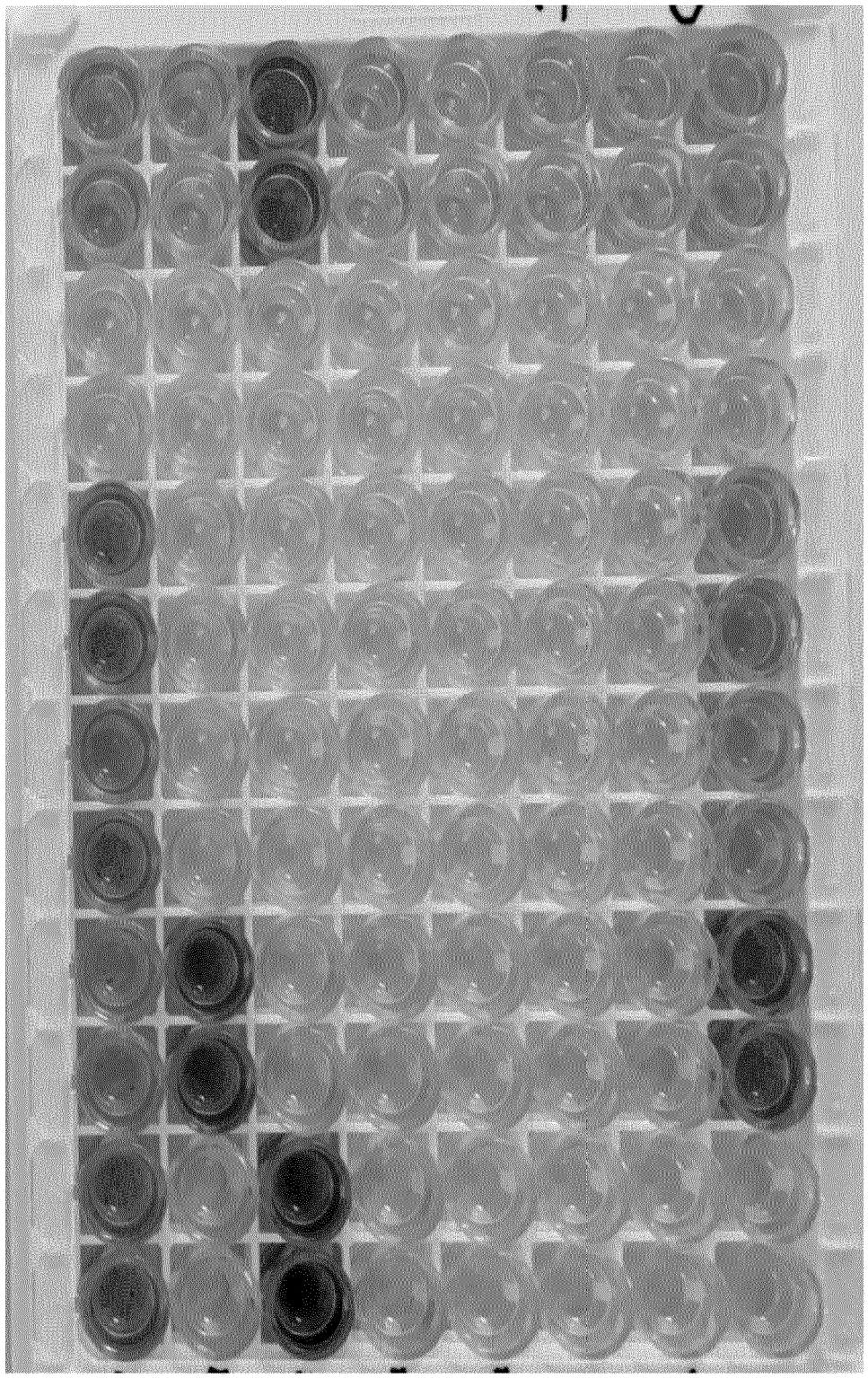

FIG. 5d shows the ELISA plate depicted in FIG. 5b in greater detail.

Figure 6:
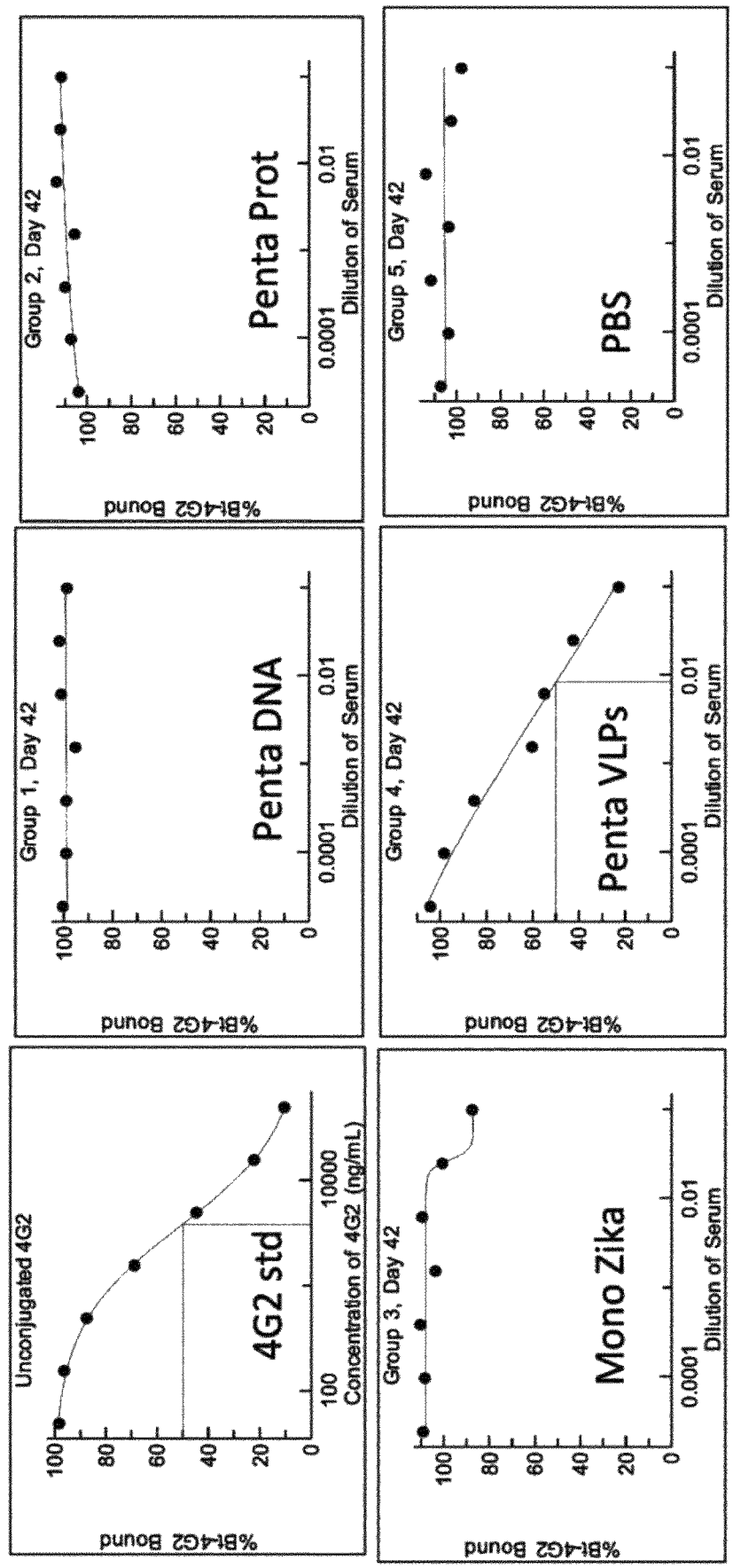

FIG. 6. Avoidance of generation of fusion-loop antibodies by the glycoengineered proteins. A further ELISA assay was developed, different to those used in FIG. 4 and FIG. 5, to detect antibodies in polyclonal sera from immunized mice, against the fusion loop. This was a competitive binding assay in which biotin-labelled 4G2 was used as a label, and unlabeled 4G2 was used as a standard. Top row left, unconjugated 4G2, x-axis concentration of 4G2 ng/mL; top row middle, Penta DNA, Group 1, Day 42, x-axis dilution of serum; top row right Penta Prot Group 2, Day 42, x-axis dilution of serum; bottom row left Mono Zika, Group 3 Day 42, X-axis dilution of serum; bottom row middle Penta VLPs, Group 4 day 42, x-axis dilution of serum; bottom row right PBS, Group 5 Day 42, x-axis dilution of serum. In each instance the y-axis was % biotinylated (Bt)-4G2 bound.

FIG. 7. Generation of neutralising antibodies by the glycoengineered proteins (PRNT).

Figure 7A:
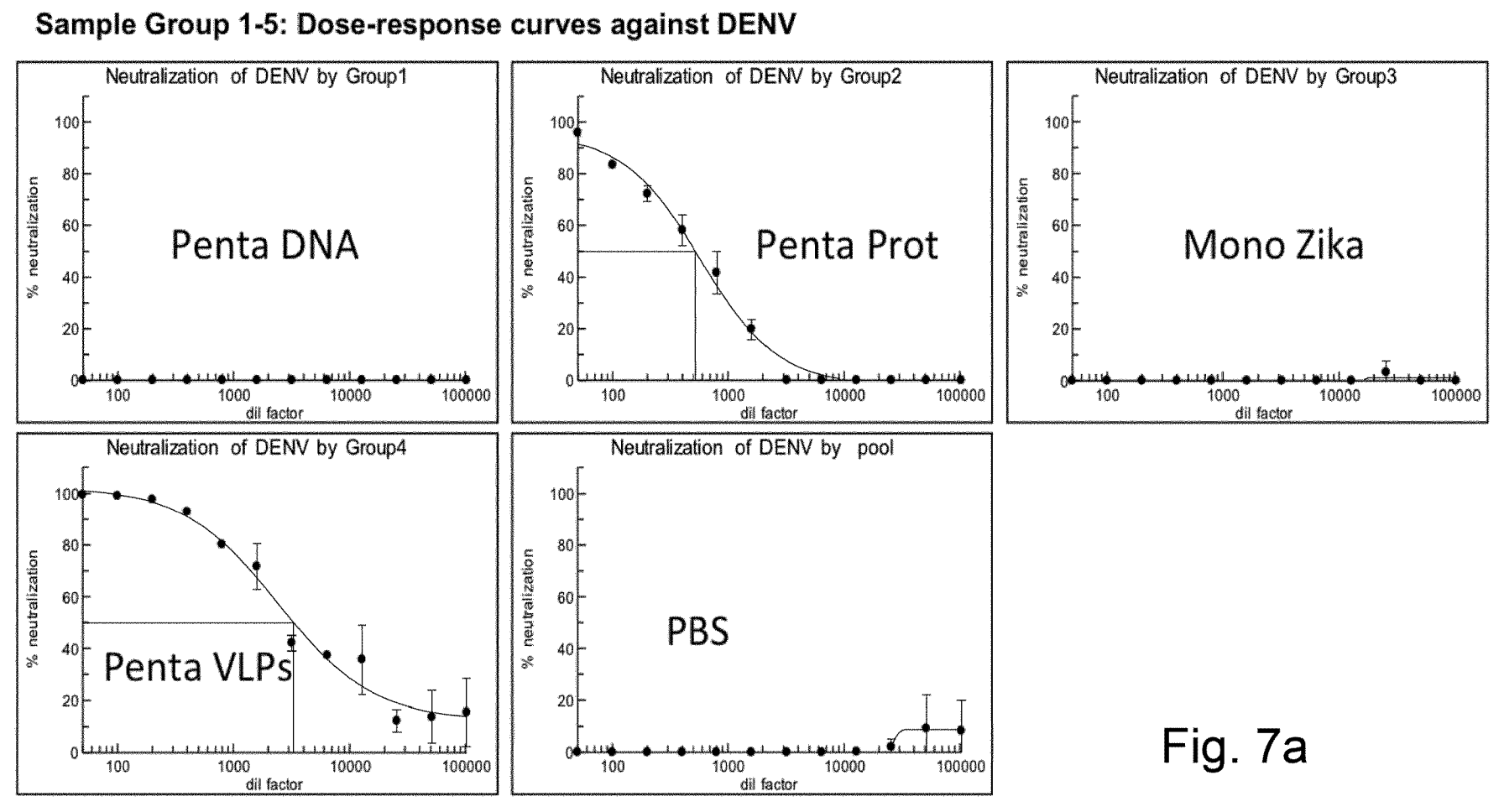

FIG. 7a shows Dengue PRNT responses for Sample groups 1 to 5 measured in pooled sera: dose response curves against DENV, Top row left Penta DNA (Neutralisation of DENV by Group 1 pool); top row middle Penta Prot (Neutralisation of DENV by Group 2 pool); top row right Mono Zika (Neutralisation of DENV by Group 3 pool); bottom row left Penta VLPs (Neutralisation of DENV by Group 4 pool); Bottom row middle PBS (Neutralisation of DENV by Group 5 pool). In each instance the x-axis is dilution factor and the y-axis shows percentage neutralisation.

Figure 7B:
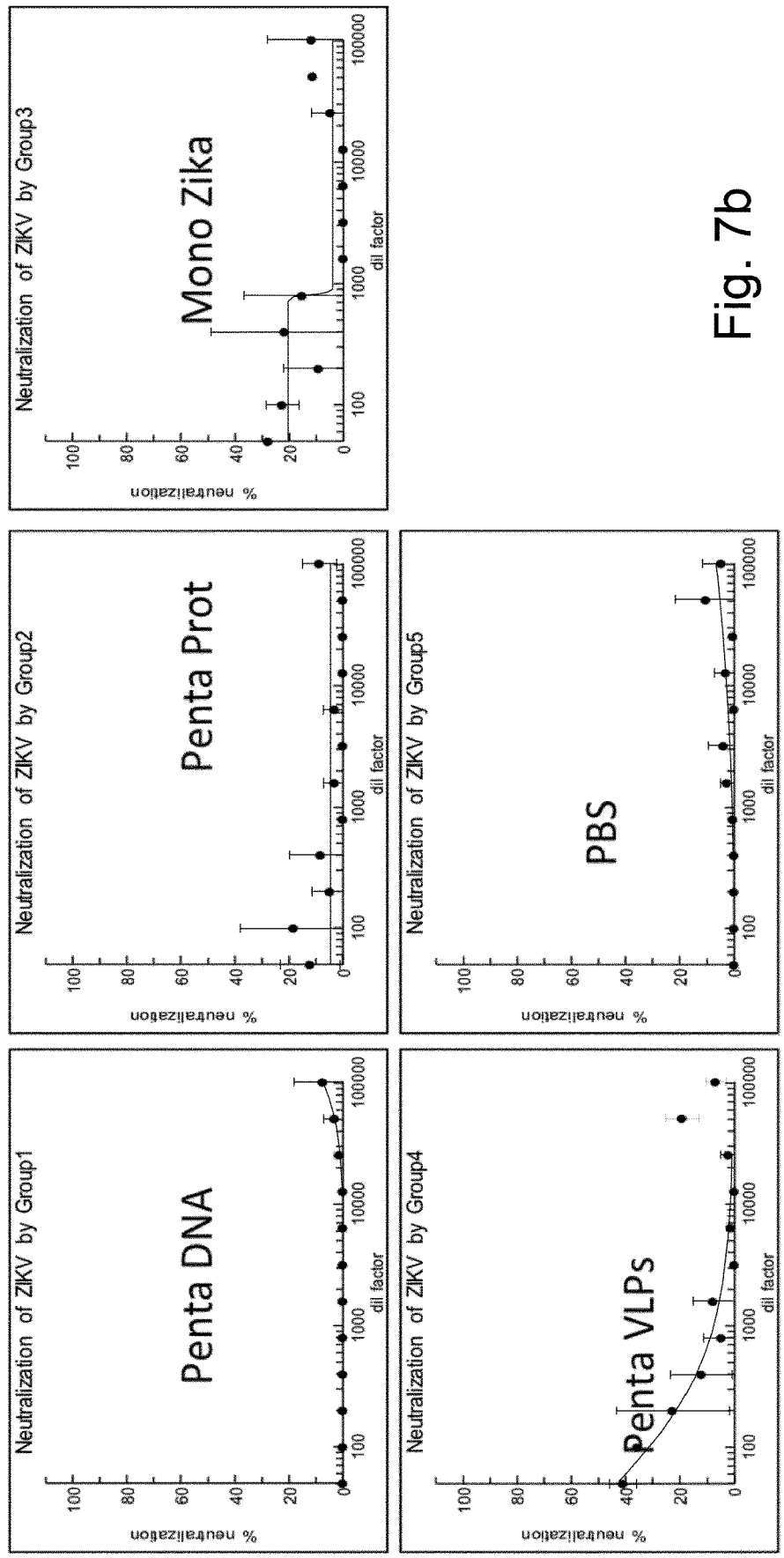

FIG. 7b shows PRNT responses for Sample groups 1 to 5 measured in pooled sera: dose response curves against ZIKV, Top row left Penta DNA (Neutralisation of ZIKV by Group 1 pool); top row middle Penta Prot (Neutralisation of ZIKV by Group 2 pool); top row right Mono Zika (Neutralisation of ZIKV by Group 3 pool); bottom row left Penta VLPs (Neutralisation of ZIKV by Group 4 pool); Bottom row middle PBS (Neutralisation of ZIKV by Group 5 pool). In each instance the x-axis is dilution factor and the y-axis shows percentage neutralisation.

Figure 8:
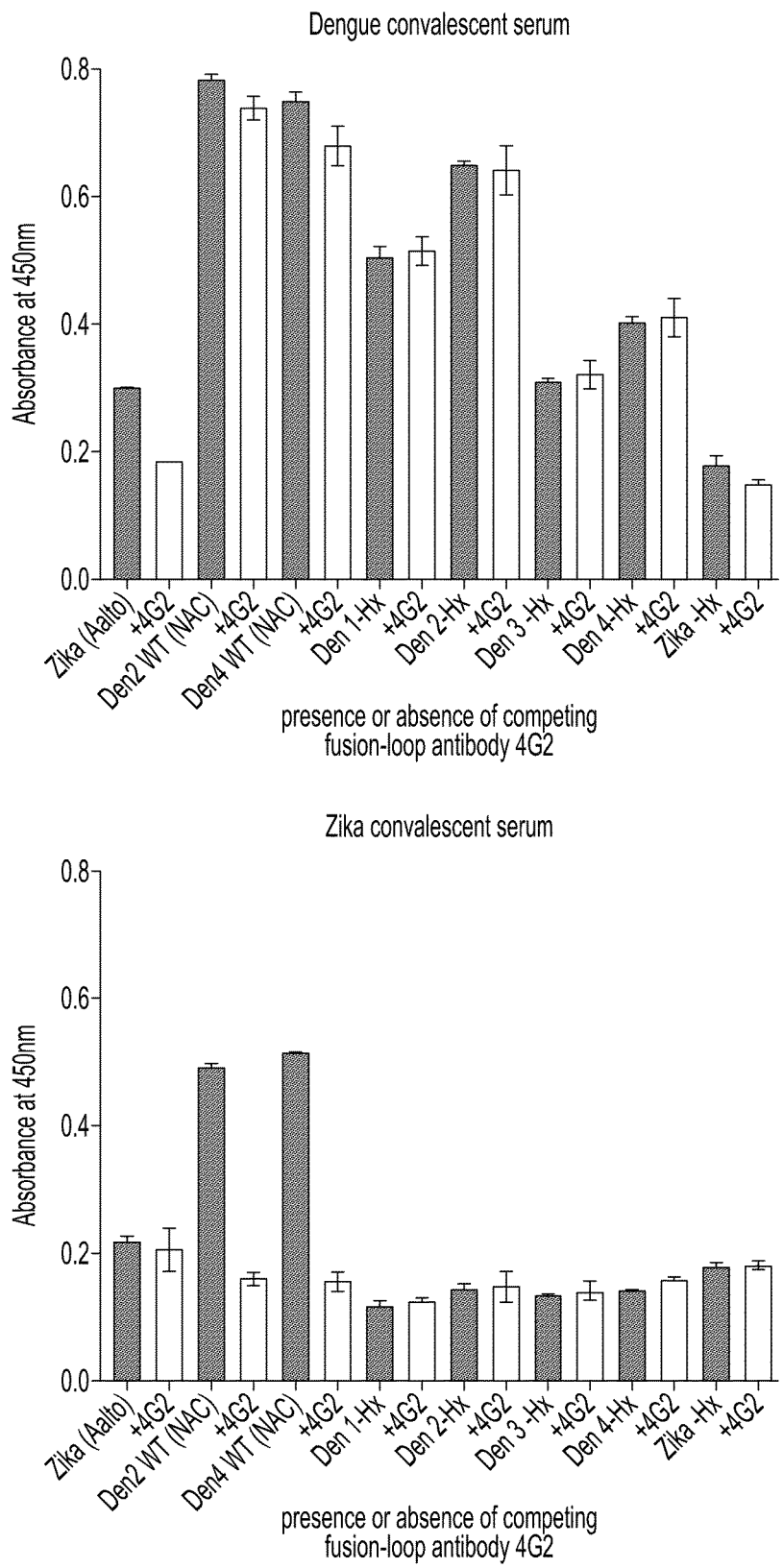

FIG. 8. Reaction of convalescent dengue and Zika sera with immobilized Zika and dengue wild-type (WT) and hyperglycosylated (HX) exodomain proteins Upper panel shows ELISA reactivity of antibodies in a dengue convalescent serum with immobilized Zika and dengue wild-type (WT) and hyperglycosylated (HX) exodomain proteins oriented on the solid phase by capture with a rabbit anti-His-tag monoclonal antibody, in the presence (grey bars, right of each pair) and absence (black bars, left of each pair) of competing mouse monoconal flavivirus fusion loop antibody 4G2 (an anti-dengue-serotype-2 cross-reactive monoclonal antibody) at a concentration of 10 ug/ml during serum incubation. Human sera were tested at a constant concentration of 1/1000.

Lower panel shows ELISA reactivity of antibodies in a Zika convalescent serum with immobilized Zika and Dengue wild-type (WT) and hyperglycosylated (HX) exodomain proteins in the presence (grey bars) and absence (black bars) of competing mouse monoclonal flavivirus fusion loop antibody 4G2. Conditions and labelling are the same as for the upper panel. Error bars are standard error of duplicate determinations.

FIG. 9 shows alternative formats for lateral flow detection of antiviral antibodies. FIG. 9A shows a single-port format for lateral flow detection of antiviral antibodies. FIG. 9B shows a two-port format for the lateral-flow detection of antiviral antibodies.

Figure 11:
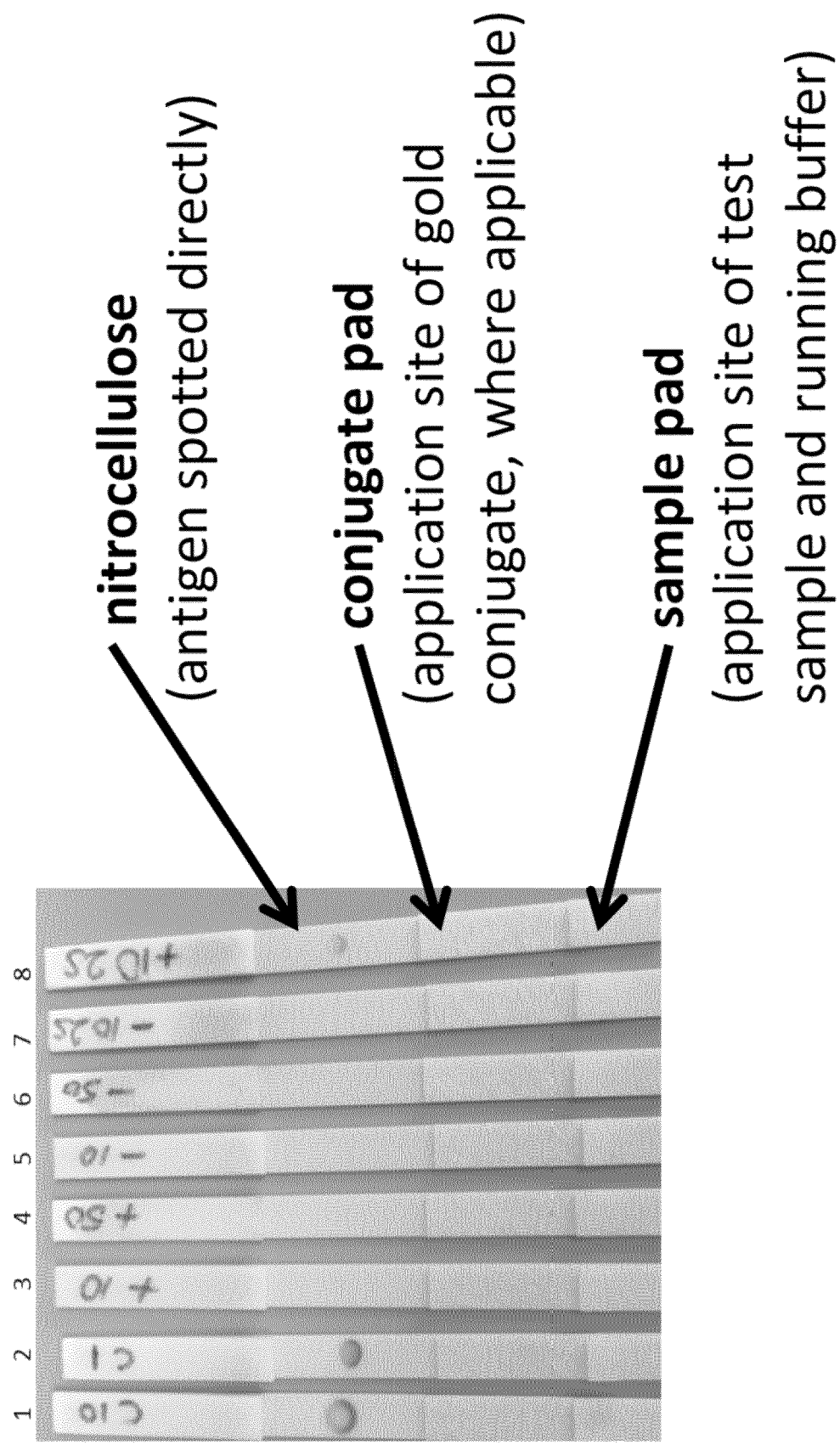

FIG. 10 shows that indirect immobilisation of mobile dengue HX exodomain antigens via anti-His-tag monoclonal antibody allows detection of neutralising antibodies in lateral flow FIG. 11 shows direct spotting/immobilisation of antigen on nitrocellulose (as distinct from capture of mobile phase antigen via anti-tag)

Figure 12:
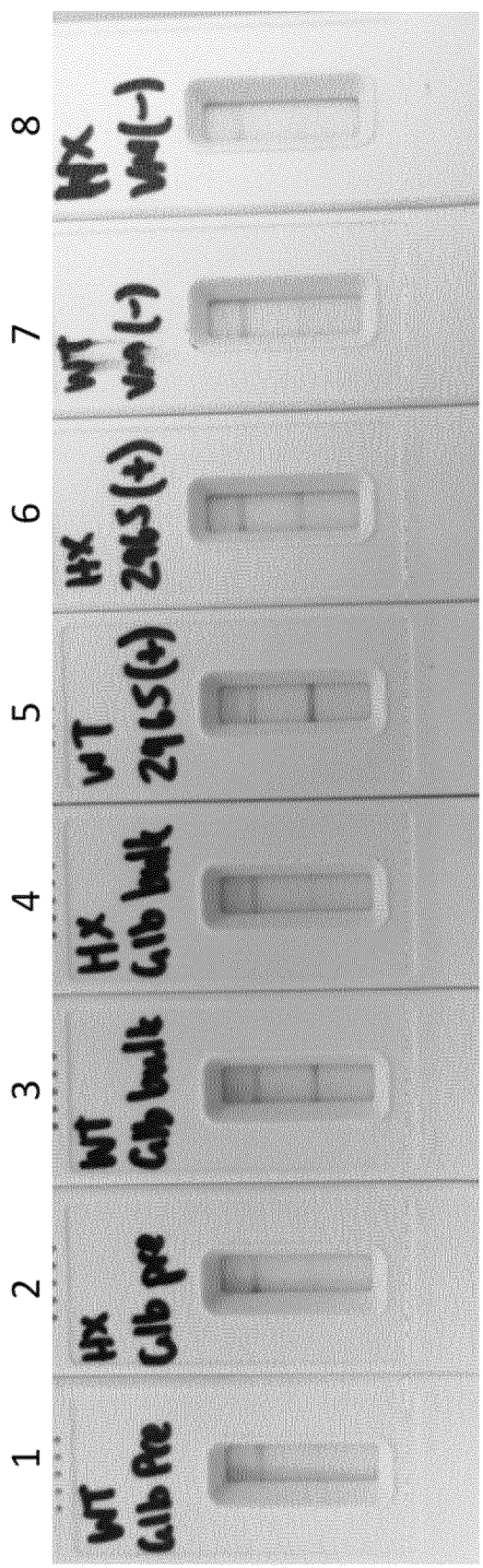

FIG. 12 shows avoidance of off-target recognition of dengue envelope antigens by Zika macaque convalescent serum IgG antibodies by using dengue-HX antigens.

Figure 13:
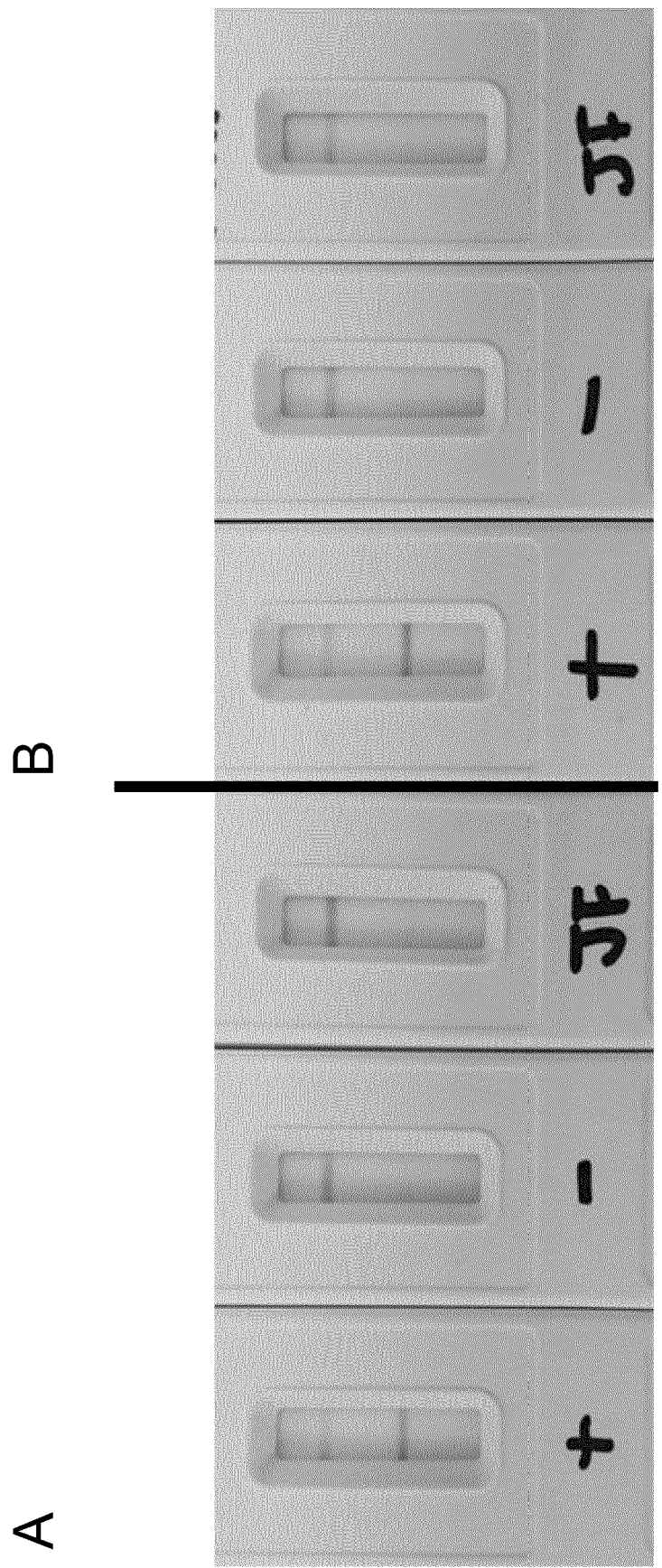

FIG. 13 shows A: Utility of HEK-cell expressed dengue HX antigens (all four dengue serotypes) and B: Utility of insect (Tni-cell) expressed HX antigens (all four dengue serotypes) can be used to similar effect in lateral flow for the detection of IgG class anti-dengue antibodies.

FIG. 14 shows utility and specificity of HX Zika and dengue antigens in lateral flow testing compared to wild type Zika antigen; FIG. 14A shows insect cell expressed dengue HX 1,2,3,4; FIG. 14B shows insect cell expressed Zika HX and FIG. 14C shows wild-type insect cell expressed Zika.

FIG. 15 shows performance of the HX antigens in lateral flow testing of human whole blood.

FIG. 16. Production of Zika HX-Strep-tag-II from insect (Tni) cells transduced with a baculovirus vector encoding the appropriate polypeptide sequence (FlashBac Ultra, Oxford Expression Technologies Ltd., UK) (A) shows samples from purification using Strep-TactinXT Superflow eluted with desthiobiotin according to manufacturer's instructions (IBA Life Sciences, Germany), (B) shows the final purified product after removal of the desthiobiotin by dialysis.

FIG. 17. Comparison of Excivion dengue-LF to SD Dengue Ag+Ab Duo. (A) tabular representation of scores of each test applied to a panel of dengue samples from Pune, India. (B) visual representation (photograph) of a range of scores of the Excivion denuge-LF test.

Figure 18:
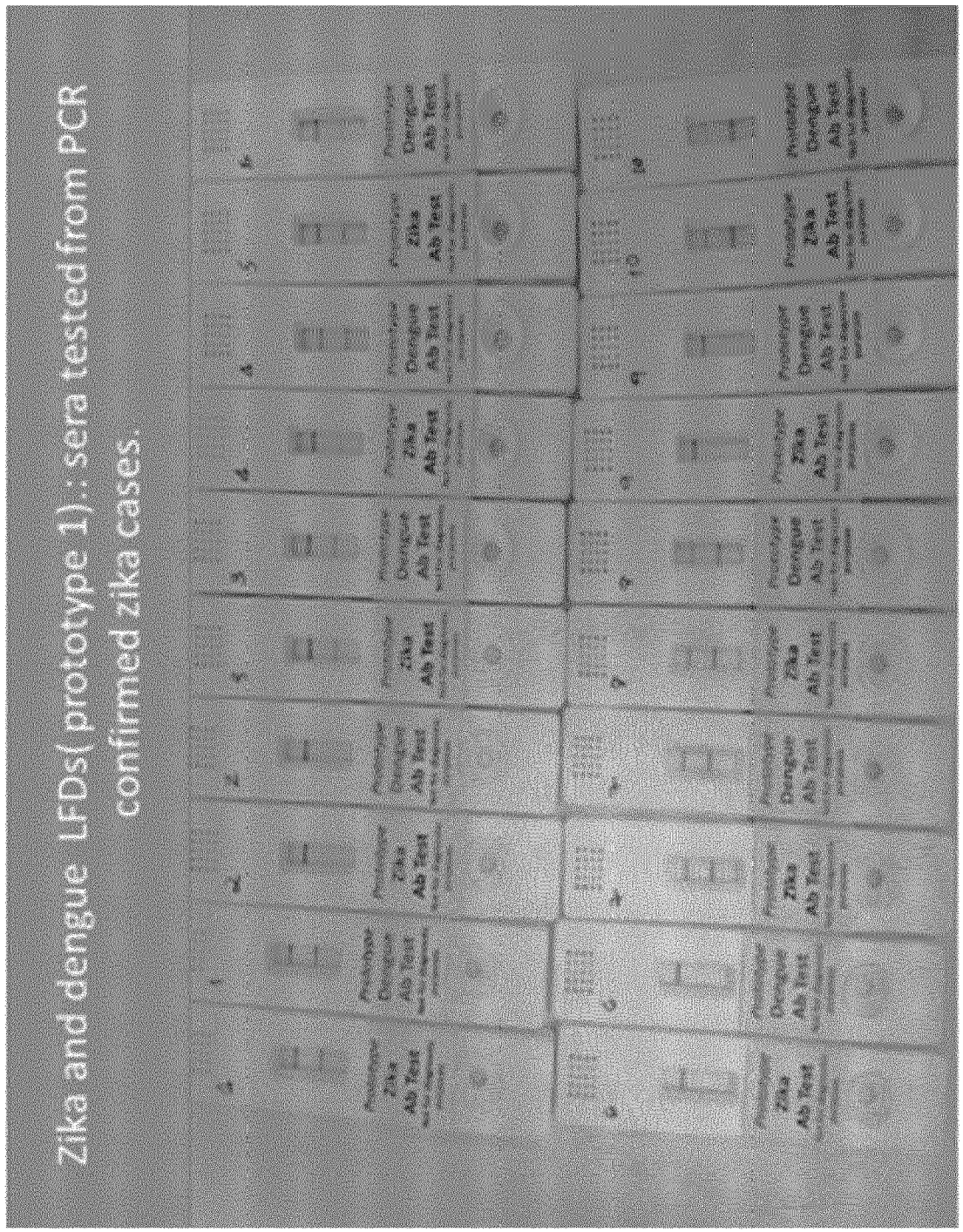

FIG. 18. Testing of early post-Zika samples from a field study in Rio de Janiero, showing a range of positivity in the Zika and dengue LF tests (prototype-1), with no pre-absorption.

Figure 19:
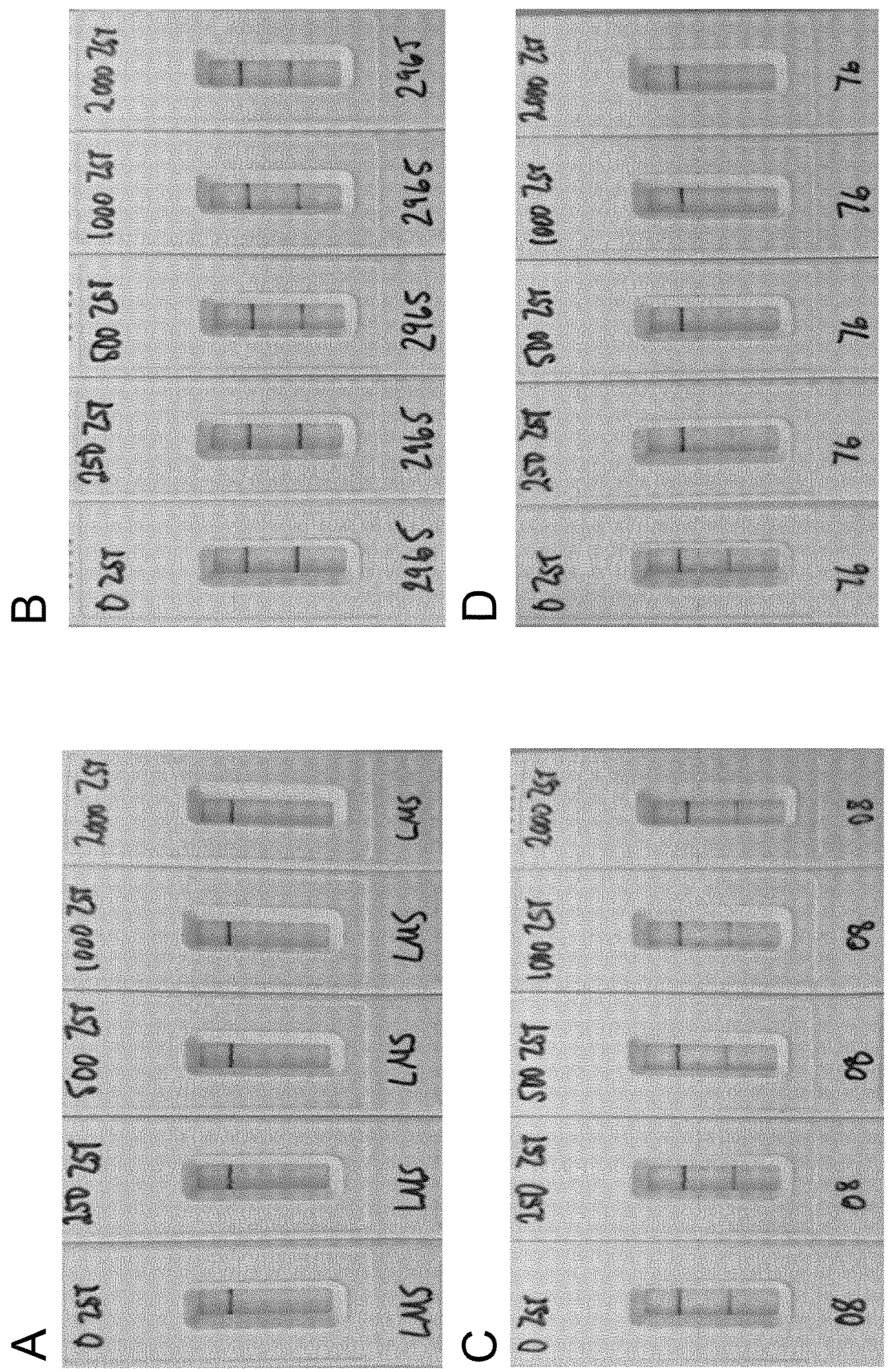
Figure 19:
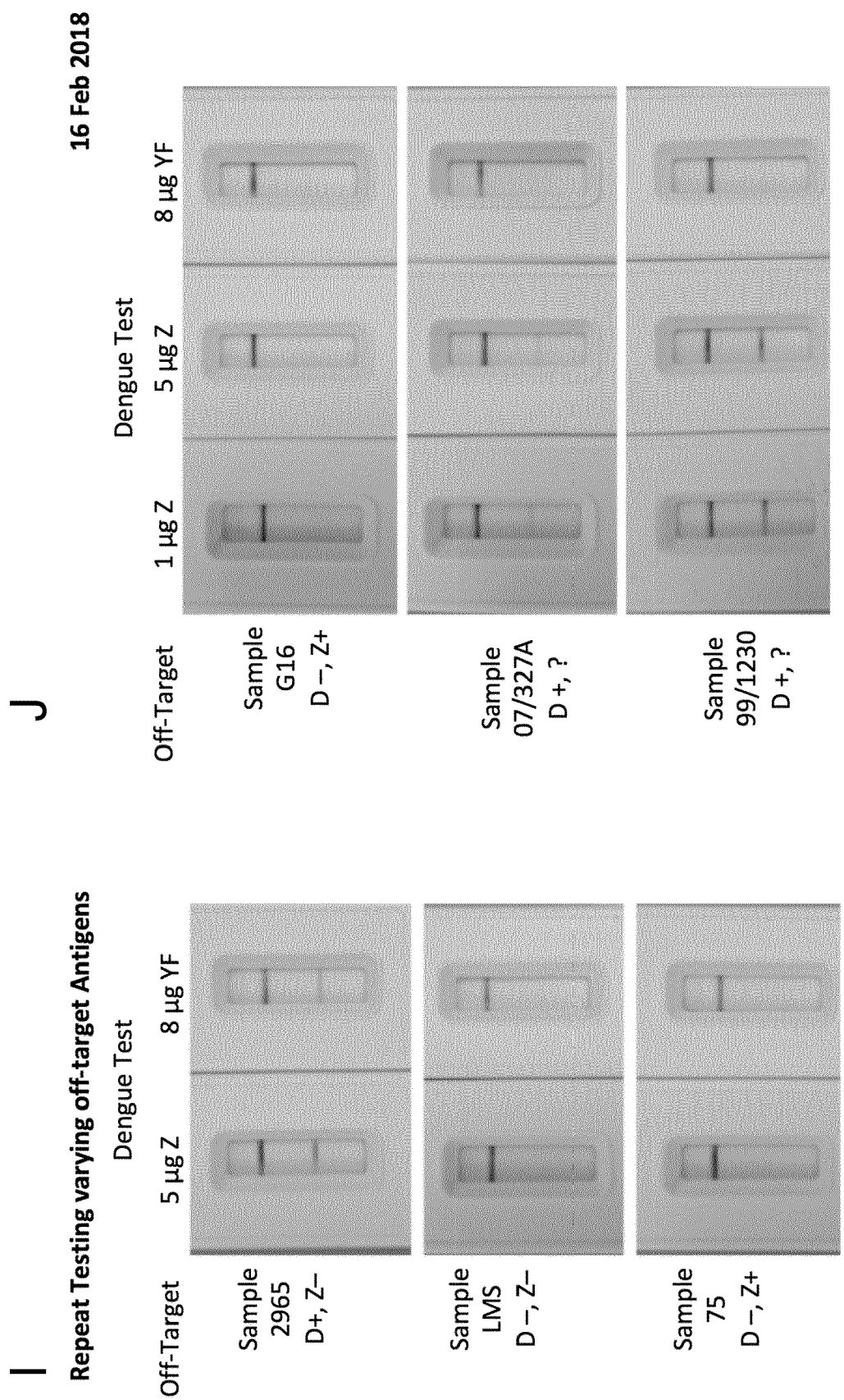
Figure 19:
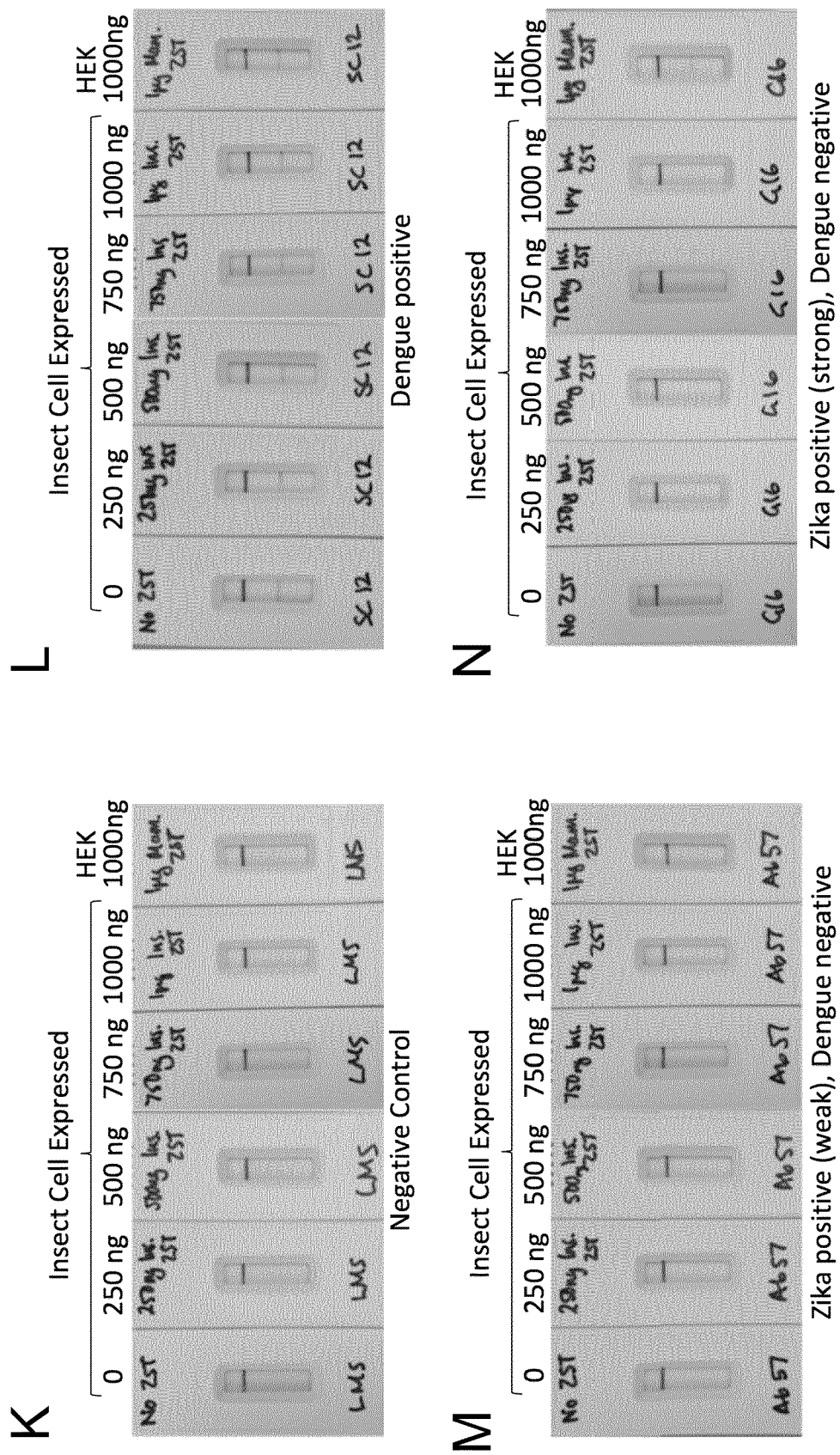
Figure 19:
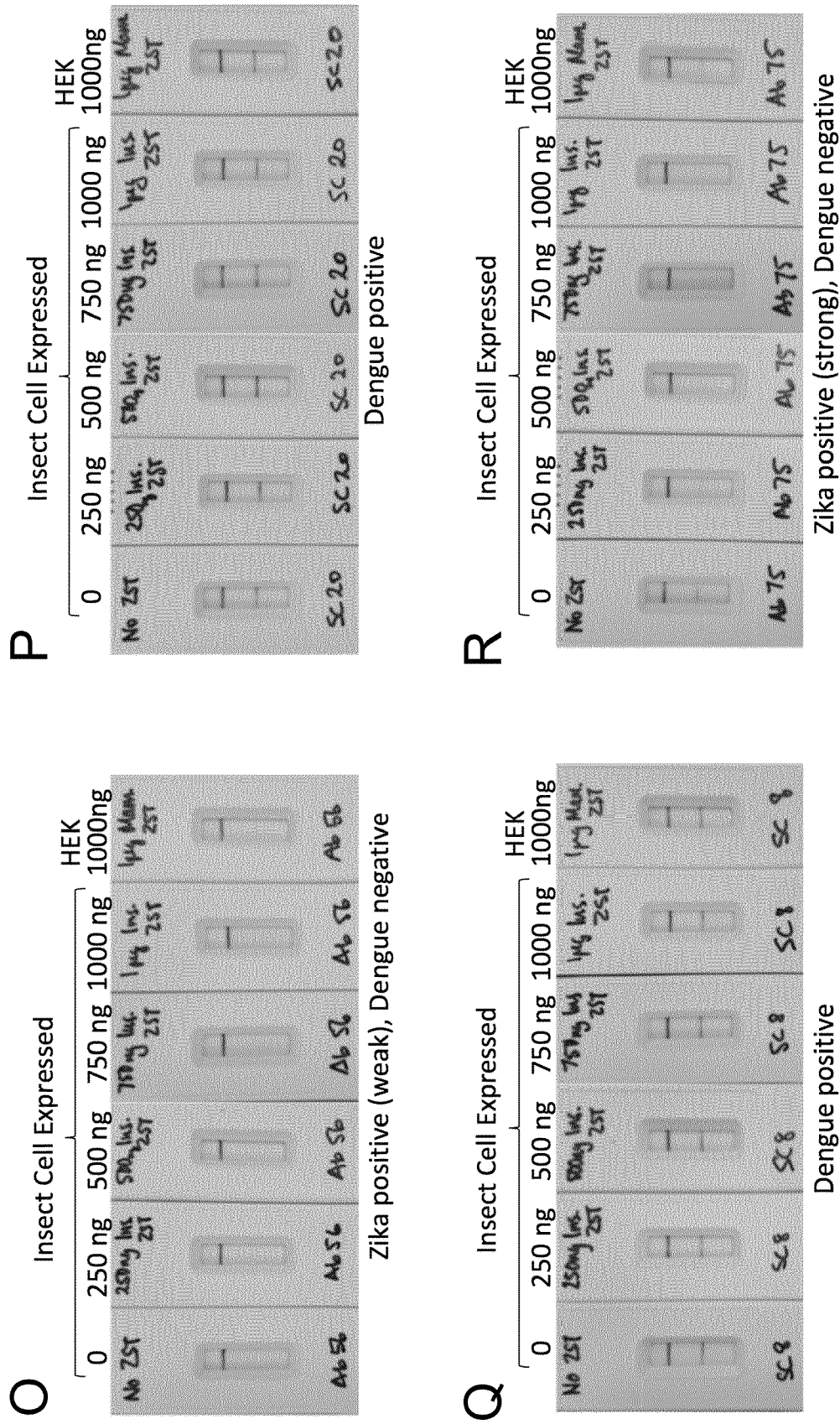

FIG. 19. A-D Titration of strep-tagged-Zika HX into Dengue Tests (A) negative control. (B) and (C) positive dengue samples (D) positive Zika (and dengue) sample, with varying amounts of strep-tagged-Zika HX (strep-Zika) added (0, 250, 500, 1000 and 2000 ng); 1000 ng appears sufficient to reduce Dengue cross-reactivity with Zika positive sample. Note: 76 is a very rare Zika-positive, Dengue-negative sample in the collection tested; (E) & (F) titration of strep-Zika into Zika Tests (50 ng His-Zika) with varying amounts of strep-Zika added (0, 25, 50, 100, 250 and 1000 ng) Sample 57 (weak Zika positive, Dengue negative) this low titre sample absorbs out completely and requires ~100 ng strep-Zika to eliminate signal, whereas Sample 76 (strong Zika positive, Den negative) requires >1000 ng strep-Zika to eliminate signal. 'Homologous Preabsorption' (E,F) was contrived as an extreme test of the effectiveness of preabsorption. Heterologous preabsorption (A to D) was easier to achieve; (G), (H), (I) & (J) repeat tests varying off target (preabsorbing) antigen YF-Ag (unlike all other antigens described in this application) was an Fc-fusion and it is possible that this may have pre-absorbed the colloidal gold conjugate (which is 'armed' with anti-human-IgG-Fc); (K) to (R) refinement of off-target pre-absorption in the LF tests using Tni-expressed insect-cell proteins, in place of HEK-expressed (mammalian-cell) expressed versions of the same proteins.

Figure 20:
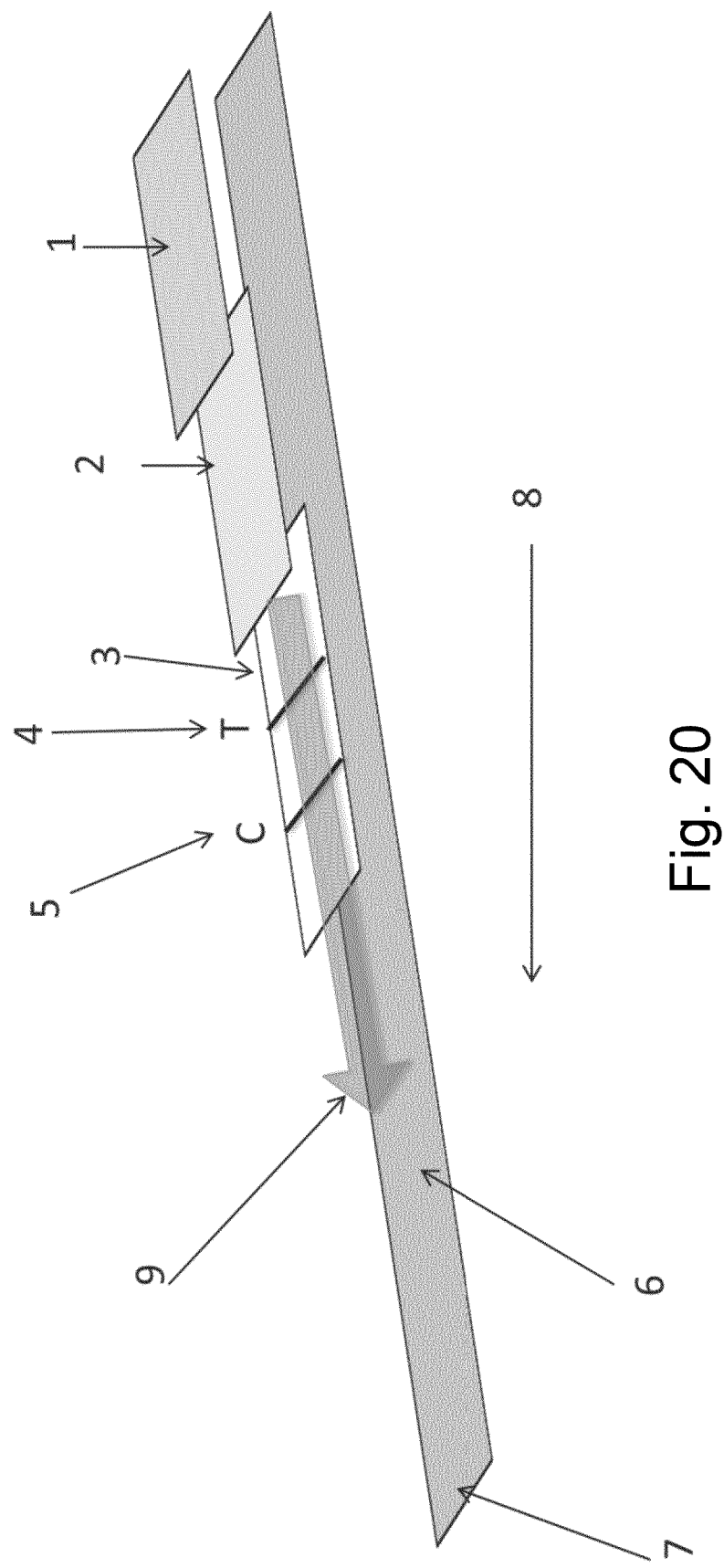

FIG. 20. Operation of strep-tagged HX antigens in an embodiment of the modified LF test design: (1) Sample Pad (with dried His-tagged antigen, plus excess Strep-tagged pre-absorbing antigen), site of single application port for sample & diluent, (2) Conjugate Pad (with dried Au-MCAB anti-IgG-Fc), (3) capture strip (e.g., nitrocellulose) (4) T (test) line (e.g., MCAB anti-His-tag), (5) C (positive control) line of human IgG, (6) backing card, (7) position of absorbent pad (not shown), (8) direction of flow along strip, (9) complexes of preabsorbing antigen (e.g. strep tagged antigen) with cross-reactive antibodies from test sample are carried invisibly past the observation window.

Figure 21:
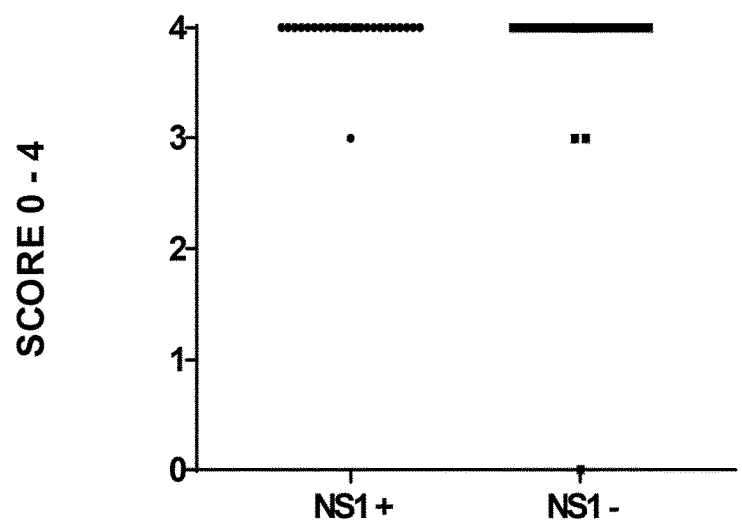
Figure 21:
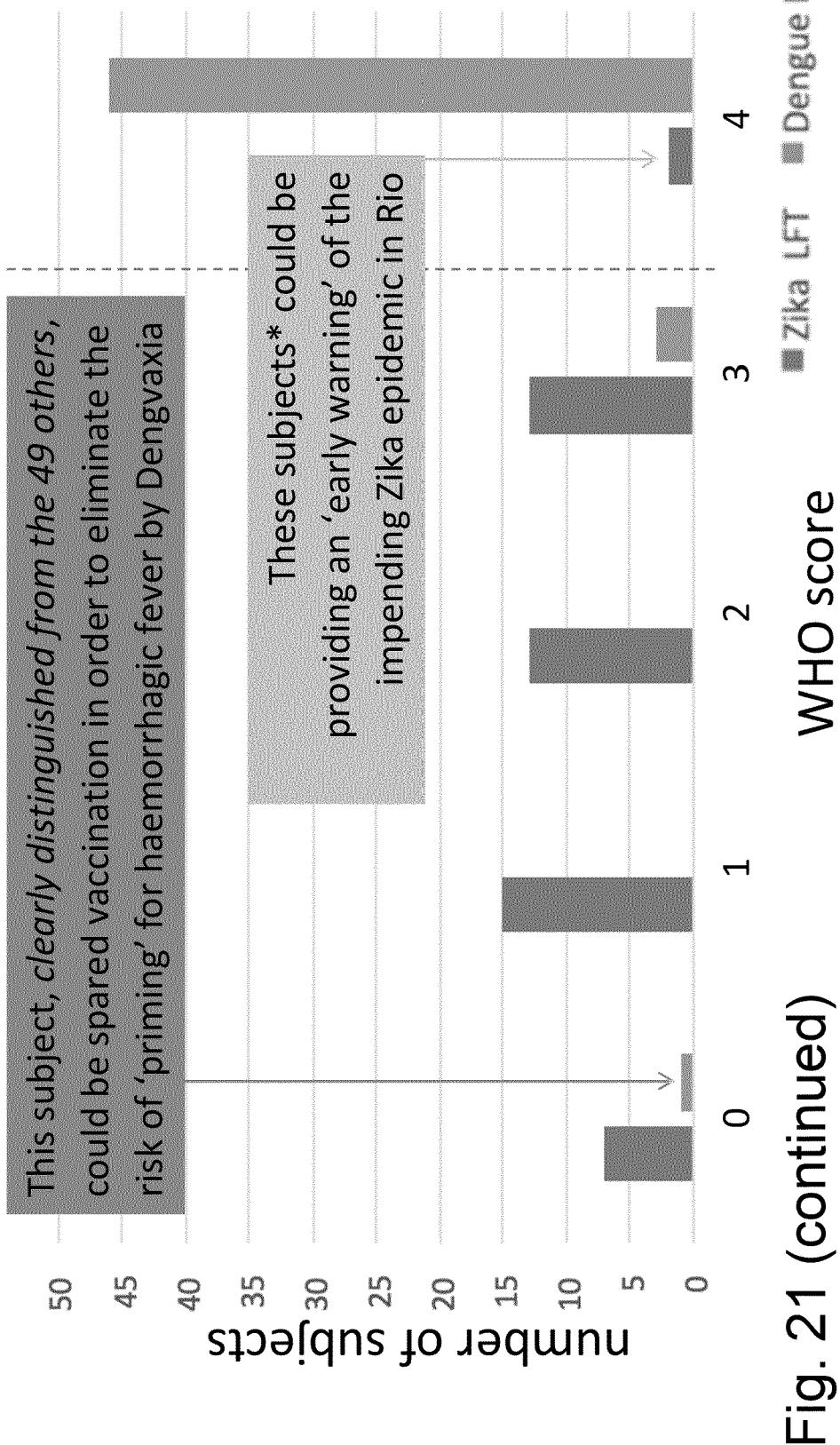

FIG. 21. (A) Zika LF compared to BOB (blockade of binding ELISA) "Sample 2016 collection", Zika LF is 100% sensitive in detecting BOB+ sera. If threshold is set at >3 (e.g. by use of a reader) it is also 100% specific. BOB however is based on a single epitope such that some of the samples scoring 1,2,3 in the LF are likely genuinely to be positive, but missed by BOB due to its recognition of only of a single epitope (i.e. sera that lack antibodies that recognize or obstruct that particular epitope). Note, eleven samples were completely negative, demonstrating a low non-specific binding of human IgG to the test line in the test.

(B) With a high threshold (set at greater than 3=positive), Zika LF of the invention markedly outperforms commercial (Euroimmun/Perkin Elmer) and bespoke (DABA) Zika ELISA assays based on measuring the NS1 protein (a test for acute Zika infection), the NS1 ELISA tests score half of this BOB-negative sample group as positive for Zika (an implausible result given the sample collection date—before significant Zika circulation had occurred) whereas the Excivion Zika LF scores 2/50=4% as positive—a more plausible result (Zika was present in Brazil in 2014 but the precise exent of its circulation is unknown);

(C) dengue LF test of the invention (setting a threshold of greater than 3=positive, as in B) scores 92% of Rio 2014 endemic sera as dengue +ve, which tallies with the 90-95% accepted value based on several published studies of dengue seropositivity in Brazil at this time. The dengue LF of the invention tallies well 92% compared to the 90-95% dengue seropositivity in this 2014 sample group from Brazil, demonstrating excellent sensitivity of the dengue-LF (confirming results from the Pune tests, which demonstrated superior sensitivity of IgG detection over the Standard Diagnostics Duo LF test, p<0.0000001).

(D) Frequency-distribution of LF scores in the Zika LF and dengue LF tests of the invention in the Rio 2014 sample set (before significant Zika circulation had occurred); one subject had a zero score in the dengue LF test and exemplifies the utility of the test in identifying dengue-negative subjects for companion-diagnostic use of the test with dengue vaccines (e.g. Dengvaxia), i.e., in order to avoid priming for dengue haemorrhagic fever this subject would be spared vaccination, the two subjects who were LF-positive for Zika in this sample set (scoring '4') may represent genuine Zika cases and the ability of the Zika LF of the invention to be used as a 'sentinel test' providing early warning of a Zika outbreak.

Figure 22:
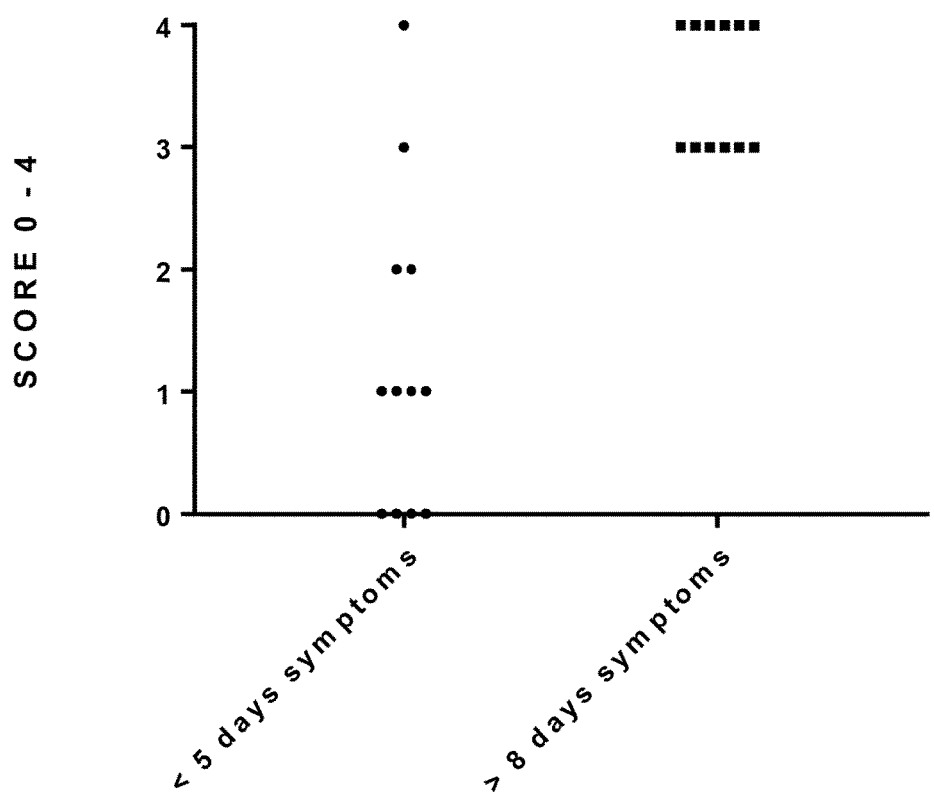

FIG. 22. Seroconversion—elevation of Zika LF scores over time in the Zika LF of the invention in paired samples from PCR-confirmed Zika cases soon after presentation with symptoms. (A) graphical representation, (B) tabular representation, in 10 cases out of 12 there was an elevation in the Zika score. In four such cases the initial score was Zero demonstrating a clear capability to detect seroconversion of subjects for Zika infection using paired samples (as soon as ten days).

EXAMPLES

Figure 1:
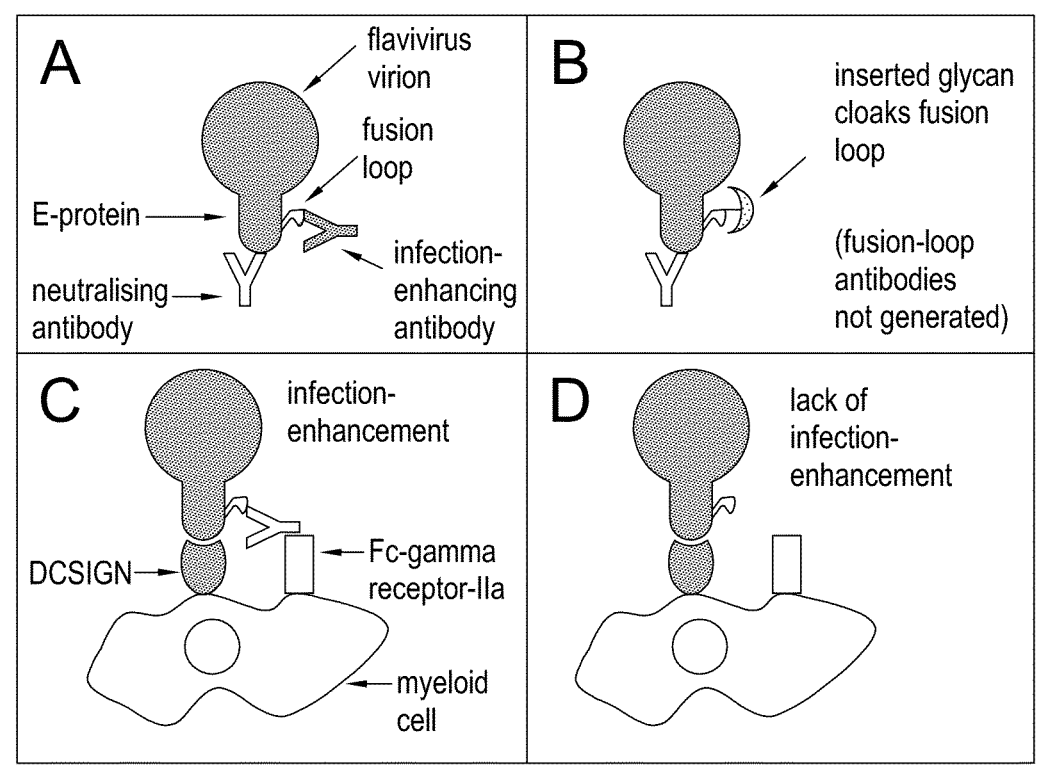

Example 1 Design of New Vaccine Immunogens Designed to Avoid the Elicitation or Stimulation of Infection-Enhancing Antibodies FIG. 1, 'A' shows the effect of vaccination with a flavivirus vaccine, such as a live attenuated vaccine known in the art comprising the four dengue serotypes DEN-1, DEN-2, DEN-3 and DEN-4. The vaccine generates a mixture of antibodies capable of virus neutralisation and other antibodies capable of antibody-dependent enhancement of infection. Antibodies capable of virus neutralisation include those that recognise sites on the receptor-interacting surface of the virion E-protein, i.e., that surface that binds to the DCSIGN lectin/receptor. (For simplicity of illustration, only the DCSIGN receptor is shown, noting that there are other receptors for dengue and flaviviruses generally). 'C' shows how infection-enhancing antibodies against the fusion loop of the E-proteins, when bound to the E-protein of the virion, are able to engage with high affinity the Fc-gamma-receptor-IIa, facilitating infection of myeloid cells. Several types of Fc-gamma receptors have been implicated in this phenomenon, even (paradoxically) including the low-affinity receptor Fc-gamma-receptor-IIb, which is normally inhibitory to myeloid cells and B-cells (Bournazos S, Signaling by Antibodies . . . Ann. Rev. Immunol 2017, 35:285-311). The result of vaccination with a live attenuated vaccine (an example of a vaccine known in the art) is the net effect of two opposing populations of antibody, one set that neutralises dengue virions, and a further set that is capable of infection enhancement. In most subjects of vaccination, neutralising antibodies overcome the effect of the infection-enhancing antibodies, such that the net effect of vaccination is protection against the four dengue serotypes. However, in subjects who do not mount a balanced response to the four serotypes, or who are immunosuppressed e.g., due to measles or HIV infection, flavivirus-infection-enhancing antibodies prevail rendering such subjects predisposed to, rather than protected against, severe infection with dengue and more prone to infection with other flaviviruses. Further, infection-enhancing antibodies in some healthy (non-immunosuppressed) dengue-vaccinated subjects cross-react with Zika virus. Those dengue-immunised subjects are now predisposed to Zika infection upon first being bitten by a Zika-infected mosquito 'C'.

Conversely, 'B' illustrates a vaccine immunogen designed in accordance with the invention. The novel immunogen, containing an E-protein wherein the fusion loop sequence has been modified and has been designed to be substituted with a glycan with the aim to generate neutralising antibodies against the E-proteins of the vaccine without generating infection-enhancing antibodies. 'D' represents occasional failure of the vaccine of the invention to elicit a protective level of antibody response in some subjects (e.g., the immunosuppressed), however, unlike other vaccine designs known in the art, the vaccine of the invention is designed to not render immunosuppressed subjects susceptible to enhanced infection with dengue or Zika viruses. Immunogens and vaccines of the present design are thereby designed to be safer on an individual subject basis and moreover to lack the potential to facilitate the epidemic spread of Zika by creating a population of subjects that have Zika-infection-enhancing antibodies, in the absence of neutralising antibodies. (WT=wild type).

Example 2 (FIG. 2) Recombinant Expression of Glycoengineered (Hyperglycosylated) Forms of Dengue and Zika Exodomain Proteins Plasmid inserts encoding various novel recombinant forms of the natural wild type (WT) exodomain sequences representative of the four dengue serotypes and of Zika and containing an $E.$ $coli$ origin of replication and a cytomegalovirus (CMV) promoter, as well as a hexahistidine C-terminal tag, were made by de novo gene synthesis (Thermofisher, GeneArt). Where two glycosylation sequons were inserted in the DNA sequence, the sequence was changed 'manually' to avoid the creation of direct DNA sequence repeats that might otherwise allow undesirable homologous recombination events.

Plasmid expression vectors pCRO21 (SEQ ID NO: 13), pCRO22 (SEQ ID NO: 14), pCRO23 (SEQ ID NO: 15), pCRO24 (SEQ ID NO: 16) and pCRO28 (SEQ ID NO: 17), coding for the mutated exodomain of the Envelope proteins of DENV1, DENV2, DENV3, DENV4 and ZIKV, respectively, were ultimately selected and produced by The Native Antigen Company, Oxford, as follows: expression cassettes were synthesized de novo to contain a 5' NotI site followed by a consensus Kozak sequence followed by the coding sequence for the first 17 amino acids of the influenza-A virus haemagglutinin protein acting as secretion signal. The Envelope protein coding sequences used, (numbering relative to the polyprotein), were 280-675 (NCBI ACA48859.1), 281-676 (NCBI ADK37484.1), 281-673 (NCBI AIH13925.1), 280-675 (NCBI ANK35835.1) and 291-696 (NCBI ARB07957.1), respectively. [Elsewhere, for ease of reference, numbering is expressed according to residue number in the E-protein, with W at 101 of the fusion loop as a reference point]. Each construct contained coding sequences for a glycine-serine linker 7 to 8 amino acids in length followed by a 6× His-tag and a stop codon. The stop codon is followed by a NheI site in each expression cassette. The mammalian expression vector pSF-CMV (Oxford Genetics, Oxford) was digested with NotI and NheI, and the 4.2 kb fragment was ligated to the 1.3 kb NotI and NheI fragments of the expression cassette harbouring maintenance vectors (pUC57). In each case, one or two additional sequons of the general formula (NXS/T) was introduced into the fusion loop of the E-protein exodomain, capable (theoretically) of encoding a functional N-linked glycosylation site. The wild-type dengue proteins naturally already have two glycosylation sites, and Zika one. None of the natural glycans are found in the fusion loop.

For small-scale preparation 15 ml aliquots of HEK293FT cells at 3e6/ml were individually transfected with pCRO21, pCRO22, pCRO23, pCRO24 or pCRO25 (SEQ ID NO: 18), 4 control transfections were performed using pSF233, pSF236, pSF237, pSF238 or pSF239. After a day, 15 ml of rescue medium was added to each transfection. At day 3 after transfection each of the 10 transfections was treated the same way as follows: 30 ml of suspension was spun at 4,000 g for 7 minutes. The resulting supernatant was filtered using a 0.22 um disc filter. The pellet was resuspended in 1 ml of PBS. The filtered supernatant was then concentrated using a Vivaspin20 (30,000 Da cutoff) as per manufacturer's instructions. Concentrate volumes ranged from 0.6 ml to 1.2 ml. All concentrates were brought up to 1.2 ml with PBS. The concentrated supernatants were subjected to Talon purification as per manufacturer's instructions using Talon HiTrap Spin (GE). Buffers for Talon capture were: Equilibration Buffer: 50 mM phosphate pH7.8, 300 mM NaCl; Wash Buffer: 50 mM phosphate pH78, 300 mM NaCl, 5 mM imidazole; Elution Buffer: 50 mM phosphate pH7.8, 300 mM NaCl, 150 mM imidazole.

Characterisation of the resulting proteins by coomassie-blue staining (FIG. 2a, FIG. 2d) and by western blot (FIG. 2b, FIG. 2c) of SDS electrophoresis gels is shown in FIG. 2.

Figure 2A:
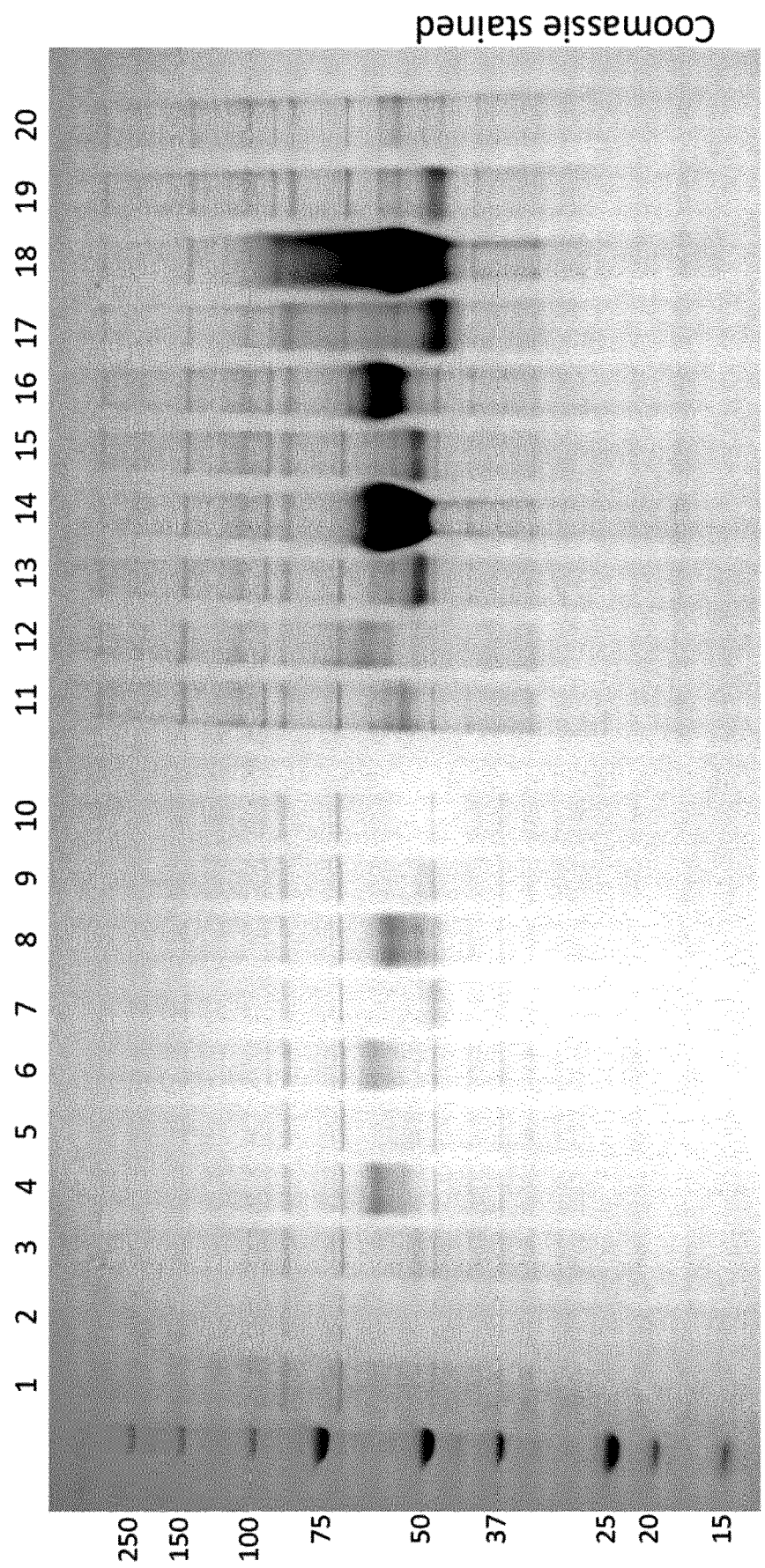
FIG. 2a: Coomassie stained gel showing evaluation of expression of dengue and Zika constructs in HEK293 cells, lanes shown as follows:
1: pSF236 transfected cells WT, 2: pCRO21 transfected cells, 3: pSF237 transfected cells WT, 4: pCRO22 transfected cells, 5: pSF238 transfected cells WT, 6: pCRO23 transfected cells, 7: pSF239 transfected cells WT, 8: pCRO24 transfected cells, 9: pSF233 transfected cells WT, 10: pCRO25 transfected cells. 11: pSF236 transfected cells WT, 12: pCRO21 transfected cells, 13: pSF237 transfected cells WT, 14: pCRO22 transfected cells, 15: pSF238 transfected cells WT, 16: pCRO23 transfected cells, 17: pSF239 transfected cells WT, 18: pCRO24 transfected cells, 19: pSF233 transfected cells WT, 20: pCRO25 transfected cells. For lanes 1 to 10, the supernatant concentrate was 1 ul/1.1 ml, for lanes 11 to 20 the supernatant concentrate Talon eluate concentration was 26 ul/400 ul.
Figure 2B:
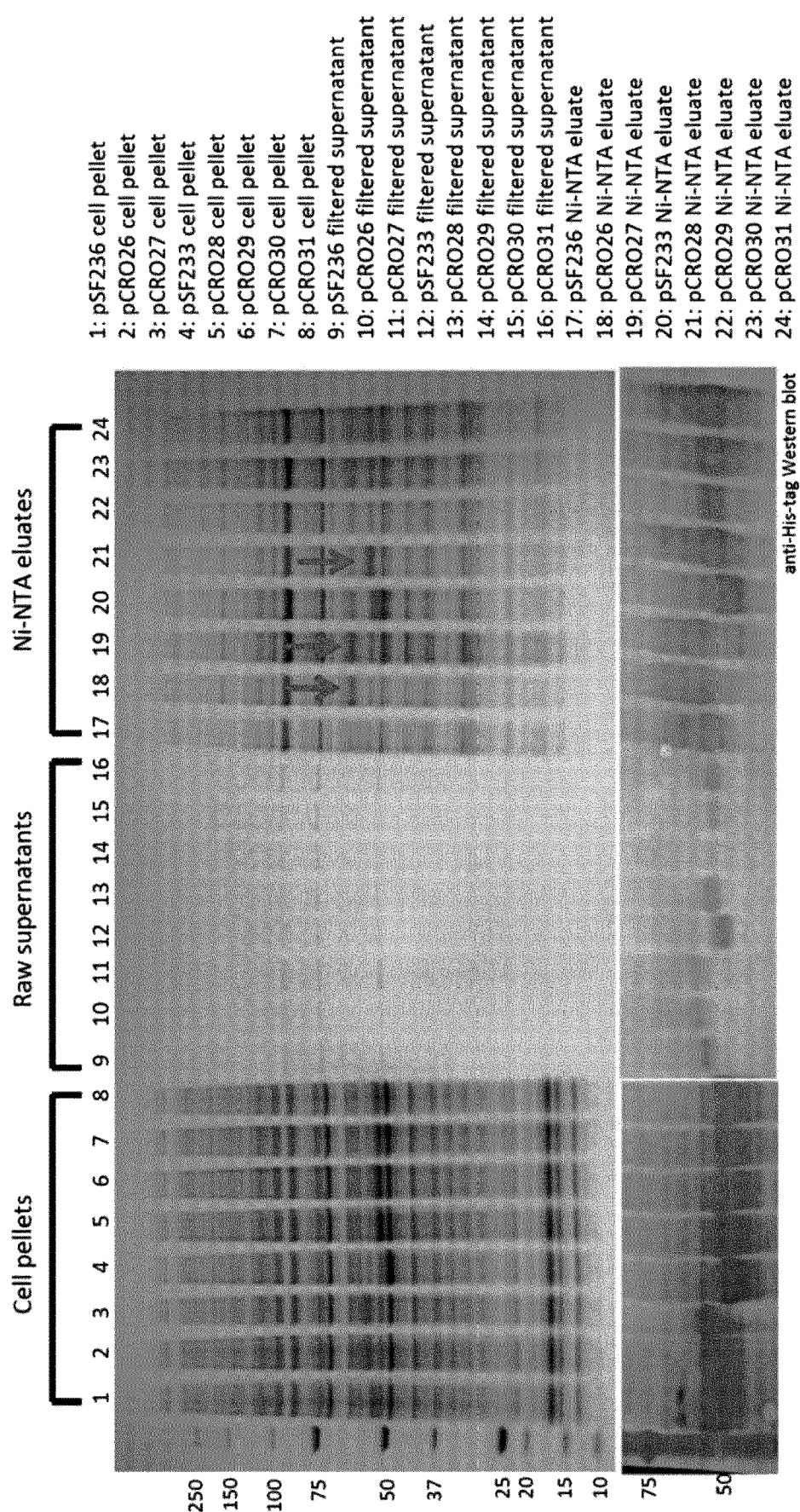
FIG. 2b: Anti-his-tag Western blot showing further expression evaluation of dengue-1 and Zika constructs. Lanes 1-8 show cell pellets, lanes 9-16 show raw (filtered) supernatants, lanes 17-24 show Ni-NTA eluates, as follows:
1: pSF236 cell pellet, 2: pCRO26 cell pellet, 3: pCRO27 cell pellet, 4: pSF233 cell pellet 5: pCRO28 cell pellet, 6: pCRO29 cell pellet, 7: pCRO30 cell pellet, 8: pCRO31 cell pellet, 9: pSF236 filtered supernatant, 10: pCRO26 filtered supernatant, 11: pCRO27 filtered supernatant, 12: pSF233 filtered supernatant, 13: pCRO28 filtered supernatant, 14: pCRO29 filtered supernatant, 15: pCRO30 filtered supernatant, 16: pCRO31 filtered supernatant, 17: pSF236 Ni-NTA eluate, 18: pCRO26 Ni-NTA eluate, 19: pCRO27 Ni-NTA eluate, 20: pSF233 Ni-NTA eluate, 21: pCRO28 Ni-NTA eluate, 22: pCRO29 Ni-NTA eluate, 23: pCRO30 Ni-NTA eluate, 24: pCRO31 Ni-NTA eluate. Three arrows indicate detected hyperglycosylated exodomain forms.
Figure 2C:
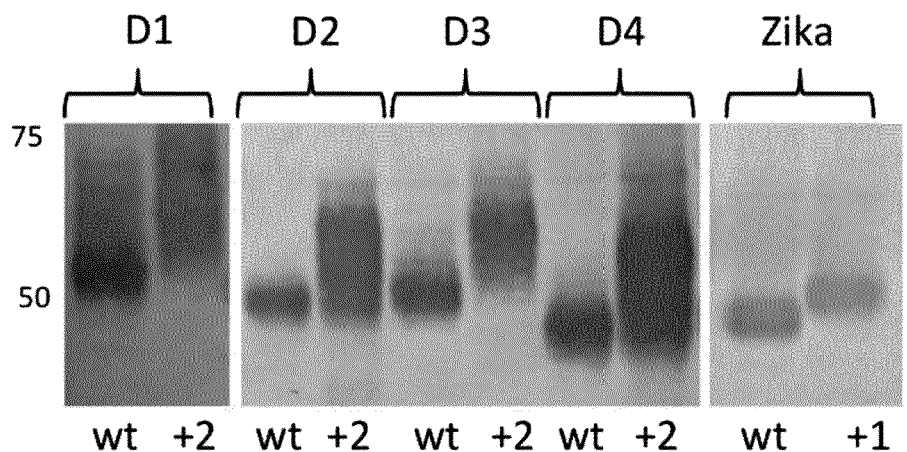
FIG. 2c shows a Western blot of the hyperglycosylated forms pCRO21, pCRO22, pCRO23, pCRO24 for dengue serotypes 1-4 (D1, D2, D3 and D4) respectively and pCRO28 for Zika. The left lane of each pair shows the wild type (wt), whereas the right lane of each pair shows the hyperglycosylated form of the dengue or Zika E-protein exodomain. +2 indicates two additional glycosylation sites/glycans, +1 indicates one additional glycosylation site/glycan.

FIG. 2c shows a Western blot with anti-His-tag monoclonal antibody of chosen constructs pCRO21 (D1), pCRO22 (D2), pCRO23 (D3), pCRO24 (D4) (for dengue serotypes 1~4 respectively) and pCRO28 for Zika, which gave rise to secreted hyperglycosylated proteins. Molecular weight increments due to glycosylation are apparent, higher for the +2 glycan dengue constructs than for the Zika +1 glycan construct, demonstrating the practical attainment of select theoretically designed constructs as expressible proteins. Wild type forms are shown on the left of each pair.

Figure 2D:
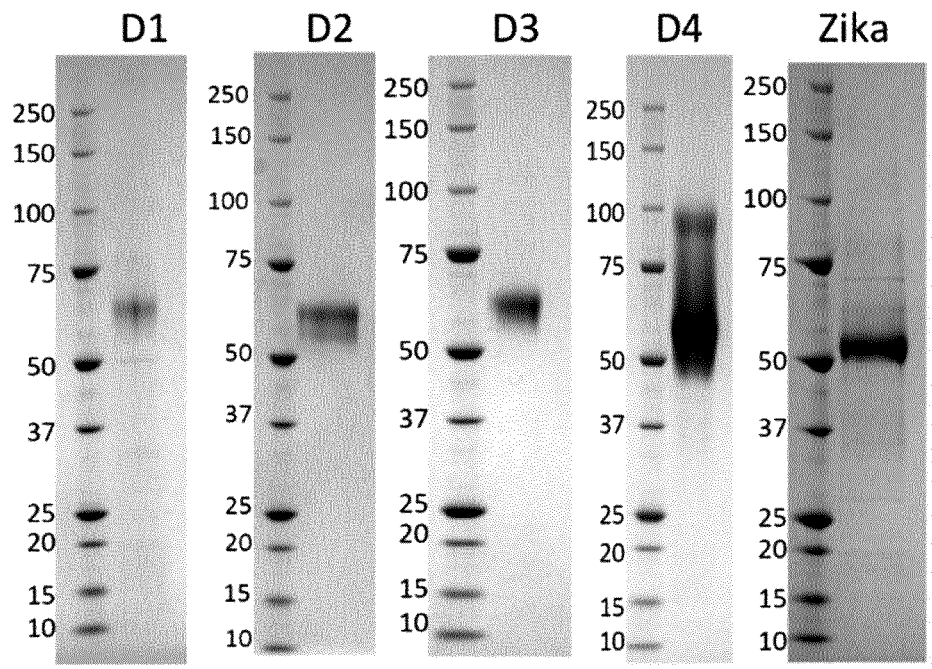
FIG. 2d shows Coomassie blue stained gels of the purified hyperglycosylated E exodomain proteins D1, D2, D3, D4 and Zika, which correspond to plasmids pCRO21, pCRO22, pCRO23, pCRO24 and pCRO28, respectively, in the sequence listings. The scale to the left is the migration position of molecular weight markers in '000s.
Figure 3A:
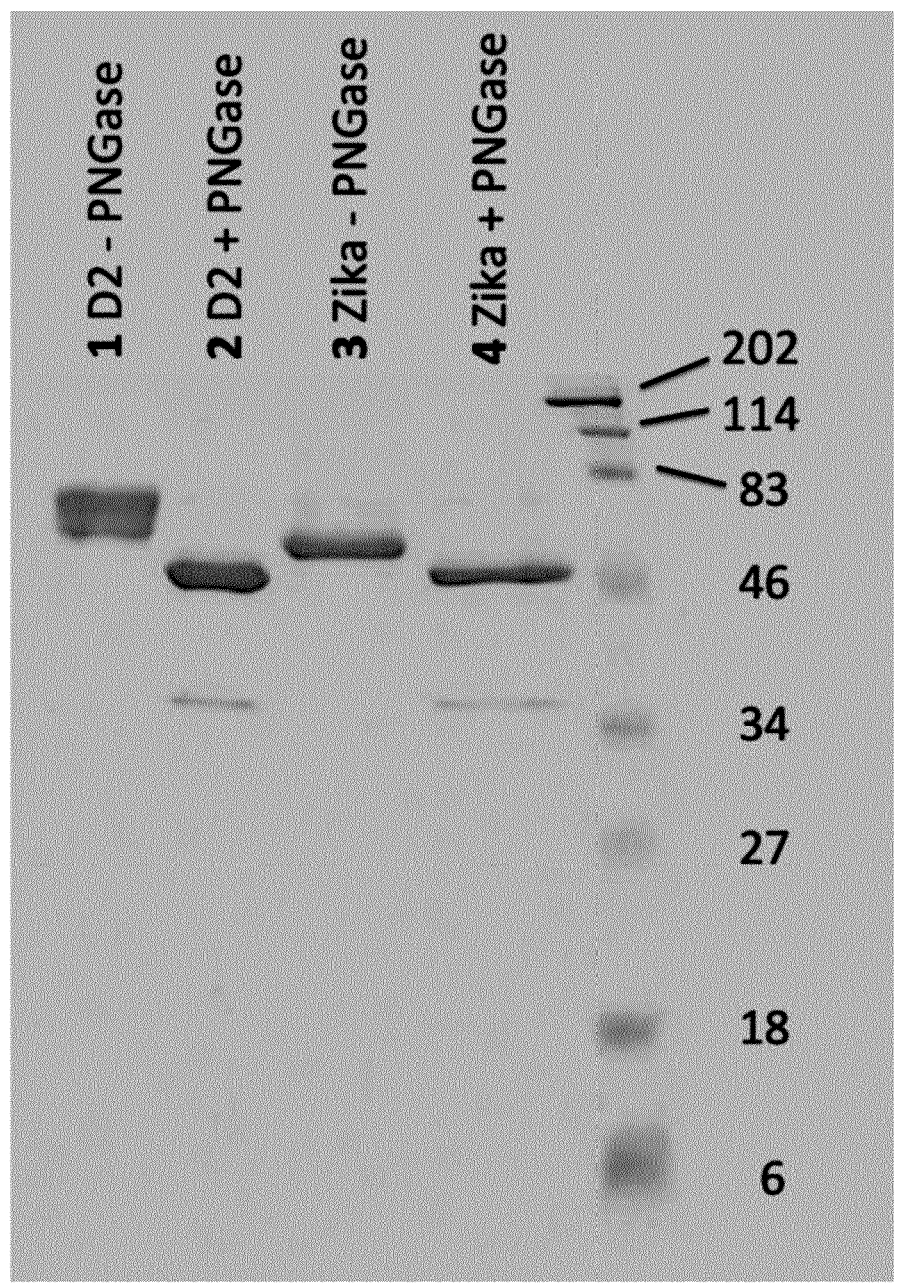
FIG. 3a shows an SDS-PAGE analysis of dengue and Zika samples prior to and after PNGase digestion.
Figure 3B:
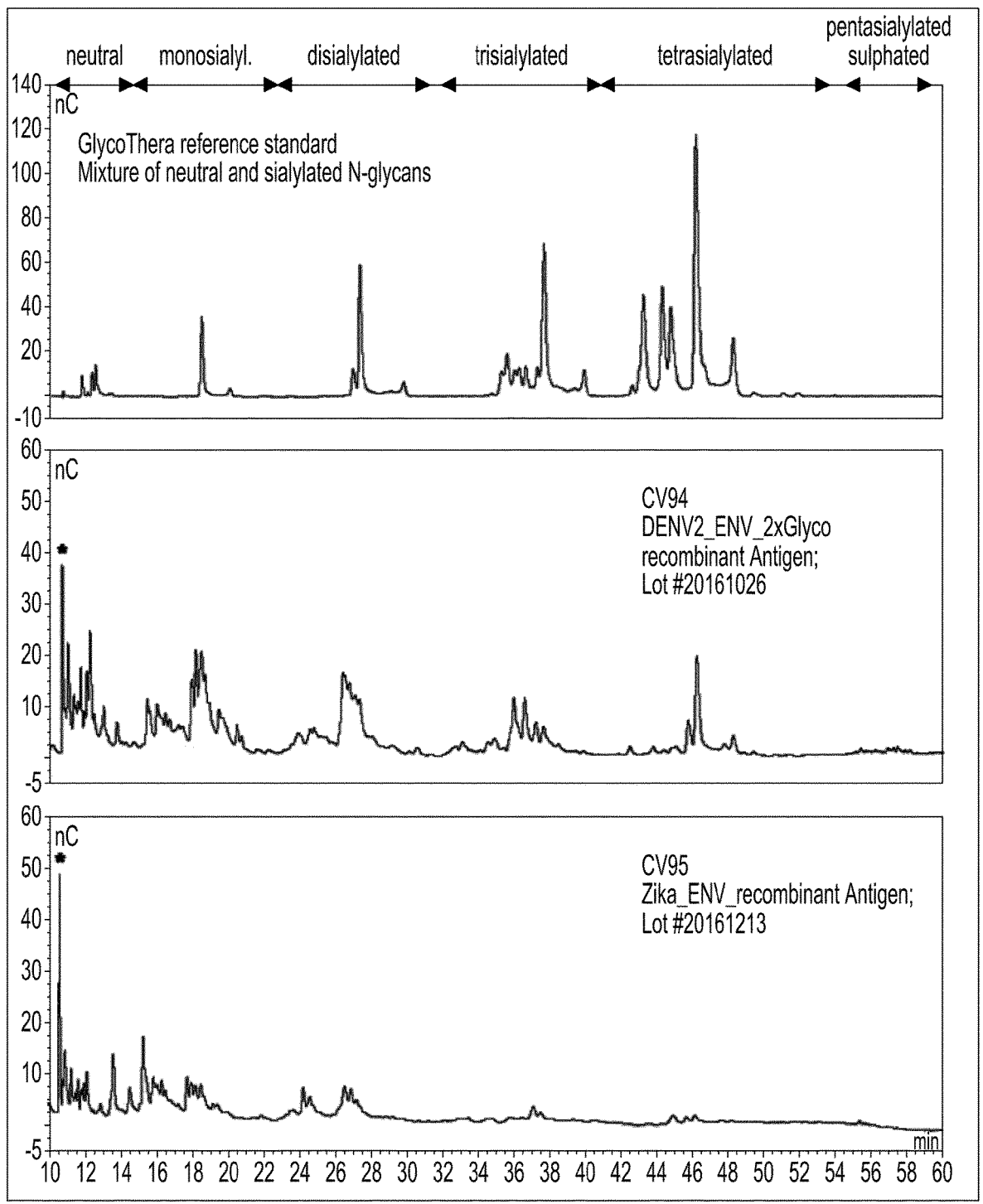
FIG. 3b shows analysis of glycans released from dengue-2 and Zika compared to reference standards by HPAEC-PAD.
Figure 3F:
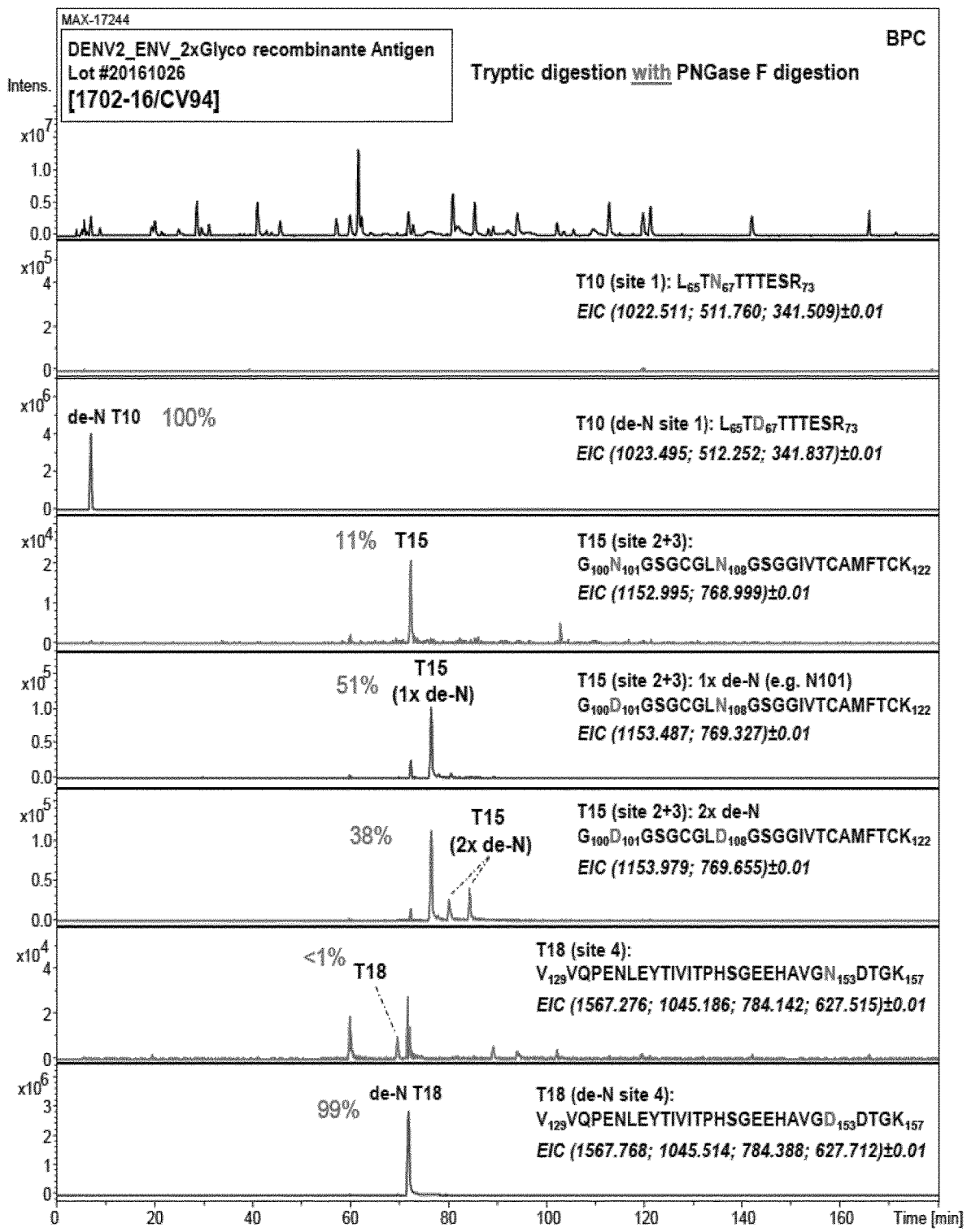
FIG. 3f shows tryptic digestion of dengue-2 with and without PNGase F digestion.
Figure 3G:
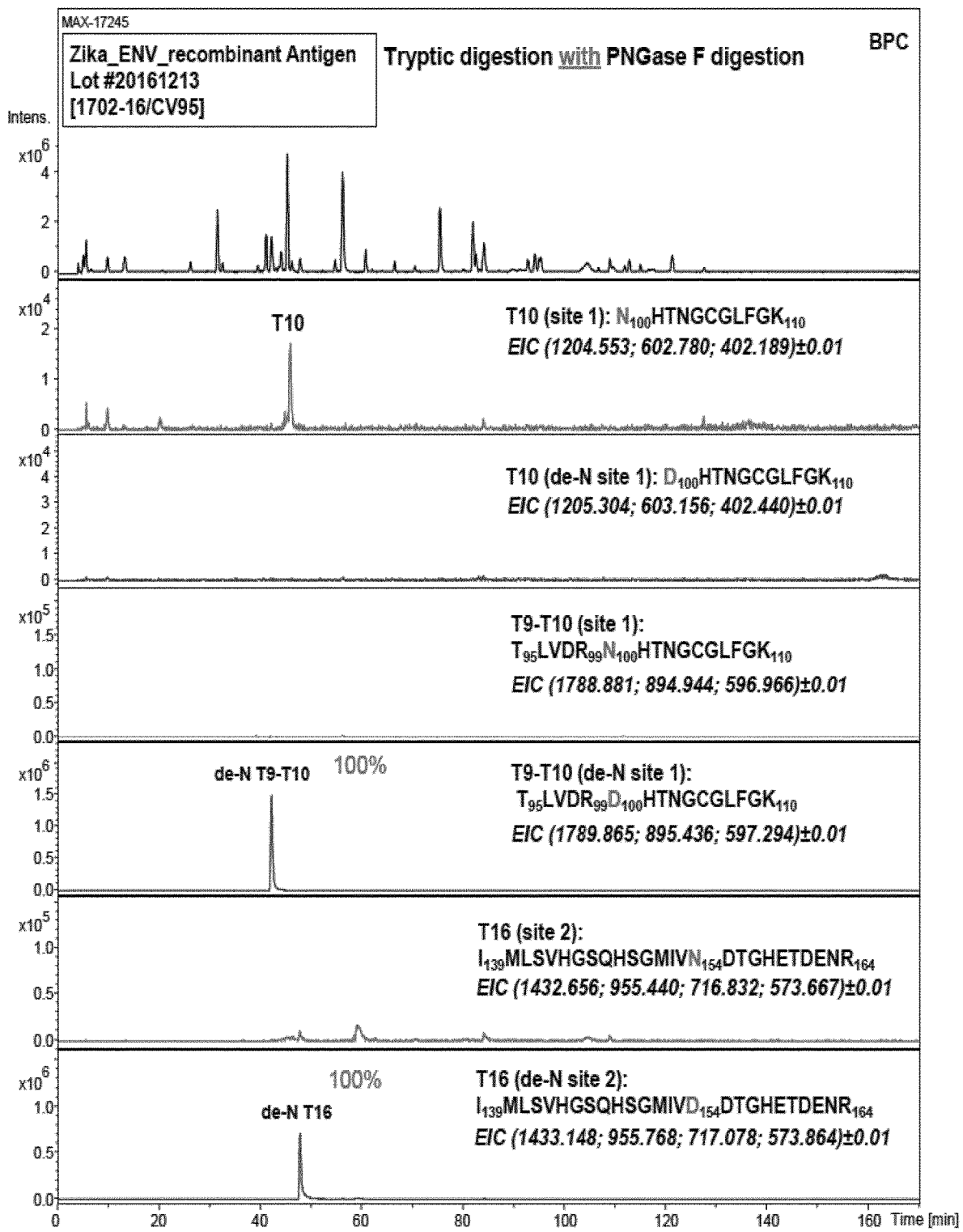
FIG. 3g shows tryptic digestion of Zika with and without PNGase digestion.
Figure 3H:
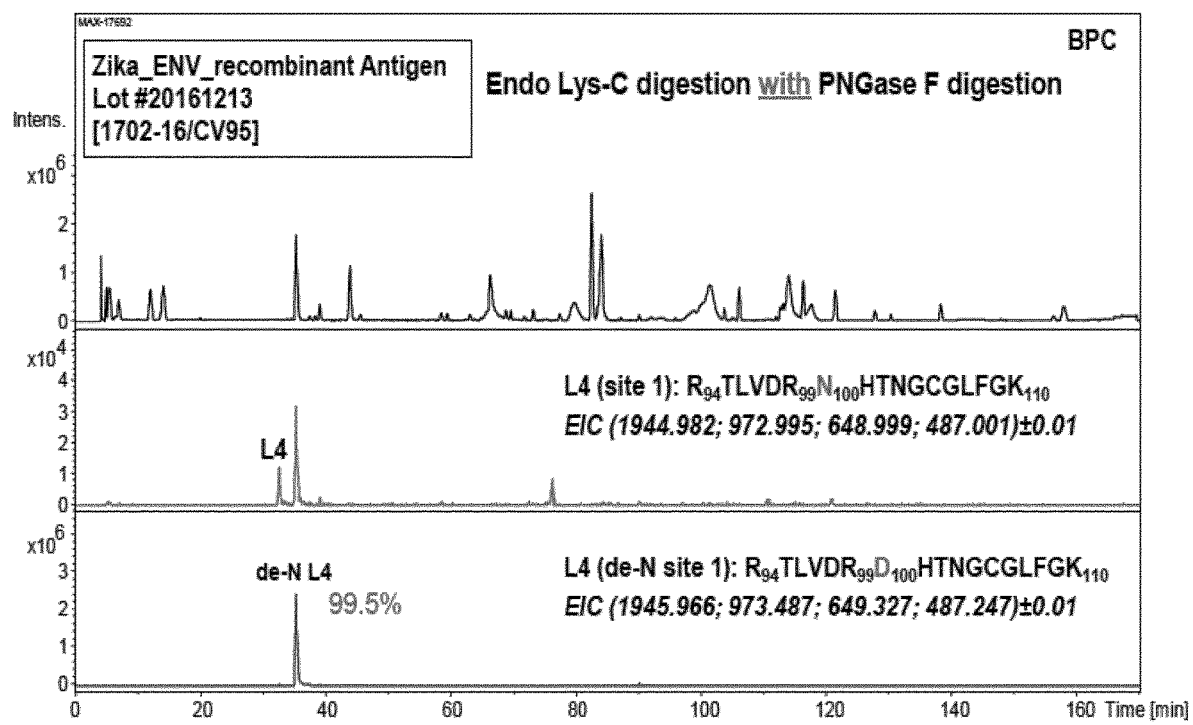
FIG. 3h shows endo-Lys-C digestion of Zika with and without PNGase digestion.

FIG. 2d shows Coomassie blue stained gels of the purified proteins, hyperglycosylated E protein exodomains from the four dengue virus strains D1, D2, D3, D4 and Zika after cobalt chelate (TALON) chromatography using cobalt chelate. Hyperglycosylated exodomains D1, D2, D3, D4 and Zika correspond to plasmids pCRO21, pCRO22, pCRO23, pCRO24 and pCRO28, respectively.

For scale-up production, the novel hyperglycosylated proteins were expressed recombinantly in human embryonic kidney cells (HEK 293) by transient transfection with linear polyethyleneimine (PEI), and purified by metal chelate affinity chromatography with a cobalt chelate (TALON®, Clontech/GE), as described as follows for the dengue-1 hyperglycosylated construct based on pCRO21. 20×1 L of HEK293 cells were transfected with DENV1_Eexo_2xglyco expression vector pCRO21. 3 days post transfection, the supernatant was harvested by centrifugation, and the cleared supernatant was 0.2 um filtered and concentrated to ~200 ml by tangential flow filtration (TFF). Immobilised metal affinity chromatography (IMAC) was performed on the TFF retentate using 5 ml HiTRAP Talon pre-packed column (GE) according to manufacturer's instructions using 20 mM sodium phosphate pH7.8 based buffer systems. DENV1_Eexo_2xglyco protein containing fractions were pooled and dialysed against 20 mM TRIS-HCl pH7.8 10 mM NaCl. Ion exchange chromatography was performed using a pre-packed 5 ml HiTrap Q HP column according to manufacturer's instructions. DENV1_Eexo_2xglyco were pooled and dialysed against DPBS pH7.4. The dialysed solution was 0.22 um filtered and vialled under sterile conditions. BCA assay and SDS-PAGE were performed according to manufacturer's instructions (Bio-Rad).

Note that three of the hyperglycosylated constructs express at levels much higher than wild type (these are the hyperglycosylated dengue serotypes 2, 3 and 4 corresponding to plasmids pCRO22, pCRO23 and pCRO24). Zika plasmid, pCRO25 did not give rise to detectable secreted protein (FIG. 2a, lane 20), although significant amounts of cell-associated protein were found (not shown).

Therefore a further round of constructs was made (see FIG. 2b) seeking to improve levels of expression of dengue-1 and Zika hyperglycosylated forms. In this instance nickel chelate chromatography was used for purification. Further constructs of dengue (pCRO26 (SEQ ID NO: 19), and pCRO27 (SEQ ID NO: 20)) and of Zika (pCRO28 (SEQ ID NO: 17), pCRO29 (SEQ ID NO: 21), pCRO30 (SEQ ID NO: 22) and pCRO31 (SEQ ID NO: 23)) were expressed and purified. Favourable expression of the plasmid construct pCRO28 was demonstrated by anti-His-tag Western blot (FIG. 2 c) and coomassie staining (FIG. 2 d).

The hyperglycosylated forms chosen were pCRO21, pCRO22, pCRO23, pCRO24 (for dengue serotypes 1-4 respectively) and pCRO28 for Zika. Hyperglycosylated exodomains D1, D2, D3, D4 and Zika correspond to plasmids pCRO21, pCRO22, pCRO23, pCRO24 and pCRO28, respectively (SEQ ID NO: 24, 25, 26, 27 and 28 respectively). Molecular weight increments due to glycosylation are apparent, higher for the +2 dengue constructs than for the Zika +1 construct.

In all, eleven plasmid constructs were made and tested for protein expression and five were selected for further investigation, based on equivalent or (in most cases) superior levels of expression compared to wild type (pCRO21, pCRO22, pCRO23, pCRO24 representing the four serotypes of dengue, and pCRO28 representing Zika).

Surprisingly, given the extremely hydrophobic nature of the fusion loop (which features the residues W, F and L exposed at the tip of the E protein in close juxtaposition at its distal end in three dimensional space) in the case of dengue, all four representative serotypes tolerated substitution of two glycans (which are hydrophilic, and radically transform the topography of this part of the protein to an extent that mere amino-acid substitutions cannot) with no penalty to levels of expression (i.e., all expressed as well as the wild type sequence, in some cases markedly better). An objective had been set of 'no less than wild type' for levels of expression in order to ensure that the proteins were not misfolded which would have resulted in eradication from the endoplasmic reticulum via the ERAD channel for proteasomal degradation. Examples of the dengue serotype-1 sequence with a single glycan in the fusion loop were also made, but it did not express any better than wild type or the species with two glycans. In the case of Zika, attempts to generate variants with two glycosylation sites into the fusion loop (following the method established for dengue) were not successful, resulting in less secretion of the recombinant protein into the culture medium than for wild type.

In the case of the Zika E-protein exodomain we therefore explored the generation of variants with a single glycan at various sites in the fusion loop. Substitution of the tryptophan (W101), as for one of the dengue sequons, with an asparagine (the N of the sequon at 101 in place of W), resulted in a level of expression of the construct that was less than for wild type. Likewise, insertion of a glycan at F108 (i.e. the N of the sequon at 108, in place of F), resulted in a level of expression of the construct that was less than for wild type. We concluded that the Zika fusion loop was less tolerant to glycan insertion, and sought a more conservative way to allow it.

Having established, in the case of Zika, that neither the W101 nor the following F of the fusion loop could be replaced with the N of an N-linked glycosylation sequon, an alternative strategy was developed, which was not modeled on the approach taken for dengue. We sought to place a single glycan as near as possible to the end of the fusion loop (based on the 3D structure PDB 5IRE). Rather than go through the process of systematically making and testing the hundreds of possible variants that might allow glycan insertion (which would have been arduous by gene synthesis or by library technologies), we contrived a hypothetical solution and tested it. We contrived to straddle the W at the apex of the fusion loop with an N-linked glycosylation sequon. However, we reasoned that may have been infeasible by insertion of the classical NXS/T sequon, because W is not tolerated at the X position of a sequon. However, although W is not tolerated in the 'X' position in the centre of a sequon, H (histidine, a relatively conserved replacement for W, having a hydrophobic-aromatic/cationic dual character) can be tolerated in the X-position. We therefore substituted the 100 position with an N, used a H in place of the W for the X-position, and used a T (which we find works better with H than S), to make a single sequon that read 'NHT' (i.e. residues 100, 101, 102, using the E-protein numbering convention rather than the polyprotein numbering convention). The resulting protein, made from plasmid pCRO28, was found to express as well as wild type, and gave greater yield on purification than wild type, indicating no impediment to expression. The other variants of Zika that we explored gave rise to low level or no secreted protein in the expression systems used.

Example 3 (FIG. 3) Characterisation of Glycans Present on the Glycoengineered Dengue Serotype-2 and Zika Proteins Glycan compositional analysis (GlycoThera, Germany) was performed on two of the selected proteins from Example 2, the dengue-2 serotype product of pCRO22 (representative of the selected dengue constructs that were all designed to carry two glycans in the fusion loop) and that of Zika (the product of pCRO28, designed to carry one glycan in the fusion loop) obtained from transfections of HEK 293.

The results of SDS-PAGE analysis of dengue and Zika samples prior to and after digestion with polypeptide N-glycosidase F (PNGase, Prozyme Inc.) are shown in FIG. 3*a*. The samples were reduced in 50 mM DTT for 5 min at 95° C. prior to SDS-PAGE analysis (15% polyacrylamide gel after coomassie blue staining) Lane 1: CV94 (pCRO22 protein, dengue-2) prior to PNGase digestion; Lane 2: CV94 after PNGase digestion; Lane 3: CV95 (pCRO28 protein, Zika) prior to PNGase digestion; Lane 4: CV95 after PNGase digestion; Lane 5: molecular weight standard. In this case the degree of decrease in apparent molecular weight (as distinct from the increment in FIG. 2*c* relative to WT) conforms to theoretical expectation based on the number of additional glycans introduced into the sequence: i.e. dengue-2 has lost four glycans in this digestion (two natural, and two introduced by sequence programming of additional sequons), whereas Zika has lost two glycans (one natural, and one introduced by sequence programming of one additional sequon). Enzymatic digestion with PNGase was conducted according to Tarentino and Plummer, Methods in Enzymology, 1994; 230; 44-57.

Glycans were released from the hyperglycosylated protein products and quantified by high-performance anion-exchange chromatography with pulsed amperometric detection (HPAEC-PAD) and normal-phase HPLC with fluorescence detection of 2-AB-labelled N-glycans, along with specific exoglycosidase treatment (FIG. 3*b*). Table 2 summarizes the results of this analysis.

TABLE 2

| | Sample | |
|---|---|---|
| Structure | DENV2_ENV_2xGlyco recombinant Antigen; Lot #20161026 mol (%) | Zika_ENV_recombinant Antigen; Lot #20161213 mol (%) |
| neutral | 16.9 | 17.0 |
| monosialylated | 30.7 | 36.9 |
| disialylated | 26.6 | 32.0 |
| trisialylated | 15.0 | 8.4 |
| tetrasialylated | 9.5 | 5.1 |
| pentasialylated/sulphated | 1.3 | 0.6 |
| sum | 100.0 | 100.0 |

Quantitative HPAEC-PAD analysis of native oligosaccharides was performed on an ICS 5000+ ion chromatography system of the Thermo Fisher Scientific Inc. (Waltham, Mass., USA; GlycoThera device-ID: HPAEC-7) using high resolution CarboPac PA200 columns. Injection of appropriate oligosaccharide reference standards was included in the analytical sequence. N-glycans were detected via electrochemical detection. The data were collected and the chromatograms were acquired by using Chromeleon Chromatography Management System Version 6.8. Native N-glycans were analyzed via HPAEC-PAD revealing mainly neutral, monosialylated, disialylated and trisialylated oligosaccharides in both preparations according to GlycoThera's reference oligosaccharide standards. (FIG. 3*b*, Table 3).

Desialylated N-glycans were analyzed via NP-HPLC after 2-AB labelling revealing predominantly complex-type N-glycans with significant permutational diversity, having proximal a 1,6-linked fucose in both samples (CV94=dengue-2, and CV95=Zika) according to GlycoThera's reference oligosaccharide standards. HPAEC-PAD mapping of native N-glycans released from dengue and Zika preparations CV94 (dengue 2 pCRO22 protein) and CV95 (pCRO28 protein) Zika (as shown in Table 2) revealed the presence of predominantly neutral (16.9% and 17.0%, respectively), monosialylated (30.7% and 36.9%, respectively), disialylated (26.6% and 32.0%, respectively) and trisialylated (15.0% and 8.4%, respectively) oligosaccharides in both samples. Significant amounts of tetrasialylated N-glycans (9.5% and 5.1%, respectively) as well as low proportions of pentasialylated/sulphated oligosaccharides (1.3% and 0.6%, respectively) were found in dengue and Zika samples CV94 and CV95; phosphorylated N-glycan structures such as oligomannosidic Man5-6GlcNAc2 glycan chains with one phosphate residue were not detected in either of the samples analyzed.

TABLE 3

N-glycan mapping of 2-AB labelled desialylated N-glycans, according to standard procedures at GlycoThera, from Dengue and Zika preparations CV94 and CV95 after sialidase treatment using normal-phase HPLC with fluorescence detection revealed the following compositions for the two proteins.

| | | Sample code | |
|---|---|---|---|
| | | CV94 | CV95 |
| | | Sample code | |
| # | N-glycan structure | DENV2_ENV_2xGlyco recombinant Antigen; Lot #20161026 mol (%) | Zika_ENV_recombinant Antigen; Lot #20161213 mol (%) |
| | complex-type N-glycans | 61.4 | 56.6 |
| 1 | diantennary w/o 2 β-Gal w/o 1 GlcNAc with α1,6-Fuc | 0.1 | 0.2 |
| 2 | diantennary w/o 2 β-Gal with α1,6-Fuc | 0.9 | 1.2 |
| 3 | diantennary w/o 1 β-Gal with α1,6-Fuc | 3.1 | 4.4 |
| 4 | diantennary w/o 1 β-Gal w/o α1,6-Fuc | 0.4 | 0.8 |
| 5 | diantennary with α1,6-Fuc | 8.1 | 8.8 |
| 6 | diantennary with α1,6-Fuc with 1x α1,3-Fuc | 5.0 | 6.1 |
| 7 | triantennary w/o 3 β-Gal with α1,6-Fuc | 0.6 | 0.4 |
| 8 | triantennary w/o 2 β-Gal with α1,6-Fuc | 1.6 | 2.9 |
| 9 | triantennary w/o 1 β-Gal with α1,6-Fuc | 3.9 | 7.5 |
| 10 | triantennary with α1,6-Fuc | 8.8 | 7.3 |
| 11 | tetraantennary w/o 4 β-Gal with α1,6-Fuc | 1.0 | 1.9 |
| 12 | tetraantennary w/o 3 β-Gal with α1,6-Fuc | 1.4 | 2.7 |
| 13 | tetraantennary w/o 2 β-Gal with α1,6-Fuc | 3.8 | 6.0 |
| 14 | tetraantennary w/o 1 β-Gal with α1,6-Fuc | 4.9 | 3.3 |
| 15 | tetraantennary with α1,6-Fuc | 15.8 | 2.6 |
| 16 | tetraantennary with one LacNAc repeat with α1,6-Fuc | 2.0 | 0.5 |
| | oligomannosidic N-glycans | 0.1 | 0.8 |
| 17 | Man5GlcNAc2 | 0.1 | 0.8 |
| | hybrid-type N-glycans | n.d.* | n.d.* |
| | not identified | 38.5 | 42.6 |
| X1 | — | 0.1 | 0.1 |
| X2 | — | 0.4 | 1.5 |
| X3 | — | 1.0 | 2.3 |
| X4 | — | 3.9 | 8.8 |
| X5 | — | 4.0 | 8.2 |
| X6 | — | 2.5 | 6.5 |
| X7 | — | 1.1 | 1.1 |
| X8 | — | 2.4 | 3.7 |
| X9 | — | 7.4 | 4.4 |
| X10 | — | 12.9 | 5.0 |
| X11 | — | 2.8 | 1.0 |
| | sum | 100.0 | 100.0 |

*n.d. = not detected.

Site Occupancy Analysis of the Glycans:

Site occupancy was determined by LC-MS measurement of tryptic peptides. The analysis was based on the LC-MS measurement of tryptic or Endo Lys-C generated peptides liberated from proteins de-N-glycosylated enzymatically by PNGase F. Since PNGaseF is a glycoamidase, the asparagine (N) becomes converted to an aspartic acid residue (D). Quantification was done by creation of extracted ion chromatograms (EICs). The EICs were generated using the theoretical m/z values of differently charged target peptides within a mass window of +/−m/z of 0.01. In order to compare the peptide intensity with the specifically modified counterpart generated by de-N-glycosylation, the area of the peak of the EIC was used. The ratio/extent of modification was then calculated as follows: extent of modification=[area under EIC of modified peptide]/([area under EIC of modified peptide]+[area under EIC of unmodified peptide]).

Sequence numbering is by protein rather than the polyprotein sequence numbering convention, with W101 (at the very tip of the fusion loop) as a useful reference point. Sites are numbered according to their appearance in the linear sequence starting at the N-terminus, such that in dengue (pCRO22, GlycoThera sample number CV94) there were two additional sequons comprising sites 2 and 3. The Occupancy of the natural WT N-glycosylation sites was confirmed to be 100% and 99% for site 1 and site 4, respectively. The added N-glycosylation sites 2 and 3 (in the fusion loop) are located on one tryptic peptide (T15) and the occupancy was 38% (both sites) and additional 51% where only one of the two sites were N-glycosylated. In all 89% of the fusion loops had at least one glycan.

In the case of Zika, the occupancy of the N-glycosylation sites was confirmed to be 99.5% and 100% for the added 'site1' (residue 100, fusion loop) and site 2 (residue 154 the glycan naturally present), respectively. Site occupancy of the programmed glycosylation sequons was deduced from PNGase digestion and its effects on the mass of tryptic peptide fragments (whereby the amide $NH_2$ group of the asparagine side chain is lost and converted to a hydroxyl group). (In the following sequences programmed sequons are in bold). In the hyperglycosylated dengue 2 exodomain the relevant tryptic peptide was T15, i.e., the 15th tryptic peptide ($GN_{101}GSGCGLN_{108}GSGGIVTCAMFTCK_{122}$ (SEQ ID NO: 35)—containing the substituted N residues at 101 and 108. In the hyperglycosylated Zika exodomain (with a single introduced glycosylation sequon 'NHT') the relevant peptide was T10 ($N_{100}HTNGCGLFGK_{110}$ (SEQ ID NO: 36)).

These findings of efficient introduction of large and complex glycans into the fusion loop of dengue and Zika exodomain proteins strengthened our expectation that these proteins would neither bind to the fusion loop, nor elicit fusion-loop antibodies, giving confidence that B-cells or antibodies capable of recognising the wild type versions of the fusion loop would not engage with the glycosylated forms of the invention. This scenario is markedly different from mere introduction of mutations into the fusion loop, because by imposing one or more large additional glycan structures into the fusion loop, the resulting variant fusion loop cannot bind antibodies or B-cell receptors or generate fusion loop antibodies reactive with the wild type versions of the fusion loop. This was fully confirmed in later examples. This strategy may also be contrasted to deleting domains I and II from the structure of the protein, as these domains also contribute neutralising epitopes and T-cell epitopes useful for anamnestic immune responses upon encounter with flaviviruses in the wild, while pre-conditioning the immune system in such a way as to avoid the dangerous dominance of the fusion loop in immune responses to natural virus infections or to other vaccines.

TABLE 4 list of m/z values used for creating Extracted-Ion-Chromatograms (EIC) for N-glycosylation-site occupancy for dengue-2

| ID | Amino Acid Range | Amino acid sequence | Theor. mass in Da | m/z values used for EIC $[M + n H]^{n+}$ |
|---|---|---|---|---|
| | | Site 1 | | |
| T10 | [65-73] | $L65TN67TTTESR73$ (SEQ ID NO: 37) | 1022.511 | 1022.511; |
| T10 | [65-73] | $L65TD67TTTESR73$ (SEQ ID NO: 38) | 1023.495 | 1023.495; |
| | | Site 2 + 3 | | |
| T15 | [100-122] | $G100N101GSGCGLN108GSGGIVTCAMFTCK122$ (SEQ ID NO: 39) | 2304.983 | 1152.995; 768.999 |
| T15 1x de-N | [100-122] | $G100D101GSGCGLN108GSGGIVTCAMFTCK122$ (SEQ ID NO: 40) OR $G100N101GSGCGLD108GSGGIVTCAMFTCK122$ (SEQ ID NO: 41) | 2305.967 | 1153.487; 769.327 |
| T15 2x de-N | [100-122] | $G100D101GSGOGLD108GSGGIVTCAMPTCK122$ (SEQ ID NO: 42) | 2306.951 | 1153.979; 769.655 |
| | | Site 4 | | |
| T18 | [129-157] | $V129VQPENLEYTIVITPHSGEEHAVGN153DTGK157$ (SEQ ID NO: 43) | 3133.544 | 1567.276; 1045.186; 784.142; 627.515 |
| T18 de-N | [129-157] | $V129VQPENLEYTIVITPHSGEEHAVGD153DTGK157$ (SEQ ID NO: 44) | 3134.528 | 1567.768; 1045.514; 784.388; 627.712 |

TABLE 5 list of m/z values used for creating Extracted-Ion-Chromatograms (EIC) for N-glycosylation-site occupancy for Zika

| ID | Amino Acid Range | Amino acid sequence | Theor. mass in Da | m/z values used for EIC $[M + n H]^{n+}$ |
|---|---|---|---|---|
| | | Site 1 | | |
| L4 | [94-110] | $R94TLVDR99N100HTNGCGLFGK110$ (SEQ ID NO: 45) | 1944.982 | 1944.98 972.99 648.92; 5; 99; |

TABLE 5-continued list of m/z values used for creating Extracted-Ion-Chromatograms
(EIC) for N-glycosylation-site occupancy for Zika

| ID | Amino Acid Range | Amino acid sequence | Theor. mass in Da | m/z values used for EIC $[M + nH]^{n+}$ |
|---|---|---|---|---|
| L4 | [94-110] | R94TLVDR99D100HTNGCGLFGK110 (SEQ ID NO: 46) | 1945.966 | 1945.96 973.48 649.36; 7; 27; |

Site 2

| T16 | [32-164]] | I$_{139}$MLSVHGSQHSGMIVN$_{154}$DTGHETDENR$_{164}$ (SEQ ID NO: 47) | 2864.305 | 1432.65 955.44 716.86; 0; 32; |
| T16 de-N | [139-164]] | I$_{139}$MLSVHGSQHSGMIVD$_{154}$DTGHETDENR$_{164}$ (SEQ ID NO: 48) | 2865.289 | 1433.14 955.76 717.08; 8; 78; |

TABLE 6 site occupancy (% occupation) for dengue-2
(sites 2 and 3 are in the fusion loop)
Rate of N-glycosylation site occupancy [%]

| | | N-glycosylation site [peptide] | | | |
|---|---|---|---|---|---|
| Sample | GT-code | Site 1 $N_{67}$ [T10] | Site 2 + 3 $N_{101}$; $N_{108}$ [T15] | Site 2 or 3 $N_{101}$ or $N_{108}$ [T15] | Site 4 $N_{153}$ [T15] |
| DENV2_ENV | CV94 | 100 | 38 | 51 | 99 |

(collectively, 89% of molecules have a glycan or two in the fusion loop. N101 replaced W101 of the WT sequence; N108 replaced F108 of the wild type sequence)

TABLE 7 site occupancy (% occupation) for Zika (site 1 is in the fusion loop)
Rate of N-glycosylation site occupancy [%]

| | | N-glycosylation site [peptide] | |
|---|---|---|---|
| Sample | GT-code | Site 1 $N_{100}$ [L4] | Site 2 $N_{154}$ [T16] |
| Zika_ENV | CV95 | 99.5 | 100 |

(99.5% of molecules have a single glycan in the fusion loop; N100 replaced G100 of the WT sequence)

Example 4 (FIG. 4) Immunogenicity of Select Glycoengineered Dengue Proteins 1, 2, 3 and 4 and Zika in Direct ELISA Female Balb-c mice were immunized with PBS (negative control) and various dengue and Zika formulations of the hyperglycosylated exodomain proteins on Alhydrogel, alone (Zika mono) and in combination (Penta-) and as naked DNA (DNA). Alhydrogel formulations of proteins were injected subcutaneously (s.c.) in a total volume of 200 ul and naked DNA (comprising plasmids pCRO21, pCRO22, pCRO23 and pCRO24 of dengue plus pCRO28 representing Zika) was injected intramuscularly (i.m.) in a total volume of 50 ul for pentavalent DNA (representing 5 micrograms of each plasmid immunogen). Pentavalent protein combinations contained 5 ug amounts per dose of each hyperglycosylated exodomain, and monovalent (Zika) contained 10 ug per dose. Mice were dosed three times, once at each of day 0, day 14 and day 21. The legend at the bottom right of FIG. 4 denotes the composition of each immunogen. The title of each panel denotes the antigen used on the solid phase ELISA plate. (Wild type recombinant VLPs were used both as immunogens, Group 4, and as antigens in FIG. 4). Mice were bled retro-orbitally at the intervals indicated and serum was collected for ELISA and PRNT assays.

The Balb-c Mice were immunized with DNA and protein representations of the glycoengineered exodomains and with the corresponding VLPs (i.e. VLPs representing the wild type sequences) from The Native Antigen Company Ltd, Oxford, UK (with no extra glycans, and exposed fusion loops) as positive control. These VLPs (see Table 8, used as both immunogens and also as test antigens in the ELISA tests of FIG. 4) also contain multiple additional epitopes not present in the exodomains, notably epitopes of the pre-membrane protein prM.

TABLE 8

| Group (n = 5) female Balb-c mice | Immunogen | Route of immu- nization | Doe | Injectate volume | Alhydrogel* adjuvant (2% w/v aqueous alhydrogel suspension) (ul) |
|---|---|---|---|---|---|
| 1 | Pentavalent glycoengineered DNA ('Penta-DNA' in figures) | i.m., in 10 mM Tris- HCl pH 7.4 | 50 ug of each plasmid (250 ug total) | 50 ul | None |
| 2 | Pentavalent glycoengineered proteins (Penta-Prot) | s.c. | 5 ug of each protein (25 ug in total) | 200 ul | 50 |

TABLE 8-continued

| Group (n = 5) female Balb-c mice | Immunogen | Route of immunization | Doe | Injectate volume | Alhydrogel* adjuvant (2% w/v aqueous alhydrogel suspension) (ul) |
|---|---|---|---|---|---|
| 3 | Monovalent Zika glycoengineered protein (Zika-mono) | s.c. | 10 ug of Zika protein | 80 ul | 20 |
| 4 | Pentavalent wild type VLP (Penta VLP) | s.c. | 5 ug of each VLP (25 ug in total) | 200 ul | 50 |
| 5 | PBS | s.c. | 0 | 200 ul | none |

There was little antibody response to naked DNA representing the five exodomains—as expected in the absence of delivery assistance from liposomal formulation, gene-gun or electroporation technology. Antibody responses to naked DNA were evident against dengue 1, 2 and 3 native VLPs, and not against Zika and dengue 4 VLPs. However these results served to demonstrate the potential utility of these DNA encoded antigens (all of them) with appropriate delivery systems. The assay is naturally more sensitive to detect immune responses to VLPs, due to the presence of additional epitopes (noted above), such that, as expected, antibody responses to the VLP antigens were uniform and very strong in the VLP-immunised 'Group 4'. However, so too were responses to the novel glycoengineered exodomain proteins of the present invention, which gave strong, balanced immune responses against all five components (dengue serotypes 1,2,3 and 4 plus Zika) with the pentavalent immunogen formulation. Responses were uniformly high to the exodomain immunogens (pentavalent protein and monovalent Zika) and there were no non-responders. Also, the response to Zika in the monovalent-Zika-hyperglycosylated-exodomain-immunized group (10 µg dose) was modestly higher than that in the pentavalent protein group where the same exodomain was used at half the dose. This finding indicates a favorable lack of competition among the serotypes in the generation of type specific immune responses (this is a known problem with live attenuated flavivirus vaccine approaches, such as Dengvaxia, where immune responses to dengue serotype 2 are problematically low).

For direct ELISA (FIG. 4) to measure murine antibodies against dengue and Zika viruses Nunc™ Flat 96-Well Microplates, Thermoscientific, Cat. No. 269620, were coated with VLPs (from The Native Antigen Company (Oxford)) at a concentration of 0.5 µg/ml in bicarbonate-carbonate buffer (pH 9.4-9.6) containing sodium bicarbonate at 4.43 g/l and sodium carbonate at 1.59 g/l, at 100 µl/well for 2 h at room temperature. Plates were aspirated and blocked with 2% neutral BSA (SigmaAldrich A7906) in Dulbecco's phosphate buffered saline (PBS, ThermoFisher-Gibco 14190136) (PBS-BSA). The blocking buffer was used as diluent for the testing of mouse sera diluted at concentrations of 1/100 and 1/10,000 (duplicates at each concentration). Plates were washed with PBS containing 0.05% Tween-20 detergent (Sigma-Aldrich) (PBS-Tween) after each incubation (blocking, diluted serum incubation, conjugate incubation) by filling and emptying the wells five times with PBS-Tween. After serum incubation and washing, a secondary antibody conjugate was applied in PBS-BSA (goat anti-mouse IgG HRP conjugate BioRad 103005) at a dilution of 1:4000. After washing the plate a final time, substrate for horseradish peroxidase (HRP) was added (3,3', 5,5'-tetramethylbenzidine, TMB, Sigma-Aldrich T00440), and stopped with 0.16M sulfuric acid after 20 min incubation at room temperature. Incubations were conducted on a mixer (Grant Bio, PMS-1000 at 500 rpm approx.). Absorbance of the stopped reaction was read at 450 nm.

Antibody responses were calibrated against fusion loop antibody 4G2 (The Native Antigen Company Ltd, Oxford) with dengue VLP representing serotype 2 on the solid phase at 0.5 micrograms per ml coating concentration. Units of antibody measurement "IgG antibody titre" are micrograms per ml 4G2-equivalent in undiluted serum, determined by interpolation of the standard curve using a four-component polynomial regression fit (AssayFit, IVD Tools). At day 42, antibody responses reached $10^4$-$10^5$ for the hyperglycosylated exodomain immunogens (a notional 10 mg per ml-100 mg per ml in neat serum). These concentrations (taken literally) are unattainably high since the IgG concentration of mouse serum is only 2-5 mg per ml, and probably reflect the higher affinity or avidity of the antibodies generated compared to the antibody, 4G2, used for standardization, or may reflect better epitope exposure (4G2's fusion loop epitope being semi-crytpic in the structure of VLPs and virions). Nevertheless the 4G2 calibration serves a useful purpose allowing the assay to be run from time to time, controlling for such variables as batch to batch variation in the conjugate—(an anti-IgG-Fc horseradish peroxidase conjugate made from polyclonal antibodies which vary by batch). This is more reliable than quoting antibody 'titres' based on a threshold absorbance value which are very conjugate-batch and antigen-batch dependent, and may vary further among conjugates sourced by different manufacturers.

A further aspect of these observations is that the antibodies generated are of the IgG class demonstrating class-switching (even at day 14) from IgM, for all of the protein immunogens. This is an essential component of the B-cell memory response, important for the development of vaccines. A further aspect of these findings is that the antibodies generated by exodomain protein immunogens (and to some extent the DNA immunogens) strongly recognize the native form of the VLP antigens, which also lack His tags, ruling out the possibility of false positives due to anti-His-tag responses. This proves that both the dengue and Zika exodomain materials represent native epitopes of the exodomain proteins that are immunogenic in generating antiviral (VLP) antibodies. These results suggest that other nucleic acid encoded forms of the hyperglycosylated exodomain species, e.g., liposomal RNA or lipoplex RNA, would also generate desirable antibody responses against virions (VLPs) and viruses.

There was specificity in the immune response to the Zika monovalent hyperglycosylated exodomain, which generated higher antibody titres against the homologous Zika VLP than to other VLPs, despite the known cross-reactivity of these various viruses with antibodies. This is a favourable result since type-specific anti-Zika antibodies are known to have better neutralizing activity generally than dengue-cross-reactive ones. Also, as seen in the antibody-responses to the Zika-monovalent hyperglycosylated exodomain at the later time points (after two or three doses), there was a degree of cross-reactivity against dengue strains that developed over time, raising the potential for generation of beneficial cross-reactive neutralizing responses, excluding the fusion loop epitope (which was not recognized by antibodies generated by hyperglycosylated exodomain species as demonstrated in the data that follows in later examples).

Example 5 (FIG. 5) Avoidance of Recognition of the Glycoengineered Proteins by Fusion Loop Antibodies, and Retention of Neutralizing Epitopes An ELISA test (of FIG. 5) was devised employing oriented capture of His-6-tagged exodomain proteins on the solid phase (the VLPs of FIG. 4 do not have His-tags).

Unless otherwise specified, conditions were the same as for the ELISA test of Example 4 and FIG. 4. 8-well strip ELISA plates (Dynex) were coated with rabbit monoclonal anti-His-6 tag (Anti-6× His Tag® antibody [HIS.H8] (ab18184) Abcam) for 1 h at room temperature and then overnight at a concentration of 1 µg/ml in bicarbonate-carbonate coating buffer. Plates were washed and then exposed to Starting Block (ThermoFisher 37538) 30 min at room temperature, and then to the various exodomain proteins, all having a C-terminal hexahistidine tag, at a concentration of 0.5 µg/ml, for 2 h at 37 degrees then at 4 degrees overnight. Antibodies were added to appropriate wells in 0.4% BSA in PBS-Tween and incubated for 2 h at 37 degrees. Next a secondary antibody conjugate (rabbit-anti-mouse-HRP IgG H&L, Abcam ab97046), for mouse antibodies, was applied in 0.4% BSA in PBS-Tween, at a dilution of 1/10,000. For human serum, the dilution factor was 1/1000 in PBS-Tween 0.4% BSA followed by goat anti-human IgG Fc (HRP) preadsorbed (Abcam ab98624) at 1/20,000. Secondary antibody HRP conjugates were incubated for 2 h at 37 degrees. The plate was washed between exposure to successive reagents. Finally TMB substrate was added and stopped after 10 min at room temperature.

Antigens were as follows: wild type dengue exodomains representing dengue serotypes 2 and 4 were from The Native Antigen Company (DENV2-ENV, DENV4-ENV); 'HX' designated exodomains (hyperglycosylated exodomains) were the selected set of Excivion exodomains of the present disclosure (pCRO21-24 for dengue, pCRO28 for Zika). Prospec Zika was a non-glycosylated bacterial exodomain from Prospec of Israel (zkv-007-a), and Aalto Zika was an insect (Sf9 cell) derived Zika exodomain (AZ6312—Lot3909). Mouse monoclonal antibodies against Zika virus exodomain were as follows: Aalto Bioreagents AZ1176-0302156-Lot3889; Z48 and Z67 were neutralizing antibodies described by Zhao et al, Cell 2016 (The Native Antigen Company ZV67 MAB12125 and ZV48 MAB12124). Antibody 4G2 is an anti-dengue-serotype-2 antibody recognizing the fusion loop (The Native Antigen Company AbFLA-VENV-4G2).

FIG. 5a demonstrates the sensitive detection of wild type exodomains of dengue 2 and 4 by antibody 4G2, giving a signal significantly above background even at very low concentrations (250 pg/ml). In contrast, the hyperglycosylated exodomains gave no detectable signal at any of the concentrations tested (5a). This side-by-side comparison of the wild-type and fusion-loop-glycosylated (HX) exodomains demonstrates that the latter fail to react with this classical fusion loop antibody (which is highly dependent on Leucine 107, Stiasny K et al., J Virol 2006 80:19 9557-68, intolerant of D, T or F at that position), even despite the presence of 11% of non-glycosylated (albeit mutated) fusion loop in the dengue-2 HX exodomain used (refer to example 3 for glycosylation site occupancy data). This demonstrates that the mutations employed, even without the glycans, are sufficient to prevent the binding of this particular fusion loop antibody (4G2). However, given the clonal diversity of human antibodies, ultimately it will be preferable to employ the glycosylated forms as an additional layer of surety that fusion loop antibodies capable of recognizing wild type fusion loops of flaviviruses will not be generated in man with these novel immunogens when used as vaccines.

The data of FIG. 5b&c also demonstrate that, in the case of Zika, the HX version of the exodomain reacts with all three Zika monoclonal antibodies, including the two neutralizing epitopes ZV48 (Z48) and ZV67 (Z67). This demonstrates that the Zika HX exodomain has retained these neutralizing epitopes, plus the Aaalto antibody epitope, despite the drastic changes wrought to the structure of the fusion loop by glycan insertion. Moreover, this Zika HX exodomain fails to react with 4G2, as do the four dengue HX exodomains, confirming that this epitope has been effectively cloaked in all five HX proteins.

The data of FIG. 5b&c, with respect to the Zika human convalescent serum tested are also diagnostically informative. This serum was a gift from Mark Page of NIBSC selected for its high PRNT activity against Zika and its high levels of Zika NS1 antibody. The data of FIG. 5b&c demonstrate that this Zika convalescent serum strongly recognizes, indeed prefers the dengue-2 wt exodomain over other antigens in the test. This observation demonstrates the diagnostic utility of the HX series of proteins, and indicates that this patient had previously also been exposed to another flavivirus other than Zika. In fact it suggests that that other flavivirus was not dengue because the Zika convalescent serum (unlike the dengue convalescent serum) fails to react with the hyperglycosylated exodomain forms of dengue. The fusion loop antibodies in the Zika convalescent serum must therefore have originated from exposure to a third flavivirus, such as yellow fever (by vaccination or infection) or West Nile virus, both of which are prevalent in Trinidad where this serum was collected.

A further aspect of the data of FIG. 5b&c are that the Zika HX antigen has the capacity to selectively inform the presence of neutralizing antibodies, since the 4G2 fusion loop epitope has been effectively cloaked, while neutralizing epitopes noted above, have been retained. The HX Zika exodomain protein and likely therefore the dengue HX exodomain proteins will therefore have the capacity to inform the development and deployment of Zika and dengue vaccines. In the case of the latter, the HX antigens of the test will be useful in identifying persons that are naïve to dengue and who might be spared vaccination with the currently licensed DengVaxia® anti-dengue vaccine, in order to reduce the risk of predisposition to subsequent dengue haemorrhagic fever (whereby the vaccine acts as a silent primary dengue infection). Such test may extend the utility of DengVaxia to younger persons (currently it is only licensed to children greater than 9 years of age), or to naïve persons in non-endemic territories such as Europe and the USA (e.g. for use in traveller populations in whom DengVaxia vaccination is not currently advocated).

Example 6 (FIG. 6) Avoidance of Generation of Fusion-Loop Antibodies by the Glycoengineered Proteins An ELISA test was established to measure the binding of polyclonal antibodies against the fusion loop (represented in this example by dengue serotype-3 VLP on solid phase ELISA plates).

A competition ELISA was set up using biotinylated 4G2 (Integrated Biotherapeutics) which was detected using streptavidin-horseradish peroxidase conjugate. Dengue serotype 3 VLP (The Native Antigen Company) which reacts with 4G2 slightly better than the immunizing serotype dengue-2 VLP was used as antigen coated at 0.5 ug per ml on the solid phase. Pooled sera (from the groups of FIG. 4) or unlabeled 4G2 (as standard) were titrated at various dilutions (from 1/10 as the top concentration of the serum pools) to determine their capacity to compete with biotinylated 4G2 for binding to the fusion loop. Similar standard curves were generated (not shown) using Zika VLP and dengue-2 VLP wild type recombinant materials as antigen, underscoring the generality of this phenomenon (cross-reactivity of fusion loop antibodies) across the flaviviruses of interest.

In this assay (FIG. 6) the ability of unlabeled 4G2 to compete for binding to solid phase antigen was demonstrated using biotinylated 4G2 and streptavidin-HRP conjugate (Kirkegaard and Perry KPL KPL 14-30-00 at 1/3000). Unless otherwise specified, conditions were as for Example 4. First, a sample of 4G2 was biotinylated according to manufacturer's instructions using the BioRad EZ-link NHS-PEG4 biotinyation kit (21455) using a molar ratio of reactants of 30:1. Unlabelled antibody and biotinylated antibody were allowed to compete in an overnight room temperature incubation for binding to solid phase antigen. Antigen-coated plates were exposed in parallel to dilutions of standard antibody (four or five-fold serial dilutions of 4G2, unlabeled). Biotinylated antibody was used at a concentration of 100 ng/ml.

FIG. 6 demonstrates that antibodies raised against pentavalent VLPs on Alhydrogel, containing VLPs of all four dengue serotypes plus Zika, generate abundant fusion loop antibodies. It can be calculated from these data (assuming similar affinities of 4G2 and raised antibodies) that the VLP-immunised sera contain approximately 100 micrograms per ml fusion loop antibody, which is the maximum amount generally for viral antibodies in a polyclonal antiserum. In contrast, none of the other groups generate significant amounts of fusion loop antibodies whose binding is mutually exclusive with 4G2. In particularly the pentavalent (HX) exodomain proteins of the present disclosure do not generate fusion loop antibodies as assessed in this test, and neither does the monovalent Zika (HX) protein, despite generating very substantial antibody responses to the VLP antigens used in the competition ELISA test. In the case of Zika, inhibition was detectable only at the highest concentration tested, indicating a >1000 fold advantage in avoidance of fusion loop antibodies compared to VLP immunogens, if this single point at 1/10 serum dilution is (for the sake of argument) deemed to be significant.

The data of FIG. 6 demonstrate that a dengue vaccine (or a Zika vaccine) of the invention would not prime for antibody responses to the conserved fusion loop. This is in contrast with natural primary dengue infections that prime for subsequent haemorrhagic fever upon encounter with a second serotype of dengue. Such antibody responses to natural primary dengue infections are poorly neutralizing or non-neutralizing at physiological concentrations of antibody and are particularly implicated in the causation of antibody-dependent enhancement of dengue infection and disease by allowing antibody-complexed virions to enter and infect myeloid cells via Fc-receptors, while failing to prevent them infecting other host cells.

Example 7 (FIG. 7) Generation of Neutralising Antibodies by the Glycoengineered Dengue and Zika Proteins Serum pools from Example 4 were tested for their ability to neutralize dengue serotype 2 and Zika viruses using Vero cells in plaque reduction neutralization tests (PRNT).

In the case of dengue, the dengue serotype 2 strain used to infect the Vero cells (D2Y98P) was a different serotype-2 strain (non-homologous) from the sequence of the immunizing dengue 2 strain of the VLPs and exodomains. In the groups expected (from Example 4) to generate dengue neutralizing antibodies (namely pentavalent protein and pentavalent VLPs, Groups 2 & 4) there was potent neutralization of the 'off target' dengue test virus. In the case of Zika there was significant (albeit partial) neutralization as expected from the results of Example 4, in groups shown to contain antibodies that recognized native Zika VLPs (namely pentavalent protein and pentavalent VLPs, Groups 2, 3 & 4). Due to limitations on sample volume, the maximum concentration of serum that was tested was 1/50, such that in interpreting these results this factor needs to be taken into consideration (i.e. that there would be higher neutralizing capability in the blood of the immunized animals).

TABLE 9

Immunogenicity Study Design

| Group (n = 5) | Vaccine* | Vaccine Schedule | Dosage | Bleeds | Readout |
|---|---|---|---|---|---|
| 1 | Pentavalent glycoengineered DNA | On days 0, 14, & 21 via IM route | 250 µg total DNA (50 µg of each) | Test bleed for serum on Days 14 & 21. Terminal bleed on Day 42. | Measurement of antibodies against ZIKV & DENV 1-4 via ELISA |
| 2 | Pentavalent glycoengineered proteins on Alhydrogel | | 25 µg total protein (5 µg each) | | |
| 3 | Monovalent Zika glycoengineered | | 10 µg protein | | |

TABLE 9-continued

Immunogenicity Study Design

| Group (n = 5) | Vaccine* | Vaccine Schedule | Dosage | Bleeds | Readout |
|---|---|---|---|---|---|
| 4 | protein on Alhydrogel Pentavalent wild type VLP on Alhydrogel | | 25 µg total VLPs (5 µg each) | | |
| 5 | PBS | | — | | |

PRNT Assay was performed as follows. Five mouse serum samples were pooled by taking an equal volume of individual samples in each group (sample description in next slide) and were then tested against ZIKV and DENV, respectively. Twelve two-fold serial dilutions of each serum sample in duplicates starting at 1:50 were prepared for the two-hour inoculation with virus. The serum-virus mix was then added to Vero cells seeded in 24-well culture plates and incubated at 37° C. in a humidified 5% $CO_2$ atmosphere. The Vero cells were fixed on 3 days post incubation (dpi) for ZIKV PRNT and 4 dpi for DENV PRNT. Viral plaque was determined by crystal violet staining.

Potent inhibition of infection by dengue was observed in the group immunized with hyperglycosylated exodomain proteins of the present disclosure (Penta-prot). Zika immunized animals generated antibodies that did not prevent dengue infection of Vero cells, illustrating the type-specific nature of antibodies generated by these novel immunogens. These Zika antibodies (from the Zika monovalent group and from the pentavalent proteins group) were significantly protective of infection of Vero cells by Zika virus. As expected, PBS-sham-immunised animals did not give rise to protective antibodies, nor did pentavalent DNA administered intramuscularly. This latter result may have been due to the low concentrations of antibodies generated by naked DNA, as expected from intramuscular injection (as distinct from gene-gun or electroporation strategies, or strategies incorporating encoded proteins as molecular adjuvants).

The results of Example 6 (generation of neutralizing antibodies) combined with those of Example 5 (lack of recognition by or generation of fusion loop antibodies) by the hyperglycosylated Exodomain proteins of the invention strongly suggest that these proteins can form the basis of a protective vaccine for dengue or Zika viruses (or, in combination, for both viruses) without the generation of fusion loop antibodies, which are particularly implicated in antibody-dependent enhancement of infection.

Example 8 (FIG. 8) Reaction of Convalescent Dengue or Zika Serum with Immobilized Zika and Dengue Wild-Type (WT) and Hyperglycosylated (HX) Exodomain Proteins The ELISA reactivity of antibodies in a dengue convalescent serum with immobilized Zika and dengue wild-type (WT) and hyperglycosylated (HX) exodomain proteins oriented on the solid phase by capture with a rabbit anti-His-tag monoclonal antibody (FIG. 8, upper panel), in the presence (grey bars, right of each pair) and absence (black bars, left of each pair) of competing mouse monoconal flavivirus fusion loop antibody 4G2 (an anti-dengue-serotype-2 monoclonal antibody) at a concentration of 10 µg/ml during serum incubation. Human sera were tested at a constant concentration of 1/1000.

The ELISA reactivity of antibodies in a Zika convalescent serum with immobilized Zika and Dengue wild-type (WT) and hyperglycosylated (HX) exodomain proteins (FIG. 8, lower panel) in the presence (grey bars) and absence (black bars) of competing mouse monoclonal flavivirus fusion loop antibody 4G2. Conditions and labelling are the same as for the upper panel. Error bars are standard error.

The results show that:

1) the HX Zika antigen of the invention is not susceptible to the off-target recognition of WT Zika exodomain by the convalescent dengue serum.

2) The off-target recognition of WT Zika exodomain (Aalto) by dengue serum is a fusion-loop directed phenomenon because it is abolished by 4G2 (anti-fusion loop monoclonal antibody) in solution phase at a concentration that causes 80% inhibition against VLPs (10 micrograms per ml). (The antigen on the solid phase in this instance is exodomain rather than VLP).

3) The 'Zika' convalescent serum does not recognize any of three Zika exodomains, but it strongly recognizes WT dengue 2 and WT dengue 4. In the Example 6 the HX Zika antigen of the invention and Aalto's Zika exodomains exhibit reaction with conformation-dependent anti-Zika neutralising antibodies). This demonstrates that this particular Zika serum (positive for Zika plaque neutralisation and Zika NS1 antibodies) is from a subject also exposed to another flavivirus. Because the Zika convalescent serum (unlike the dengue convalescent serum) does not recognize the fusion-loop-cloaked exodomains, it can be concluded that this other flavivirus is not dengue.

4) The off-target recognition of WT dengue-2 and dengue-4 exodomains by the human Zika convalescent serum is not seen with the HX-cloaked dengue exodomains of the invention. This suggests that it is fusion loop directed and would show false positive in other flavivirus diagnostic tests that do not use glycan-cloaked proteins in accordance with the invention.

5) The off-target recognition of WT dengue-2 and dengue-4 exodomains by the human Zika convalescent serum is blocked completely by 4G2 showing that it is a fusion loop directed phenomenon.

6) The dengue convalescent serum recognizes WT 2 & 4 indiscriminately, but clearly prefers the d2 exodomain out of the set of 4. This demonstrates that the fusion loop antigens of the invention have superior selectivity (compared to their wild type equivalent forms) to discriminate between dengue serotypes, due to the glycan cloaking of the fusion loop.

Examples of Diagnostic Use

Various formats of lateral flow test for the detection of antibodies are possible. A widely-used design for the detection of antibodies against viral antigens is to place a line (or spot) of antigen 'directly' on a strip of nitrocellulose, and then allow blood/serum/plasma or oral fluid to seep up the strip by capillary action, hydrating a dried nanoparticulate gold reagent, wherein the particles are coated with an antibody (e.g. anti-IgG, anti-IgM), typically followed by a wash buffer. As the reagents proceed along the nitrocellulose strip, specific antibodies are arrested by the antigen, and some of the gold particles are likewise arrested by binding to specific antibodies immobilised on the antigen, excess particles proceeding beyond the observation window—resulting in a brown or pink line in the observation window of the test cassette indicating the presence of specific antibody. In some embodiments of this format, a two-port system is used, one port for the sample application (proximal to the antigen line), and a second port, more distal, for the application of the diluent. Additionally, a control line (or spot) may be used to verify the fluidic performance the test and the functionality of the gold conjugate. This may be formed of a line of purified antibody or of human serum containing the antibody type appropriate to the anti-Ig conjugated nanoparticulate gold reagent. In preliminary studies with this format, we were successful in demonstrating the diagnostic utility of wild type, and the superior specificity of HX versions of the four dengue envelope proteins and Zika. In addition, aware of the phenomenon of surface denaturation of proteins (Sen, Yamaguchi, & Tahara, 2008) which is more common in our experience with nitrocellulose (viz. lateral flow) as a solid phase compared to polystyrene (viz. ELISA) we were influenced in the current lateral flow design by our earlier ELISA studies (see above), to employ indirect immobilisation of the HX envelope proteins. Indirect immobilisation had proven more sensitive in ELISA studies than direct immobilisation of the antigen on the solid phase. To this end we explored the use of anti-His-tag antibodies recognizing the C-terminal hexahistidine tag on the HX proteins described herein as an indirect means to attach the antigens to the solid phase (Example 9).

Example 9: Alternative Formats for Lateral Flow Detection of Antiviral Antibodies Test Composition (Common to Both Formats A and B of this Example 9)

Absorbent pad—Whatman CF5 (22 mm)

Nitrocellulose—MDI 15μ SS12 (25 mm)

Sample pad—Ahlstrom 8964 (20 mm)—Sample pad can be treated with a red blood cell arresting agent. This can be anti-glycophorin A (AGA) at a suitable concentration (suitable concentrations are known in the art). Pad is soaked with anti-glycophorin A and dried for 24 hrs at 25° C. in low humidity.

Conjugate pad—Ahlstrom 8815 (Format (A) 20 mm, Format (B) 45 mm)—Conjugate pad is soaked with 0.1M Tris-HCl pH8.0 containing 0.25% Tween 20 and 0.5% bovine serum albumin (BSA) and dried overnight at 37° C. followed by 24 hrs at 25° C. in low humidity Cassette—Kanani Biologicals, India Gold conjugate (detector) 40 nm colloidal gold (BBI Solutions of Cardiff, Wales, UK) conjugated to anti-human-IgG at 100 units per test on the conjugate pad, dried for 24 hrs at 25° C. in low humidity. Advantageously the conjugate is made from affinity-purified IgG (e.g., from goat or rabbit) or a suitable monoclonal antibody such as a pan-subclass-reactive IgG antibody or a monoclonal anti-IgM antibody. Such antibodies are known in the art and are available from Sigma, AbCAM or Merck-Millipore. Gold conjugates (where applicable) were applied in 2 mM tetrasodium borate, 10% sucrose, 0.95% sodium azide pH 9.0.

Running Buffer was prepared from Oxoid PBS pH 7.3 tablets using deionised water (NaCl 0.137M, KCl 0.003M, disodium hydrogen phosphate 0.008M, potassium dihydrogen phosphate 0.0015M), containing additionally 0.5% Tween-20 and (where indicated) 0.5% PEG 20K (average Mn 20,000) CAS Number 25322-68-3.

Antigens

The antigens used were as follows: (in 'direct' formats, antigen was applied directly to the nitrocellulose strip in Oxoid-PBS without additives and dried as above; in 'indirect' formats, where antigen was applied to the sample application pad, antigens were applied in Oxoid-PBS without additives and dried as above).

Dengue HX antigen D1: Hyperglycosylated exodomain D1 (from pCRO21) (SEQ ID NO: 24)

Dengue HX antigen D2: Hyperglycosylated exodomain D2 (from pCRO22) (SEQ ID NO: 25)

Dengue HX antigen D3: Hyperglycosylated exodomain D3 (from pCRO23) (SEQ ID NO: 26)

Dengue HX antigen D4 Hyperglycosylated exodomain D4 (from pCRO24) (SEQ ID NO: 27)

Zika HX antigen: Hyperglycosylated exodomain Zika (from pCRO28) (SEQ ID NO: 28)

The alignment of the E-protein fusion loop amino acids 98-110 of a group of wild-type sequences of flaviviruses and recombinant analogue sequences of the invention is shown in Table 1, for each of the Dengue HX antigens D1-D4 the hyperglycosylated exodomain fusion loop sequence was DRGNGSGCGLNGS (SEQ ID NO: 2) for the Zika HX antigen the hyperglycosylated exodomain fusion loop sequence was RNHTNGCGLFGK (SEQ ID NO: 5) Dengue HX antigens D1, D2, D3 and D4 at 100 ng each antigen per test on the sample pad, dried for 24 hrs at 25° C. in low humidity.

Zika HX antigen at 50 ng per test on the sample pad, dried for 24 hrs at 25° C. in low humidity.

Nitrocellulose

Test Line—Mouse mab anti-6×His at 0.3 mg/mL (RT0266 Bioxcell)

Control Line—Human IgG at 0.75 mg/mL (Sigma-Aldrich-Merck 18640—IgG from human serum)

A: Single Port Format for Lateral Flow Detection of Antiviral Antibodies

As shown in FIG. 9A the lateral flow test strip comprises an adhesive backing card onto which the various components are attached. In this format the sample (e.g. a serum sample or a blood sample) is applied to the sample pad port where it dissolves the antigen(s) which are previously dried into the sample pad (as a line orthogonal to the strip or as a spot) from a solution in a suitable diluent such as Dulbecco's phosphate buffered saline pH 7.4 (PBS). Running buffer is then applied to the sample pad port to chase the resulting solution of reactants through the conjugate pad (containing the detector molecules, e.g. colloidal-gold-labelled anti-IgG, likewise dried) and onto the nitrocellulose. Thus the sample, antigens and detector molecules flow onto the nitrocellulose in unison and have time to react in solution phase (which is more conducive to antigen-antibody reaction than solid phase reactions due to the diffusibility of reactants). The reactants (antigen-specific antibodies, antigens, detector molecules/conjugate) then flow onto the nitrocellulose where the meet with a stripe of anti-His-tag monoclonal antibody which arrests passing antigen molecules and associated antibodies from the serum, plus detector molecules such as gold-anti-IgG conjugate. This stripe of anti-His-tag monoclonal antibody comprises the 'test line' indicative of the presence of antigen-specific antibodies. There follows a control line composed of human IgG (or human IgM) as appropriate to the antibody class under test. The purpose of the control line is to arrest excess conjugate demonstrating the satisfactory fluidic performance of the test and the functionality of the gold anti-Ig conjugate. The main advantage of the single port format is that it is easier to manufacture and execute. (Note: single port format can be run in a two-port cassette, below, if needed).

B: Two-Port Format for the Lateral-Flow Detection of Antiviral Antibodies

As shown in FIG. 9B, in this format the sample pad and conjugate pad are physically separate, as are their fluidic paths to the nitrocellulose strip, effected by a strip of double-sided adhesive tape. The sample is applied to the sample pad port where it interacts with the antigens. Running buffer is then applied to the sample pad port to chase the sample onto the nitrocellulose. Once the sample solvent front has reached the distal end of the observation window, another sample of buffer is added to the test, this time to the conjugate pad port—in order to release the detector molecules which flow onto the nitrocellulose where they can bind the previously run sample/antigen complex located at the test line. In so doing, the solvated conjugate avoids depletion by non-specific binding to human antibodies that have bound non-specifically in the sample pad. This format also has the advantage that a beneficial separation of antigen-bound and excess free human antiviral antibody is achieved, before conjugate arrives, minimising futile pre-absorption of the conjugate by binding in solution phase to non-antigen-specific antibodies, to the benefit of sensitivity. A disadvantage of this format is that it is more complex to manufacture.

Example 10: Indirect Immobilisation of Mobile Dengue HX Exodomain Antigens Via Anti-His-Tag Monoclonal Antibody Allows Detection of Neutralising Antibodies in Lateral Flow A: Using the test format of Example 9A (two ports used) 15 ul of normal human plasma (spiked with a two-fold serial dilution of human dengue monoclonal neutralising antibodies DV78 and DV18 (Absolute Antibody Ltd., Oxford UK) in equal amounts, from 1 to 0.0078 ug) was added to the square sample pad port, and allowed to incubate at room temperature for 3 minutes. Next, 45 ul of running buffer was added to the sample port, and the device was run for a further 17 minutes. 90 ul of running buffer was then added to the round port to release the gold anti-human-IgG conjugate. The test was read after a total of run time of 40 minutes. This demonstration illustrates a sensitive capability of this test format to detect neutralising anti-dengue antibodies (DV78 and DV18 recognise epitopes in the DI and DII of dengue virus), 7.8 ng of specific antibody was detectable. In this particular example HX versions of dengue-2 and dengue-4 exodomains were used.

B: Results obtained in this format with control serum NM (not exposed to flavivirus infection or vaccination) and a dengue positive serum '2965' are shown in FIG. 10B, demonstrating positivity in the dengue reference serum and negativity in the control. All tests used 500 ng of mouse anti-His-tag monoclonal antibody. The antigen spot on the sample pad was 1.5 ug. 50 units of anti-human IgG gold conjugate were used per test. Note: there was no prozone effect ('prozone' defined as negative reaction at higher concentrations of specific antiviral antibody) which is a common problem in lateral flow tests. This suggests that false negatives are not likely to be a problem for this format.

(In the examples A and B above, both antigen and anti-His-tag antibody were spotted manually).

Example 10 demonstrates the utility of the HX dengue exodomains 2 and 4, in serodiagnosis of dengue in lateral flow format. It also demonstrates the advantage and utility of capturing the antigen (initially mobile) using an anti-tag antibody. A monoclonal anti-His-tag antibody was used, although there are other tag-antibody pairs that could be used (such as FLAGtag and StrepTag-II). (Such additional pairs can be used to multiplex the assay, whereby a second line of anti-tag would recognize a second tag on a second antigen involved in the test, a third a third etc.). By using a tag antibody for capture of the mobile antigen (and antigen-antibody-complexes and antigen-antibody-colloidal gold conjugate materials), a prozone effect is avoided. This contrasts to an alternative scenario where one might have used an antigen-specific (e.g. murine) monoclonal antibody for the purpose of arrest at the test line or spot. In this latter alternative scenario, the test is defeated by the presence (if present) of an antibody in the test sample against the same or overlapping epitope as is recognized by the antigen-specific capture antibody. (Such adverse competition for antigen binding can be mitigated by the use of multiple monoclonal or a polyclonal affinity purified antigen specific antibody, but cannot be eliminated by this means). In the Example 10 and elsewhere in other examples we have detected IgG antibodies by virtue of a colloidal gold conjugate with surface bound anti-human-IgG. However, it should be apparent that other antibody classes and subclasses can be detected in this way (e.g. IgM, IgA and subclasses of IgG) by use of appropriately specific antibodies on the colloidal gold reagent, and likewise by use of corresponding pure antibodies comprising the control line (i.e. IgM for an IgM test, IgA for an IgA test, IgG for an IgG subclass-1 for an IgG subclass-1 test etc.). For tests designed to measure IgG, when using a monoclonal or affinity-purified anti-IgG colloidal gold conjugate, it is important to choose one that has a balanced reactivity across the IgG subclasses, in order to give a representative signal in the lateral flow tests. Such antibodies are known in the art, and are commercially available.

The antigens used in serodiagnostic tests are sometimes more expensive than antibodies when antibodies are used in such tests. This is particularly important in lateral flow tests targeting mass markets. (This is a feature of improvements in recent years in the facile production of monoclonal antibodies in particular, e.g. by transient expression in HEK cells, where the antibodies can be produced at high yield, e.g. several grams per litre of culture). Therefore, an additional advantage of exploiting anti-tag antibodies for indirect antigen-capture in lateral flow tests is that the test is made more economic with respect to antigen costs in manufacturing. The economic advantage of this approach is further enhanced by the stronger recognition of indirectly-immobilised antigen (via anti-tag antibody), compared to that deposited directly on the lateral flow strip (e.g. a nitrocellulose strip).

A further feature of Example 10 is demonstration that the HX class of flavivirus exodomain antigens (having glycans in the fusion loop) have intact neutralising epitopes throughout the molecule (except, as noted above, for the fusion loop—in which the epitope is glycan-cloaked). Thus as described above it was demonstrated for Zika HX exodomain that immobilisation via its His-tag allowed functional display of two neutralising epitopes, namely those recognised by murine monoclonal antibodies ZV48 and ZV67 (human antibodies from Absolute Antibody Ltd., Oxford).

Example 10 demonstrates that HX versions of dengue-2 and dengue-4 exodomains functionally display epitopes recognized by DV78 and DV18, which are located in domains [I and II]. These data and arguments strongly support the use of the HX antigens in serodiagnostic tests, in particular point-of-care serodiagnostic tests, for the detection and measurement of neutralising antibodies. Antibodies against the fusion loop, which dominate the antibody response, are poorly neutralising and rapidly decline to concentrations that enhance infection. The point-of-care diagnostics described here for dengue and Zika can therefore be used to measure vaccine performance, e.g. to determine whether an additional dose may be needed, or how well a vaccine is performing in a subject already exposed to another flavivirus by reason of infection or vaccination (e.g. with yellow fever or dengue vaccines). They may also be combined (dengue and Zika, by using different tag/anti-tag pairs, e.g. His-tagged dengue antigen being captured by an anti-His-tag line, and FLAG-tagged Zika antigen being captured by an anti-FLAG antibody).

Example 11: Direct Spotting/Immobilisation of Antigen on Nitrocellulose (as Distinct from Capture of Mobile Phase Antigen Via Anti-Tag)

FIG. 11 depicts a 'stick-based' (no cassette) prototype lateral flow experiment in which antigens were immobilised directly by spotting onto the nitrocellulose strip (unlike the other Examples in this patent application). Sticks were compiled with sample application pad and absorbent pad at the bottom and top respectively (direction of flow is bottom to top). In this format, wild type dengue-1 and dengue-2 exodomain antigens (from The Native Antigen Company) were used. These antigens generate a strong fusion-loop dominated signal that has been subtracted (by glycan cloaking) in other Examples in this patent application. Sticks 1&2 were spotted with normal serum 'NM' (2 ul of a 1/10 dilution in PBS for '1' and 2 ul of a 1/100 dilution for '2'). These serum-spotted sticks were used to verify the satisfactory performance of the anti-IgG-colloidal-gold conjugate, and did not contain exodomain antigens. 50 units of gold conjugate were used in all sticks. Remaining sticks were spotted directly with a mixture of 0.75 ug each of wild type dengue-2 and dengue-4 exodomains in a total volume of 2 ul (a total amount of 1.5 micrograms of antigen). Unlike the Example 9B, in this (prototype) experiment the anti-IgG-colloidal-gold was applied in liquid form, followed by 40 ul of running buffer to clear unbound gold conjugate from the nitrocellulose strip (except in 1&2 where 100 ul was used). In sticks 3-6, the conjugate was run immediately after application of neat serum samples, whereas in sticks 7&8, the serum sample and conjugate were run with an intervening running-buffer wash, with the intent that excess free IgG in the sample would be washed beyond the antigen spot by the time the conjugate reached it, increasing the specific signal of the test. 10 ul or 50 ul volumes of serum were used as indicated; '−'=NM negative control serum; '+'=2623 dengue positive serum. In the case of sticks 7&8 the conjugate was run only after both sample and running-buffer wash (wash volumes of 100 ul or 60 ul respectively) had completed their passage up the nitrocellulose strip as evident by the completion of transit of the solvent front.

Results: 1&2 verify the performance of the conjugate in expected rank of intensity; 3 showed a very faint signal (not visible in the photograph), likewise 4; 5&6, controls for non-specific binding of reactants, were negative; 7&8 (negative and positive test sera) gave the desired result, i.e. negative in 7, positive in 8. These findings demonstrate (in the case of directly applied immobile antigen) the value of an intervening wash, because signal was weak (not evident on photograph) when no wash was used. Moreover, relatively large amounts of antigen were required, even of the strongly reactive fusion-loop-intact forms, in this test configuration. (Where reagents or solutions are not defined in this Example, they are the same as in Example 9).

Example 11 demonstrates the utility of direct immobilisation by spotting of exodomain antigens on nitrocellulose, as distinct from having them in the mobile phase of the test (which is the format in all other Examples in this application). Direct spotting/immobilisation of antigen on nitrocellulose (as distinct from capture of mobile phase antigen via anti-tag) was effective, but less sensitive than indirect immobilisation of mobile antigen via anti-tag antibody.

In Example 11 wild type antigens are used (dengue-2 and dengue-4) but it is clear that HX versions of flavivirus antigens could be used in this format. In the format of Example 11 it would be possible to improve sensitivity by use of luminescent detection, as described (Laing, 1986), or using fluorophore-labelled anti-human-Ig, with a fluorophore such as a quantum dot or a lanthanide which have high quantum efficiency and low photobleaching, as well as a favourable Stokes shift (particularly in the case of lanthanides such as Europium chelates). Europium chelates are also amenable to time resolved fluorescence which is more sensitive because the fluorescence measurement is made once the light source is turned off, and does not contribute noise to the signal. Clearly these sensitive luminescent and fluorescent methods could be applied to other Examples given in this patent application, if desirable or necessary.

Example 12: Avoidance of Off-Target Recognition of Dengue Envelope Antigens by Zika Macaque Convalescent Serum IgG Antibodies by Using Dengue-HX Antigens As shown in FIG. 12, lateral flow tests were configured according to the format of Example 9B (two separate ports were used for sample and conjugate), using either wild type (WT) or fusion-loop glycosylated 'HX' dengue-2 and dengue-4 antigens. Lower line is the test line, upper line is control line to verify conjugate performance. Serum samples were tested against these two types of dengue antigen (wild type and HX) as follows: 1, G16 macaque pre-immune serum vs. wild type dengue antigens; 2 G16 macaque pre-immune versus HX dengue antigens; 3, G16 Zika-convalescent serum versus wild type dengue antigens; 4 G16 macaque Zika convalescent serum versus HX dengue antigens; 5, dengue human serum 2965 vs. wild type dengue antigens; 6, dengue human serum 2965 vs. HX dengue antigens; 7, VM control human serum vs. wild type dengue antigens; 8, VM control human serum vs. HX dengue antigens.

These results show a strong off-target recognition of wild type dengue antigens by the Zika convalescent serum which is not exhibited by the tests conducted with the HX versions of the same antigens, which nevertheless correctly identify the dengue positive human serum. The macaque 'G16' was bred in captivity and cannot have been exposed to dengue. The strong 'quasi specific' recognition of the WT dengue antigens by the macaque serum is a true antigen-specific reaction, explained by reaction of anti-Zika antibodies in the macaque serum with the dengue fusion loop, which is effectively cloaked (masked) by glycosylation in the case of the HX antigens. Results by test are 1 negative; 2 negative;

3 positive; 4 weakly positive (much less than false positive in 3); 5, positive; 6 positive; 7 weak positive; 8 negative. 100 ng of each antigen (200 ng total) was used in each test. '8', using HX versions of the dengue antigens, was negative as expected (desirable result) whereas '7' gave rise to a weak non-specific binding reaction of this non-flavivirus exposed subject (VM) to the wild-type version of the antigen (undesirable result).

Example 12 demonstrates the superior performance of dengue-HX antigens (combined dengue-2 and dengue-4 HX antigens) compared to their wild type equivalents, the wild type versions showing strong off-target recognition by anti-Zika antibodies. In this example a captive-bred macaque was used. This obviates the uncertainty, in the case of human sera, that a person may also have been exposed to dengue as well as Zika, because there is high co-endemicity of Zika and dengue such that the majority of Zika-exposed human subjects will also have been exposed to dengue.

Example 13: Equivalent Performance of Mammalian and Insect-Expressed (Tni Cell) Dengue 1, 2, 3, 4 HX Antigens, and Avoidance of False Positivity with Yellow Fever Vaccinated Subjects HX versions of the four dengue proteins were made in either human embryonic kidney cells or in insect (Tni) cells using a secretory-type baculovirus vector expression system (Flash-Bac Ultra) according to manufacturer's instructions. FIG. 13 shows the results for A (left panel) HEK-cell expressed dengue HX antigens and B (right panel) Tni-cell expressed HX antigens. In each case (HEK or Tni) the protein sequences are identical, and the genetic code usage and DNA sequence of the expressed proteins likewise identical. Example 13 demonstrates that the antigenicity of the dengue HX antigens is preserved when they are expressed in an insect cell system. This is so despite the differences in glycan structure that obtain between human and insect systems. Specific reactivity of the antigens is maintained with dengue positive but not dengue negative serum, and there was no off-target recognition, under the conditions used, of the dengue and Zika naïve yellow-fever vaccinated subject JF, which had shown positive in previous tests, (not shown).

Example 14: Utility and Specificity of HX Zika and Dengue Antigens in Lateral Flow Testing Compared to Wild Type Zika Antigen In this example the reactivity of HX versions of the complete set of dengue antigens 1, 2, 3 &4 (as a mixture) and of the HX Zika antigen are compared for a dengue positive serum +D=serum 2965, and a Zika positive serum +Z (G16 macacque Zika convalescent serum, and a control human serum positive for neither.

FIG. 14A shows insect-cell-expressed dengue HX 1,2,3,4. The insect-expressed HX dengue antigens show a strong reaction with the human dengue positive serum, but not with the negative control serum or with the Zika convalescent serum.

FIG. 14B shows insect cell expressed Zika HX. The HX-Zika antigen reacts very strongly with the Zika convalescent serum, and shows a weak reactivity towards the dengue positive serum;

FIG. 14C shows that the wild type insect cell expressed Zika antigen (which like the HX versions has a His tag) reacts weakly with the Zika convalescent serum, and shows minimal cross-reactivity with the dengue positive serum. In these tests 100 ng of each antigen was used, 100 units of gold conjugate, 0.5% PEG20K was used in the running buffer. JF is a serum from a subject who was vaccinated against yellow fever, and which had shown false-positive positive in previous tests. The loss of residual false positivity or cross-reaction with yellow fever is ascribed to the use of 0.5% PEG20K in the running buffer as a carrier.

Example 14 demonstrates utility and specificity of HX Zika and dengue antigens in lateral flow testing compared to wild type Zika antigen. In this example insect-cell expressed dengue and Zika antigens were used. The extremely strong reaction seen with the HX version of the insect-expressed Zika antigen can be traded off with respect to specificity, by using less antigen in the test or less anti-His-tag antibody in the test line, in order to render the weak off-target recognition of dengue HX antigens undetectable (i.e. invisible).

Example 15: Performance of the HX Antigens in Lateral Flow Testing of Human Whole Blood Example 15 demonstrates the performance of various configurations of the test with whole blood, all based on the format of Example 9A (using a single port). For a point-of-care test it is most useful and convenient if it can be conducted using blood without the need for plasma or serum separation. First it was investigated whether it was advantageous to use an anti-glycophorin antibody in the sample pad to absorb-out red blood cells preventing them from running on the nitrocellulose and complicating the reading of the device. It was found that the anti-glycophorin antibody reduced the signal of the test to an unacceptable degree. However, it is noted that it may nevertheless be advantageous to include a lesser amount of such an antibody in the sample pad, in order to absorb out heterophile antibodies (human anti-mouse-IgG antibodies) that occasionally give false positives in tests using mouse monoclonal antibodies. In the format of Example 15, without anti-glycophorin antibody, specific reactivity of dengue positive samples was demonstrated without problems of false positivity due to yellow fever vaccination in five subjects. Also in this format, there was sensitive detection of dengue neutralising antibodies D18 and D78.

A: The test requirement for anti-glycophorin A (AGA) in the dengue test was investigated. Tests were run according to Example 9A, but also including 0.5% PEG20K in the running buffer. Samples were made from serum mixed with an equal volume of centrifuge-sedimented red cell fraction from whole normal blood. 10 ul samples of blood were used. 100 ng of each HX dengue antigen was used and 100 units of anti-human-IgG gold conjugate. FIG. 15A right panel shows deconstruction of the tests after running, demonstrating that in the absence of the AGA the red blood cells reach the nitrocellulose, but this does not interfere with the test aesthetics or interpretation.

B: Tests were run as in 15A above including testing of serum JF, a yellow-fever vaccine. No AGA was used. There was minimal breakthrough of red blood cells into the test window (FIG. 15B).

C: Tests were run as above in 15A and 15B, with 5 ul of negative sample which had been spiked with various levels of D18/D78 antibodies (Absolute Antibody Ltd., Oxford) in equal mixture. 100 ul of running buffer was used as chase. All tests used 100 ng of each dengue insect derived HX antigen and 100 units of anti-human-IgG gold conjugate.

The results are shown in FIG. 15C. Although not immediately obvious from the photograph, the signal was detectable down to 15.6 ng.

D: Blood samples were made up by replacing the plasma of a normal blood sample from which red blood cells were sedimented, with various plasmas (negative, positive and yellow-fever vaccinated) and resuspended. 100 ul of running buffer was used as chase. 100 ng of each of the four insect-derived dengue HX antigens were used, plus 100 units of anti-hu-IgG gold conjugate. "+" is the positive control used in the various previous test examples above. A very favourable profile of positivity was observed—all positive samples gave a positive test line, none of the yellow fever vaccinated subjects or the negative control subject, gave a positive test line (FIG. 15D).

Example 16: Production of all Seven HX Proteins in Insect-Cells (Tni) and Comparison of Insect-Expressed (Tni) Proteins to Human Expressed (HEK) HX Proteins HX proteins were initially produced in HEK cells, however it was difficult to achieve efficient expression of some of the proteins. To seek to improve protein expression, HX proteins were produced in Tni insect cells in the 'Flash-Bac-Ultra' baculovirus system of Oxford Expression Technologies Ltd. According to the manufacturer's instructions. Protein purification was performed using Strep-TactinXT® Superflow® system (IBA Lifesciences), according to the manufacturer's instructions.

The results of expression of Zika HX-Strep-tag-II from insect (Tni) cells are shown in FIG. 16 in which expression of 10.5 mg Zika HX-Strep-tag-II was achieved (expression of 1.5 mg was achieved in HEK cells)

In Tni cells, an approximately 10-fold improvement in productivity (relative to expression in HEK or CHO) was achieved for the 'difficult-to produce' dengue-1-HX and Zika-HX antigens, which now expressed at levels approaching those of the most abundantly-expressed antigens such as dengue-2-HX. High levels of expression have been achieved subsequently in CHO cells, by optimising signal sequence and by cell-line development.

As it was possible that the HEK-expressed antigens might differ from the baculovirus-expressed forms (notably these cell lines produce different glycan structures), bridging studies were performed with the lateral flow tests to determine if these differences influenced the performance of the test with human sera, or whether there were differences in reactivity in ELISA format with panels of monoclonal antibodies.

The antigenic integrity of insect (Tni) expressed HX forms of the dengue and Zika proteins (having one or more glycans in the fusion loop) was probed with a panel of murine anti-Zika monoclonal antibodies (some of which had known specificity and properties), and with 4G2—a flavivirus cross-reactive antibody which was raised against dengue-2 wild type and which recognizes the conserved fusion loop (Table A). This was done in order to ensure that the data generated earlier on the HEK-expressed proteins would translate effectively when the insect (Tni) expressed antigens were used in the LF tests, in place of the HEK-expressed proteins. These studies confirmed that the baculovirus-produced antigens were equivalent to the HEK-expressed forms in their recognition by well-characterised murine monoclonal antibodies. Also, glycan analyses were conducted on the baculovirus-expressed proteins which confirmed that the fusion-loop planting efficiency of the glycans was the same for the baculovirus-expressed as was the case for the HEK-expressed proteins, although the glycans were, as expected, different between insect and HEK expression.

TABLE 10

Recognition (absorbance values) of baculovirus-expressed and HEK- expressed HX and wt dengue and Zika antigens by murine MCABs

| | Ab type | | | | | |
|---|---|---|---|---|---|---|
| | Neutralising | Neutralising | Enhancing | neut. &/enh. | Unknown | enhancing anti-D2 Fusion-loop Aba |
| | ab name | | | | | |
| | ZV48 | ZV67 | ZKA78 | ZKA64 | Aalto a Z ab | 4G2 |
| insect D1HX | 0.0 | 0.1 | 0.0 | 0.2 | 0.2 | 0.1 |
| insect D2HX | 0.0 | 0.1 | 0.0 | 0.2 | 0.1 | 0.1 |
| insect D3HX | 0.0 | 0.1 | 0.0 | 0.2 | 0.3 | 0.1 |
| insect D4HX | 0.0 | 0.1 | 0.0 | 0.1 | 0.1 | 0.1 |
| insect ZHX | 1.1 | 1.5 | 0.0 | 0.7 | 2.0 | 0.1 |
| insect Z-wt | 1.1 | 1.2 | 1.4 | 0.8 | 1.0 | 0.9 |
| HEK D1HX | 0.0 | 0.1 | 0.0 | 0.1 | 0.1 | 0.1 |
| HEK D2HX | 0.0 | 0.0 | 0.0 | 0.1 | 0.1 | 0.1 |
| HEK D3HX | 0.0 | 0.0 | 0.0 | 0.1 | 0.1 | 0.1 |
| HEK D4HX | 0.0 | 0.0 | 0.0 | 0.1 | 0.1 | 0.1 |
| HEK ZHX | 1.2 | 1.1 | 0.0 | 0.9 | 3.1 | 0.1 |

Antigenic 'audit' of HEK vs Tni-expressed HX proteins, vs Zika-wildtype. Tni-expressed antigen had an equivalent recognition profile to the equivalent HEK-expressed material with murine MCABs, were recognized by neutralizing antibody but not by cross-reactive enhancing antibody and were able to detect neutralising antibody, thus had the capability to be used to assess exposure to flavivirus and inform vaccine use. There was a very similar profile of reactivity of our Zika antigen secreted from insect (Tni) cells in the baculovirus system, compared to the equivalent antigen secreted from HEK cells. Notably, in both cases, the 'HX' forms (into which glycosylation sites have been introduced and which have been modified post-translationally by glycosylation) were recognized appropriately by four conformation-sensitive anti-Zika E protein antibodies, but not by dengue-cross-reactive antibodies ZKA78 and 4G2 (which strongly recognize wild-type Zika).

Example 17: Comparison of Excivion Dengue-LF to SD Dengue Ag+Ab Duo (Field Study Done in Pune, India)

Comparison of Excivion dengue-LF prototype test of the invention to the SD BIOLINE Dengue DUO® (SDB DD)

NS1 Ag and IgG/IgM ICT (SD Dengue Ag+Ab Duo) test was performed in a field study carried out in Pune, India.

The manufacturer's instructions for the use of SD BIO-LINE Dengue DUO® (SDB DD) NS1 Ag and IgG/IgM ICT (Standard Diagnostics, Inc., Korea) were followed, and are described previously (Wang S M, Sekaran S D. Early diagnosis of dengue infection using a commercial Dengue Duo rapid test kit for the detection of NS1, IgM, and IgG. Am J Trop Med Hyg. 2010; 83(3):690-5).

The Excivion dengue-LF prototype test (without preabsorption).

The Excivion dengue-LF test was used to perform 47 tests on the sera tested previously with SD Dengue LF test (FIG. 17). The line intensities seen with the Excivion –Omega dengue-LF test were described by the observer as "very, very strong" compared to SD Duo. Cases of discrepancy, where the Excivion –Omega dengue-LF test scored IgG+ and SD scored IgG−, were confirmed to be true dengue +ve for the Excivion tests by evidence of NS1 or dengue IgM positivity in the SD test.

Excivion –Omega dengue-LF test had "increased sensitivity for IgG". (statistical analysis: Wilcoxon Matched Pairs Test N 47 T 0. Z 5.23162 p-level 1.6803E-7).

Example 18: Test Performance of Early Test Prototypes

The performance of early test prototypes (no preabsorption) was assessed first with panels of sera available from commercial and academic sources. Tests were performed using dengue and Zika serum and plasma panels collected in endemic territories or from returning traveller populations including Thailand, the Dominican Republic, USA and UK-Trinidad, collected before and 'after' the advent of Zika as a pandemic disease, although it became apparent that Zika had arrived in Brazil in 2013 (earlier than previously thought). The test was also demonstrated to work with whole blood, its intended use.

Tests were also performed on NIBSC sera, noted above, from non-human primates that had been exposed only to Zika. The specificity seen in earlier ELISA tests with the NIBSC primate sera, was replicated in the LF format Zika test. These primate Zika-convalescent sera were positive in the Zika LF test, but negative in the dengue LF test, employing our proprietary 'HX' antigens. In contrast, the wild type Zika antigen (i.e. without cloaking of the fusion loop) gave rise to false-positives with dengue sera when used in LF-tests. These findings confirmed the superior diagnostic accuracy of our HX antigens over the wild-type (natural) equivalent proteins, in a lateral-flow (as well as ELISA) context.

FIG. 18 shows testing of early post-Zika samples from the Rio field study showing a range of positivity in the Zika and dengue LF tests (prototype-1), with no preabsorption. The samples were from subjects with Zika, whose Zika infection had been confirmed by PCR. Zika IgG was detected in 8/10 samples, as the samples were taken early after infection, little IgG expected. Some double –ve samples (2,6,9) confirmed specificity by proving that normal human IgG present in these samples was not binding non-specifically to the test line. All Zika-positive samples (Z+) were also dengue-positive (D+). The sensitivity of Z-LF prototype 1 test was demonstrated, but distinction between dengue and Zika was not confirmed by these data.

When human sera were used in the LF tests, we found that the tests had excellent sensitivity (judged initially by spiking normal human sera with monoclonal anti-Zika and anti-dengue antibodies). However, we found that there was a significant false-positivity rate in both the Zika and dengue LF tests, employing our HX antigens, when endemic panels of sera were tested. We attributed these false positives to 'mosaic' epitopes representing short segments of identity in amino-acid sequence common between dengue and Zika viruses (and to a lesser extent with other human flaviviruses), less immune-dominant than the fusion-loop. We were able to obviate false signals due to yellow fever vaccination by increasing the 'stringency' of the test (via manipulating running-buffer composition), however this was not sufficient to abolish all false signals originating from (putative) dengue-only and Zika-only sera. We then embarked on a modified strategy of test design, which incorporated 'off-target-pre-absorption' to deal with remaining cross-reactions.

Example 19 Characterisation of Off-Target Pre-Absorption

Preabsorption is a well-established technique which is sometimes used in serological analyses to prevent signals being generated by cross-reactive antibodies. In the case of flaviviruses this is difficult to achieve, but our advent of cloaking the fusion loop and obviating signals from the major cross-reactive site of this family of viruses makes it possible to exploit preabsorption to minimize signals from cross-reactive antibodies in LF tests for Zika and dengue. In the Zika test we have described Zika as the target antigen, and preabsorbing dengue antigen as the 'off-target' antigen. In the dengue test we have described (below) dengue 1,2,3,4 as the target antigen and Zika as the off-target antigen. Because the mosaic epitopes (defined above) were present in sequence alignments across Zika and all four strains of dengue, we used dengue-2-HX for preabsorption instead of all four dengue serotypes. In configuring tests with preabsorbing antigens it was necessary to construct versions of dengue-2-HX (SEQ ID NO: 2) and Zika-HX (SEQ ID NO: 5) that had either no tag or a different tag than a His tag, otherwise they would contribute signal in the test from cross-reactive antibodies. For this reason we constructed Strep-tag-II versions of the dengue-2-HX and Zika-HX antigens. HX versions were used for preabsorption because they were more productive than the wild type versions in recombinant expression. By configuring the tests in this way we were able to engineer the capture and blockade of antigen combining sites of cross-reactive antibodies with Strep-tag-II versions of the off-target antigens, whereby such antigen-antibody complexes were not captured by the anti-His-tag line and ran off the end of the observation window of the test without contributing signal.

TABLE 11

Comparison of LF tests with and without off-target-preabsorption, vs. commercial ELISAs

| | Commercial ELISA Tests | | | | | | | | Den LF | | Z LF | | Concur D | Concur Z |
|---|---|---|---|---|---|---|---|---|---|---|---|---|---|---|
| | Z | | D | | Chik | | WNV | | D | D + Z | Z | Z + D | (with | (with |
| Sample | M | G | M | G | M | G | M | G | G | G | G | G | abs'n) | abs'n) |
| 55 | + | + | − | + | + | + | − | + | +++ | +++ | +++ | +++ | Green | Green |
| 56 | + | + | − | − | − | − | − | − | − | − | + | + | Green | Green |
| 57 | + | + | − | − | − | − | − | − | − | − | ++ | + | Green | Green |
| 58 | + | + | − | + | − | − | − | + | +++ | +++ | +++ | +++ | Green | Green |
| 59 | + | − | + | + | − | − | − | − | + | + | − | − | Green | Green |
| 60 | + | − | − | − | − | − | − | − | − | − | − | − | Green | Green |
| 63 | − | − | − | + | − | − | − | − | ++ | ++ | + | − | Green | Green |
| 64 | − | − | + | − | − | − | − | − | + | + | − | − | Green | Green |
| 65 | − | − | − | + | − | − | − | − | + | − | + | − | Red | Green |
| 66 | − | − | − | + | + | + | − | − | ++ | + | − | − | Green | Green |
| 67 | − | − | − | + | + | + | − | ? | ++ | + | ++ | − | Green | Green |
| 68 | − | + | − | + | + | + | − | ? | +++ | ++ | +++ | − | Green | Red |
| 69 | − | − | − | + | + | + | − | − | ++ | + | +++ | − | Green | Green |
| 70 | − | − | − | + | + | + | − | + | + | + | ++ | − | Green | Green |
| 71 | − | − | − | − | − | − | + | − | − | − | − | − | Green | Green |
| 72 | − | − | ? | + | − | − | + | + | − | − | − | − | Red | Green |
| 73 | − | − | − | − | − | − | + | ? | − | − | − | − | Green | Green |
| 74 | − | − | − | − | − | − | + | − | − | − | − | − | Green | Green |
| 75 | − | − | − | + | − | − | + | + | + | − | +++ | ++ | Red | Red |
| 76 | − | − | − | + | − | − | − | + | − | − | − | − | Red | Green |

Comparative studies conducted with commercial ELISA tests on endemic sera positive for various flaviviruses: The performance of the Zika and dengue LF tests, with and without 'off-target' preabsorption' was compared to that of commercial ELISA tests. In the dengue LF, Zika-HX was used for absorption; in the Zika LF, dengue-2HX was used for off-target preabsorption. Under these circumstances there was good agreement (depicted by light shading (green) in concur D, and concur Z columns) with the commercial ELISA tests.

As multiple-exposure (and cross-reactivity of antibodies) was expected to be commonplace in endemic areas, it was desirable to employ tests with off-target pre-absorption. Thus we set about determining what amounts of off-target antigen would be needed in each of the pair of LF devices (one Zika and one Dengue test making up the pair), and found that 1 ug per device was adequate for the dengue test, and 5 ug per device for the Zika test (these larger amounts of antigen compare to 200 ng amounts of the test antigen in each device). In the case of the Zika test, off-target preabsorption using all four dengue antigens in Strep-tag form was considered, but after comparison of the sequences and X-ray structures of the wild-type Zika and dengue antigens, it was concluded that use of dengue-2-HX-Strep-tag alone would be sufficient for off-target pre-absorption, because the 'islands of identity' in the dengue and Zika HX sequences (comprising residual cross-reactive 'mosaic' epitopes) were essentially the same across all four dengue serotypes, additionally the dengue-2-HX was easiest to produce. Pre-absorption with the panel sera with dengue-2-HX was successful and provided LF Zika devices, equipped with off-target pre-absorption built into the LF device for the field testing in Brazil (which were tested alongside the analogously configured dengue LF test devices).

FIG. 19 shows the characterisation of off-target pre-absorption to establish, in Lateral Flow (LF), how much antigen was needed to preabsorb cross reactive antibodies to minimize interference with test results.

Example 20 Modified LF Test Design

In a particular embodiment, the Zika test contained non-His-tagged (Strep-tagged) dengue antigen, and (conversely) the dengue test contained Strep-tagged Zika antigen, the off-target antigens were included to bind to cross-reactive antibodies, but not result in gold-particle-arrest (visually detectable signal) on the test line (which was effected by an anti-His-tag antibody). Because the HX antigens were much easier to produce, the off-target antigens were made as HX (rather than wild-type) forms.

In conventional LF tests for this purpose, test line has an anti-Ig (anti-IgM or anti-IgG) and the gold conjugate is labelled with antigen, giving rise to arrest of gold particles by human antibodies that bridge the solid-phase anti-Ig of the test line with gold particles. In our preferred configuration, the test-line is monoclonal-anti-His-tag. Off-target antigens (for pre-absorption) are Strep-tagged (using StrepTag-II), allowing them to flow past the test line. Of a number of architectures tested, we found this configuration to be most sensitive, while simple and easy to manufacture. By use of monoclonal and recombinant reagents exclusively, it is 'infinitely' scalable.

A depiction of embodiments of the LF test devices is given in FIG. 20.

Example 21 Clinical Field Studies in Rio
(Flavivirus Reference Laboratory, Oswaldo Cruz)

In the devices used in the clinical field studies in Rio, the LF tests used 1 ug of Zika-HX and 5 ug of den-2-HX for off-target-pre-absorption of cross-reactive antibodies.

In field testing conducted in Rio de Janiero, the Zika test was found to be 100% sensitive (positive in 50 samples out of 50) in detecting cases of Zika confirmed by PCR (in samples from 2016) that were found to be positive in the blockade of binding assay 'BOB', a recently developed 'second generation' Zika ELISA assay based on blockade of NS1 monoclonal antibody binding, regarded as the most reliable laboratory-based test for Zika antibodies (Balmaseda A et al Proc Natl Acad Sci USA. 2017 Aug. 1; 114(31):8384-8389. doi: 10.1073/pnas.1704984114. Epub 2017 Jul. 17).

Using our tests all of these samples were strongly and unambiguously (++++) positive (whereas in the BOB test they exhibited a range of positivity). This result tallied with our own observations with panel sera in which our LF tests were found (in the case of dengue) to be very significantly more sensitive than Standard Diagnostics' LF test with respect to IgG detection. Our Zika test was also very good at detecting seroconversion (elevation of antibodies indicative of recent infection) in serial samples (p<0.01) FIG. 22. The very few 'dengue negative' Zika samples from the seroconversion panel in Brazil showed the clear development of test lines after a matter of days post-infection, from a 'zero' background. Using a threshold WHO score of '1' as positive, our Zika LF was positive in 7/25 cases (28%) of BOB-negative 2016 sera. However, some of these sera may reasonably be expected to be covertly Zika-positive by dint of having antibodies against sites other than the single epitope measured in this assay. Choosing a positive threshold score of >3, the results of our Zika LF are precisely the same in calling Zika positives or negatives as the BOB assay (i.e. the best laboratory test available for the purpose). In fact these results indicate that our test is more-sensitive than the BOB assay, which may allow a tradeoff of this sensitivity for certain applications.

In the Rio field testing, the earliest sera we were able to obtain were from 2014, which was believed to be before significant Zika circulation had occurred in Rio, although it has recently been recognized that Zika was, in fact, circulating in Brazil in 2013, meaning that there could be some Zika cases in this sample set collected in 2014. We found a 4% positivity rate for Zika (calling any result >3 as positive) with our LF test in this group. However, two tests for Zika NS1 antigen put this figure even higher—at 50%. This result indicated that our Zika test is more specific than the commercial NS1-based Zika ELISA tests, which are false positive in 50% of cases. With respect to our dengue LF test, we found a positivity of 92% (46/50) in the 2014 samples, which tallies with an expected 90-95% dengue seropositivity in the general (Rio) population from various literature studies. The results of testing are shown in FIG. 21.

CONCLUSION

We have developed a pair of cheap, simple point-of-care devices for detecting and distinguishing prior dengue or Zika infection, the devices are convenient, do not require a laboratory environment for their performance. The performance of the tests is better than previous commercial LFs and ELISAs and they will find many uses in the diagnosis and monitoring of these infections, including their demonstrated use as a 'companion diagnostic' with potential to increase the safety of use of vaccines.

Sequence Listing Free Text

SEQ ID NO: 1 DRGWGNGCGLFGK

SEQ ID NO: 2 DRGNGSGCGLNGS,

SEQ ID NO: 3 DRGNGSGCGLFGK

SEQ ID NO: 4 DRGWGNGCGLNGS

SEQ ID NO: 5 DRNHTNGCGLFGK.

SEQ ID NO: 6 DRGWGNGCGNHTK

SEQ ID NO: 7 pCR025 fragment CKRTLVDRGNGSGCGLNGSGSLVTCAKFA

SEQ ID NO: 8 pCR029 fragment CKRTLVDRGWGNGCGNHTKGSLVTCAKFA

SEQ ID NO: 9 pCR030 fragment CKRTLVDRGNGSGCGLFGKGSLVTCAKFA

SEQ ID NO: 10 pCR031 fragment CKRTLVDRGWGNGCGLNGSGSLVTCAKFA

SEQ ID NO: 11 DRGWGNNCTLFGK

SEQ ID NO: 12 DRGWGNNCSLFGK

```
pCR021 (SEQ ID NO: 13)
ORIGIN
     1 GCGATCGCGG CTCCCGACAT CTTGGACCAT TAGCTCCACA GGTATCTTCT TCCCTCTAGT
    61 GGTCATAACA GCAGCTTCAG CTACCTCTCA ATTCAAAAAA CCCCTCAAGA CCCGTTTAGA
   121 GGCCCCAAGG GGTTATGCTA TCAATCGTTG CGTTACACAC ACAAAAACC AACACACATC
   181 CATCTTCGAT GGATAGCGAT TTTATTATCT AACTGCTGAT CGAGTGTAGC CAGATCTAGT
   241 AATCAATTAC GGGGTCATTA GTTCATAGCC CATATATGGA GTTCCGCGTT ACATAACTTA
   301 CGGTAAATGG CCCGCCTGGC TGACCGCCCA ACGACCCCCG CCCATTGACG TCAATAATGA
   361 CGTATGTTCC CATAGTAACG CCAATAGGGA CTTTCCATTG ACGTCAATGG GTGGAGTATT
   421 TACGGTAAAC TGCCCACTTG GCAGTACATC AAGTGTATCA TATGCCAAGT ACGCCCCCTA
   481 TTGACGTCAA TGACGGTAAA TGGCCCGCCT GGCATTATGC CCAGTACATG ACCTTATGGG
   541 ACTTTCCTAC TTGGCAGTAC ATCTACGTAT TAGTCATCGC TATTACCATG CTGATGCGGT
   601 TTTGGCAGTA CATCAATGGG CGTGGATAGC GGTTTGACTC ACGGGGATTT CCAAGTCTCC
   661 ACCCCATTGA CGTCAATGGG AGTTTGTTTT GGCACCAAAA TCAACGGGAC TTTCCAAAAT
   721 GTCGTAACAA CTCCGCCCCA TTGACGCAAA TGGGCGGTAG GCGTGTACGG TGGGAGGTCT
   781 ATATAAGCAG AGCTGGTTTA GTGAACCGTC AGATCAGATC TTTGTCGATC CTACCATCCA
   841 CTCGACACAC CCGCCAGCgg ccgccaccat gaaggccaat ctactggtgt tgctgtgtgc
   901 cctttgcggcg gcagatgcca tgcggtgcgt ggggatcggc aatcgcgatt ttgtagaagg
   961 actatctggt gccacgtggg tcgatgtggt tcttgaacac gggtcatgcg tgaccacgat
  1021 ggctaaggat aagccgacct tggacatcga actactgaaa accgaggtca caaaccctgc
  1081 tgtgctccgc aagctgtgca tcgaggctaa gatttccaac acaactactg atagccgctg
  1141 ccccacccaa ggcgaggcga ccctcgttga agagcaggac agcaacttcg tgtgtcgccg
```

-continued

```
1201 gactttcgtg gaccgcggta atgggtccgg atgcggactt aacggatctg gttccttact
1261 gacttgcgcc aaatttaagt gcgtgactaa gttagagggg aaaatcgttc agtatgagaa
1321 cttaaaatac tcggtgatag ttaccgtgca cacaggcgac cagcatcaag ttgggaacga
1381 aacgacagag cacgggacaa tagcgaccat taccccacag gctccaacga gcgaaattca
1441 gctgacagac tacggtgcac tcaccctgga ctgtagccca cggaccgggc tagactttaa
1501 cgagatggtg ctcctgacta tgaaggaaaa gtcatggttg gtgcacaagc agtggttcct
1561 tgatcttcca ttgccctgga cctctggcgc ttcgacctca caagagactt ggaacaggca
1621 ggacttgctc gtgacattca aaacggctca cgctaaaaag caagaggtcg tggttctggg
1681 gagtcaggaa ggcgctatgc ataccgcgtt aacaggggct acagagatcc agaccagtgg
1741 aacaaccact attttcgccg ggcatcttaa gtgtaggctg aagatggata agttgaccct
1801 gaaaggtatg tcatatgtga tgtgcaccgg tagtttcaaa ctggagaaag aagtggccga
1861 aacccagcat ggaacagtac tggtgcaagt caaatatgag ggcaccgatg caccatgtaa
1921 aatacccttc agcgcacaag acgagaaggg agttacccag aacggtaggc tgataacagc
1981 caatccaatc gtcaccgata aggagaaacc agtaaacatc gaaaccgagc caccttcgg
2041 cgaaagctac atcgtggtcg gcgctggcga gaaagcactt aagctgagct ggtttaagaa
2101 aggtagcacg ggcggcggca gccatcatca ccatcatcac tgagctagcT TGACTGACTG
2161 AGATACAGCG TACCTTCAGC TCACAGACAT GATAAGATAC ATTGATGAGT TTGGACAAAC
2221 CACAACTAGA ATGCAGTGAA AAAAATGCTT TATTTGTGAA ATTTGTGATG CTATTGCTTT
2281 ATTTGTAACC ATTATAAGCT GCAATAAACA AGTTAACAAC AACAATTGCA TTCATTTTAT
2341 GTTTCAGGTT CAGGGGGAGG TGTGGGAGGT TTTTTAAAGC AAGTAAAACC TCTACAAATG
2401 TGGTATTGGC CCATCTCTAT CGGTATCGTA GCATAACCCC TTGGGGCCTC TAAACGGGTC
2461 TTGAGGGGTT TTTTGTGCCC CTCGGGCCGG ATTGCTATCT ACCGGCATTG GCGCAGAAAA
2521 AAATGCCTGA TGCGACGCTG CGCGTCTTAT ACTCCCACAT ATGCCAGATT CAGCAACGGA
2581 TACGGCTTCC CCAACTTGCC CACTTCCATA CGTGTCCTCA TTACCAGAAA TTTATCCTTA
2641 AGGTCGTCAG CTATCCTGCA GGCGATCTCT CGATTTCGAT CAAGACATTC CTTTAATGGT
2701 CTTTTCTGGA CACCACTAGG GGTCAGAAGT AGTTCATCAA ACTTTCTTCC CTCCCTAATC
2761 TCATTGGTTA CCTTGGGCTA TCGAAACTTA ATTAACCAGT CAAGTCAGCT ACTTGGCGAG
2821 ATCGACTTGT CTGGGTTTCG ACTACGCTCA GAATTGCGTC AGTCAAGTTC GATCTGGTCC
2881 TTGCTATTGC ACCCGTTCTC CGATTACGAG TTTCATTTAA ATCATGTGAG CAAAAGGCCA
2941 GCAAAAGGCC AGGAACCGTA AAAAGGCCGC GTTGCTGGCG TTTTTCCATA GGCTCCGCCC
3001 CCCTGACGAG CATCACAAAA ATCGACGCTC AAGTCAGAGG TGGCGAAACC CGACAGGACT
3061 ATAAAGATAC CAGGCGTTTC CCCCTGGAAG CTCCCTCGTG CGCTCTCCTG TTCCGACCCT
3121 GCCGCTTACC GGATACCTGT CCGCCTTTCT CCCTTCGGGA AGCGTGGCGC TTTCTCATAG
3181 CTCACGCTGT AGGTATCTCA GTTCGGTGTA GGTCGTTCGC TCCAAGCTGG GCTGTGTGCA
3241 CGAACCCCCC GTTCAGCCCG ACCGCTGCGC CTTATCCGGT AACTATCGTC TTGAGTCCAA
3301 CCCGGTAAGA CACGACTTAT CGCCACTGGC AGCAGCCACT GGTAACAGGA TTAGCAGAGC
3361 GAGGTATGTA GGCGGTGCTA CAGAGTTCTT GAAGTGGTGG CCTAACTACG GCTACACTAG
3421 AAGAACAGTA TTTGGTATCT GCGCTCTGCT GAAGCCAGTT ACCTTCGGAA AAAGAGTTGG
3481 TAGCTCTTGA TCCGGCAAAC AAACCACCGC TGGTAGCGGT GGTTTTTTTG TTTGCAAGCA
3541 GCAGATTACG CGCAGAAAAA AAGGATCTCA AGAAGATCCT TTGATCTTTT CTACGGGGTC
3601 TGACGCTCAG TGGAACGAAA ACTCACGTTA AGGGATTTTG GTCATGAGAT TATCAAAAAG
3661 GATCTTCACC TAGATCCTTT TAAATTAAAA ATGAAGTTTT AAATCAATCT AAAGTATATA
3721 TGAGTAAACT TGGTCTGACA GTTACCAATG CTTAATCAGT GAGGCACCTA TCTCAGCGAT
3781 CTGTCTATTT CGTTCATCCA TAGTTGCATT TAAATTTCCG AACTCTCCAA GGCCCTCGTC
3841 TGGAAAATCTT CAAACCTTTC GTCCGATCCA TCTTGCAGAC TACCTCTCA ACGAACTATC
3901 GCAAGTCTCT TGGCCGGCCT TGCGCCTTGG CTATTGCTTG GCAGCGCCTA TCGCCAGGTA
3961 TTACTCCAAT CCCGAATATC CGAGATCGGG ATCACCCGAG AGAAGTTCAA CCTACATCCT
4021 CAATCCCGAT CTATCCGAGA TCCGAGGAAT ATCGAAATCG GGGCGCGCCT GGTGTACCGA
4081 GAACGATCCT CTCAGTGCGA GTCTCGACGA TCCATATCGT TGCTTGGCAG TCAGCCAGTC
4141 GGAATCCAGC TTGGGACCCA GGAAGTCCAA TCGTCAGATA TTGTACTCAA GCCTGGTCAC
4201 GGCAGCGTAC CGATCTGTTT AAACCTAGAT ATTGATAGTC TGATCGGTCA ACGTATAATC
4261 GAGTCCTAGC TTTTGCAAAC ATCTATCAAG AGACAGGATC AGCAGGAGGC TTTCGCATGA
4321 GTATTCAACA TTTCCGTGTC GCCCTTATTC CCTTTTTTGC GGCATTTTGC CTTCCTGTTT
4381 TTGCTCACCC AGAAACGCTG GTGAAAGTAA AAGATGCTGA AGATCAGTTG GGTGCGCGAG
4441 TGGGTTACAT CGAACTGGAT CTCAACAGCG GTAAGATCCT TGAGAGTTTT CGCCCCGAAG
4501 AACGCTTTCC AATGATGAGC ACTTTTAAAG TTCTGCTATG TGGCGCGGTA TTATCCCGTA
4561 TTGACGCCGG GCAAGAGCAA CTCGGTCGCC GCATACACTA TTCTCAGAAT GACTTGGTTG
4621 AGTATTCACC AGTCACAGAA AAGCATCTTA CGGATGGCAT GACAGTAAGA GAATTATGCA
4681 GTGCTGCCAT AACCATGAGT GATAACACTG CGGCCAACTT ACTTCTGACA ACGATTGGAG
4741 GACCGAAGGA GCTAACCGCT TTTTTGCACA ACATGGGGGA TCATGTAACT CGCCTTGATC
4801 GTTGGGAACC GGAGCTGAAT GAAGCCATAC CAAACGACGA GCGTGACACC ACGATGCCTG
4861 TAGCAATGGC AACAACCTTG CGTAAACTAT TAACTGGCGA ACTACTTACT CTAGCTTCCC
4921 GGCAACAGTT GATAGACTGG ATGGAGGCGG ATAAAGTTGC AGGACCACTT CTGCGCTCGG
4981 CCCTTCCGGC TGGCTGGTTT ATTGCTGATA AATCTGGAGC CGGTGAGCGT GGGTCTCGCG
5041 GTATCATTGC AGCACTGGGG CCAGATGGTA AGCCCTCCCG TATCGTAGTT ATCTACACGA
5101 CGGGGAGTCA GGCAACTATG GATGAACGAA ATAGACAGAT CGCTGAGATA GGTGCCTCAC
5161 TGATTAAGCA TTGGTAACCG ATTCTAGGTG CATTGGCGCA GAAAAAAATG CCTGATGCGA
5221 CGCTGCGCGT CTTATACTCC CACATATGCC AGATTCAGCA ACGGATACGG CTTCCCCAAC
5281 TTGCCCACTT CCATACGTGT CCTCCTTACC AGAAATTTAT CCTTAAGATC CCGAATCGTT
5341 TAAACTCGAC TCTGGCTCTA TCGAATCTCC GTCGTTTCGA GCTTACGCGA ACAGCCGTGG
5401 CGCTCATTTG CTCGTCGGGC ATCGAATCTC GTCAGCTATC GTCAGCTTAC CTTTTTGGCA
5461
``` pCR022 (SEQ ID NO: 14)
ORIGIN

```
   1 GCGATCGCGG CTCCCGACAT CTTGGACCAT TAGCTCCACA GGTATCTTCT TCCCTCTAGT
  61 GGTCATAACA GCAGCTTCAG CTACCTCTCA ATTCAAAAAA CCCCTCAAGA CCCGTTTAGA
```

```
 121 GGCCCCAAGG GGTTATGCTA TCAATCGTTG CGTTACACAC ACAAAAAACC AACACACATC
 181 CATCTTCGAT GGATAGCGAT TTTATTATCT AACTGCTGAT CGAGTGTAGC CAGATCTAGT
 241 AATCAATTAC GGGGTCATTA GTTCATAGCC CATATATGGA GTTCCGCGTT ACATAACTTA
 301 CGGTAAATGG CCCGCCTGGC TGACCGCCCA ACGACCCCCG CCCATTGACG TCAATAATGA
 361 CGTATGTTCC CATAGTAACG CCAATAGGGA CTTTCCATTG ACGTCAATGG GTGGAGTATT
 421 TACGGTAAAC TGCCCACTTG GCAGTACATC AAGTGTATCA TATGCCAAGT ACGCCCCCTA
 481 TTGACGTCAA TGACGGTAAA TGGCCCGCCT GGCATTATGC CCAGTACATG ACCTTATGGG
 541 ACTTTCCTAC TTGGCAGTAC ATCTACGTAT TAGTCATCGC TATTACCATG CTGATGCGGT
 601 TTTGGCAGTA CATCAATGGG CGTGGATAGC GGTTTGACTC ACGGGGATTT CCAAGTCTCC
 661 ACCCCATTGA CGTCAATGGG AGTTTGTTTT GGCACCAAAA TCAACGGGAC TTTCCAAAAT
 721 GTCGTAACAA CTCCGCCCCA TTGACGCAAA TGGGCGGTAG GCGTGTACGG TGGGAGGTCT
 781 ATATAAGCAG AGCTGGTTTA GTGAACCGTC AGATCAGATC TTTGTCGATC CTACCATCCA
 841 CTCGACACAC CCGCCAGCgg ccgccaccat gaaggccaat ctactggtgt tgctgtgtgc
 901 ccttgcggcg gcagatgcca tgcgctgcat cgggatcagc aatcgcgact ttgtggaagg
 961 agtcagcggc ggatcatggg tggacatcgt gcttgagcac ggcagctgcg tgaccactat
1021 ggcaaagaat aagccgactc tggattttga actcattaaa accgaggcga agcagcccgc
1081 aactctgagg aagtactgca tcgaggccaa actgactaac actaccaccg aatcacggtg
1141 cccgacccaa ggcgaaccga gcctgaacga agagcaggat aagagatttg tctgcaagca
1201 ctcaatggtg gaccggggga atggatccgg ctgcggactg aacggatctg ggggcattgt
1261 gacttgcgca atgttcacct gtaaaaagaa caggtgctgc agccagagaa
1321 cctggaatac accattgtca ttactccaca ttccggagag gaacacgccg tcggcaacga
1381 cactggaaaa catgggaagg aaattaagat cacccccgcag tcgtcaatta ccgaggcaga
1441 actcaccggg tacggcactg tcactatgga gtgctcaccg agaactgggt tggatttcaa
1501 tgagatggtg ctcctacaga tggagaacaa ggcatggctc gtgcaccggc aatggtttct
1561 cgacctgccg ctgccttggc tccctgggc cgacactcaa ggctcgaatt ggattcagaa
1621 ggaaacgctg gtcacgttca agaaccccca tgccaagaag caagacgtgg tggtcctggg
1681 ctcgcaagaa ggagctatgc acaccgctct gaccggcgcg accgaaatcc aaatgtcatc
1741 aggcaacctc ctgttcactg gccacctcaa atgccgggta agaatggata agctgcaact
1801 gaaaggtatg tcctactcga tgtgcaccgg taaatttaaa gtggtgaaag agatcgctga
1861 aactcagcac ggtaccatcg tcatcagggt gcagtacgag ggagacggct cacctgcaa
1921 aatcccttc gaaatcatgg acctcgaaaa gagacacgtg ctgggccgcc tgatcaccgt
1981 taacccgatc gtgaccgaga aagacagccc ggtgaatatt gaagcggaac ctccgttcgg
2041 cgacagctac atcattaccg gcgtggaacc gggccagctg aagcttaatt ggttcaaaaa
2101 ggggtccagc ggcggcggca gccatcatca ccatcatcac tgagctagCT TGACTGACTG
2161 AGATACAGCG TACCTTCAGC TCACAGACAT GATAAGATAC ATTGATGAGT TTGGACAAAC
2221 CACAACTAGA ATGCAGTGAA AAAAATGCTT TATTTGTGAA ATTTGTGATG CTATTGCTTT
2281 ATTTGTAACC ATTATAAGCT GCAATAAACA AGTTAACAAC AACAATTGCA TTCATTTTAT
2341 GTTTCAGGTT CAGGGGGAGG TGTGGGAGGT TTTTTAAAGC AAGTAAAACC TCTACAAATG
2401 TGGTATTGGC CCATCTCTAT CGGTATCGTA GCATAACCCC TTGGGGCCTC TAAACGGGTC
2461 TTGAGGGGTT TTTTGTGCCC CTCGGGCCGG ATTGCTATCT ACCGGCATTG GCGCAGAAAA
2521 AAATGCCTGA TGCGACGCTG CGCGTCTTAT ACTCCCACAT ATGCCAGATT CAGCAACGGA
2581 TACGGCTTCC CCAACTTGCC CACTTCCATA CGTGTCCTCC TTACCAGAAA TTTATCCTTA
2641 AGGTCGTCAG CTATCCTGCA GGCGATCTCT CGATTTCGAT CAAGACATTC CTTTAATGGT
2701 CTTTTCTGGA CACCACTAGG GGTCAGAAGT AGTTCATCAA ACTTTCTTCC CTCCCTAATC
2761 TCATTGGTTA CCTTGGGCTA TCGAAACTTA ATTAACCAGT CAAGTCAGCT ACTTGGCGAG
2821 ATCGACTTGT CTGGGTTTCG ACTACGCTCA GAATTGCGTC AGTCAAGTTC GATCTGGTCC
2881 TTGCTATTGC ACCCGTTCTC CGATTACGAG TTTCATTTAA ATCATGTGAG CAAAAGGCCA
2941 GCAAAAGGCC AGGAACCGTA AAAAGGCCGC GTTGCTGGCG TTTTTCCATA GGCTCCGCCC
3001 CCCTGACGAG CATCACAAAA ATCGACGCTC AAGTCAGAGG TGGCGAAACC CGACAGGACT
3061 ATAAAGATAC CAGGCGTTTC CCCCTGGAAG CTCCCTCGTG CGCTCTCCTG TTCCGACCCT
3121 GCCGCTTACC GGATACCTGT CCGCCTTTCT CCCTTCGGGA AGCGTGGCGC TTTCTCATAG
3181 CTCACGCTGT AGGTATCTCA GTTCGGTGTA GGTCGTTCGC TCCAAGCTGG GCTGTGTGCA
3241 CGAACCCCCC GTTCAGCCCG ACCGCTGCGC CTTATCCGGT AACTATCGTC TTGAGTCCAA
3301 CCCGGTAAGA CACGACTTAT CGCCACTGGC AGCAGCCACT GGTAACAGGA TTAGCAGAGC
3361 GAGGTATGTA GGCGGTGCTA CAGAGTTCTT GAAGTGGTGG CCTAACTACG GCTACACTAG
3421 AAGAACAGTA TTTGGTATCT GCGCTCTGCT GAAGCCAGTT ACCTTCGGAA AAAGAGTTGG
3481 TAGCTCTTGA TCCGGCAAAC AAACCACCGC TGGTAGCGGT GGTTTTTTTG TTTGCAAGCA
3541 GCAGATTACG CGCAGAAAAA AAGGATCTCA AGAAGATCCT TTGATCTTTT CTACGGGGTC
3601 TGACGCTCAG TGGAACGAAA ACTCACGTTA AGGGATTTTG GTCATGAGAT TATCAAAAAG
3661 GATCTTCACC TAGATCCTTT TAAATTAAAA ATGAAGTTTT AAATCAATCT AAAGTATATA
3721 TGAGTAAACT TGGTCTGACA GTTACCAATG CTTAATCAGT GAGGCACCTA TCTCAGCGAT
3781 CTGTCTATTT CGTTCATCCA TAGTTGCATT TAAATTTCCG AACTCTCCAA GGCCCTCGTC
3841 GGAAAATCTT CAAACCTTTC GTCCGATCCA TCTTGCAGGC TACCTCTCGA ACGAACTATC
3901 GCAAGTCTCT TGGCCGGCCT TGCGCCTTGG CTATTGCTTG GCAGCGCCTA TCGCCAGGTA
3961 TTACTCCAAT CCCGAATATC CGAGATCGGG ATCACCCGAG AGAAGTTCAA CCTACATCCT
4021 CAATCCCGAT CTATCCGAGA TCCGAGGAAT ATCGAAATCG GGGCGCGCCT GGTGTACCGA
4081 GAACGATCCT CTCAGTGCGA GTCTCGACGA TCCATATCGT TGCTTGGCAG TCAGCCAGTC
4141 GGAATCCAGC TTGGGACCCA GGAAGTCCAA TCGTCAGATA TTGTACTCAA GCCTGGTCAC
4201 GGCAGCGTAC CGATCTGTTT AAACCTAGAT ATTGATAGTC TGATCGGTCA ACGTATAATC
4261 GAGTCCTAGC TTTTGCAAAC ATCTATCAAG AGACAGGATC AGCAGGAGGC TTTCGCATGA
4321 GTATTCAACA TTTTCGTGTC GCCCTTATTC CCTTTTTTGC GGCATTTTGC CTTCCTGTTT
4381 TTGCTCACCC AGAAACGCTG GTGAAAGTAA AAGATGCTGA AGATCAGTTG GGTGCGCGAG
4441 TGGGTTACAT CGAACTGGAT CTCAACAGCG GTAAGATCCT TGAGAGTTTT CGCCCCGAAG
4501 AACGCTTTCC AATGATGAGC ACTTTTAAAG TTCTGCTATG TGGCGCGGTA TTATCCCGTA
4561 TTGACGCCGG GCAAGAGCAA CTCGGTCGCC GCATACACTA TTCTCAGAAT GACTTGGTTG
4621 AGTATTCACC AGTCACAGAA AAGCATCTTA CGGATGGCAT GACAGTAAGA GAATTATGCA
4681 GTGCTGCCAT AACCATGAGT GATAACACTG CGGCCAACTT ACTTCTGACA ACGATTGGAG
```

```
4741 GACCGAAGGA GCTAACCGCT TTTTTGCACA ACATGGGGGA TCATGTAACT CGCCTTGATC
4801 GTTGGGAACC GGAGCTGAAT GAAGCCATAC CAAACGACGA GCGTGACACC ACGATGCCTG
4861 TAGCAATGGC AACAACCTTG CGTAAACTAT TAACTGGCGA ACTACTTACT CTAGCTTCCC
4921 GGCAACAGTT GATAGACTGG ATGGAGGCGG ATAAAGTTGC AGGACCACTT CTGCGCTCGG
4981 CCCTTCCGGC TGGCTGGTTT ATTGCTGATA AATCTGGAGC CGGTGAGCGT GGGTCTCGCG
5041 GTATCATTGC AGCACTGGGG CCAGATGGTA AGCCCTCCCG TATCGTAGTT ATCTACACGA
5101 CGGGGAGTCA GGCAACTATG GATGAACGAA ATAGACAGAT CGCTGAGATA GGTGCCTCAC
5161 TGATTAAGCA TTGGTAACCG ATTCTAGGTG CATTGGCGCA GAAAAAAATG CCTGATGCGA
5221 CGCTGCGCGT CTTATACTCC CACATATGCC AGATTCAGCA ACGGATACGG CTTCCCCAAC
5281 TTGCCCACTT CCATACGTGT CCTCCTTACC AGAAATTTAT CCTTAAGATC CCGAATCGTT
5341 TAAACTCGAC TCTGGCTCTA TCGAATCTCC GTCGTTTCGA GCTTACGCGA ACAGCCGTGG
5401 CGCTCATTTG CTCGTCGGGC ATCGAATCTC GTCAGCTATC GTCAGCTTAC CTTTTTGGCA
5461 pCR023 (SEQ ID NO: 15)
ORIGIN
   1 GCGATCGCGG CTCCCGACAT CTTGGACCAT TAGCTCCACA GGTATCTTCT TCCCTCTAGT
  61 GGTCATAACA GCAGCTTCAG CTACCTCTCA ATTCAAAAAA CCCCTCAAGA CCCGTTTAGA
 121 GGCCCCAAGG GGTTATGCTA TCAATCGTTG CGTTACACAC ACAAAAAACC AACACACATC
 181 CATCTTCGAT GGATAGCGAT TTTATTATCT AACTGCTGAT CGAGTGTAGC CAGATCTAGT
 241 AATCAATTAC GGGGTCATTA GTTCATAGCC CATATATGGA GTTCCGCGTT ACATAACTTA
 301 CGGTAAATGG CCCGCCTGGC TGACCGCCCA ACGACCCCCG CCCATTGACG TCAATAATGA
 361 CGTATGTTCC CATAGTAACG CCAATAGGGA CTTTCCATTG ACGTCAATGG GTGGAGTATT
 421 TACGGTAAAC TGCCCACTTG GCAGTACATC AAGTGTATCA TATGCCAAGT ACGCCCCCTA
 481 TTGACGTCAA TGACGGTAAA TGGCCCGCCT GGCATTATGC CCAGTACATG ACCTTATGGG
 541 ACTTTCCTAC TTGGCAGTAC ATCTACGTAT TAGTCATCGC TATTACCATG CTGATGCGGT
 601 TTTGGCAGTA CATCAATGGG CGTGGATAGC GGTTTGACTC ACGGGGATTT CCAAGTCTCC
 661 ACCCCATTGA CGTCAATGGG AGTTTGTTTT GGCACCAAAA TCAACGGGAC TTTCCAAAAT
 721 GTCGTAACAA CTCCGCCCCA TTGACGCAAA TGGGCGGTAG GCGTGTACGG TGGGAGGTCT
 781 ATATAAGCAG AGCTGGTTTA GTGAACCGTC AGATCAGATC TTTGTCGATC CTACCATCCA
 841 CTCGACACAC CCGCCAGCgg ccgccaccat gaaggccaat ctactggtgt tgctgtgtgc
 901 ccttgcggcg gcagatgcca tgagatgtgt gggcgtgggg aaccgcgact tgtcgaagg
 961 attaagtggc gcgaccgggg tagacgtcgt gctggacgac ggagggtgcg tcacaaccat
1021 ggccaagaac aagcccaccc ttgacattga acttcaaaag acagaagcta ctcagctggc
1081 tacactgcgc aagctgtgca tagagggaaa aatcaccaac ataactacgg actcgaggtg
1141 tcccacacag ggtgaagcgg tcttgcctga agaacaggat cagaattatg tttgtaaaca
1201 tacttatgta gacaggggga atggatccgg gtgcgtgctg aacggatctg gttccctagt
1261 cacatgcgct aagttccagt gcctcgagcc tatcgaaggt aaagtggtcc agtacgagaa
1321 tcttaagtac accgtgatca tcacggtcca tacaggagat caacaccagg ttggaaacga
1381 gacccaagga gtcactgccg aaatcacacc gcaggccagc acgacggagg ctattttgcc
1441 ggagtatggg acactgggac tggaatgctc ccctaggacg ggactagatt ttaatgagat
1501 gattctgctg acaatgaaga acaaggcttg gatggtgcat cgtcaatggt tctttgatct
1561 gccactgccg tgggcagccg gcgccacgac agagaccccca acctggaatc gaaaagagct
1621 gctggtcaca ttcaaaaacg cacacgccaa aaagcaagaa gtggtagtgc ttggctccca
1681 ggaaggtgcc atgcacactg cactcacagg ggctactgaa attcagaatt caggaggcac
1741 ttctatttc gccggccacc tcaaatgccg gttaaagatg gacaagctgg aactgaaagg
1801 tatgtcgtac gcaatgtgca ctaatacatt tgtgctaaag aaggaagtct ccgagactca
1861 gcacgggaca atactgatta aggtggaata caaaggtgag gatgctccct gtaagatccc
1921 cttctctact gaggatggtc agggcaaagc tcataatgat cggttgatca cagcgaatcc
1981 agtggttaca aagaaggagg agccagtgaa tatcgaagca gaacctccct tcggtgagtc
2041 aaacattgtc atcggtatcg gagataacgc tcttaagata aactggtaca aaaagggatc
2101 tagcggcggc ggcagccatc atcaccatca tcactgagct agCTTGACTG ACTGAGATAC
2161 AGCGTACCTT CAGCTCACAG ACATGATAAG ATACATTTGA GAGTTTGGAC AAACCACAAC
2221 TAGAATGCAG TGAAAAAAAT GCTTTATTTG TGAAATTTGT GATGCTATTG CTTTATTTGT
2281 AACCATTATA AGCTGCAATA AACAAGTTAA CAACAACAAT TGCATTCATT TTATGTTTCA
2341 GGTTCAGGGG GAGGTGTGGG AGGTTTTTTA AAGCAAGTAA AACCTCTACA AATGTGGTAT
2401 TGGCCCATCT CTATCGGTAT CGTAGCATAA CCCCTTGGGG CCTCTAAACG GGTCTTGAGG
2461 GGTTTTTTGT GCCCCTCGGG CCGGATTGCT ATCTACCGGC ATTGGCGCAG AAAAAAATGC
2521 CTGATGCGAC GCTGCGCGTC TTATACTCCC ACATATGCCA GATTCAGCAA CGGATACGGC
2581 TTCCCCAACT TGCCCACTTC CATACGTGTC CTCCTTACCA GAAATTTATC CTTAAGGTCG
2641 TCAGCTATCC TGCAGGCGAT CTCTCGATTT CGATCAGACC ATTCCTTTAA TGGTCTTTTC
2701 TGGACACCAC TAGGGGTCAG AAGTAGTTCA TCAAACTTTC TTCCCTCCCT AATCTCATTG
2761 GTTACCTTGG GCTATCGAAA CTTAATTAAC CAGTCAAGTC AGCTACTTGG CGAGATCGAC
2821 TTGTCTGGGT TTCGACTACG CTCAGAATTG CGTCAGTCAA GTTCGATCTG GTCCTTGCTA
2881 TTGCACCCGT TCTCCGATTA CGAGTTTCAT TTAAATCATG TGAGCAAAAG GCCAGCAAAA
2941 GGCCAGGAAC CGTAAAAAGG CCGCGTTGCT GGCGTTTTTC CATAGGCTCC GCCCCCCTGA
3001 CGAGCATCAC AAAAATCGAC GCTCAAGTCA GAGGTGGCGA AACCCGACAG GACTATAAAG
3061 ATACCAGGCG TTTCCCCCTG GAAGCTCCCT CGTGCGCTCT CCTGTTCCGA CCCTGCCGCT
3121 TACCGGATAC CTGTCCGCCT TTCTCCCTTC GGGAAGCGTG GCGCTTTCTC ATAGCTCACG
3181 CTGTAGGTAT CTCAGTTCGG TGTAGGTCGT TCGCTCCAAG CTGGGCTGTG TGCACGAACC
3241 CCCCGTTCAG CCCGACCGCT GCGCCTTATC CGGTAACTAT CGTCTTGAGT CCAACCCGGT
3301 AAGACACGAC TTATCGCCAC TGGCAGCAGC CACTGGTAAC AGGATTAGCA GAGCGAGGTA
3361 TGTAGGCGGT GCTACAGAGT TCTTGAAGTG GTGGCCTAAC TACGGCTACA CTAGAAGAAC
3421 AGTATTTGGT ATCTGCGCTC TGCTGAAGCC AGTTACCTTC GGAAAAGAG TTGGTAGCTC
3481 TTGATCCGGC AAACAAACCA CCGCTGGTAG CGGTGGTTTT TTTGTTTGCA AGCAGCAGAT
3541 TACGCGCAGA AAAAAGGGAT CTCAAGAAGA TCCTTTGATC TTTTCTACGG GGTCTGACGC
3601 TCAGTGGAAC GAAAACTCAC GTTAAGGGAT TTTGGTCATG AGATTATCAA AAAGGATCTT
```

Sequence Listing Free Text

```
3661 CACCTAGATC CTTTTAAATT AAAAATGAAG TTTTAAATCA ATCTAAAGTA TATATGAGTA
3721 AACTTGGTCT GACAGTTACC AATGCTTAAT CAGTGAGGCA CCTATCTCAG CGATCTGTCT
3781 ATTTCGTTCA TCCATAGTTG CATTTAAATT TCCGAACTCT CCAAGGCCCT CGTCGGAAAA
3841 TCTTCAAACC TTTCGTCCGA TCCATCTTGC AGGCTACCTC TCGAACGAAC TATCGCAAGT
3901 CTCTTGGCCG GCCTTGCGCC TTGGCTATTG CTTGGCAGCG CCTATCGCCA GGTATTACTC
3961 CAATCCCGAA TATCCGAGAT CGGGATCACC CGAGAGAAGT TCAACCTACA TCCTCAATCC
4021 CGATCTATCC GAGATCCGAG GAATATCGAA ATCGGGGCGC GCCTGGTGTA CCGAGAACGA
4081 TCCTCTCAGT GCGAGTCTCG ACGATCCATA TCGTTGCTTG GCAGTCAGCC AGTCGGAATC
4141 CAGCTTGGGA CCCAGGAAGT CCAATCGTCA GATATTGTAC TCAAGCCTGG TCACGGCAGC
4201 GTACCGATCT GTTTAAACCT AGATATTGAT AGTCTGATCG GTCAACGTAT AATCGAGTCC
4261 TAGCTTTTGC AAACATCTAT CAAGAGACAG GATCAGCAGG AGGCTTTCGC ATGAGTATTC
4321 AACATTTCCG TGTCGCCCTT ATTCCCTTTT TTGCGGCATT TTGCCTTCCT GTTTTTGCTC
4381 ACCCAGAAAC GCTGGTGAAA GTAAAAGATG CTGAAGATCA GTTGGGTGCG CGAGTGGGTT
4441 ACATCGAACT GGATCTCAAC AGCGGTAAGA TCCTTGGAGA TTTTCGCCCC GAAGAACGCT
4501 TTCCAATGAT GAGCACTTTT AAAGTTCTGC TATGTGGCGC GGTATTATCC CGTATTGACG
4561 CCGGGCAAGA GCAACTCGGT CGCCGCATAC ACTATTCTCA GAATGACTTG GTTGAGTATT
4621 CACCAGTCAC AGAAAAGCAT CTTACGGATG GCATGACAGT AAGAGAATTA TGCAGTGCTG
4681 CCATAACCAT GAGTGATAAC ACTGCGGCCA ACTTACTTCT GACAACGATT GGAGGACCGA
4741 AGGAGCTAAC CGCTTTTTTG CACAACATGG GGGATCATGT AACTCGCCTT GATCGTTGGG
4801 AACCGGAGCT GAATGAAGCC ATACCAAACG ACGAGCGTGA CACCACGATG CCTGTAGCAA
4861 TGGCAACAAC CTTGCGTAAA CTATTAACTG GCGAACTACT TACTCTAGCT TCCCGGCAAC
4921 AGTTGATAGA CTGGATGGAG GCGGATAAAG TTGCAGGACC ACTTCTGCGC TCGGCCCTTC
4981 CGGCTGGCTG GTTTATTGCT GATAAATCTG GAGCCGGTGA GCGTGGGTCT CGCGGTATCA
5041 TTGCAGCACT GGGGCCAGAT GGTAAGCCCT CCCGTATCGT AGTTATCTAC ACGACGGGGA
5101 GTCAGGCAAC TATGGATGAA CGAAATAGAC AGATCGCTGA GATAGGTGCC TCACTGATTA
5161 AGCATTGGTA ACCGATTCTA GGTGCATTGG CGCAGAAAAA AATGCCTGAT GCGACGCTGC
5221 GCGTCTTATA CTCCCACATA TGCCAGATTC AGCAACGGAT ACGGCTTCCC CAACTTGCCC
5281 ACTTCCATAC GTGTCCTCCT TACCAGAAAT TTATCCTTAA GATCCCGAAT CGTTTAAACT
5341 CGACTCTGGC TCTATCGAAT CTCCGTCGTT TCGAGCTTAC GCGAACAGCC GTGGCGCTCA
5401 TTTGCTCGTC GGGCATCGAA TCTCGTCAGC TATCGTCAGC TTACCTTTTT GGCA
//
pCR024 (SEQ ID NO: 16)
ORIGIN
   1 GCGATCGCGG CTCCCGACAT CTTGGACCAT TAGCTCCACA GGTATCTTCT TCCCTCTAGT
  61 GGTCATAACA GCAGCTTCAG CTACCTCTCA ATTCAAAAAA CCCCTCAAGA CCCGTTTAGA
 121 GGCCCCAAGG GGTTATGCTA TCAATCGTTG CGTTACACAC ACAAAAAACC AACACACATC
 181 CATCTTCGAT GGATAGCGAT TTTATTATCT AACTGCTGAT CGAGTGTAGC CAGATCTAGT
 241 AATCAATTAC GGGGTCATTA GTTCATAGCC CATATATGGA GTTCCGCGTT ACATAACTTA
 301 CGGTAAATGG CCCGCCTGGC TGACCGCCCA ACGACCCCCG CCCATTGACG TCAATAATGA
 361 CGTATGTTCC CATAGTAACG CCAATAGGGA CTTTCCATTG ACGTCAATGG GTGGAGTATT
 421 TACGGTAAAC TGCCCACTTG GCAGTACATC AAGTGTATCA TATGCCAAGT ACGCCCCCTA
 481 TTGACGTCAA TGACGGTAAA TGGCCCGCCT GGCATTATGC CCAGTACATG ACCTTATGGG
 541 ACTTTCCTAC TTGGCAGTAC ATCTACGTAT TAGTCATCGC TATTACCATG CTGATGCGGT
 601 TTTGGCAGTA CATCAATGGG CGTGGATAGC GGTTTGACTC ACGGGGATTT CCAAGTCTCC
 661 ACCCCATTGA CGTCAATGGG AGTTTGTTTT GGCACCAAAA TCAACGGGAC TTTCCAAAAT
 721 GTCGTAACAA CTCCGCCCCA TTGACGCAAA TGGGCGGTAG GCGTGTACGG TGGGAGGTCT
 781 ATATAAGCAG AGCTGGTTTA GTGAACCGTC AGATCAGATC TTTGTCGATC CTACCATCCA
 841 CTCGACACAC CCGCCAGCgg ccgccaccat gaaggccaat ctactggtgt tgctgtgtgc
 901 ccttgcggcg gcagatgcca tgcgatgcgt ggggtgggc aatagagatt tcgtggaagg
 961 ggtgtctgga ggggcatggg tggatctggt gctgagcac ggcggatgtg tcacaactat
1021 ggcccagggg aagccaaccc tggatttcga gctaactaag accacagcta aggaggtagc
1081 cctgcttcgg acttactgta ttgaggcatc catctctaac atcaccaccg ccacgagatg
1141 cccgacacag ggcgaaccct acttgaagga agaacaggat cagcagtaca tttgccggcg
1201 cgatgttgtt gatagaggca atggctccgg gtgtggcctc aacggctctg gtggggtggt
1261 cacctgtgcc aagttcagct gttctggcaa gatcacggga aatctggtgc aaattgaaaa
1321 ttgggaatat acggtcgttg tgactgtcca caatggcgat acacatgctg tgggcaacga
1381 taccagtaac cacgcgtca ccgcgatgat aactcccgag agcccatctg ttgaagttaa
1441 actgcccgat tacggagagt tgacactcga ctgcgaaccg aggtctgaa tagatttcaa
1501 cgagatgata cttatgaaaa tgaagaaaaa gacctggctc gtacacaagc agtggttttt
1561 ggatttgccc ctcccttgga ccgcaggggc cgataccagc gaggtgcatt ggaattacaa
1621 agagcgcatg gtgactttca aagtgcccca gcaaagggta caagatgtga ctgtattagg
1681 atcacaggaa ggcgctatgc attccgccct ggctggtgcc acggaggtgg attcaggaga
1741 cggtaaccat atgtttgctg gccacctcaa atgtaaggtc cgcatggaaa aacttcgcat
1801 taaggaatg tcctacgca tgtgctcagg aaagttctct atcgacaagg aaatggccga
1861 gactcagcat ggaacgactg tagtcaaggt gaaatatgaa ggtgccgggg cgccttgcaa
1921 ggtgccaatc gaaatccgaa acgttaacaa ggagaaggtg gttgggagga ttataagtag
1981 cactccgctc gcagagaaca ccaatagcgt gactaacata gaactggagc ccccttttgg
2041 ggatagctac attgtgattg gagtagggaa tagtgcacta acattgcact ggttcagaaa
2101 agggtcttca ggcggcgca gccatcatca ccatcatcac tgagctagCT TGACTGACTG
2161 AGATACAGCG TACCTTCAGC TCACAGACAT GATGAGT TTGGACAAAC
2221 CACAACTAGA ATGCAGTGAA AAAATGCTT TATTTGTGAA ATTTGTGATG CTATTGCTTT
2281 ATTTGTAACC ATTATAAGCT GCAATAAACA AGTTAACAAC AACAATTGCA TTCATTTTAT
2341 GTTTCAGGTT CAGGGGGAGG TGTGGGAGGT TTTTTAAAGC AAGTAAAACC TCTACAAATG
2401 TGGTATTGGC CCATCTCTAT CGGTATCGTA GCATAACCCC TTGGGGCCTC TAAACGGGTC
2461 TTGAGGGGTT TTTTGTGCCC CTCGGGCCGG ATTGCTATCT ACCGGCATTG GCGCAGAAAA
2521 AAATGCCTGA TGCGACGCTG CGCGTCTTAT ACTCCCACAT ATGCCAGATT CAGCAACGGA
```

-continued

Sequence Listing Free Text

```
2581 TACGGCTTCC CCAACTTGCC CACTTCCATA CGTGTCCTCC TTACCAGAAA TTTATCCTTA
2641 AGGTCGTCAG CTATCCTGCA GGCGATCTCT CGATTTCGAT CAAGACATTC CTTTAATGGT
2701 CTTTTCTGGA CACCACTAGG GGTCAGAAGT AGTTCATCAA ACTTTCTTCC CTCCCTAATC
2761 TCATTGGTTA CCTTGGGCTA TCGAAACTTA ATTAACCAGT CAAGTCAGCT ACTTGGCGAG
2821 ATCGACTTGT CTGGGTTTCG ACTACGCTCA GAATTGCGTC AGTCAAGTTC GATCTGGTCC
2881 TTGCTATTGC ACCCGTTCTC CGATTACGAG TTTCATTTAA ATCATGTGAG CAAAAGGCCA
2941 GCAAAAGGCC AGGAACCGTA AAAAGGCCGC GTTGCTGGCG TTTTTCCATA GGCTCCGCCC
3001 CCCTGACGAG CATCACAAAA ATCGACGCTC AAGTCAGAGG TGGCGAAACC CGACAGGACT
3061 ATAAAGATAC CAGGCGTTTC CCCCTGGAAG CTCCCTCGTG CGCTCTCCTG TTCCGACCCT
3121 GCCGCTTACC GGATACCGTG CCGCCTTTCT CCCTTCGGGA AGCGTGGCGC TTTCTCATAG
3181 CTCACGCTGT AGGTATCTCA GTTCGGTGTA GGTCGTTCGC TCCAAGCTGG GCTGTGTGCA
3241 CGAACCCCCC GTTCAGCCCG ACCGCTGCGC CTTATCCGGT AACTATCGTC TTGAGTCCAA
3301 CCCGGTAAGA CACGACTTAT CGCCACTGGC AGCAGCCACT GGTAACAGGA TTAGCAGAGC
3361 GAGGTATGTA GGCGGTGCTA CAGAGTTCTT GAAGTGGTGG CCTAACTACG GCTACACTAG
3421 AAGAACAGTA TTTGGTATCT GCGCTCTGCT GAAGCCAGTT ACCTTCGGAA AAAGAGTTGG
3481 TAGCTCTTGA TCCGGCAAAC AAACCACCGC TGGTAGCGGT GGTTTTTTTG TTTGCAAGCA
3541 GCAGATTACG CGCAGAAAAA AAGGATCTCA AGAAGATCCT TTGATCTTTT CTACGGGGTC
3601 TGACGCTCAG TGGAACGAAA ACTCACGTTA AGGGATTTTG GTCATGAGAT TATCAAAAAG
3661 GATCTTCACC TAGATCCTTT TAAATTAAAA ATGAAGTTTT AAATCAATCT AAAGTATATA
3721 TGAGTAAACT TGGTCTGACA GTTACCAATG CTTAATCAGT GAGGCACCTA TCTCAGCGAT
3781 CTGTCTATTT CGTTCATCCA TAGTTGCATT TAAATTTCCG AACTCTCCAA GGCCCTCGTC
3841 GGAAAATCTT CAAACCTTTC GTCCGATCCA TCTTGCAGGC TACCTCTCGA ACGAACTATC
3901 GCAAGTCTCT TGGCCGGCCT TGCGCCTTGG CTATTGCTTG GCAGCGCCTA TCGCCAGGTA
3961 TTACTCCAAT CCCGAATATC CGAGATCGGG ATCACCCAGG AGAAGTTCAA CCTACATCCT
4021 CAATCCCGAT CTATCCGAGA TCCGAGGAAT ATCGAAATCG GGGCGCGCCT GGTGTACCGA
4081 GAACGATCCT CTCAGTGCGA GTCTCGACGA TCCATATCGT TGCTTGGCAG TCAGCCAGTC
4141 GGAATCCAGC TTGGGACCCA GGAAGTCCAA TCGTCAGATA TTGTACTCAA GCCTGGTCAC
4201 GGCAGCGTAC CGATCTGTTT AAACCTAGAT ATTGATAGTC TGATCGGTCA ACGTATAATC
4261 GAGTCCTAGC TTTTGCAAAC ATCTATCAAG AGACAGGATC AGCAGGAGGC TTTCGCATGA
4321 GTATTCAACA TTTCCGTGTC GCCCTTATTC CCTTTTTTGC GGCATTTTGC CTTCCTGTTT
4381 TTGCTCACCC AGAAACGCTG GTGAAAGTAA AAGATGCTGA AGATCAGTTG GGTGCGCGAG
4441 TGGGTTACAT CGAACTGGAT CTCAACAGCG GTAAGATCCT TGAGAGTTTT CGCCCCGAAG
4501 AACGCTTTCC AATGATGAGC ACTTTTAAAG TTCTGCTATG TGGCGCGGTA TTATCCCGTA
4561 TTGACGCCGG GCAAGAGCAA CTCGGTCGCC GCATACACTA TTCTCAGAAT GACTTGGTTG
4621 AGTATTCACC AGTCACAGAA AAGCATCTTA CGGATGGCAT GACAGTAAGA GAATTATGCA
4681 GTGCTGCCAT AACCATGAGT GATAACACTG CGGCCAACTT ACTTCTGACA ACGATTGGAG
4741 GACCGAAGGA GCTAACCGCT TTTTTGCACA ACATGGGGGA TCATGTAACT CGCCTTGATC
4801 GTTGGGAACC GGAGCTGAAT GAAGCCATAC CAAACGACGA GCGTGACACC ACGATGCCTG
4861 TAGCAATGGC AACAACCTTG CGTAAACTAT TAACTGGCGA ACTACTTACT CTAGCTTCCC
4921 GGCAACAGTT GATAGACTGG ATGGAGGCGG ATAAAGTTGC AGGACCACTT CTGCGCTCGG
4981 CCCTTCCGGC TGGCTGGTTT ATTGCTGATA AATCTGGAGC CGGTGAGCGT GGGTCTCGCG
5041 GTATCATTGC AGCACTGGGG CCAGATGGTA AGCCCTCCCG TATCGTAGTT ATCTACACGA
5101 CGGGGAGTCA GGCAACTATG GATGAACGAA ATAGACAGAT CGCTGAGATA GGTGCCTCAC
5161 TGATTAAGCA TTGGTAACCG ATTCTAGGTG CATTGGCGCA GAAAAAAATG CCTGATGCGA
5221 CGCTGCGCGT CTTATACTCC CACATATGCC AGATTCAGCA ACGGATACGG CTTCCCCAAC
5281 TTGCCCACTT CCATACGTGT CCTCCTTACC AGAAATTTAT CCTTAAGATC CCGAATCGTT
5341 TAAACTCGAC TCTGGCTCTA TCGAATCTCC GTCGTTCGA GCTTACGCGA ACAGCCGTGG
5401 CGCTCATTTG CTCGTCGGGC ATCGAATCTC GTCAGCTATC GTCAGCTTAC CTTTTTGGCA
5461
```

//
pCR028 (SEQ ID NO: 17)
ORIGIN
```
   1 GCGATCGCGG CTCCCGACAT CTTGGACCAT TAGCTCCACA GGTATCTTCT TCCCTCTAGT
  61 GGTCATAACA GCAGCTTCAG CTACCTCTCA ATTCAAAAAA CCCCTCAAGA CCCGTTTAGA
 121 GGCCCCAAGG GGTTATGCTA TCAATCGTTG CGTTACACAC ACAAAAAACC AACACACATC
 181 CATCTTCGAT GGATAGCGAT TTTATTATCT AACTGCTGAT CGAGTGTAGC CAGATCTAGT
 241 AATCAATTAC GGGGTCATTA GTTCATAGCC CATATATGGA GTTCCGCGTT ACATAACTTA
 301 CGGTAAATGG CCCGCCTGGC TGACCGCCCA ACGACCCCCG CCCATTGACG TCAATAATGA
 361 CGTATGTTCC CATAGTAACG CCAATAGGGA CTTTCCATTG ACGTCAATGG GTGGAGTATT
 421 TACGGTAAAC TGCCCACTTG GCAGTACATC AAGTGTATCA TATGCCAAGT ACGCCCCCTA
 481 TTGACGTCAA TGACGGTAAA TGGCCCGCCT GGCATTATGC CCAGTACATG ACCTTATGGG
 541 ACTTTCCTAC TTGGCAGTAC ATCTACGTAT TAGTCATCGC TATTACCATG CTGATGCGGT
 601 TTTGGCAGTA CATCAATGGG CGTGGATAGC GGTTTGACTC ACGGGGATTT CCAAGTCTCC
 661 ACCCCATTGA CGTCAATGGG AGTTTGTTTT GGCACCAAAA TCAACGGGAC TTTCCAAAAT
 721 GTCGTAACAA CTCCGCCCCA TTGACGCAAA TGGGCGGTAG GCGTGTACGG TGGGAGGTCT
 781 ATATAAGCAG AGCTGGTTTA GTGAACCGTC AGATCAGATC TTTGTCGATC CTACCATCCA
 841 CTCGACACAC CGCCAGCGg ccgccaccat gaaggccaat ctactggtgt tgctgtgtgc
 901 ccttgcggcg gcagatgccA TCAGGTGCAT TGGAGTCAGC AACAGGGACT TCGTCGAAGG
 961 CATGTCCGGC GGCACCTGGG TGGATGTGGT GCTCGAACAC GGCGGATGCG TGACCGTCAT
1021 GGCCCAGGAC AAGCCTACCG TCGATATTGA GCTGGTGACC ACCACAGTGA GCAACATGGC
1081 CGAAGTGAGA AGCTACTGCT ATGAGGCCTC CATCAGCGAT ATGGCTTCCG ATTCCAGATG
1141 CCCCACACAG GGAGAGGCTT ATCTGGACAA ACAGTCCGAC ACCCAGTACG TCTGCAAAAG
1201 AACCCTGGTG GACAGAaacc acaccAACGG ATGCGGCCTG TTCGGCAAAG GCAGCCTCGT
1261 GACATGTGCC AAGTTCGCCT GCAGCAAAAA GATGACCGGC AAGTCCATCC AGCCCGAGAA
1321 CCTGGAATAC AGGATCATGC TGTCCGTGCA TGGATCCCAG CACTCCGGCA TGATCGTCAA
1381 CGATACCGGC CACGAGACCG ACGAGAACAG GGCTAAAGTG GAGATCACCC CCAACAGCCC
```

Sequence Listing Free Text

```
1441 TAGAGCCGAA GCTACACTGG GCGGCTTCGG AAGCCTGGGC CTGGATTGCG AACCCAGGAC
1501 CGGCCTGGAT TTCAGCGACC TGTATTACCT GACCATGAAC AATAAGCACT GGCTGGTGCA
1561 CAAGGAATGG TTCCACGACA TCCCCCTGCC TTGGCATGCT GGCGCCGATA CCGGCACACC
1621 TCACTGGAAC AATAAGGAAG CCCTGGTCGA GTTTAAGGAC GCCCACGCCA AAAGACAGAC
1681 CGTGGTGGTG CTGGGAAGCC AGGAGGGAGC TGTCCACACA GCCCTGGCCG GAGCTCTGGA
1741 AGCCGAGATG GATGGCGCCA AGGGCAGGCT GAGCTCCGGC CACCTGAAAT GCAGGCTCAA
1801 GATGGACAAG CTGAGGCTGA AGGGCGTGAG CTACAGCCTG TGCACCGCCG CTTTCACCTT
1861 TACCAAGATC CCTGCCGAGA CACTGCACGG CACCGTCACC GTGGAGGTGC AATACGCCGG
1921 AACCGATGGA CCTTGCAAAG TGCCTGCCCA GATGGCTGTG GATATGCAGA CCCTCACACC
1981 CGTCGGCAGG CTGATCACCG CCAATCCCGT CATTACCGAG TCCACCGAGA ACAGCAAGAT
2041 GATGCTcGAG CTCGATCCCC CCTTTGGCGA CAGCTACATT GTGATCGGCG TGGGCGAGAA
2101 GAAGATCACC CACCATTGGC ACAGAAGCGG CTCCACAggg ggtagcggtg gtagcggagg
2161 tagccatcac caccatcacc actgagctag CTTGACTGAC TGAGATACAG CGTACCTTCA
2221 GCTCACAGAC ATGATAAGAT ACATTGATGA GTTTGGACAA ACCACAACTA GAATGCAGTG
2281 AAAAAAATGC TTTATTTGTG AAATTTGTGA TGCTATTGCT TTATTTGTAA CCATTATAAG
2341 CTGCAATAAA CAAGTTAACA ACAACAATTG CATTCATTTT ATGTTTCAGG TTCAGGGGGA
2401 GGTGTGGGAG GTTTTTTAAA GCAAGTAAAA CCTCTACAAA TGTGGTATTG GCCCATCTCT
2461 ATCGGTATCG TAGCATAACC CCTTGGGGCC TCTAAACGGG TCTTGAGGGG TTTTTTGTGC
2521 CCCTCGGGCC GGATTGCTAT CTACCGGCAT TGGCGCAGAA AAAAATGCCT GATGCGACGC
2581 TGCGCGTCTT ATACTCCCAC ATATGCCAGA TTCAGCAACG GATACGGCTT CCCCAACTTG
2641 CCCACTTCCA TACGTGTCCT CCTTACCAGA AATTTATCCT TAAGGTCGTC AGCTATCCTG
2701 CAGGCGATCT CTCGATTTCG ATCAAGACAT TCCTTTAATG GTCTTTTCTG GACACCACTA
2761 GGGGTCAGAA GTAGTTCATC AAACTTTCTT CCCTCCCTAA TCTCATTGGT TACCTTGGGC
2821 TATCGAAACT TAATTAACCA GTCAAGTCAG CTACTTGGTG AGATCGACTT GTCTGGGTTT
2881 CGACTACGCT CAGAATTGCG TCAGTCAAGT TCGATCTGGT CCTTGCTATT GCACCCGTTC
2941 TCCGATTACG AGTTTCATTT AAATCATGTG AGCAAAAGGC CAGCAAAAGG CCAGGAACCG
3001 TAAAAAGGCC GCGTTGCTGG CGTTTTTCCA TAGGCTCCGC CCCCCTGACG AGCATCACAA
3061 AAATCGACGC TCAAGTCAGA GGTGGCGAAA CCCGACAGGA CTATAAAGAT ACCAGGCGTT
3121 TCCCCCTGGA AGCTCCCTCG TGCGCTCTCC TGTTCCGACC CTGCCGCTTA CCGGATACCT
3181 GTCCGCCTTT CTCCCTTCGG AAGCGTGGCG CTTTCTCAT AGCTCACGCT GTAGGTATCT
3241 CAGTTCGGTG TAGGTCGTTC GCTCCAAGCT GGGCTGTGTG CACGAACCCC CCGTTCAGCC
3301 CGACCGCTGC GCCTTATCCG GTAACTATCG TCTTGAGTCC AACCCGGTAA GACACGACTT
3361 ATCGCCACTG GCAGCAGCCA CTGGTAACAG GATTAGCAGA GCGAGGTATG TAGGCGGTGC
3421 TACAGAGTTC TTGAAGTGGT GGCCTAACTA CGGCTACACT AGAAGAACAG TATTTGGTAT
3481 CTGCGCTCTG CTGAAGCCAG TTACCTTCGG AAAAAGAGTT GGTAGCTCTT GATCCGGCAA
3541 ACAAACCACC GCTGGTAGCG GTGGTTTTTT TGTTTGCAAG CAGCAGATTA CGCGCAGAAA
3601 AAAAGGATCT CAAGAAGATC CTTTGATCTT TTCTACGGGG TCTGACGCTC AGTGGAACGA
3661 AAACTCACGT TAAGGGATTT TGGTCATGAG ATTATCAAAA AGGATCTTCA CCTAGATCCT
3721 TTTAAATTAA AAATGAAGTT TTAAATCAAT CTAAAGTATA TATGAGTAAA CTTGGTCTGA
3781 CAGTTACCAA TGCTTAATCA GTGAGGCACC TATCTCACG ATCGTCTAT TTCGTTCATC
3841 CATAGTTGCA TTTAAATTTC CGAACTCTCC AAGGCCCTCG TCGGAAAATC TTCAAACCTT
3901 TCGTCCGATC CATCTTGCAG GCTACCTCTC GAACGAACTA TCGCAAGTCT CTTGGCCGGC
3961 CTTGCGCCTT GGCTATTGCT TGGCAGCGCC TATCGCCAGG TATTACTCCA ATCCCGAATA
4021 TCCGAGATCG GGATCACCCG AGAGAAGTTC AACCTACATC CTCAATCCCG ATCTATCCGA
4081 GATCCGAGGA ATATCGAAAT CGGGGCGCGC CTGGTGATCC GAGAACGATC CTCTCAGTGC
4141 GAGTCTCGAC GATCCATATC GTTGCTTGGC AGTCAGCCAG TCGGAATCCA GCTTGGGACC
4201 CAGGAAGTCC AATCGTCAGA TATTGTACTC AAGCCTGGTC ACGGCAGCGT ACCGATCTGT
4261 TTAAACCTAG ATATTGATAG TCTGATCGGT CAACGTATAA TCGAGTCCTA GCTTTTGCAA
4321 ACATCTATCA AGAGACAGGA TCAGCAGGAG GCTTTCGCAT CATTTCCGTG
4381 TCGCCCTTAT TCCCTTTTTT GCGGCATTTT GCCTTCCTGT TTTTGCTCAC CCAGAAACGC
4441 TGGTGAAAGT AAAAGATGCT GAAGATCAGT TGGGTGCGCG AGTGGGTTAC ATCGAACTGG
4501 ATCTCAACAG CGGTAAGATC CTTGAGAGTT TTCGCCCCGA AGAACGCTTT CCAATGATGA
4561 GCACTTTTAA AGTTCTGCTA TGTGGCGCGG TATTATCCGG TATTGACGCC GGGCAAGAGC
4621 AACTCGGTCG CCGCATACAC TATTCTCAGA ATGACTTGGT TGAGTATTCA CCAGTCACAG
4681 AAAAGCATCT TACGGATGGC ATGACAGTAA GAGAATTATG CAGTGCTGCC ATAACCATGA
4741 GTGATAACAC TGCGGCCAAC TTACTTCTGA CAACGATTGG AGGACCGAAG GAGCTAACCG
4801 CTTTTTTGCA CAACATGGGG GATCATGTAA CTCGCCTTGA TCGTTGGGAA CCGGAGCTGA
4861 ATGAAGCCAT ACCAAACGAC GAGCGTGACA CCACGATGCC TGTAGCAATG GCAACAACCT
4921 TGCGTAAACT ATTAACTGGC GAACTACTTA CTCTAGCTTC CCGGCAACAG TTGATAGACT
4981 GGATGGAGGC GGATAAAGTT GCAGGACCAC TTCTGCGCTC GGCCCTTCCG GCTGGCTGGT
5041 TTATTGCTGA TAAATCTGGA GCCGGTGAGC GTGGGTCTCG CGGTATCATT GCAGCACTGG
5101 GGCCAGATGG TAAGCCCTCC CGTATCGTAG TTATCTACAC GACGGGGAGT CAGGCAACTA
5161 TGGATGAACG AAATAGACAG ATCGCTGAGA TAGGTGCCTC ACTGATTAAG CATTGGTAAC
5221 CGATTCTAGG TGCATTGGCG CAGAAAAAAA TGCCTGATGC GACGCTGCGC GTCTTATACT
5281 CCCACATATG CCAGATTCAG CAACGGATAC GGCTTCCCCA ACTTGCCCAC TTCCATACGT
5341 GTCCTCCTTA CCAGAAATTT ATCCTTAAGA TCCCGAATCG TTTAAACTCG ACTCTGGCTC
5401 TATCGAATCT CCGTCGTTTC GAGCTTACGC GAACAGCCGT GGCGCTCATT TGCTCGTCGG
5461 GCATCGAATC TCGTCAGCTA TCGTCAGCTT ACCTTTTGG CA pCR025 (SEQ ID NO: 18)
ORIGIN
   1 GCGATCGCGG CTCCCGACAT CTTGGACCAT TAGCTCCACA GGTATCTTCT TCCCTCTAGT
  61 GGTCATAACA GCAGCTTCAG CTACCTCTCA ATTCAAAAAA CCCCTCAAGA CCCGTTTAGA
 121 GGCCCCAAGG GGTTATGCTA TCAATCGTTG CGTTACACAC ACAAAAAACC AACACACATC
 181 CATCTTCGAT GGATAGCGAT TTTATTATCT AACTGCTGAT CGAGTGTAGC CAGATCTAGT
 241 AATCAATTAC GGGGTCATTA GTTCATAGCC CATATATGGA GTTCCGCGTT ACATAACTTA
 301 CGGTAAATGG CCCGCCTGGC TGACCGCCCA ACGACCCCCG CCCATTGACG TCAATAATGA
```

-continued

Sequence Listing Free Text

```
361 CGTATGTTCC CATAGTAACG CCAATAGGGA CTTTCCATTG ACGTCAATGG GTGGAGTATT
421 TACGGTAAAC TGCCCACTTG GCAGTACATC AAGTGTATCA TATGCCAAGT ACGCCCCCTA
481 TTGACGTCAA TGACGGTAAA TGGCCCGCCT GGCATTATGC CCAGTACATG ACCTTATGGG
541 ACTTTCCTAC TTGGCAGTAC ATCTACGTAT TAGTCATCGC TATTACCATG CTGATGCGGT
601 TTTGGCAGTA CATCAATGGG CGTGGATAGC GGTTTGACTC ACGGGGATTT CCAAGTCTCC
661 ACCCCATTGA CGTCAATGGG AGTTTGTTTT GGCACCAAAA TCAACGGGAC TTTCCAAAAT
721 GTCGTAACAA CTCCGCCCCA TTGACGCAAA TGGGCGGTAG GCGTGTACGG TGGGAGGTCT
781 ATATAAGCAG AGCTGGTTTA GTGAACCGTC AGATCAGATC TTTGTCGATC CTACCATCCA
841 CTCGACACAC CCGCCAGCgg ccgccaccat gaaggccaat ctactggtgt tgctgtgtgc
901 ccttgcggcg gcagatgcca tcaggtgcat tggagtcagc aacagggact tcgtcgaagg
961 catgtccggc ggcacctggg tggatgtggt gctcgaacac ggcggatgcg tgaccgtcat
1021 ggcccaggac aagcctaccg tcgatattga gctggtgacc accacagtga gcaacatggc
1081 cgaagtgaga agctactgct atgaggcctc catcagcgat atggcttccg attccagatg
1141 ccccacacag ggagaggctt atctggacaa acagtccgac acccagtacg tctgcaaaag
1201 aaccctggtg gacagaggca atggatccgg atgcggcctg aacggctctg gcagcctcgt
1261 gacatgtgcc aagttcgcct gcagcaaaaa gatgaccggc aagtccatcc agcccgagaa
1321 cctggaatac aggatcatgc tgtccgtgca tggatcccag cactccggca tgatcgtcaa
1381 cgataccggc cacgagaccg acgagaacag ggctaaagtg gagatcaccc ccaacagccc
1441 tagagccgaa gctacactgg gcggcttcgg aagcctgggc ctggattgcg aacccaggac
1501 cggcctggat ttcagcgacc tgtattacct gaccatgaac aataagcact ggctggtgca
1561 caaggaatgg ttccacgaca tccccctgcc ttggcatgct ggcgccgata ccggcacacc
```

```
1621 tcactggaac aataaggaag ccctggtcga gtttaaggac gcccacgcca aaagacagac
1681 cgtggtggtg ctgggaagcc aggagggagc tgtccacaca gccctggccg gagctctgga
1741 agccgagatg gatggcgcca agggcaggct gagctccggc cacctgaaat gcaggctcaa
1801 gatggacaag ctgaggctga agggcgtgag ctacagcctg tgcaccgccg ctttcacctt
1861 taccaagatc cctgccgaga cactgcacgg caccgtcacc gtggaggtgc aatacgccgg
1921 aaccgatgga ccttgcaaag tgcctgccca gatggctgtg gatatgcaga ccctcacacc
1981 cgtcggcagg ctgatcaccg ccaatcccgt cattaccgag tccaccgaga acagcaagat
2041 gatgctcgag ctcgatcccc cctttggcga cagctacatt gtgatcggcg tgggcgagaa
2101 gaagatcacc caccattggc acagaagcgg ctccacaggg ggtagcggtg gtagcggagg
2161 tagccatcac caccatcacc actgagctag CTTGACTGAC TGAGATACAG CGTACCTTCA
2221 GCTCACAGAC ATGATAAGAT ACATTGATGA GTTTGGACAA ACCACAACTA GAATGCAGTG
2281 AAAAAAATGC TTTATTTGTG AAATTTGTGA TGCTATTGCT TTATTTGTAA CCATTATAAG
2341 CTGCAATAAA CAAGTTAACA ACAACAATTG CATTCATTTT ATGTTTCAGG TTCAGGGGGA
2401 GGTGTGGGAG GTTTTTTAAA GCAAGTAAAA CCTCTACAAA TGTGGTATTG GCCCATCTCT
2461 ATCGGTATCG TAGCATAACC CCTTGGGGCC TCTAAACGGG TCTTGAGGGG TTTTTTGTGC
2521 CCCTCGGGCC GGATTGCTAT CTACCGGCAT TGGCGCAGAA AAAAATGCCT GATGCGACGC
2581 TGCGCGTCTT ATACTCCCAC ATATGCCAGA TTCAGCAACG GATACGGCTT CCCCAACTTG
2641 CCCACTTCCA TACGTGTCCT CCTTACCAGA AATTTATCCT TAAGGTCGTC AGCTATCCTG
2701 CAGGCGATCT CTCGATTTCG ATCAAGACAT TCCTTTAATG GTCTTTTCTG GACACCACTA
2761 GGGGTCAGAA GTAGTTCATC AAACTTTCTT CCCTCCCTAA TCTCATTGGT TACCTTGGGC
2821 TATCGAAACT TAATTAACCA GTCAAGTCAG CTACTTGGCG AGATCGACTT GTCTGGGTTT
2881 CGACTACGCT CAGAATTGCG TCAGTCAAGT TCGATCTGGT CCTTGCTATT GCACCCGTTC
2941 TCCGATTACG AGTTTCATTT AAATCATGTG AGCAAAAGGC CAGCAAAAGG CCAGGAACCG
3001 TAAAAAGGCC GCGTTGCTGG CGTTTTTCCA TAGGCTCCGC CCCCCTGACG AGCATCACAA
3061 AAATCGACGC TCAAGTCAGA GGTGGCGAAA CCCGACAGGA CTATAAAGAT ACCAGGCGTT
3121 TCCCCCTGGA AGCTCCCTCG TGCGCTCTCC TGTTCCGACC CTGCCGCTTA CCGGATACCT
3181 GTCCGCCTTT CTCCCTTCGG GAAGCGTGGC GCTTTCTCAT AGCTCACGCT GTAGGTATCT
3241 CAGTTCGGTG TAGGTCGTTC GCTCCAAGCT GGGCTGTGTG CACGAACCCC CCGTTCAGCC
3301 CGACCGCTGC GCCTTATCCG GTAACTATCG TCTTGAGTCC AACCCGGTAA GACACGACTT
3361 ATCGCCACTG GCAGCAGCCA CTGGTAACAG GATTAGCAGA GCGAGGTATG TAGGCGGTGC
3421 TACAGAGTTC TTGAAGTGGT GGCCTAACTA CGGCTACACT AGAAGAACAG TATTTGGTAT
3481 CTGCGCTCTG CTGAAGCCAG TTACCTTCGG AAAAAGAGTT GGTAGCTCTT GATCCGGCAA
3541 ACAAACCACC GCTGGTAGCG GTGGTTTTTT TGTTTGCAAG CAGCAGATTA CGCGCAGAAA
3601 AAAAGGATCT CAAGAAGATC CTTTGATCTT TTCTACGGGG TCTGACGCTC AGTGGAACGA
3661 AAACTCACGT TAAGGGATTT TGGTCATGAG ATTATCAAAA AGGATCTTCA CCTAGATCCT
3721 TTTAAATTAA AAATGAAGTT TTAAATCAAT CTAAAGTATA TATGAGTAAA CTTGGTCTGA
3781 CAGTTACCAA TGCTTAATCA GTGAGGCACC TATCTCAGCG ATCTGTCTAT TTCGTTCATC
3841 CATAGTTGCA TTTAAATTTC CGAACTCTCC AAGGCCCTCG TCGGAAAATC TTCAAACCTT
3901 TCGTCCGATC CATCTTGCAG GCTACCTCTC GAACGAACTA TCGCAAGTCT CTTGGCCGGC
3961 CTTGCGCCTT GGCTATTGCT TGGCAGCGCC TATCGCCAGG TATTACTCCA ATCCCGAATA
4021 TCCGAGATCG GGATCACCCG AGAGAAGTTC AACCTACATC CTCAATCCCG ATCTATCCGA
4081 GATCCGAGGA ATATCGAAAT CGGGGCGCGC CTGGTGTACC GAGAACGATC CTCTCAGTGC
4141 GAGTCTCGAC GATCCATATC GTTGCTTGGC AGTCAGCCAG TCGGAATCCA GCTTGGGACC
4201 CAGGAAGTCC AATCGTCAGA TATTGTACTC AAGCCTGGTC ACGGCAGCGT ACCGATCTGT
4261 TTAAACCTAG ATATTGATAG TCTGATCGGT CAACGTATAA TCGAGTCCTA GCTTTTGCAA
4321 ACATCTATCA AGAGACAGGA TCAGCAGGAG GCTTTCGCAT GAGTATTCAA CATTTCCGTG
4381 TCGCCCTTAT TCCCTTTTTT GCGGCATTTT GCCTTCCTGT TTTTGCTCAC CCAGAAACGC
4441 TGGTGAAAGT AAAAGATGCT GAAGATCAGT TGGGTGCGCG AGTGGGTTAC ATCGAACTGG
4501 ATCTCAACAG CGGTAAGATC CTTGAGAGTT TTCGCCCCGA AGAACGCTTT CCAATGATGA
4561 GCACTTTTAA AGTTCTGCTA TGTGGCGCGG TATTATCCCG TATTGACGCC GGGCAAGAGC
4621 AACTCGGTCG CCGCATACAC TATTCTCAGA ATGACTTGGT TGAGTATTCA CCAGTCACAG
4681 AAAAGCATCT TACGGATGGC ATGACAGTAA GAGAATTATG CAGTGCTGCC ATAACCATGA
4741 GTGATAACAC TGCGGCCAAC TTACTTCTGA CAACGATTGG AGGACCGAAG GAGCTAACCG
4801 CTTTTTTGCA CAACATGGGG GATCATGTAA CTCGCCTTGA TCGTTGGGAA CCGGAGCTGA
4861 ATGAAGCCAT ACCAAACGAC GAGCGTGACA CCACGATGCC TGTAGCAATG GCAACAACCT
4921 TGCGTAAACT ATTAACTGGC GAACTACTTA CTCTAGCTTC CCGGCAACAG TTGATAGACT
```

-continued

Sequence Listing Free Text

```
4981 GGATGGAGGC GGATAAAGTT GCAGGACCAC TTCTGCGCTC GGCCCTTCCG GCTGGCTGGT
5041 TTATTGCTGA TAAATCTGGA GCCGGTGAGC GTGGGTCTCG CGGTATCATT GCAGCACTGG
5101 GGCCAGATGG TAAGCCCTCC CGTATCGTAG TTATCTACAC GACGGGGAGT CAGGCAACTA
5161 TGGATGAACG AAATAGACAG ATCGCTGAGA TAGGTGCCTC ACTGATTAAG CATTGGTAAC
5221 CGATTCTAGG TGCATTGGCG CAGAAAAAAA TGCCTGATGC GACGCTGCGC GTCTTATACT
5281 CCCACATATG CCAGATTCAG CAACGGATAC GGCTTCCCCA ACTTGCCCAC TTCCATACGT
5341 GTCCTCCTTA CCAGAAATTT ATCCTTAAGA TCCCGAATCG TTTAAACTCG ACTCTGGCTC
5401 TATCGAATCT CCGTCGTTTC GAGCTTACGC GAACAGCCGT GGCGCTCATT TGCTCGTCGG
5461 GCATCGAATC TCGTCAGCTA TCGTCAGCTT ACCTTTTTGG CA
``` pCR026 (SEQ ID NO: 19)
ORIGIN

```
   1 GCGATCGCGG CTCCCGACAT CTTGGACCAT TAGCTCCACA GGTATCTTCT TCCCTCTAGT
  61 GGTCATAACA GCAGCTTCAG CTACCTCTCA ATTCAAAAAA CCCCTCAAGA CCCGTTTAGA
 121 GGCCCCAAGG GGTTATGCTA TCAATCGTTG CGTTACACAC ACAAAAAACC AACACACATC
 181 CATCTTCGAT GGATAGCGAT TTTATTATCT AACTGCTGAT CGAGTGTAGC CAGATCTAGT
 241 AATCAATTAC GGGGTCATTA GTTCATAGCC CATATATGGA GTTCCGCGTT ACATAACTTA
 301 CGGTAAATGG CCCGCCTGGC TGACCGCCCA ACGACCCCCG CCCATTGACG TCAATAATGA
 361 CGTATGTTCC CATAGTAACG CCAATAGGGA CTTTCCATTG ACGTCAATGG GTGGAGTATT
 421 TACGGTAAAC TGCCCACTTG GCAGTACATC AAGTGTATCA TATGCCAAGT ACGCCCCCTA
 481 TTGACGTCAA TGACGGTAAA TGGCCCGCCT GGCATTATGC CCAGTACATG ACCTTATGGG
 541 ACTTTCCTAC TTGGCAGTAC ATCTACGTAT TAGTCATCGC TATTACCATG CTGATGCGGT
 601 TTTGGCAGTA CATCAATGGG CGTGGATAGC GGTTTGACTC ACGGGGATTT CCAAGTCTCC
 661 ACCCCATTGA CGTCAATGGG AGTTTGTTTT GGCACCAAAA TCAACGGGAC TTTCCAAAAT
 721 GTCGTAACAA CTCCGCCCCA TTGACGCAAA TGGGCGGTAG GCGTGTACGG TGGGAGGTCT
 781 ATATAAGCAG AGCTGGTTTA GTGAACCGTC AGATCAGATC TTTGTCGATC CTACCATCCA
 841 CTCGACACAC CCGCCAGCgg ccgccaccat gaaggccaat ctactggtgt tgctgtgtgc
 901 ccttgcggcg gcagatgcca tgcggtgcgt ggggatcggc aatcgcgatt ttgtagaagg
 961 actatctggt gccacgtggg tcgatgtggt tcttgaacac gggtcatgcg tgaccacgat
1021 ggctaaggat aagccgacct tggacatcga actactgaaa accgaggtca caaaccctgc
1081 tgtgctccgc aagctgtgca tcgaggctaa gatttccaac acaactactg atagccgctg
1141 ccccacccaa ggcgaggcga ccctcgttga agagcaggac agcaacttcg tgtgtcgccg
1201 gacttttcgtg gaccgcggta atgggtccgg atgcggactt TTTGGAAAgg gttccttact
1261 gacttgcgcc aaatttaagt gcgtgactaa gttagagggg aaaatcgttc agtatgagaa
1321 cttaaaatac tcggtgatag ttaccgtgca cacaggcgac cagcatcaag ttgggaacga
1381 aacgacagag cacgggacaa tagcgaccat taccccacag gctccaacga gcgaaattca
1441 gctgacagac tacggtgcac tcaccctgga ctgtagccca cggacccggc tagactttaa
1501 cgagatggtg ctcctgacta tgaaggaaaa gtcatggttg gtgcacaagc agtggttcct
1561 tgatcttcca ttgccctgga cctctggcgc ttcgacctca caagagactt ggaacaggca
1621 ggacttgctc gtgacattca aaacggctca cgctaaaaag caagaggtcg tggttctggg
1681 gagtcaggaa ggcgctatgc ataccgcgtt aacagagatc acagagatcc agaccagtgg
1741 aacaaccact attttcgccg ggcatcttaa gtgtaggctg aagatggata agttgaccct
1801 gaaaggtatg tcatatgtga tgtgcaccgg tagtttcaaa ctggagaaag aagtggccga
1861 aacccagcat ggaacagtac tggtgcaagt caaatatgag ggcaccgatg caccatgtaa
1921 aataccctcc agcgcacaag acgagaaggg agttaaccag aacggtaggc tgataacagc
1981 caatccaatc gtcaccgata aggagaaacc agtaaacatc gaaaccgagc caccccttcgg
2041 cgaaagctac atcgtggtcg gcgctggcga gaaagcactt aagctgagct ggtttaagaa
2101 aggtagcacg ggcggcggca gccatcatca ccatcatcac tgagctagCT TGACTGACTG
2161 AGATACAGCG TACCTTCAGC TCACAGACAT GATAAGATAC ATTGATGAGT TTGGACAAAC
2221 CACAACTAGA ATGCAGTGAA AAAAATGCTT TATTTGTGAA ATTTGTGATG CTATTGCTTT
2281 ATTTGTAACC ATTATAAGCT GCAATAAACA AGTTAACAAC AACAATTGCA TTCATTTTAT
2341 GTTTCAGGTT CAGGGGGAGG TGTGGGAGGT TTTTTAAAGC AAGTAAAACC TCTACAAATG
2401 TGGTATTGGC CCATCTCTAT CGGTATCGTA GCATAACCCC TTGGGGCCTC TAAACGGGTC
2461 TTGAGGGGTT TTTTGTGCCC CTCGGGCCGG ATTGCTATCT ACCGGCATTG GCGCAGAAAA
2521 AAATGCCTGA TGCGACGCTG CGCGTCTTAT ACTCCCACAT ATGCCAGATT CAGCAACGGA
2581 TACGGCTTCC CCAACTTGCC CACTTCCATA CGTGTCCTCC TTACCAGAAA TTTATCCTTA
2641 AGGTCGTCAG CTATCCTGCA GGCGATCTCT CGATTTCGAT CAAGACATTC CTTTAATGGT
2701 CTTTTCTGGA CACCACTAGG GGTCAGAAGT AGTTCATCAA ACTTTCTTCC CTCCCTAATC
2761 TCATTGGTTA CCTTGGGCTA TCGAAACTTA ATTAACCAGT CAAGTCAGCT ACTTGGCGAG
2821 ATCGACTTGT CTGGGTTTCG ACTACGCTCA GAATTGCGTC AGTCAAGTTC GATCTGGTCC
2881 TTGCTATTGC ACCCGTTCTC CGATTACGAG TTTCATTTAA ATCATGTGGA CAAAAGGCCA
2941 GCAAAAGGCC AGGAACCGTA AAAAGGCCGC GTTGCTGGCA TTTTTCCATA GGCTCCGCCC
3001 CCCTGACGAG CATCACAAAA ATCGACGCTC AAGTCAGAGG TGGCGAAACC CGACAGGACT
3061 ATAAAGATAC CAGGCGTTTC CCCCTGGAAG CTCCCTCGTG CGCTCTCCTG TTCCGACCCT
3121 GCCGCTTACC GGATACCTGT CCGCCTTTCT CCCTTCGGGA AGCGTGGCGC TTTCTCATAG
3181 CTCACGCTGT AGGTATCTCA GTTCGGTGTA GGTCGTTCGC TCCAAGCTGG GCTGTGTGCA
3241 CGAACCCCCC GTTCAGCCCG ACCGCTGCGC CTTATCCGGT AACTATCGTC TTGAGTCCAA
3301 CCCGGTAAGA CACGACTTAT CGCCACTGGC AGCAGCCACT GGTAACAGGA TTAGCAGAGC
3361 GAGGTATGTA GGCGGTGCTA CAGAGTTCTT GAAGTGGTGG CCTAACTACG GCTACACTAG
3421 AAGAACAGTA TTTGGTATCT GCGCTCTGCT GAAGCCAGTT ACCTTCGGAA AAAGAGTTGG
3481 TAGCTCTTGA TCCGGCAAAC AAACCACCGC TGGTAGCGGT GGTTTTTTTG TTTGCAAGCA
3541 GCAGATTACG CGCAGAAAAA AAGGATCTCA AGAAGATCCT TTGATCTTTT CTACGGGGTC
3601 TGACGCTCAG TGGAACGAAA ACTCACGTTA AGGGATTTTG GTCATGAGAT TATCAAAAAG
3661 GATCTTCACC TAGATCCTTT TAAATTAAAA ATGAAGTTTT AAATCAATCT AAAGTATATA
3721 TGAGTAAACT TGGTCTGACA GTTACCAATG CTTAATCAGT GAGGCACCTA TCTCAGCGAT
3781 CTGTCTATTT CGTTCATCCA TAGTTGCATT TAAATTTCCG AACTCTCCAA GGCCCTCGTC
3841 GGAAAATCTT CAAACCTTTC GTCCGATCCA TCTTGCAGGC TACCTCTCGA ACGAACTATC
```

-continued

| Sequence Listing Free Text | | | | | |
|---|---|---|---|---|---|
| 3901 | GCAAGTCTCT | TGGCCGGCCT | TGCGCCTTGG | CTATTGCTTG | GCAGCGCCTA | TCGCCAGGTA |
| 3961 | TTACTCCAAT | CCCGAATATC | CGAGATCGGG | ATCACCCGAG | AGAAGTTCAA | CCTACATCCT |
| 4021 | CAATCCCGAT | CTATCCGAGA | TCCGAGGAAT | ATCGAAATCG | GGGCGCCCTA | GGTGTACCGA |
| 4081 | GAACGATCCT | CTCAGTGCGA | GTCTCGACGA | TCCATATCGT | TGCTTGGCAG | TCAGCCAGTC |
| 4141 | GGAATCCAGC | TTGGGACCCA | GGAAGTCCAA | TCGTCAGATA | TTGTACTCAA | GCCTGGTCAC |
| 4201 | GGCAGCGTAC | CGATCTGTTT | AAACCTAGAT | ATTGATAGTC | TGATCGGTCA | ACGTATAATC |
| 4261 | GAGTCCTAGC | TTTTGCAAAC | ATCTATCAAG | AGACAGGATC | AGCAGGAGGC | TTTCGCATGA |
| 4321 | GTATTCAACA | TTTCCGTGTC | GCCCTTATTC | CCTTTTTTGC | GGCATTTTGC | CTTCCTGTTT |
| 4381 | TTGCTCACCC | AGAAACGCTG | GTGAAAGTAA | AAGATGCTGA | AGATCAGTTG | GGTGCGCGAG |
| 4441 | TGGGTTACAT | CGAACTGGAT | CTCAACAGCG | GTAAGATCCT | TGAGAGTTTT | CGCCCCGAAG |
| 4501 | AACGCTTTCC | AATGATGAGC | ACTTTTAAAG | TTCTGCTATG | TGGCGCGGTA | TTATCCCGTA |
| 4561 | TTGACGCCGG | GCAAGAGCAA | CTCGGTCGCC | GCATACACTA | TTCTCAGAAT | GACTTGGTTG |
| 4621 | AGTATTCACC | AGTCACAGAA | AAGCATCTTA | CGGATGGCAT | GACAGTAAGA | GAATTATGCA |
| 4681 | GTGCTGCCAT | AACCATGAGT | GATAACACTG | CGGCCAACTT | ACTTCTGACA | ACGATTGGAG |
| 4741 | GACCGAAGGA | GCTAACCGCT | TTTTTGCACA | ACATGGGGGA | TCATGTAACT | CGCCTTGATC |
| 4801 | GTTGGGAACC | GGAGCTGAAT | GAAGCCATAC | CAAACGACGA | GCGTGACACC | ACGATGCCTG |
| 4861 | TAGCAATGGC | AACAACCTTG | CGTAAACTAT | TAACTGGCGA | ACTACTTACT | CTAGCTTCCC |
| 4921 | GGCAACAGTT | GATAGACTGG | ATGGAGGCGG | ATAAAGTTGC | AGGACCACTT | CTGCGCTCGG |
| 4981 | CCCTTCCGGC | TGGCTGGTTT | ATTGCTGATA | AATCTGGAGC | CGGTGAGCGT | GGGTCTCGCG |
| 5041 | GTATCATTGC | AGCACTGGGG | CCAGATGGTA | AGCCCTCCCG | TATCGTAGTT | ATCTACACGA |
| 5101 | CGGGGAGTCA | GGCAACTATG | GATGAACGAA | ATAGACAGAT | CGCTGAGATA | GGTGCCTCAC |
| 5161 | TGATTAAGCA | TTGGTAACCG | ATTCTAGGTG | CATTGGCGCA | GAAAAAAATG | CCTGATGCGA |
| 5221 | CGCTGCGCGT | CTTATACTCC | CACATATGCC | AGATTCAGCA | ACGGATACGG | CTTCCCCAAC |
| 5281 | TTGCCCACTT | CCATACGTGT | CCTCCTTACC | AGAAATTTAT | CCTTAAGATC | CCGAATCGTT |
| 5341 | TAAACTCGAC | TCTGGCTCTA | TCGAATCTCC | GTCGTTTCGA | GCTTACGCGA | ACAGCCGTGG |
| 5401 | CGCTCATTTG | CTCGTCGGGC | ATCGAATCTC | GTCAGCTATC | GTCAGCTTAC | CTTTTTGGCA |
| 5461 | | | | | | | pCR027 (SEQ ID NO: 20)
ORIGIN

| 1 | GCGATCGCGG | CTCCCGACAT | CTTGGACCAT | TAGCTCCACA | GGTATCTTCT | TCCCTCTAGT |
|---|---|---|---|---|---|---|
| 61 | GGTCATAACA | GCAGCTTCAG | CTACCTCTCA | ATTCAAAAAA | CCCCTCAAGA | CCCGTTTAGA |
| 121 | GGCCCCAAGG | GGTTATGCTA | TCAATCGTTG | CGTTACACAC | ACAAAAAACC | AACACACATC |
| 181 | CATCTTCGAT | GGATAGCGAT | TTTATTATCT | AACTGCTGAT | CGAGTGTAGC | CAGATCTAGT |
| 241 | AATCAATTAC | GGGGTCATTA | GTTCATAGCC | CATATATGGA | GTTCCGCGTT | ACATAACTTA |
| 301 | CGGTAAATGG | CCCGCCTGGC | TGACCGCCCA | ACGACCCCCG | CCCATTGACG | TCAATAATGA |
| 361 | CGTATGTTCC | CATAGTAACG | CCAATAGGGA | CTTTCCATTG | ACGTCAATGG | GTGGAGTATT |
| 421 | TACGGTAAAC | TGCCCACTTG | GCAGTACATC | AAGTGTATCA | TATGCCAAGT | ACGCCCCCTA |
| 481 | TTGACGTCAA | TGACGGTAAA | TGGCCCGCCT | GGCATTATGC | CCAGTACATG | ACCTTATGGG |
| 541 | ACTTTCCTAC | TTGGCAGTAC | ATCTACGTAT | TAGTCATCGC | TATTACCATG | CTGATGCGGT |
| 601 | TTTGGCAGTA | CATCAATGGG | CGTGGATAGC | GGTTTGACTC | ACGGGGATTT | CCAAGTCTCC |
| 661 | ACCCCATTGA | CGTCAATGGG | AGTTTGTTTT | GGCACCAAAA | TCAACGGGAC | TTTCCAAAAT |
| 721 | GTCGTAACAA | CTCCGCCCCA | TTGACGCAAA | TGGGCGGTAG | GCGTGTACGG | TGGGAGGTCT |
| 781 | ATATAAGCAG | AGCTGGTTTA | GTGAACCGTC | AGATCAGATC | TTTGTCGATC | CTACCATCCA |
| 841 | CTCGACACAC | CCGCCAGCgg | ccgccaccat | gaaggccaat | ctactggtgt | tgctgtgtgc |
| 901 | ccttgcggcg | gcagatgcca | tgcggtgcgt | ggggatcggc | aatcgcgatt | ttgtagaagg |
| 961 | actatctggt | gccacgtggg | tcgatgtggt | tcttgaacac | gggtcatgcg | tgaccacgat |
| 1021 | ggctaaggat | aagccgacct | tggacatcga | actactgaaa | accgaggtca | caaaccctgc |
| 1081 | tgtgctccgc | aagctgtgca | tcgaggctaa | gatttccaac | acaactactg | atagccgctg |
| 1141 | ccccaccca a | ggcgaggcga | ccctcgttga | agagcaggac | agcaacttcg | tgtgtcgccg |
| 1201 | gactttcgtg | gaccgcggtT | GGGGGAATgg | atgcggactt | aacggatctg | gttccttact |
| 1261 | gacttgcgcc | aaatttaagt | gcgtgactaa | gttagagggg | aaaatcgttc | agtatgagaa |
| 1321 | cttaaaatac | tcggtgatag | ttaccgtgca | cacaggcgac | cagcatcaag | ttgggaacga |
| 1381 | aacgacagag | cacgggacaa | tagcgaccat | taccccacag | gctccaacga | gcgaaattca |
| 1441 | gctgacagac | tacggtgcac | tcaccctgga | ctgtagccca | cggaccgggc | tagactttaa |
| 1501 | cgagatggtg | ctcctgacta | tgaaggaaaa | gtcatggttg | gtgcacaagc | agtggttcct |
| 1561 | tgatctteca | cctctggcgc | ttcgacctca | caagagactt | ggaacaggca | |
| 1621 | ggacttgctc | gtgacattca | aaacggctca | cgctaaaaag | caagaggtcg | tggttctggg |
| 1681 | gagtcaggaa | ggcgctatgc | ataccgcgtt | aacaggggct | acagagatcc | agaccagtgg |
| 1741 | aacaaccact | attttcgccg | ggcatcttaa | gtgtaggctg | aagatggata | agttgaccct |
| 1801 | gaaaggtatg | tcatatgtga | tgtgtaccgg | tagtttcaaa | ctggagaaag | aagtggccga |
| 1861 | aacccagcat | ggaacagtac | tggtgcaagt | caaatatgag | ggcaccgatg | caccatgtaa |
| 1921 | aataccctte | agcgcacaag | acgagaaggg | agttaccagg | aacggtaggc | tgataacagc |
| 1981 | caatccaatc | gtcaccgata | aggagaaacc | agtaaacatc | gaaaccgagc | caccottcgg |
| 2041 | cgaaagctac | atcgtggtcg | gcgctggcga | gaaagcactt | aagctgagct | ggtttaagaa |
| 2101 | aggtagcacg | ggcggcggca | gccatcatca | ccatcatcac | tgagctagcT | TGACTGACTG |
| 2161 | AGATACAGCG | TACCTTCAGC | TCACAGACAT | GATAAGATAC | ATTGATGAGT | TTGGACAAAC |
| 2221 | CACAACTAGA | ATGCAGTGAA | AAAAATGCTT | TATTTGTGAA | ATTTGTGATG | CTATTGCTTT |
| 2281 | ATTTGTAACC | ATTATAAGCT | GCAATAAACA | AGTTAACAAC | AACAATTGCA | TTCATTTTAT |
| 2341 | GTTTCAGGTT | CAGGGGGAGG | TGTGGGAGGT | TTTTTAAAGC | AAGTAAAACC | TCTACAAATG |
| 2401 | TGGTATTGGC | CCATCTCTAT | CGGTATCGTA | GCATAACCCC | TTGGGGCCTC | TAAACGGGTC |
| 2461 | TTGAGGGGTT | TTTTGTGCCC | CTCGGGCCGG | ATTGCTATCT | ACCGGCATTG | GCGCAGAAAA |
| 2521 | AAATGCCTGA | TGCGACGCTG | CGCGTCTTAT | ACTCCCACAT | ATGCCAGATT | CAGCAACGGA |
| 2581 | TACGGCTTCC | CCAACTTGCC | CACTTCCATA | CGTGTCCTCC | TTACCAGAAA | TTTATCCTTA |
| 2641 | AGGTCGTCAG | CTATCCTGCA | GGCGATCTCT | CGATTTCGAT | CAAGACATTC | CTTTAATGGT |
| 2701 | CTTTTCTGGA | CACCACTAGG | GGTCAGAAGT | AGTTCATCAA | ACTTTCTTCC | CTCCCTAATC |
| 2761 | TCATTGGTTA | CCTTGGGCTA | TCGAAACTTA | ATTAACCAGT | CAAGTCAGCT | ACTTGGCGAG |

-continued

Sequence Listing Free Text

```
2821 ATCGACTTGT CTGGGTTTCG ACTACGCTCA GAATTGCGTC AGTCAAGTTC GATCTGGTCC
2881 TTGCTATTGC ACCCGTTCTC CGATTACGAG TTTCATTTAA ATCATGTGAG CAAAAGGCCA
2941 GCAAAAGGCC AGGAACCGTA AAAAGGCCGC GTTGCTGGCG TTTTTCCATA GGCTCCGCCC
3001 CCCTGACGAG CATCACAAAA ATCGACGCTC AAGTCAGAGG TGGCGAAACC CGACAGGACT
3061 ATAAAGATAC CAGGCGTTTC CCCCTGGAAG CTCCCTCGTG CGCTCTCCTG TTCCGACCCT
3121 GCCGCTTACC GGATACCTGT CCGCCTTTCT CCCTTCGGGA AGCGTGGCGC TTTCTCATAG
3181 CTCACGCTGT AGGTATCTCA GTTCGGTGTA GGTCGTTCGC TCCAAGCTGG GCTGTGTGCA
3241 CGAACCCCCC GTTCAGCCCG ACCGCTGCGC CTTATCCGGT AACTATCGTC TTGAGTCCAA
3301 CCCGGTAAGA CACGACTTAT CGCCACTGGC AGCAGCCACT GGTAACAGGA TTAGCAGAGC
3361 GAGGTATGTA GGCGGTGCTA CAGAGTTCTT GAAGTGGTGG CCTAACTACG GCTACACTAG
3421 AAGAACAGTA TTTGGTATCT GCGCTCTGCT GAAGCCAGTT ACCTTCGGAA AAAGAGTTGG
3481 TAGCTCTTGA TCCGGCAAAC AAACCACCGC TGGTAGCGGT GGTTTTTTTG TTTGCAAGCA
3541 GCAGATTACG CGCAGAAAAA AAGGATCTCA AGAAGATCCT TTGATCTTTT CTACGGGGTC
3601 TGACGCTCAG TGGAACGAAA ACTCACGTTA AGGGATTTTG GTCATGAGAT TATCAAAAAG
3661 GATCTTCACC TAGATCCTTT TAAATTAAAA ATGAAGTTTT AAATCAATCT AAAGTATATA
3721 TGAGTAAACT TGGTCTGACA GTTACCAATG CTTAATCAGT GAGGCACCTA TCTCAGCGAT
3781 CTGTCTATTT CGTTCATCCA TAGTTGCATT TAAATTTCCG AACTCTCCAA GGCCCTCGTC
3841 GGAAAATCTT CAAACCTTTC GTCCGATCCA TCTTGCAGGC TACCTCTCGA ACGAACTATC
3901 GCAAGTCTCT TGGCCGGCCT TGCGCCTTGG CTATTGCTTG GCAGCGCCTA TCGCCAGGTA
3961 TTACTCCAAT CCCGAATATC CGAGATCGGG ATCACCCGAG AGAAGTTCAA CCTACATCCT
4021 CAATCCCGAT CTATCCGAGA TCCGAGGAAT ATCGAAATCG GGGCGCGCCT GGTGTACCGA
4081 GAACGATCCT CTCAGTGCGA GTCTCGACGA TCCATATCGT TGCTTGGCAG TCAGCCAGTC
4141 GGAATCCAGC TTGGGACCCA GGAAGTCCAA TCGTCAGATA TTGTACTCAA GCCTGGTCAC
4201 GGCAGCGTAC CGATCTGTTT AAACCTAGAT ATTGATGATC TGATCGGTCA ACGTATAATC
4261 GAGTCCTAGC TTTTGCAAAC ATCTATCAAG AGACAGGATC AGCAGGAGGC TTTCGCATGA
4321 GTATTCAACA TTTCCGTGTC GCCCTTATTC CCTTTTTTGC GGCATTTTGC CTTCCTGTTT
4381 TTGCTCACCC AGAAACGCTG GTGAAAGTAA AAGATGCTGA AGATCAGTTG GGTGCGCGAG
4441 TGGGTTACAT CGAACTGGAT CTCAACAGCG GTAAGATTTC TGAGAGTTTT CGCCCCGAAG
4501 AACGCTTTCC AATGATGAGC ACTTTTAAAG TTCTGCTATG TGGCGCGGTA TTATCCCGTA
4561 TTGACGCCGG GCAAGAGCAA CTCGGTCGCC GCATACACTA TTCTCAGAAT GACTTGGTTG
4621 AGTATTCACC AGTCACAGAA AAGCATCTTA CGGATGGCAT GACAGTAAGA GAATTATGCA
4681 GTGCTGCCAT AACCATGAGT GATAACACTG CGGCCAACTT ACTTCTGACA ACGATTGGAG
4741 GACCGAAGGA GCTAACCGCT TTTTTGCACA ACATGGGGGA TCATGTAACT CGCCTTGATC
4801 GTTGGGAACC GGAGCTGAAT GAAGCCATAC CAAACGACGA GCGTGACACC ACGATGCCTG
4861 TAGCAATGGC AACAACCTTG CGTAAACTAT TAACTGGCGA ACTACTTACT CTAGCTTCCC
4921 GGCAACAGTT GATAGACTGG ATGGAGGCGG ATAAAGTTGC AGGACCACTT CTGCGCTCGG
4981 CCCTTCCGGC TGGCTGGTTT ATTGCTGATA AATCTGGAGC CGGTGAGCGT GGGTCTCGCG
5041 GTATCATTGC AGCACTGGGG CCAGATGGTA AGCCCTCCCG TATCGTAGTT ATCTACACGA
5101 CGGGGAGTCA GGCAACTATG GATGAACGAA ATAGACAGAT CGCTGAGATA GGTGCCTCAC
5161 TGATTAAGCA TTGGTAACCG ATTCTAGGTG CATTGGCGCA GAAAAAAATG CCTGATGCGA
5221 CGCTGCGCGT CTTATACTCC CACATATGCC AGATTCAGCA ACGGATACGG CTTCCCCAAC
5281 TTGCCCACTT CCATACGTGT CCTCCTTACC AGAAATTTAT CCTTAAGATC CCGAATCGTT
5341 TAAACTCGAC TCTGGCTCTA TCGAATCTCC GTCGTTTCGA GCTTACGCGA ACAGCCGTGG
5401 CGCTCATTTG CTCGTCGGGC ATCGAATCTC GTCAGCTATC GTCAGCTTAC CTTTTTGGCA
5461
```

//
pCR029 (SEQ ID NO: 21)
ORIGIN

```
   1 GCGATCGCGG CTCCCGACAT CTTGGACCAT TAGCTCCACA GGTATCTTCT TCCCTCTAGT
  61 GGTCATAACA GCAGCTTCAG CTACCTCTCA ATTCAAAAAA CCCCTCAAGA CCCGTTTAGA
 121 GGCCCCAAGG GGTTATGCTA TCAATCGTTG CGTTACACAC ACAAAAAACC AACACACATC
 181 CATCTTCGAT GGATAGCGAT TTTATTATCT AACTGCATGA TCGAGTGTAC CAGATCTAGT
 241 AATCAATTAC GGGGTCATTA GTTCATAGCC CATATATGGA GTTCCGCGTT ACATAACTTA
 301 CGGTAAATGG CCCGCCTGGC TGACCGCCCA ACGACCCCCG CCCATTGACG TCAATAATGA
 361 CGTATGTTCC CATAGTAACG CCAATAGGGA CTTTCCATTG ACGTCAATGG GTGGAGTATT
 421 TACGGTAAAC TGCCCACTTG GCAGTACATC AAGTGTATCA TATGCCAAGT ACGCCCCCTA
 481 TTGACGTCAA TGACGGTAAA TGGCCCGCCT GGCATTATGC CCAGTACATG ACCTTATGGG
 541 ACTTTCCTAC TTGGCAGTAC ATCTACGTAT TAGTCATCGC TATTACCATG CTGATGCGGT
 601 TTTGGCAGTA CATCAATGGG CGTGGATAGC GGTTTGACTC ACGGGGATTT CCAAGTCTCC
 661 ACCCCATTGA CGTCAATGGG AGTTTGTTTT GGCACCAAAA TCAACGGGAC TTTCCAAAAT
 721 GTCGTAACAA CTCCGCCCCA TTGACGCAAA TGGGCGGTAG GCGTGTACGG TGGGAGGTCT
 781 ATATAAGCAG AGCTGGTTTA GTGAACCGTC AGATCAGATC TTTGTCGATC CTACCATCCA
 841 CTCGACACAC CCGCCAGCgg ccgccaccat gaaggccaat ctactggtgt tgctgtgtgc
 901 ccttgcggcg gcagatgccA TCAGGTGCAT TGGAGTCAGC AACAGGGACT TCGTCGAAGG
 961 CATGTCCGGC GGCACCTGGG TGGATGTGGT GCTCGAACAC GGCGGATGCG TGACGGTCAT
1021 GGCCCAGGAC AAGCCTACCG TCGATATTGA GCTGGTGACC ACCACAGTGA GCAACATGGC
1081 CGAAGTGAGA AGCTACTGCT ATGAGGCCTC CATCAGCGAT ATGGCTTCCG ATTCCAGATG
1141 CCCCACACAG GGAGAGGCTT ATCTGGACAA ACAGTCCGAC ACCCAGTACG TCTGCAAAAG
1201 AACCCTGGTG GACAGAGGCT GGGGAAACGG ATGCGGCaac cacaccAAAG GCAGCCTCGT
1261 GACATGTGCC AAGTTCGCCT GCAGCAAAAA GATGACGGGC AAGTCCATCC AGCCCGAGAA
1321 CCTGGAATAC AGGATCATGC TGTCCGTGCA TGGATCCCAG CACTCCGGCA TGATCGTCAA
1381 CGATACCGGC CACGAGACCG ACGAGAACAG GGCTAAAGTG GAGATCACCC CAACAGCCC
1441 TAGAGCCGAA GCTACACTGG GCGGCTTCGG AAGCCTGGGC CTGGATTGCG AACCCAGGAC
1501 CGGCCTGGAT TTCAGCGACC TGTATTACCT GACCATGAAC AATAAGCACT GGCTGGTGCA
1561 CAAGGAATGG TTCCACGACA TCCCCCTGCC TTGGCATGCT GGCGCCGATA CCGGCACACC
1621 TCACTGGAAC AATAAGGAAG CCCTGGTCGA GTTTAAGGAC GCCCACGCCA AAAGACAGAC
```

```
1681 CGTGGTGGTG CTGGGAAGCC AGGAGGGAGC TGTCCACACA GCCCTGGCCG GAGCTCTGGA
1741 AGCCGAGATG GATGGCGCCA AGGGCAGGCT GAGCTCCGGC CACCTGAAAT GCAGGCTCAA
1801 GATGGACAAG CTGAGGCTGA AGGGCGTGAG CTACAGCCTG TGCACCGCCG CTTTCACCTT
1861 TACCAAGATC CCTGCCGAGA CACTGCACGG CACCGTCACC GTGGAGGTGC AATACGCCGG
1921 AACCGATGGA CCTTGCAAAG TGCCTGCCCA GATGGCTGTG GATATGCAGA CCCTCACACC
1981 CGTCGGCAGG CTGATCACCG CCAATCCCGT CATTACCGAG TCCACCGAGA ACAGCAAGAT
2041 GATGCTcGAG CTCGATCCCC CCTTTGGCGA CAGCTACATT GTGATCGGCG TGGGCGAGAA
2101 GAAGATCACC CACCATTGGC ACAGAAGCGG CTCCACAggg ggtagcggtg gtagcggagg
2161 tagccatcac caccatcacc actgagctag CTTGACTGAC TGAGATACAG CGTACCTTCA
2221 GCTCACAGAC ATGATAAGAT ACATTGATGA GTTTGGACAA ACCACAACTA GAATGCAGTG
2281 AAAAAAATGC TTTATTTGTG AAATTTGTGA TGCTATTGCT TTATTTGTAA CCATTATAAG
2341 CTGCAATAAA CAAGTTAACA ACAACAATTG CATTCATTTT ATGTTTCAGG TTCAGGGGGA
2401 GGTGTGGGAG GTTTTTTAAA GCAAGTAAAA CCTCTACAAA TGTGGTATTG GCCCATCTCT
2461 ATCGGTATCG TAGCATAACC CCTTGGGGCC TCTAAACGGG TCTTGAGGGG TTTTTTGTGC
2521 CCCTCGGGCC GGATTGCTAT CTACCGGCAT TGGCGCAGAA AAAAATGCCT GATGCGACGC
2581 TGCGCGTCTT ATACTCCCAC ATATGCCAGA TTCAGCAACG GATACGGCTT CCCCAACTTG
2641 CCCACTTCCA TACGTGTCCT CCTTACCAGA AATTTATCCT TAAGGTCGTC AGCTATCCTG
2701 CAGGCGATCT CTCGATTTCG ATCAAGACAT TCCTTTAATG GTCTTTTCTG GACACCACTA
2761 GGGGTCAGAA GTAGTTCATC AAACTTTCTT CCCTCCCTAA TCTCATTGGT TACCTTGGGC
2821 TATCGAAACT TAATTAACCA GTCAAGTCAG CTACTTGTACC AGATCGACTT GTCTGGGTTT
2881 CGACTACGCT CAGAATTGCG TCAGTCAAGT TCGATCTGGT CCTTGCTATT GCACCCGTTC
2941 TCCGATTACG AGTTTCATTT AAATCATGTG AGCAAAAGGC CAGCAAAAGG CCAGGAACCG
3001 TAAAAAGGCC GCGTTGCTGG CGTTTTTCCA TAGGCTCCGC CCCCCTGACG AGCATCACAA
3061 AAATCGACGC TCAAGTCAGA GGTGGCGAAA CCCGACAGGA CTATAAAGAT ACCAGGCGTT
3121 TCCCCCTGGA AGCTCCCTCG TGCGCTCTCC TGTTCCGACC CTGCCGCTTA CCGGATACCT
3181 GTCCGCCTTT CTCCCTTCGG GAAGCGTGGC GCTTTCTCAT AGCTCACGCT GTAGGTATCT
3241 CAGTTCGGTG TAGGTCGTTC GCTCCAAGCT GGGCTGTGTG CACGAACCCC CCGTTCAGCC
3301 CGACCGCTGC GCCTTATCCG GTAACTATCG TCTTGAGTCC AACCCGGTAA GACACGACTT
3361 ATCGCCACTG GCAGCAGCCA CTGGTAACAG GATTAGCAGA GCGAGGTATG TAGGCGGTGC
3421 TACAGAGTTC TTGAAGTGGT GGCCTAACTA CGGCTACACT AGAAGAACAG TATTTGGTAT
3481 CTGCGCTCTG CTGAAGCCAG TTACCTTCGG AAAAAGAGTT GGTAGCTCTT GATCCGGCAA
3541 ACAAACCACC GCTGGTAGCG GTGGTTTTTT TGTTTGCAAG CAGCAGATTA CGCGCAGAAA
3601 AAAAGGATCT CAAGAAGATC CTTTGATCTT TTCTACGGGG TCTGACGCTC AGTGGAACGA
3661 AAACTCACGT TAAGGGATTT TGGTCATGAG ATTATCAAAA AGGATCTTCA CCTAGATCCT
3721 TTTAAATTAA AAATGAAGTT TTAAATCAAT CTAAAGTATA TATGAGTAAA CTTGGTCTGA
3781 CAGTTACCAA TGCTTAATCA GTGAGGCACC TATCTCAGCG ATCTGTCTAT TTCGTTCATC
3841 CATAGTTGCA TTTAAATTTC CGAACTCTCC AAGGCCCTCG TCGGAAAATC TTCAAACCTT
3901 TCGTCCGATC CATCTTGCAG GCTACCTCTC GAACGAACTA TCGCAAGTCT CTTGGCCGGC
3961 CTTGCGCCTT GGCTATTGCT TGGCAGCGCC TATCGCCAGG TATTACTCCA ATCCCGAATA
4021 TCCGAGATCG GGATCACCCG AGAGAAGTTC AACCTACATC CTCAATCCCG ATCTATCCGA
4081 GATCCGAGGA ATATCGAAAT CGGGGCGCGC CTGGTGTACC GAGAACGATC CTCTCAGTGC
4141 GAGTCTCGAC GATCCATATC GTTGCTTGGC AGTCAGCCAG TCGGAATCCA GCTTGGGACC
4201 CAGGAAGTCC AATCGTCAGA TATTGTACTC AAGCCTGGTC ACGGCAGCGT ACCGATCTGT
4261 TTAAACCTAG ATATTGATAG TCTGATCGGT CAACGTATAA TCGAGTCCTA GCTTTTGCAA
4321 ACATCTATCA AGAGACAGGA TCAGCAGGAG GCTTTCGACT GAGTATTCAA CATTTCCGTG
4381 TCGCCCTTAT TCCCTTTTTT GCGGCATTTT GCCTTCCTGT TTTTGCTCAC CCAGAAACGC
4441 TGGTGAAAGT AAAAGATGCT GAAGATCAGT TGGGTGCGCG AGTGGGTTAC ATCGAACTGG
4501 ATCTCAACAG CGGTAAGATC CTTGAGAGTT TTCGCCCCGA AGAACGCTTT CCAATGATGA
4561 GCACTTTTAA AGTTCTGCTA TGTGGCGCGG TATTATCCGA TATTGACGCC GGGCAAGAGC
4621 AACTCGGTCG CCGCATACAC TATTCTCAGA ATGACTTGGT TGAGTATTCA CCAGTCACAG
4681 AAAAGCATCT TACGGATGGC ATGACAGTAA GAGAATTATG CAGTGCTGCC ATAACCATGA
4741 GTGATAACAC TGCGGCCAAC TTACTTCTGA CAACGATTGG AGGACCGAAG GAGCTAACCG
4801 CTTTTTTGCA CAACATGGGG GATCATGTAA CTCGCCTTGA TCGTTGGGAA CCGGAGCTGA
4861 ATGAAGCCAT ACCAAACGAC GAGCGTGACA CCACGATGCC TGTAGCAATG GCAACAACCT
4921 TGCGTAAACT ATTAACTGGC GAACTACTTA CTCTAGCTTC CCGGCAACAG TTGATAGACT
4981 GGATGGAGGC GGATAAAGTT GCAGGACCAC TTCTGCGCTC GGCCCTTCCG GCTGGCTGGT
5041 TTATTGCTGA TAAATCTGGA GCCGGTGAGC GTGGGTCTCG CGGTATCATT GCAGCACTGG
5101 GGCCAGATGG TAAGCCCTCC CGTATCGTAG TTATCTACAC GACGGGGAGT CAGGCAACTA
5161 TGGATGAACG AAATAGACAG ATCGCTGAGA TAGGTGCCTC ACTGATTAAG CATTGGTAAC
5221 CGATTCTAGG TGCATTGGCG CAGAAAAAAA TGCCTGATGC GACGCTGCGC GTCTTATACT
5281 CCCACATATG CCAGATTCAG CAACGGATAC GGCTTCACCA ACTTGCCCAC TTCCATACGT
5341 GTCCTCCTTA CCAGAAATTT ATCCTTAAGA TCCCGAATCG TTTAAACTCG ACTCTGGCTC
5401 TATCGAATCT CCGTCGTTTC GAGCTTACGC GAACAGCCGT GGCGCTCATT TGCTCGTCGG
5461 GCATCGAATC TCGTCAGCTA TCGTCAGCTT ACCTTTTTGG
//
pCR030 (SEQ ID NO: 22)
ORIGIN
    1 GCGATCGCGG CTCCCGACAT CTTGGACCAT TAGCTCCACA GGTATCTTCT TCCCTCTAGT
   61 GGTCATAACA GCAGCTTCAG CTACCTCTCA ATTCAAAAAA CCCCTCAAGA CCCGTTTAGA
  121 GGCCCCAAGG GGTTATGCTA TCAATCGTTG CGTTACACAC ACAAAAAACC AACACACATC
  181 CATCTTCGAT GGATAGCGAT TTTATTATCT AACTGCTGAT CGAGTGTAGC CAGATCTAGT
  241 AATCAATTAC GGGGTCATTA GTTCATAGCC CATATATGGA GTTCCGCGTT ACATAACTTA
  301 CGGTAAATGG CCCGCCTGGC TGACCGCCCA ACGACCCCCG CCCATTGACG TCAATAATGA
  361 CGTATGTTCC CATAGTAACG CCAATAGGGA CTTTCCATTG ACGTCAATGG GTGGAGTATT
  421 TACGGTAAAC TGCCCACTTG GCAGTACATC AAGTGTATCA TATGCCAAGT ACGCCCCCTA
  481 TTGACGTCAA TGACGGTAAA TGGCCCGCCT GGCATTATGC CCAGTACATG ACCTTATGGG
```

```
 541 ACTTTCCTAC TTGGCAGTAC ATCTACGTAT TAGTCATCGC TATTACCATG CTGATGCGGT
 601 TTTGGCAGTA CATCAATGGG CGTGGATAGC GGTTTGACTC ACGGGGATTT CCAAGTCTCC
 661 ACCCCATTGA CGTCAATGGG AGTTTGTTTT GGCACCAAAA TCAACGGGAC TTTCCAAAAT
 721 GTCGTAACAA CTCCGCCCCA TTGACGCAAA TGGGCGGTAG GCGTGTACGG TGGGAGGTCT
 781 ATATAAGCAG AGCTGGTTTA GTGAACCGTC AGATCAGATC TTTGTCGATC CTACCATCCA
 841 CTCGACACAC CCGCCAGCgg ccgccaccat gaaggccaat ctactggtgt tgctgtgtgc
 901 ccttgcggcg gcagatgccA TCAGGTGCAT TGGAGTCAGC AACAGGGACT TCGTCGAAGG
 961 CATGTCCGGC GGCACCTGGG TGGATGTGGT GCTCGAACAC GGCGGATGCG TGACCGTCAT
1021 GGCCCAGGAC AAGCCTACCG TCGATATTGA GCTGGTGACC ACCACAGTGA GCAACATGGC
1081 CGAAGTGAGA AGCTACTGCT ATGAGGCCTC CATCAGCGAT ATGGCTTCCG ATTCCAGATG
1141 CCCCACACAG GGAGAGGCTT ATCTGGACAA ACAGTCCGAC ACCCAGTACG TCTGCAAAAG
1201 AACCCTGGTG GACAGAGGCa acggatccGG ATGCGGCCTG TTCGGCAAAG GCAGCCTCGT
1261 GACATGTGCC AAGTTCGCCT GCAGCAAAAA GATGACCGGC AAGTCCATCC AGCCCGAGAA
1321 CCTGGAATAC AGGATCATGC TGTCCGTGCA TGGATCCCAG CACTCCGGCA TGATCGTCAA
1381 CGATACCGGC CACGAGACCG ACGAGAACAG GGCTAAAGTG GAGATCACCC CCAACAGCCC
1441 TAGAGCCGAA GCTACACTGG GCGGCTTCGG AAGCCTGGGC CTGGATTGCG AACCCAGGAC
1501 CGGCCTGGAT TTCAGCGACC TGTATTACCT GACCATGAAC AATAAGCACT GGCTGGTGCA
1561 CAAGGAATGG TTCCACGACA TCCCCCTGCC TTGGCATGCT GGCGCCGATA CCGGCACACC
1621 TCACTGGAAC AATAAGGAAG CCCTGGTCGA GTTTAAGGAC GCCCACGCCA AAGACAGAC
1681 CGTGGTGGTG CTGGGAAGCC AGGAGGGAGC TGTCCACACA GCCCTGGCCG GAGCTCTGGA
1741 AGCCGAGATG GATGCGCCA AGGGCAGGCT GAGCTCCGGC CACCTGAAAT GCAGGCTCAA
1801 GATGGACAAG CTGAGGCTGA AGGGCGTGAG CTACAGCCTG TGCACCGCCG CTTTCACCTT
1861 TACCAAGATC CCTGCCGAGA CACTGCACGG CACCGTCACC GTGGAGGTGC AATACGCCGG
1921 AACCGATGGA CCTTGCAAAG TGCCTGCCCA GATGGCTGTG GATATGCAGA CCCTCACACC
1981 CGTCGGCAGG CTGATCACCG CCAATCCCGT CATTACCGAG TCCACCGAGA ACAGCAAGAT
2041 GATGCTcGAG CTCGATCCCC CCTTTGGCGA CAGCTACATT GTGATCGGCG TGGGCGAGAA
2101 GAAGATCACC CACCATTGGC ACAGAAGCGG CTCCACAggg ggtagcggtg gtagcggagg
2161 tagccatcac caccatcacc actgagctag CTTGACTACG TGAGATACAG CGTACCTTCA
2221 GCTCACAGAC ATGATAAGAT ACATTGATGA GTTTGGACAA ACCACAACTA GAATGCAGTG
2281 AAAAAAATGC TTTATTTGTG AAATTTGTGA TGCTATTGCT TTATTTGTAA CCATTATAAG
2341 CTGCAATAAA CAAGTTAACA ACAACAATTG CATTCATTTT ATGTTTCAGG TTCAGGGGGA
2401 GGTGTGGGAG GTTTTTTAAA GCAAGTAAAA CCTCTACAAA TGTGGTATTG GCCCATCTCT
2461 ATCGGTATCG TAGCATAACC CCTTGGGGCC TCTAAACGGG TCTTGAGGGG TTTTTTGTGC
2521 CCCTCGGGCC GGATTGCTAT CTACCGGCAT TGGCGCAGAA AAAAATGCCT GATGCGACGC
2581 TGCGCGTCTT ATACTCCCAC ATATGCCAGA TTCAGCAACG GATACGGCTT CCCCAACTTG
2641 CCCACTTCCA TACGTGTCCT CCTTACCAGA AATTTATCCT TAAGGTCGTC AGCTATCCTG
2701 CAGGCGATCT CTCGATTTCG ATCAAGACAT TCCTTTAATG GTCTTTTCTG GACACCACTA
2761 GGGGTCAGAA GTAGTTCATC AAACTTTCTT CCCTCCCTAA TCTCATTGGT TACCTTGGGC
2821 TATCGAAACT TAATTAACCA GTCAAGTCAG CTACTTGGCG AGATCGACTT GTCTGGGTTT
2881 CGACTACGCT CAGAATTGCG TCAGTCAAGT TCGATCTGGT CCTTGCTATT GCACCCGTTC
2941 TCCGATTACG AGTTTCATTT AAATCATGTG AGCAAAAGGC CAGCAAAAGG CCAGGAACCG
3001 TAAAAAGGCC GCGTTGCTGG CGTTTTTCCA TAGGCTCCGC CCCCCTGACG AGCATCACAA
3061 AAATCGACGC TCAAGTCAGA GGTGGCGAAA CCCGACAGGA CTATAAAGAT ACCAGGCGTT
3121 TCCCCCTGGA AGCTCCCTCG TGCGCTCTCC TGTTCCGACC CTGCCGCTTA CCGGATACCT
3181 GTCCGCCTTT CTCCCTTCGG GAAGCGTGGC GCTTTCTCAT AGCTCACGCT GTAGGTATCT
3241 CAGTTCGGTG TAGGTCGTTC GCTCCAAGCT GGGCTGTGTG CACGAACCCC CCGTTCAGCC
3301 CGACCGCTGC GCCTTATCCG GTAACTATCG TCTTGAGTCC AACCCGGTAA GACACGACTT
3361 ATCGCCACTG GCAGCAGCCA CTGGTAACAG GATTAGCAGA GCGAGGTATG TAGGCGGTGC
3421 TACAGAGTTC TTGAAGTGGT GGCCTAACTA CGGCTACACT AGAAGAACAG TATTTGGTAT
3481 CTGCGCTCTG CTGAAGCCAG TTACCTTCGG AAAAAGAGTT GGTAGCTCTT GATCCGGCAA
3541 ACAAACCACC GCTGGTAGCG GTGGTTTTTT TGTTTGCAAG CAGCAGATTA CGCGCAGAAA
3601 AAAAGGATCT CAAGAAGATC CTTTGATCTT TTCTACGGGG TCTGACGCTC AGTGGAACGA
3661 AAACTCACGT TAAGGGATTT TGGTCATGAG ATTATCAAAA AGGATCTTCA CCTAGATCCT
3721 TTTAAATTAA AAATGAAGTT TTAAATCAAT CTAAAGTATA TATGAGTAAA CTTGGTCTGA
3781 CAGTTACCAA TGCTTAATCA GTGAGGCACC TATCTCAGCG ATCGTCTAT TTCGTTCATC
3841 CATAGTTGCA TTTAAATTTC CGAACTCTCC AAGGCCCTCG TCGGAAAATC TTCAAACCTT
3901 TCGTCCGATC CATCTTGCAG GCTACCTCTC GAACGAACTA TCGCAAGTCT CTTGGCCGGC
3961 CTTGCGCCTT GGCTATTGCT TGGCAGCGCC TATCGCCAGG TATTACTCCA ATCCCGAATA
4021 TCCGAGATCG GGATCACCCG AGAGAAGTTC AACCTACATC CTCAATCCCG ATCTATCCGA
4081 GATCCGAGGA ATATCGAAAT CGGGGCGCGC CTGGTGTACC GAGAACGATC CTCTCAGTGC
4141 GAGTCTCGAC GATCCATATC GTTGCTTGGC AGTCAGCCAG TCGGAATCCA GCTTGGGACC
4201 CAGGAAGTCC AATCGTCAGA TATTGTACTC AAGCCTGGTC ACGGCAGCGT ACCGATCTGT
4261 TTAAACCTAG ATATTGATAG TCTGATCGGT CAACGTATAA TCGAGTCCTA GCTTTTGCAA
4321 ACATCTATCA AGAGACAGGA TCAGCAGGAG GCTTTCGCAT GAGTATTCAA CATTTCCGTG
4381 TCGCCCTTAT TCCCTTTTTT GCGGCATTTT GCCTTCCTGT TTTTGCTCAC CCAGAAACGC
4441 TGGTGAAAGT AAAAGATGCT GAAGATCAGT TGGGTGCCGG AGTGGGTTAC ATCGAACTGG
4501 ATCTCAACAG CGGTAAGATC CTTGAGAGTT TTCGCCCCGA AGAACGCTTT CCAATGATGA
4561 GCACTTTTAA AGTTCTGCTA TGTGGCGCGG TATTATCCCG TATTGACGCC GGGCAAGAGC
4621 AACTCGGTCG CCGCATACAC TATTCTCAGA ATGACTTGGT TGAGTATTCA CCAGTCACAG
4681 AAAAGCATCT TACGGATGGC ATGACAGTAA GAGAATTATG CAGTGCTGCC ATAACCATGA
4741 GTGATAACAC TGCGGCCAAC TTACTTCTGA CAACGATTGG AGGACCGAAG GAGCTAACCG
4801 CTTTTTTGCA CAACATGGGG GATCATGTAA CTCGCCTTGA TCGTTGGGAA CCGGAGCTGA
4861 ATGAAGCCAT ACCAAACGAC GAGCGTGACA CCACGATGCC TGTAGCAATG GCAACAACCT
4921 TGCGTAAACT ATTAACTGGC GAACTACTTA CTCTAGCTTC CCGGCAACAG TTGATAGACT
4981 GGATGGAGGC GGATAAAGTT GCAGGACCAC TTCTGCGCTC GGCCCTTCCG GCTGGCTGGT
5041 TTATTGCTGA TAAATCTGGA GCCGGTGAGC GTGGGTCTCG CGGTATCATT GCAGCACTGG
5101 GGCCAGATGG TAAGCCCTCC CGTATCGTAG TTATCTACAC GACGGGGAGT CAGGCAACTA
```

| | | | | |
|---|---|---|---|---|
|5161 TGGATGAACG|AAATAGACAG|ATCGCTGAGA|TAGGTGCCTC|ACTGATTAAG|CATTGGTAAC|
|5221 CGATTCTAGG|TGCATTGGCG|CAGAAAAAAA|TGCCTGATGC|GACGCTGCGC|GTCTTATACT|
|5281 CCCACATATG|CCAGATTCAG|CAACGGATAC|GGCTTCCCCA|ACTTGCCCAC|TTCCATACGT|
|5341 GTCCTCCTTA|CCAGAAATTT|ATCCTTAAGA|TCCCGAATCG|TTTAAACTCG|ACTCTGGCTC|
|5401 TATCGAATCT|CCGTCGTTTC|GAGCTTACGC|GAACAGCCGT|GGCGCTCATT|TGCTCGTCGG|
|5461 GCATCGAATC|TCGTCAGCTA|TCGTCAGCTT|ACCTTTTTGG|CA| |

//
pCR031 (SEQ ID NO: 23)
ORIGIN

| | | | | | |
|---|---|---|---|---|---|
|1 GCGATCGCGG|CTCCCGACAT|CTTGGACCAT|TAGCTCCACA|GGTATCTTCT|TCCCTCTAGT|
|61 GGTCATAACA|GCAGCTTCAG|CTACCTCTCA|ATTCAAAAAA|CCCCTCAAGA|CCCGTTTAGA|
|121 GGCCCCAAGG|GGTTATGCTA|TCAATCGTTG|CGTTACACAC|ACAAAAAACC|AACACACATC|
|181 CATCTTCGAT|GGATAGCGAT|TTTATTATCT|AACTGCTGAT|CGAGTGTAGC|CAGATCTAGT|
|241 AATCAATTAC|GGGGTCATTA|GTTCATAGCC|CATATATGGA|GTTCCGCGTT|ACATAACTTA|
|301 CGGTAAATGG|CCCGCCTGGC|TGACCGCCCA|ACGACCCCCG|CCCATTGACG|TCAATAATGA|
|361 CGTATGTTCC|CATAGTAACG|CCAATAGGGA|CTTTCCATTG|ACGTCAATGG|GTGGAGTATT|
|421 TACGGTAAAC|TGCCCACTTG|GCAGTACATC|AAGTGTATCA|TATGCCAAGT|ACGCCCCTA|
|481 TTGACGTCAA|TGACGGTAAA|TGGCCCGCCT|GGCATTATGC|CCAGTACATG|ACCTTATGGG|
|541 ACTTTCCTAC|TTGGCAGTAC|ATCTACGTAT|TAGTCATCGC|TATTACCATG|CTGATGCGGT|
|601 TTTGGCAGTA|CATCAATGGG|CGTGGATAGC|GGTTTGACTC|ACGGGGATTT|CCAAGTCTCC|
|661 ACCCCATTGA|CGTCAATGGG|AGTTTGTTTT|GGCACCAAAA|TCAACGGGAC|TTTCCAAAAT|
|721 GTCGTAACAA|CTCCGCCCCA|TTGACGCAAA|TGGGCGGTAG|GCGTGTACGG|TGGGAGGTCT|
|781 ATATAAGCAG|AGCTGGTTTA|GTGAACCGTC|AGATCAGATC|TTTGTCGATC|CTACCATCCA|
|841 CTCGACACAC|CCGCCAGCGg|ccgccaccat|gaaggccaat|ctactggtgt|tgctgtgtgc|
|901 ccttgcggcg|gcagatgccA|TCAGGTGCAT|TGGAGTCAGC|AACAGGGACT|TCGTCGAAGG|
|961 CATGTCCGGC|GGCACCTGGG|TGGATGTGGT|GCTCGAACAC|GGCGGATGCG|TGACCGTCAT|
|1021 GGCCCAGGAC|AAGCCTACCG|TCGATATTGA|GCTGTGACCA|ACCACAGTGA|GCAACATGGC|
|1081 CGAAGTGAGA|AGCTACTGCT|ATGAGGCCTC|CATCAGCGAT|ATGGCTTCCG|ATTCCAGATG|
|1141 CCCCACACAG|GGAGAGGCTT|ATCTGGACAA|ACAGTCCGAC|ACCCAGTACG|TCTGCAAAAG|
|1201 AACCCTGGTG|GACAGAGGCT|GGGGAAACGG|ATGCGGCCTG|aacggatcCG|GCAGCCTCGT|
|1261 GACATGTGCC|AAGTTCGCCT|GCAGCAAAAA|GATGACCGGC|AAGTCCATCC|AGCCCGAGAA|
|1321 CCTGGAATAC|AGGATCATGC|TGTCCGTGCA|TGGATCCCGA|CACTCCGGCA|TGATCGTCAA|
|1381 CGATACCGGC|CACGAGACCG|ACGAGAACAG|GGCTAAAGTG|GAGATCACCC|CCAACAGCCC|
|1441 TAGAGCCGAA|GCTACACTGG|GCGGCTTCGG|AAGCCTGGGC|CTGGATTGCG|AACCCAGGAC|
|1501 CGGCCTGGAT|TTCAGCGACC|TGTATTACCT|GACCATGAAC|AATAAGCACT|GGCTGGTGCA|
|1561 CAAGGAATGG|TTCCACGACA|TCCCCCTGCC|TTGGCATGCT|GGCGCCGATA|CCGGCACACC|
|1621 TCACTGGAAC|AATAAGGAAG|CCCTGGTCGA|GTTTAAGGAC|GCCCACGCCA|AAAGACAGAC|
|1681 CGTGGTGGTG|CTGGGAAGCC|AGGAGGGAGC|TGTCCACACA|GCCCTGGCCG|GAGCTCTGGA|
|1741 AGCCGAGATG|GATGCGCCA|AGGGCAGGCT|GAGCTCCGGC|CACCTGAAAT|GCAGGCTCAA|
|1801 GATGGACAAG|CTGAGGCTGA|AGGGCGTGAG|CTACAGCCTG|TGCACCGCCG|CTTTCACCTT|
|1861 TACCAAGATC|CCTGCCGAGA|CACTGCACGG|CACCGTCACC|GTGGAGGTGC|AATACGCCGG|
|1921 AACCGATGGA|CCTTGCAAAG|TGCCTGCCCA|GATGGCTGTG|GATATGCAGA|CCCTCACACC|
|1981 CGTCGGCAGG|CTGATCACCG|CCAATCCCGT|CATTACCGAG|TCCACCGAGA|ACAGCAAGAT|
|2041 GATGCtCGAG|CTCGATCCCC|CCTTTGGCGA|CAGCTACATT|GTGATCGGCG|TGGGCGAGAA|
|2101 GAAGATCACC|CACCATTGGC|ACAGAAGCGG|CTCCACAggg|ggtagcggtg|gtagcggagg|
|2161 tagccatcac|caccatcacc|actgagctag|CTTGACTGAC|TGAGATACAG|CGTACCTTCA|
|2221 GCTCACAGAC|ATGATAAGAT|ACATTGATGA|GTTTGGACAA|ACCACAACTA|GAATGCAGTG|
|2281 AAAAAAATGC|TTTATTTGTG|AAATTTGTGA|TGCTATTGCT|TTATTTGTAA|CCATTATAAG|
|2341 CTGCAATAAA|CAAGTTAACA|ACAACAATTG|CATTCATTTT|ATGTTTCAGG|TTCAGGGGGA|
|2401 GGTGTGGGAG|GTTTTTTAAA|GCAAGTAAAA|CCTCTACAAA|TGTGGTATTG|GCCCATCTCT|
|2461 ATCGGTATCG|TAGCATAACC|CCTTGGGGCC|TCTAAACGGG|TCTTGAGGGG|TTTTTTGTGC|
|2521 CCCTCGGGCC|GGATTGCTAT|CTACCGGCAT|TGGCGCAGAA|AAAAATGCCT|GATGCGACGC|
|2581 TGCGCGTCTT|ATACTCCCAC|ATATGCCAGA|TTCAGCAACG|GATACGGCTT|CCCCAACTTG|
|2641 CCCACTTCCA|TACGTGTCCT|CCTTACCAGA|AATTTATCCT|TAAGGTCGTC|AGCTATCCTG|
|2701 CAGGCGATCT|CTCGATTTCG|ATCAAGACAT|TCCTTTAATG|GTCTTTTCTG|GACACCACTA|
|2761 GGGGTCAGAA|GTAGTTCATC|AAACTTTCTT|CCCTCCCTAA|TCTCATTGGT|TACCTTGGGC|
|2821 TATCGAAACT|TAATTAACCA|GTCAAGTCAG|CTACTTGGCG|AGATCGACTT|GTCTGGGTTT|
|2881 CGACTACGCT|CAGAATTGCG|TCAGTCAAGT|TCGATCTGGT|CCTTGCTATT|GCACCCGTTC|
|2941 TCCGATTACG|AGTTTCATTT|AAATCATGTG|AGCAAAAGGC|CAGCAAAAGG|CCAGGAACCG|
|3001 TAAAAAGGCC|GCGTTGCTGG|CGTTTTTCCA|TAGGCTCCGC|CCCCCTGACG|AGCATCACAA|
|3061 AAATCGACGC|TCAAGTCAGA|GGTGGCGAAA|CCCGACAGGA|CTATAAAGAT|ACCAGGCGTT|
|3121 TCCCCCTGGA|AGCTCCCTCG|TGCGCTCTCC|TGTTCCGACC|CTGCCGCTTA|CCGGATACCT|
|3181 GTCCGCCTTT|CTCCCTTCGG|GAAGCGTGGC|GCTTTCTCAT|AGCTCACGCT|GTAGGTATCT|
|3241 CAGTTCGGTG|TAGGTCGTTC|GCTCCAAGCT|GGGCTGTGTG|CACGAACCCC|CCGTTCAGCC|
|3301 CGACCGCTGC|GCCTTATCCG|GTAACTATCG|TCTTGAGTCC|AACCCGGTAA|GACACGACTT|
|3361 ATCGCCACTG|GCAGCAGCCA|CTGGTAACAG|GATTAGCAGA|GCGAGGTATG|TAGGCGGTGC|
|3421 TACAGAGTTC|TTGAAGTGGT|GGCCTAACTA|CGGCTACACT|AGAAGAACAG|TATTTGGTAT|
|3481 CTGCGCTCTG|CTGAAGCCAG|TTACCTTCGG|AAAAAGAGTT|GGTAGCTCTT|GATCCGGCAA|
|3541 ACAAACCACC|GCTGGTAGCG|GTGGTTTTTT|TGTTTGCAAG|CAGCAGATTA|CGCGCAGAAA|
|3601 AAAAGGATCT|CAAGAAGATC|CTTTGATCTT|TTCTACGGGG|TCTGACGCTC|AGTGGAACGA|
|3661 AAACTCACGT|TAAGGGATTT|TGGTCATGAG|ATTATCAAAA|AGGATCTTCA|CCTAGATCCT|
|3721 TTTAAATTAA|AAATGAAGTT|TTAAATCAAT|CTAAAGTATA|TATGAGTAAA|CTTGGTCTGA|
|3781 CAGTTACCAA|TGCTTAATCA|GTGAGGCACC|TATCTCAGCG|ATCTGTCTAT|TTCGTTCATC|
|3841 CATAGTTGCA|TTTAAATTTC|CGAACTCTCC|AAGGCCCTCG|TCGAAAATC|TTCAAACCTT|
|3901 TCGTCCGATC|CATCTTGCAG|GCTACCTCTC|GAACGAACTA|TCGCAAGTCT|CTTGGCCGGC|
|3961 CTTGCGCCTT|GGCTATTGCT|TGGCAGCGCC|TATCGCCAGG|TATTACTCCA|ATCCCGAATA|

Sequence Listing Free Text

```
4021 TCCGAGATCG GGATCACCCG AGAGAAGTTC AACCTACATC CTCAATCCCG ATCTATCCGA
4081 GATCCGAGGA ATATCGAAAT CGGGGCGCGC CTGGTGTACC GAGAACGATC CTCTCAGTGC
4141 GAGTCTCGAC GATCCATATC GTTGCTTGGC AGTCAGCCAG TCGGAATCCA GCTTGGGACC
4201 CAGGAAGTCC AATCGTCAGA TATTGTACTC AAGCCTGGTC ACGGCAGCGT ACCGATCTGT
4261 TTAAACCTAG ATATTGATAG TCTGATCGGT CAACGTATAA TCGAGTCCTA GCTTTTGCAA
4321 ACATCTATCA AGAGACAGGA TCAGCAGGAG GCTTTCGCAT GAGTATTCAA CATTTCCGTG
4381 TCGCCCTTAT TCCCTTTTTT GCGGCATTTT GCCTTCCTGT TTTTGCTCAC CCAGAAACGC
4441 TGGTGAAAGT AAAAGATGCT GAAGATCAGT TGGGTGCGCG AGTGGGTTAC ATCGAACTGG
4501 ATCTCAACAG CGGTAAGATC CTTGAGAGTT TTCGCCCCGA AGAACGCTTT CCAATGATGA
4561 GCACTTTTAA AGTTCTGCTA TGTGGCGCGG TATTATCCCG TATTGACGCC GGGCAAGAGC
4621 AACTCGGTCG CCGCATACAC TATTCTCAGA ATGACTTGGT TGAGTATTCA CCAGTCACAG
4681 AAAAGCATCT TACGGATGGC ATGACAGTAA GAGAATTATG CAGTGCTGCC ATAACCATGA
4741 GTGATAACAC TGCGGCCAAC TTACTTCTGA CAACGATTGG AGGACCGAAG GAGCTAACCG
4801 CTTTTTTGCA CAACATGGGG GATCATGTAA CTCGCCTTGA TCGTTGGGAA CCGGAGCTGA
4861 ATGAAGCCAT ACCAAACGAC GAGCGTGACA CCACGATGCC TGTAGCAATG GCAACAACCT
4921 TGCGTAAACT ATTAACTGGC GAACTACTTA CTCTAGCTTC CCGGCAACAG TTGATAGACT
4981 GGATGGAGGC GGATAAAGTT GCAGGACCAC TTCTGCGCTC GGCCCTTCCG GCTGGCTGGT
5041 TTATTGCTGA TAAATCTGGA GCCGGTGAGC GTGGGTCTCG CGGTATCATT GCAGCACTGG
5101 GGCCAGATGG TAAGCCCTCC CGTATCGTAG TTATCTACAC GACGGGGAGT CAGGCAACTA
5161 TGGATGAACG AAATAGACAG ATCGCTGAGA TAGGTGCCTC ACTGATTAAG CATTGGTAAC
5221 CGATTCTAGG TGCATTGGCG CAGAAAAAAA TGCCTGATGC GACGCTGCGC GTCTTATACT
5281 CCCACATATG CCAGATTCAG CAACGGATAC GGCTTCCCCA ACTTGCCCAC TTCCATACGT
5341 GTCCTCCTTA CCAGAAATTT ATCCTTAAGA TCCCGAATCG TTTAAACTCG ACTCTGGCTC
5401 TATCGAATCT CCGTCGTTTC GAGCTTACGC GAACAGCCGT GGCGCTCATT TGCTCGTCGG
5461 GCATCGAATC TCGTCAGCTA TCGTCAGCTT ACCTTTTTGG CA
```

//

Hyperglycosylated exodomain D1 (from pCR021) (SEQ ID NO: 24)

Hyperglycosylated exodomain D2 (from pCR022) (SEQ ID NO: 25)

Hyperglycosylated exodomain D3 (from pCR023) (SEQ ID NO: 26)

Hyperglycosylated exodomain D4 (from pCR024) (SEQ ID NO: 27)

Hyperglycosylated exodomain Zika(from pCR028) (SEQ ID NO: 28)

SEQ ID NO: 24 >DENV1_Eexo = pCR021
MRCVGIGNRDFVEGLSGATWVDVVLEHGSCVTTMAKDKPTLDIELLKTEVTNPAVLRKLCIEAKISNTTTDSRCP
TQGEATLVEEQDSNFVCRRTFVDRGNGSGCGLNGSGSLLTCAKFKCVTKLEGKIVQYENLKYSVIVTVHTGDQHQ
VGNETTEHGTIATITPQAPTSEIQLTDYGALTLDCSPRTGLDFNEMVLLTMKEKSWLVHRQWFLDLPLPWTSGAS
TSQETWNRQDLLVTFKTAHAKKQEVVVLGSQEGAMHTALTGATEIQTSGTTTIFAGHLKCRLKMDKLTLKGMSYV
MCTGSFKLEKEVAETQHGTVLVQVKYEGTDAPCKIPFSAQDEKGVTQNGRLITANPIVTDKEKPVNIETEPPFGE
SYIVVGAGEKALKLSWFKKGSTGGGSHHHHHH SEQ ID NO: 25 >DENV2_Eexo = pCR022
MRCIGISNRDFVEGVSGGSWVDIVLEHGSCVTTMAKNKPTLDFELIKTEAKQPATLRKYCIEAKLTNTTTESRCP
TQGEPSLNEEQDKRFVCKHSMVDRGNGSGCGLNGSGGIVTCAMFTCKKNMEGKVVQPENLEYTIVITPHSGEEHA
VGNDTGKHGKEIKITPQSSITEAELTGYGTVTMECSPRTGLDFNEMVLLQMENKAWLVHRQWFLDLPLPWLPGAD
TQGSNWIQKETLVTFKNPHAKKQDVVVLGSQEGAMHTALTGATEIQMSSGNLLFTGHLKCRLRMDKLQLKGMSYS
MCTGKFKVVKEIAETQHGTIVIRVQYEGDGSPCKIPFEIMDLEKRHVLGRLITVNPIVTEKDSPVNIEAEPPFGD
SYIIIGVEPGQLKLNWFKKGSSGGGSHHHHHH SEQ ID NO: 26 >DENV3_Eexo = pCR023
MRCVGVGNRDFVEGLSGATWVDVVLEHGGCVTTMAKNKPTLDIELQKTEATQLATLRKLCIEGKITNITTDSRCP
TQGEAVLPEEQDQNYVCKHTYVDRGNGSGCGLNGSGSLVTCAKFQCLEPIEGKVVQYENLKYTVIITVHTGDQHQ
VGNETQGVTAEITPQASTTEAILPEYGTLGLECSPRTGLDFNEMILLTMKNKAWMVHRQWFFDLPLPWASGATTE
TPTWNRKELLVTFKNAHAKKQEVVVLGSQEGAMHTALTGATEIQNSGGTSIFAGHLKCRLKMDKLELKGMSYAMC
TNTFVLKKEVSETQHGTILIKVEYKGEDAPCKIPFSTEDGQGKAHNGRLITANPVVTKKEEPVNIEAEPPFGESN
IVIGIGDNALKINWYKKGSSGGGSHHHHHH SEQ ID NO: 27 >DENV4_Eexo = pCR024
MRCVGVGNRDEVEGVSGGAWVDLVLEHGGCVTTMAQGKPTLDFELTKTTAKEVALLRTYCIEASISNITTATRCP
TQGEPYLKEEQDQQYICRRDVVDRGNGSGCGLNGSGGVVTCAKFSCSGKITGNLVQIENLEYTVVVTVHNGDTHA
VGNDTSNHGVTAMITPRSPSVEVKLPDYGELTLDCEPRSGIDFNEMILMKMKKKTWLVHKQWFLDLPLPWTAGAD
TSEVHWNYKERMVTFKVPHAKRQDVTVLGSQEGAMHSALAGATEVDSGDGNHMFAGHLKCKVRMEKLRIKGMSYT
MCSGKFSIDKEMAETQHGTTVVKVKYEGAGAPCKVPIEIRDVNKEKVVGRIISSTPLAENTNSVTNIELEPPFGD
SYIVIGVGNSALTLHWFRKGSSGGGSHHHHHH SEQ ID NO: 28 >ZIKV_Eexo = pCR025
IRCIGVSNRDFVEGMSGGTWVDVVLEHGGCVTVMAQDKPTVDIELVTTTVSNMAEVRSYCYEASISDMASDSRCP
TQGEAYLDKQSDTQYVCKRTLVDRGNGSGCGLNGSGSLVTCAKFACSKKMTGKSIQPENLEYRIMLSVHGSQHSG
MIVNDTGHETDENRAKVEITPNSPRAEATLGGEGSLGLDCEPRTGLDFSDLYYLTMNNKHWLVHKEWFHDIPLPW
HAGADTGTPHWNNKEALVEFKDAHAKRQTVVVLGSQEGAVHTALAGALEAEMDGAKGRLSSGHLKCRLKMDKLRL
KGVSYSLCTAAFFTKIPAETLHGTVTVEVQYAGTDGPCKVPAQMAVDMQTLTPVGRLITANPVITESTENSKMM
LELDPPFGDSYIVIGVGEKKITHHWHRSGSTGGSGGSGGSHHHHHH

Sequence Listing Free Text

SEQ ID NO: 29 >DENV1_Eexo 2.1 (single sequon W101N;N103S) [= insert for pCR026 plasmid]
MRCVGIGNRDFVEGLSGATWVDVVLEH Vaccine. *Evolution: Education and Outreach,* 4(4), 635-643. http://doi.org/10.1007/s12052-011-0365-y Kostyuchenko, V. A., Lim, E. X. Y., Zhang, S., Fibriansah, G., Ng, T.-S., Ooi, J. S. G., et al. (2016). Structure of the thermally stable Zika virus. *Nature.* http://doi.org/10.1038/nature17994

Laing, P., Bacon, A., McCormack, B., Gregoriadis, G., Frisch, B., & Schuber, F. (2006). The "co-delivery" approach to liposomal vaccines: application to the development of influenza-A and hepatitis-B vaccine candidates. *Journal of Liposome Research,* 16(3), 229-235. http://doi.org/10.1080/08982100600880432

Paul, L. M., Carlin, E. R., Jenkins, M. M., Tan, A. L., Barcellona, C. M., Nicholson, C. O., et al. (2016). *Dengue Virus Antibodies Enhance Zika Virus Infection* (p. 050112). Cold Spring Harbor Labs Journals.

Ramsauer, K., Schwameis, M., Firbas, C., Müllner, M., Putnak, R. J., Thomas, S. J., et al. (2015). Immunogenicity, safety, and tolerability of a recombinant measles-virus-based chikungunya vaccine: a randomised, double-blind, placebo-controlled, active-comparator, first-in-man trial. *The Lancet. Infectious Diseases,* 15(5), 519-527. http://doi.org/10.1016/S1473-3099(15)70043-5

Roby J A et al., (2013) West Nile Virus Genome with Glycosylated Envelope Protein and Deletion of Alpha Helices 1, 2, and 4 in the Capsid Protein Is Noninfectious and Efficiently Secretes Subviral Particles . . . " *J Virol* Vol 87(23), 13063-16069

Roby J A et al., (2014) Increased expression of capsid protein in trans enhances production of single-round infectious particles by West Nile virus DNA vaccine candidate. *J Gen Virol,* 95, 2176-2019.

Russell, P. K. (2016). The Zika Pandemic—A Perfect Storm? *PLoS Neglected Tropical Diseases,* 10(3). http://doi.org/10.1371/journal.pntd.0004589

Sirohi, D., Chen, Z., Sun, L., Klose, T., Pierson, T. C., Rossmann, M. G., & Kuhn, R. J. (2016). The 3.8 A resolution cryo-EM structure of Zika virus. *Science,* 352 (6284), 467-470. http://doi.org/10.1126/science.aaf5316

Tregoning, J. S., & Kinnear, E. (2014). Using Plasmids as DNA Vaccines for Infectious Diseases. *Microbiology Spectrum,* 2(6). http://doi.org/10.1128/microbiolspec.PLAS-0028-2014

Tretyakova, I., Nickols, B., Hidajat, R., Jokinen, J., Lukashevich, I. S., & Pushko, P. (2014). Plasmid DNA initiates replication of yellow fever vaccine in vitro and elicits virus-specific immune response in mice. *Virology,* 468-470, 28-35. http://doi.org/10.1016/j.virol.2014.07.050

Alaniz, A. J., Bacigalupo, A., & Cattan, P. E. (2017). Spatial quantification of the world population potentially exposed to Zika virus. *International Journal of Epidemiology,* 1-10. http://doi.org/10.1093/ije/dyw366

Beltramello, M., Williams, K. L., Simmons, C. P., Macagno, A., Simonelli, L., Quyen, N. T. H., et al. (2010). The Human Immune Response to Dengue Virus Is Dominated by Highly Cross-Reactive Antibodies Endowed with Neutralizing and Enhancing Activity. *Cell Host & Microbe,* 8(3), 271-283. http://doi.org/10.1016/j.chom.2010.08.007

Chang, H.-H., Huber, R. G., Bond, P. J., Grad, Y. H., Camerini, D., Maurer-Stroh, S., & Lipsitch, M. (2017). Systematic analysis of protein identity between Zika virus and other arthropod-borne viruses. *Bulletin of the World Health Organization,* 95(7), 517-5251. http://doi.org/10.2471/BLT.16.182105

Dejnirattisai, W., Supasa, P., Wongwiwat, W., Rouvinski, A., Barba-Spaeth, G., Duangchinda, T., et al. (2016). Dengue virus sero-cross-reactivity drives antibody-dependent enhancement of infection with zika virus. *Nature Immunology,* 17(9), 1102-1108. http://doi.org/10.1038/ni.3515

Dejnirattisai, W., Wongwiwat, W., Supasa, S., Zhang, X., Dai, X., Rouvinsky, A., et al. (2014). A new class of highly potent, broadly neutralizing antibodies isolated from viremic patients infected with dengue virus. *Nature Immunology,* 16(2), 170-177. http://doi.org/10.1038/ni.3058

Dengue-yellow fever sera cross-reactivity; challenges for diagnosis.—PubMed—NCBI. (2017, Aug. 14). Dengue-yellow fever sera cross-reactivity; challenges for diagnosis.—PubMed—NCBI. Retrieved Aug. 22, 2017, from message:%3CA85487139-6B59-4645-8CEA-093E63DEB692@excivion.com%3E Ferguson, N. M., Rodríguez-Barraquer, I., Dorigatti, I., Mier-Y-Teran-Romero, L., Laydon, D. J., & Cummings, D. A. T. (2016). Benefits and risks of the Sanofi-Pasteur dengue vaccine: Modeling optimal deployment. *Science,* 353(6303), 1033-1036. http://doi.org/10.1126/science.aaf9590

Flasche, S., Jit, M., Rodríguez-Barraquer, I., Coudeville, L., Recker, M., Koelle, K., et al. (2016). The Long-Term Safety, Public Health Impact, and Cost-Effectiveness of Routine Vaccination with a Recombinant, Live-Attenuated Dengue Vaccine (Dengvaxia): A Model Comparison Study. *PLOS Medicine,* 13(11), e1002181-19. http://doi.org/10.1371/journal.pmed.1002181

Guzman, M. G., Alvarez, M., & Halstead, S. B. (2013). Secondary infection as a risk factor for dengue hemorrhagic fever/dengue shock syndrome: an historical perspective and role of antibody-dependent enhancement of infection. *Archives of Virology,* 158(7), 1445-1459. http://doi.org/10.1007/s00705-013-1645-3

Hadinegoro, S. R., Arredondo-García, J. L., Capeding, M. R., Deseda, C., Chotpitayasunondh, T., Dietze, R., et al. (2015). Efficacy and Long-Term Safety of a Dengue Vaccine in Regions of Endemic Disease. *The New England Journal of Medicine,* 373(13), 1195-1206. http://doi.org/10.1056/NEJMoa1506223

Halstead, S. B. (2014). Dengue Antibody-Dependent Enhancement: Knowns and Unknowns. *Microbiology Spectrum,* 2(6), 1-24. http://doi.org/10.1128/microbiolspec.AID-0022-2014

Halstead, S. B. (2017a). ?term=Achieving+safe%2C+effective%2C+and+durable+Zika+virus. *The Lancet. Infectious Diseases,* 17(11), e378-e382. http://doi.org/10.1016/S1473-3099(17)30362-6

Halstead, S. B. (2017b). ?term=Biologic+Evidence+Required+Halstead+SB. *Emerging Infectious Diseases,* 23(4), 569-573. http://doi.org/10.3201/eid2304.161879

Hofer, U. (2016). Viral Pathogenesis: Tracing the steps of Zika virus. *Nature Reviews Microbiology,* 14(7), 401-401. http://doi.org/10.1038/nrmicro.2016.80

Katzelnick, L. C., Gresh, L., Halloran, M. E., Mercado, J. C., Kuan, G., Gordon, A., et al. (2017). Antibody-dependent enhancement of severe dengue disease in humans. *Science*, eaan6836. http://doi.org/10.1126/science.aan6836

Lai, C. Y., Tsai, W. Y., Lin, S. R., Kao, C. L., Hu, H. P., King, C. C., et al. (2008). Antibodies to Envelope Glycoprotein of Dengue Virus during the Natural Course of Infection Are Predominantly Cross-Reactive and Recognize Epitopes Containing Highly Conserved Residues at the Fusion Loop of Domain II. *Journal of Virology,* 82(13), 6631-6643. http://doi.org/10.1128/JVI.00316-08

Laing, P. (1986). Luminescent visualization of antigens on blots. *Journal of Immunological Methods,* 92(2), 161-165.

Ling, Y., Chen, J., Huang, Q., Hu, Y., Zhu, A., Ye, S., et al. (2016). Yellow Fever in a Worker Returning to China from Angola, March 2016. *Emerging Infectious Diseases,* 22(7), 1317-1318. http://doi.org/10.3201/eid2207.160469

Lucey, D., Cummins, H., & Sholts, S. (2017). Congenital Zika Syndrome in 2017. *Jama,* 3/7(13), 1368. http://doi.org/10.1001/jama.2017.1553

Medina, M. T., & Medina-Montoya, M. (2017). New spectrum of the neurologic consequences of Zika. *Journal of the Neurological Sciences.* http://doi.org/10.1016/j.jns.2017.10.046

Mir, D., Delatorre, E., Bonaldo, M., Lourenço-de-Oliveira, R., Vicente, A. C., & Bello, G. (2017). Phylodynamics of Yellow Fever Virus in the Americas: new insights into the origin of the 2017 Brazilian outbreak. *Scientific Reports,* 7(1), 198. http://doi.org/10.1038/s41598-017-07873-7

Paul, L. M., Carlin, E. R., Jenkins, M. M., Tan, A. L., Barcellona, C. M., Nicholson, C. O., et al. (2016). *Dengue Virus Antibodies Enhance Zika Virus Infection* (p. 050112). Cold Spring Harbor Labs Journals.

Priyamvada, L., Quicke, K. M., Hudson, W. H., Onlamoon, N., Sewatanon, J., Edupuganti, S., et al. (n.d.). Human antibody responses after dengue virus infection are highly cross-reactive to Zika virus. Pnas.org.

Russell, P. K. (2016). The Zika Pandemic—A Perfect Storm? *PLoS Neglected Tropical Diseases,* 10(3). http://doi.org/10.1371/journal.pntd.0004589

Sariol, C. A., Nogueira, M. L., & Vasilakis, N. (2017). A Tale of Two Viruses: Does Heterologous Flavivirus Immunity Enhance Zika Disease? *Trends in Microbiology.* http://doi.org/10.1016/j.tim.2017.10.004

Screaton, G., Mongkolsapaya, J., Yacoub, S., & Roberts, C. (2015). New insights into the immunopathology and control of dengue virus infection. *Nature Reviews Immunology,* 15(12), 745-759. http://doi.org/doi:10.1038/nri3916

Sen, P., Yamaguchi, S., & Tahara, T. (2008). New Insight into the Surface Denaturation of Proteins: Electronic Sum Frequency Generation Study of Cytochrome c at Water Interfaces. *The Journal of Physical Chemistry B,* 112(43), 13473-13475. http://doi.org/10.1021/jp8061288

Sirohi, D., Chen, Z., Sun, L., Klose, T., Pierson, T. C., Rossmann, M. G., & Kuhn, R. J. (2016). The 3.8 A resolution cryo-EM structure of Zika virus. *Science,* 352 (6284), 467-470. http://doi.org/10.1126/science.aaf5316

Smith, D. R. (2016). Waiting in the wings: The potential of mosquito transmitted flaviviruses to emerge. *Critical Reviews in Microbiology,* 43(4), 405-422. http://doi.org/10.1080/1040841X.2016.1230974

Willis, E., & Hensley, S. E. (2017). Characterization of Zika virus binding and enhancement potential of a large panel of flavivirus murine monoclonal antibodies. *Virology,* 508, 1-6. http://doi.org/10.1016/j.virol.2017.04.031

---

The invention claimed is:

1. An isolated recombinant analogue of a flavivirus E-protein comprising an analogue of a flavivirus E-protein fusion loop, wherein the analogue of the flavivirus E-protein fusion loop comprises at least one glycosylation site for an N-linked glycan that is not present in a natural flavivirus E-protein fusion loop sequence, wherein the at least one glycosylation site is an N-linked glycosylation sequon (Asn-X-Ser/Thr) and the Asn (N) residue of the sequon occupies any of positions 98-110 (DRGWGNGCGLFGK; SEQ ID NO: 1) of the natural flavivirus E-protein fusion loop amino acid sequence, wherein X is any amino acid residue except proline and Ser/Thr denotes a serine or threonine residue, wherein the analogue is configured for use in an in vitro method for specific detection of anti-flavivirus antibody, diagnosis of flavivirus infection and/or to investigate exposure to flavivirus.

2. The isolated recombinant analogue of a flavivirus E-protein according to claim 1, wherein the analogue of the flavivirus E-protein fusion loop comprises two glycosylation sites that are not present in a natural flavivirus E-protein fusion loop.

3. The isolated recombinant analogue of a flavivirus E-protein of claim 1 which is glycosylated with a glycan at one or at both of the introduced glycosylation sites in the analogue of the flavivirus E-protein fusion loop.

4. The isolated recombinant analogue of a flavivirus E-protein of claim 1 wherein the glycan is an N-linked glycan.

5. The isolated recombinant analogue of a flavivirus E-protein of claim 1, comprising an N-linked glycosylation sequon (Asn-X-Ser/Thr) such that an Asn (N) residue of the sequon occupies any of positions 98-101 and/or 106-110.

6. The isolated recombinant analogue of a flavivirus E-protein of claim 1, wherein X is selected from any of the following 13 amino acid residues Gly, His, Asn, Gln, Tyr, Val, Ala, Met, Ile, Lys, Arg, Thr or Ser.

7. The isolated recombinant analogue of a flavivirus E-protein of claim 1, wherein the flavivirus E-protein is a dengue virus E-protein and the Asn (N) residue of the sequon occupies position 101, 108 or both 101 and 108 of the amino acid sequence of the flavivirus E-protein fusion loop or the flavivirus E-protein is a Zika E-protein and the Asn (N) residue of the sequon occupies position 100 of the amino acid sequence of the flavivirus E-protein fusion loop.

8. The isolated recombinant analogue of a flavivirus E-protein of claim 1, wherein the flavivirus is a dengue virus and the amino acid sequence of the analogue flavivirus E-protein fusion loop 98-110 is selected from: DRGNGSGCGLNGS (SEQ ID NO: 2), DRGNGSGCGLFGK (SEQ ID NO: 3) and DRGWGNGCGLNGS (SEQ ID NO: 4).

9. The isolated recombinant analogue of a flavivirus E-protein of claim 1, wherein the flavivirus is a Zika virus and the amino acid sequence of the analogue flavivirus E-protein fusion loop 98-110 is DRNHTNGCGLFGK (SEQ ID NO: 5).

10. A test kit comprising an isolated recombinant analogue of a flavivirus E-protein of claim 1 and a reagent capable of detecting an immunological (antigen-antibody) complex which contains said isolated analogue or binding molecule.

11. The test kit according to claim 10, wherein said analogue and/or binding molecule is immobilized on a solid support.

12. The test kit according to claim 11, wherein the solid support is a microplate well.

13. The test kit according to claim 10, wherein said immunological complex which contains said isolated analogue or binding molecule is detected by lateral flow.

14. The test kit according to claim 10, wherein said kit comprises a test device comprising lateral flow test strip comprising:
a sample pad for application of a liquid sample,
a conjugate pad comprising a detector conjugate for conjugation of anti-flavivirus antibody in the liquid sample,
a capture strip comprising a capture means to capture detector conjugate-anti-flavivirus antibody complex
and
an absorbent pad,
the pads and strip being arranged to permit capillary flow communication with each other.

15. The test kit according to claim 10, wherein said kit comprises a test device comprising a lateral flow test strip comprising:
a sample pad for application of a liquid sample, said sample pad comprising a first test antigen with a first tag and one or more second pre-absorbing antigen(s) optionally with a second tag,
a conjugate pad comprising a detector conjugate for conjugation of anti-flavivirus antibody in the liquid sample,
a capture strip comprising a capture means to capture detector conjugate-anti-flavivirus antibody complex via the first tag,
and
an absorbent pad,
the pads and strip being arranged to permit capillary flow communication with each other,
wherein the first antigen comprises a glycosylated analogue of a Zika E-protein fusion loop of claim 1 and the second pre-absorbing antigen(s) comprises one or more glycosylated analogue of a Dengue E-protein fusion loop of claim 1, or
wherein the first antigen comprises a glycosylated analogue of a Dengue E-protein fusion loop of claim 1 and the second pre-absorbing antigen comprises a glycosylated analogue of a Zika E-protein fusion loop of claim 1.

16. The test kit according to claim 14 wherein the capture means for capture of the detector conjugate-anti-flavivirus antibody complex is an antigen comprising a recombinant analogue of a flavivirus E-protein of claim 1.

17. The test kit according to claim 14, wherein the capture means is provided as a line on the capture strip.

18. The test kit according to claim 14, wherein the liquid sample is a biological sample.

19. The test kit according to claim 18, wherein the liquid sample is a biological sample selected from blood, plasma, serum, saliva, oral fluid and CSF.

20. A method for detection of a flavivirus antibody in a sample comprising contacting the sample with a) a recombinant analogue of a flavivirus E-protein of claim 1 and b) a reagent capable of detecting an immunological (antigen-antibody) complex which contains the recombinant analogue.

* * * * *

SEQUENCE LISTING

```
<160> NUMBER OF SEQ ID NOS: 130

<210> SEQ ID NO 1
<211> LENGTH: 13
<212> TYPE: PRT
<213> ORGANISM: Flavivirus

<400> SEQUENCE: 1

Asp Arg Gly Trp Gly Asn Gly Cys Gly Leu Phe Gly Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Modified Flavivirus E protein fusion loop
      98-110 fragment

<400> SEQUENCE: 2

Asp Arg Gly Asn Gly Ser Gly Cys Gly Leu Asn Gly Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Modified Flavivirus E protein fusion loop
      98-110 fragment

<400> SEQUENCE: 3

Asp Arg Gly Asn Gly Ser Gly Cys Gly Leu Phe Gly Lys
1               5                   10

<210> SEQ ID NO 4
<211> LENGTH: 13
<212> TYPE: PRT
```

<213> ORGANISM: Artificial Sequence
<220> FEATURE:
<223> OTHER INFORMATION: Modified Flavivirus E protein fusion loop
      98-110 fragment

<400> SEQUENCE: 4

Asp Arg Gly Trp Gly Asn Gly Cys Gly Leu Asn Gly Ser
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Modified Flavivirus E protein fusion loop
      98-110 fragment

<400> SEQUENCE: 5

Asp Arg Asn His Thr Asn Gly Cys Gly Leu Phe Gly Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Modified Flavivirus E protein fusion loop
      98-110 fragment

<400> SEQUENCE: 6

Asp Arg Gly Trp Gly Asn Gly Cys Gly Asn His Thr Lys
1               5                   10

<210> SEQ ID NO 7
<211> LENGTH: 29
<212> TYPE: PRT
<213> ORGANISM: Artificial Sequence
<220> FEATURE:
<223> OTHER INFORMATION: pCRO25-encoded amino acid sequence containing
      recombinant analogue of flavivirus E protein fusion loop 98-110 of
      SEQ ID NO:2

<400> SEQUENCE: 7

Cys Lys Arg Thr Leu Val Asp Arg Gly Asn Gly Ser Gly Cys Gly Leu
1               5                   10                  15

Asn Gly Ser Gly Ser Leu Val Thr Cys Ala Lys Phe Ala
            20                  25

<210> SEQ ID NO 8
<211> LENGTH: 29
<212> TYPE: PRT
<213> ORGANISM: Artificial Sequence
<220> FEATURE:
<223> OTHER INFORMATION: pCRO29 -encoded amino acid sequence containing
      recombinant analogue of flavivirus E protein fusion loop 98-110
      fragment of SEQ ID NO: 6

<400> SEQUENCE: 8

Cys Lys Arg Thr Leu Val Asp Arg Gly Trp Gly Asn Gly Cys Gly Asn
1               5                   10                  15

His Thr Lys Gly Ser Leu Val Thr Cys Ala Lys Phe Ala
            20                  25

<210> SEQ ID NO 9
<211> LENGTH: 29
<212> TYPE: PRT
<213> ORGANISM: Artificial Sequence

```
<220> FEATURE:
<223> OTHER INFORMATION: pCRO30-encoded amino acid sequence containing
      recombinant analogue of flavivirus E protein fusion loop 98-110
      fragment of SEQ ID NO: 3

<400> SEQUENCE: 9

Cys Lys Arg Thr Leu Val Asp Arg Gly Asn Gly Ser Gly Cys Gly Leu
1               5                   10                  15

Phe Gly Lys Gly Ser Leu Val Thr Cys Ala Lys Phe Ala
            20                  25

<210> SEQ ID NO 10
<211> LENGTH: 29
<212> TYPE: PRT
<213> ORGANISM: Artificial Sequence
<220> FEATURE:
<223> OTHER INFORMATION: pCRO31-encoded amino acid sequence containing
      recombinant analogue of flavivirus E protein fusion loop 98-110
      fragment of SEQ ID NO: 4

<400> SEQUENCE: 10

Cys Lys Arg Thr Leu Val Asp Arg Gly Trp Gly Asn Gly Cys Gly Leu
1               5                   10                  15

Asn Gly Ser Gly Ser Leu Val Thr Cys Ala Lys Phe Ala
            20                  25

<210> SEQ ID NO 11
<211> LENGTH: 13
<212> TYPE: PRT
<213> ORGANISM: Artificial Sequence
<220> FEATURE:
<223> OTHER INFORMATION: Modified flavivirus E protein fusion loop
      98-110 fragment

<400> SEQUENCE: 11

Asp Arg Gly Trp Gly Asn Asn Cys Thr Leu Phe Gly Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Modified flavivirus E protein fusion loop
      98-110 fragment

<400> SEQUENCE: 12

Asp Arg Gly Trp Gly Asn Asn Cys Ser Leu Phe Gly Lys
1               5                   10

<210> SEQ ID NO 13
<211> LENGTH: 5460
<212> TYPE: DNA
<213> ORGANISM: Artificial Sequence
<220> FEATURE:
<223> OTHER INFORMATION: Plasmid expression vector pCRO21

<400> SEQUENCE: 13
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
```

```
cggtaaatgg cccgcctggc tgaccgccca acgaccccg cccattgacg tcaataatga    360
cgtatgttcc catagtaacg ccaataggga cttcccattg acgtcaatgg gtggagtatt    420
tacggtaaac tgcccacttg gcagtacatc aagtgtatca tatgccaagt acgcccccta    480
ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag cgtgtacgg tgggaggtct    780
atataagcag agctggttta gtgaaccgtc agatcagatc tttgtcgatc ctaccatcca    840
ctcgacacac cgccagcgg ccgccaccat gaaggccaat ctactggtgt tgctgtgtgc    900
ccttgcggcg gcagatgcca tgcggtgcgt ggggatcggc aatcgcgatt ttgtagaagg    960
actatctggt gccacgtggg tcgatgtggt tcttgaacac gggtcatgcg tgaccacgat   1020
ggctaaggat aagccgacct tggacatcga actactgaaa accgaggtca caaaccctgc   1080
tgtgctccgc aagctgtgca tcgaggctaa gatttccaac acaactactg atagccgctg   1140
cccccacccca ggcgaggcga ccctcgttga agagcaggac agcaacttcg tgtgtcgccg   1200
gactttcgtg gaccgcggta atgggtccgg atgcggactt aacggatctg gttccttact   1260
gacttgcgcc aaatttaagt gcgtgactaa gttaggg aaaatcgttc agtatgagaa   1320
cttaaaatac tcggtgatag ttaccgtgca cacaggcgac cagcatcaag ttgggaacga   1380
aacgacagag cacgggacaa tagcgaccat taccccacag gctccaacga gcgaaattca   1440
gctgacagac tacggtgcac tcaccctgga ctgtagccca cggaccgggc tagactttaa   1500
cgagatggtg ctcctgacta tgaaggaaaa gtcatggttg gtgcacaagc agtggttcct   1560
tgatcttcca ttgccctgga cctctggcgc ttcgacctca aagagactt ggaacaggca   1620
ggacttgctc gtgacattca aaacggctca cgctaaaaag caagaggtcg tggttctggg   1680
gagtcaggaa ggcgctatgc ataccgcgtt aacaggggct acagagatcc agaccagtgg   1740
aacaaccact attttcgccg ggcatcttaa gtgtaggctg aagatggata agttgaccct   1800
gaaaggtatg tcatatgtga tgtgcaccgg tagtttcaaa ctggagaaag aagtggccga   1860
aacccagcat ggaacagtac tggtgcaagt caaatatgag gcaccgatg caccatgtaa   1920
aataccttc agcgcacaag acgagaaggg agttacccag aacggtaggc tgataacagc   1980
caatccaatc gtcaccgata aggagaaacc agtaaacatc gaaaccgagc cacccttcgg   2040
cgaaagctac atcgtggtcg gcgctggcga gaaagcactt aagctgagct ggtttaagaa   2100
aggtagcacg ggcggcggca gccatcatca ccatcatcac tgagctagct tgactgactg   2160
agatacagcg taccttcagc tcacagacat gataagatac attgatgagt ttggacaaac   2220
cacaactaga atgcagtgaa aaaaatgctt tatttgtgaa atttgtgatg ctattgcttt   2280
atttgtaacc attataagct gcaataaaca agttaacaac aacaattgca ttcattttat   2340
gtttcaggtt caggggggagg tgtgggaggt ttttaaagc aagtaaaacc tctacaaatg   2400
tggtattggc ccatctctat cggtatcgta gcataacccc ttggggcctc taaacgggtc   2460
ttgaggggtt ttttgtgccc ctcggccggg attgctatct accggcattg cgcagaaaa   2520
aaatgcctga tgcgacgctg cgcgtcttat actcccacat atgccagatt cagcaacgga   2580
tacggcttcc ccaacttgcc cacttccata cgtgtcctcc ttaccagaaa tttatcctta   2640
aggtcgtcag ctatcctgca ggcgatctct cgatttcgat caagacattc ctttaatggt   2700
```

```
cttttctgga caccactagg ggtcagaagt agttcatcaa actttcttcc ctccctaatc    2760
tcattggtta ccttgggcta tcgaaactta attaaccagt caagtcagct acttggcgag    2820
atcgacttgt ctgggtttcg actacgctca gaattgcgtc agtcaagttc gatctggtcc    2880
ttgctattgc acccgttctc cgattacgag tttcatttaa atcatgtgag caaaaggcca    2940
gcaaaaggcc aggaaccgta aaaaggccgc gttgctggcg ttttccata ggctccgccc     3000 ccctgacgag catcacaaaa atcgacgctc aagtcagagg tggcgaaacc cgacaggact    3060
ataaagatac caggcgtttc ccctggaag ctccctcgtg cgctctcctg ttccgaccct     3120
gccgcttacc ggatacctgt ccgcctttct cccttcggga agcgtggcgc tttctcatag    3180
ctcacgctgt aggtatctca gttcggtgta ggtcgttcgc tccaagctgg gctgtgtgca    3240
cgaacccccc gttcagcccg accgctgcgc cttatccggt aactatcgtc ttgagtccaa    3300
cccggtaaga cacgacttat cgccactggc agcagccact ggtaacagga ttagcagagc    3360
gaggtatgta ggcggtgcta cagagttctt gaagtggtgg cctaactacg gctacactag    3420
aagaacagta tttggtatct gcgctctgct gaagccagtt accttcggaa aaagagttgg    3480
tagctcttga tccggcaaac aaaccaccgc tggtagcggt ggtttttttg tttgcaagca    3540
gcagattacg cgcagaaaaa aaggatctca agaagatcct ttgatcttt ctacggggtc     3600 tgacgctcag tggaacgaaa actcacgtta agggattttg gtcatgagat tatcaaaaag    3660
gatcttcacc tagatccttt taaattaaaa atgaagtttt aaatcaatct aaagtatata    3720
tgagtaaact tggtctgaca gttaccaatg cttaatcagt gaggcaccta tctcagcgat    3780
ctgtctattt cgttcatcca tagttgcatt taaatttccg aactctccaa ggccctcgtc    3840
ggaaaatctt caaacctttc gtccgatcca tcttgcaggc tacctctcga cgaactatc     3900 gcaagtctct tggccggcct tgcgccttgg ctattgcttg cagcgcctta tcgccaggta    3960
ttactccaat cccgaatatc cgagatcggg atcacccgag agaagttcaa cctacatcct    4020
caatcccgat ctatccgaga tccgaggaat atcgaaatcg gggcgcgcct ggtgtaccga    4080
gaacgatcct ctcagtgcga gtctcgacga tccatatcgt tgcttggcag tcagccagtc    4140
ggaatccagc ttgggaccca ggaagtccaa tcgtcagata ttgtactcaa gcctggtcac    4200
ggcagcgtac cgatctgttt aaacctagat attgatagtc tgatcggtca acgtataatc    4260
gagtcctagc ttttgcaaac atctatcaag agacaggatc agcaggaggc tttcgcatga    4320
gtattcaaca tttccgtgtc gcccttattc cttttttgc ggcattttgc cttcctgttt     4380
ttgctcaccc agaaacgctg gtgaaagtaa aagatgctga agatcagttg ggtgcgcgag    4440
tgggttacat cgaactggat ctcaacagcg gtaagatcct tgagagtttt cgccccgaag    4500
aacgctttcc aatgatgagc acttttaaag ttctgctatg tggcgcggta ttatcccgta    4560
ttgacgccgg gcaagagcaa ctcggtcgcc gcatacacta ttctcagaat gacttggttg    4620
agtattcacc agtcacagaa aagcatctta cggatggcat gacagtaaga gaattatgca    4680
gtgctgccat aaccatgagt gataacactg cggccaactt acttctgaca acgattggag    4740
gaccgaagga gctaaccgct ttttgcaca acatggggga tcatgtaact cgccttgatc     4800
gttgggaacc ggagctgaat gaagccatac caaacgacga gcgtgacacc acgatgcctg    4860
tagcaatggc aacaaccttg cgtaaactat taactggcga actacttact ctagcttccc    4920
ggcaacagtt gatagactgg atggaggcgg ataaagttgc aggaccactt ctgcgctcgg    4980
cccttccggc tggctggttt attgctgata aatctggagc cggtgagcgt gggtctcgcg    5040
```

```
gtatcattgc agcactgggg ccagatggta agccctcccg tatcgtagtt atctacacga    5100
cggggagtca ggcaactatg gatgaacgaa atagacagat cgctgagata ggtgcctcac    5160
tgattaagca ttggtaaccg attctaggtg cattggcgca gaaaaaaatg cctgatgcga    5220
cgctgcgcgt cttatactcc cacatatgcc agattcagca acggatacgg cttccccaac    5280
ttgcccactt ccatacgtgt cctccttacc agaaatttat ccttaagatc ccgaatcgtt    5340
taaactcgac tctggctcta tcgaatctcc gtcgtttcga gcttacgcga acagccgtgg    5400
cgctcatttg ctcgtcgggc atcgaatctc gtcagctatc gtcagcttac cttttttggca   5460

<210> SEQ ID NO 14
<211> LENGTH: 5460
<212> TYPE: DNA
<213> ORGANISM: Artificial Sequence
<220> FEATURE:
<223> OTHER INFORMATION: Plasmid expression vector pCRO22

<400> SEQUENCE: 14
gcgatcgcgg ctcccgacat cttgaccat tagctccaca ggtatcttct tccctctagt      60
ggtcataaca gcagcttcag ctacctctca attcaaaaaa cccctcaaga cccgtttaga    120
ggccccaagg ggttatgcta tcaatcgttg cgttacacac acaaaaaacc aacacacatc    180
catcttcgat ggatagcgat tttattatct aactgctgat cgagtgtagc cagatctagt    240
aatcaattac ggggtcatta gttcatagcc catatatgga gttccgcgtt acataactta    300
cggtaaatgg cccgcctggc tgaccgccca acgaccccg cccattgacg tcaataatga    360
cgtatgttcc catagtaacg ccaatagggga ctttccattg acgtcaatgg gtggagtatt    420
tacggtaaac tgcccacttg gcagtacatc aagtgtatca tatgccaagt acgccccta    480 ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac cgccagcgg ccgccaccat gaaggccaat ctactggtgt tgctgtgtgc    900
ccttgcggcg gcagatgcca tgcgctgcat cgggatcagc aatcgcgact ttgtggaagg    960
agtcagcggc ggatcatggg tggacatcgt gcttgagcac ggcagctgcg tgaccactat    1020
ggcaaagaat aagccgactc tggattttga actcattaaa accgaggcga agcagcccgc    1080
aactctgagg aagtactgca tcgaggccaa actgactaac actaccaccg aatcacggtg    1140
cccgacccaa ggcgaaccga gcctgaacga agagcaggat aagagatttg tctgcaagca    1200
ctcaatggtg gaccggggga atggatccgg ctgcggactg aacggatctg ggggcattgt    1260
gacttgcgca atgttcacct gtaaaaagaa catggagggc aaggtcgtgc agccagagaa    1320
cctggaatac accattgtca ttactccaca ttccggagag gaacacgccg tcggcaacga    1380
cactggaaaa catgggaagg aaattaagat caccccgcag tcgtcaatta ccgaggcaga    1440
actcaccggg tacggcactg tcactatgga gtgctcaccg agaactgggt tggatttcaa    1500
tgagatggtg ctcctacaga tggagaacaa ggcatggctc gtgcaccggc aatggttct    1560 cgacctgccg ctgccttggc tccctgggc cgacactcaa ggctcgaatt ggattcagaa    1620
ggaaacgctg gtcacgttca agaaccccca tgccaagaag caagacgtgg tggtcctggg    1680
```

```
ctcgcaagaa ggagctatgc acaccgctct gaccggcgcg accgaaatcc aaatgtcatc    1740
aggcaacctc ctgttcactg gccacctcaa atgccggctg agaatggata agctgcaact    1800
gaaaggtatg tcctactcga tgtgcaccgg taaatttaaa gtggtgaaag agatcgctga    1860
aactcagcac ggtaccatcg tcatcagggt gcagtacgag ggagacggct caccctgcaa    1920 aatcccttc gaaatcatgg acctcgaaaa gagacacgtg ctgggccgcc tgatcaccgt    1980
taacccgatc gtgaccgaga agacagcccc ggtgaatatt gaagcggaac tcccgttcgg    2040
cgacagctac atcattatcg gcgtggaacc gggccagctg aagcttaatt ggttcaaaaa    2100
ggggtccagc ggcggcggca gccatcatca ccatcatcac tgagctagct tgactgactg    2160
agatacagcg taccttcagc tcacagacat gataagatac attgatgagt ttggacaaac    2220
cacaactaga atgcagtgaa aaaaatgctt tatttgtgaa atttgtgatg ctattgcttt    2280
atttgtaacc attataagct gcaataaaca agttaacaac acaattgca ttcatttat    2340 gtttcaggtt caggggggagg tgtgggaggt tttttaaagc aagtaaaacc tctacaaatg    2400
tggtattggc ccatctctat cggtatcgta gcataacccc ttggggcctc taaacgggtc    2460
ttgaggggtt ttttgtgccc ctcgggccgg attgctatct accggcattg gcgcagaaaa    2520
aaatgcctga tgcgacgctg cgcgtcttat actcccacat atgccagatt cagcaacgga    2580
tacggcttcc ccaacttgcc cacttccata cgtgtcctcc ttaccagaaa tttatcctta    2640
aggtcgtcag ctatcctgca ggcgatctct cgatttcgat caagacattc ctttaatggt    2700
cttttctgga caccactagg ggtcagaagt agttcatcaa actttcttcc ctccctaatc    2760
tcattggtta ccttgggcta tcgaaactta attaaccagt caagtcagct acttggcgag    2820
atcgacttgt ctgggtttcg actacgctca gaattgcgtc agtcaagttc gatctggtcc    2880
ttgctattgc acccgttctc cgattacgag tttcatttaa atcatgtgag caaaaggcca    2940 gcaaaggcc aggaaccgta aaaaggccgc gttgctggcg ttttttccata ggctccgccc    3000 ccctgacgag catcacaaaa atcgacgctc aagtcagagg tggcgaaacc cgacaggact    3060
ataaagatac caggcgtttc cccctggaag ctccctcgtg cgctctcctg ttccgaccct    3120
gccgcttacc ggatacctgt ccgcctttct cccttcggga agcgtggcgc tttctcatag    3180
ctcacgctgt aggtatctca gttcggtgta ggtcgttcgc tccaagctgg gctgtgtgca    3240 cgaaccccc gttcagcccg accgctgcgc cttatccggt aactatcgtc ttgagtccaa    3300
cccggtaaga cacgacttat cgccactggc agcagccact ggtaacagga ttagcagagc    3360
gaggtatgta ggcggtgcta cagagttctt gaagtggtgg cctaactacg gctacactag    3420
aagaacagta tttggtatct gcgctctgct gaagccagtt accttcggaa aaagagttgg    3480
tagctcttga tccggcaaac aaaccaccgc tggtagcggt ggtttttttg tttgcaagca    3540
gcagattacg cgcagaaaaa aaggatctca agaagatcct ttgatctttt ctacggggtc    3600
tgacgctcag tggaacgaaa actcacgtta agggattttg gtcatgagat tatcaaaaag    3660
gatcttcacc tagatccttt taaattaaaa atgaagtttt aaatcaatct aaagtatata    3720
tgagtaaact tggtctgaca gttaccaatg cttaatcagt gaggcaccta tctcagcgat    3780
ctgtctattt cgttcatcca tagttgcatt taaatttccg aactctccaa ggccctcgtc    3840
ggaaaatctt caaacctttc gtccgatcca tcttgcaggc tacctctcga acgaactatc    3900
gcaagtctct tggccggcct tgcgccttgg ctattgcttg gcagcgccta tcgccaggta    3960
ttactccaat cccgaatatc cgagatcggg atcacccgag agaagttcaa cctacatcct    4020
```

```
caatcccgat ctatccgaga tccgaggaat atcgaaatcg gggcgcgcct ggtgtaccga    4080
gaacgatcct ctcagtgcga gtctcgacga tccatatcgt tgcttggcag tcagccagtc    4140
ggaatccagc ttgggaccca ggaagtccaa tcgtcagata ttgtactcaa gcctggtcac    4200
ggcagcgtac cgatctgttt aaacctagat attgatagtc tgatcggtca acgtataatc    4260
gagtcctagc ttttgcaaac atctatcaag agacaggatc agcaggaggc tttcgcatga    4320
gtattcaaca tttccgtgtc gcccttattc cctttttgc ggcattttgc cttcctgttt     4380
ttgctcaccc agaaacgctg gtgaaagtaa aagatgctga agatcagttg ggtgcgcgag    4440
tgggttacat cgaactggat ctcaacagcg gtaagatcct tgagagtttt cgccccgaag    4500
aacgctttcc aatgatgagc acttttaaag ttctgctatg tggcgcggta ttatcccgta    4560
ttgacgccgg gcaagagcaa ctcggtcgcc gcatacacta ttctcagaat gacttggttg    4620
agtattcacc agtcacagaa aagcatctta cggatggcat gacagtaaga gaattatgca    4680
gtgctgccat aaccatgagt gataacactg cggccaactt acttctgaca acgattggag    4740
gaccgaagga gctaaccgct tttttgcaca acatggggga tcatgtaact cgccttgatc    4800
gttgggaacc ggagctgaat gaagccatac caaacgacga gcgtgacacc acgatgcctg    4860
tagcaatggc aacaaccttg cgtaaactat taactggcga actacttact ctagcttccc    4920
ggcaacagtt gatagactgg atggaggcgg ataaagttgc aggaccactt ctgcgctcgg    4980
cccttccggc tggctggttt attgctgata atctggagc cggtgagcgt gggtctcgcg     5040
gtatcattgc agcactgggg ccagatggta agccctcccg tatcgtagtt atctacacga    5100
cggggagtca ggcaactatg gatgaacgaa atagacagat cgctgagata ggtgcctcac    5160
tgattaagca ttggtaaccg attctaggtg cattggcgca gaaaaaaatg cctgatgcga    5220
cgctgcgcgt cttatactcc cacatatgcc agattcagca acggatacgg cttccccaac    5280
ttgcccactt ccatacgtgt cctccttacc agaaatttat ccttaagatc ccgaatcgtt    5340
taaactcgac tctggctcta tcgaatctcc gtcgtttcga gcttacgcga acagccgtgg    5400
cgctcatttg ctcgtcgggc atcgaatctc gtcagctatc gtcagcttac cttttggca    5460
```

<210> SEQ ID NO 15
<211> LENGTH: 5454
<212> TYPE: DNA
<213> ORGANISM: Artificial Sequence
<220> FEATURE:
<223> OTHER INFORMATION: Plasmid expression vector pCRO23

<400> SEQUENCE: 15

```
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgaccccg cccattgacg tcaataatga      360
cgtatgttcc catagtaacg ccaataggga ctttccattg acgtcaatgg gtggagtatt    420
tacggtaaac tgcccacttg gcagtacatc aagtgtatca tatgccaagt acgcccccta     480
ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
```

```
acccccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac ccgccagcgg ccgccaccat gaaggccaat ctactggtgt tgctgtgtgc    900
ccttgcggcg gcagatgcca tgagatgtgt gggcgtgggg aaccgcgact ttgtcgaagg    960
attaagtggc gcgacctggg tagacgtcgt gctggagcac ggagggtgcg tcacaaccat   1020
ggccaagaac aagcccaccc ttgacattga acttcaaaag acagaagcta ctcagctggc   1080
tacactgcgc aagctgtgca tagagggaaa aatcaccaac ataactacgg actcgaggtg   1140
tcccacacag ggtgaagcgg tcttgcctga agaacaggat cagaattatg tttgtaaaca   1200
tacttatgta gacaggggga atggatccgg gtgcggtctg aacggatctg gttccctagt   1260
cacatgcgct aagttccagt gcctcgagcc tatcgaaggt aaagtggtcc agtacgagaa   1320
tcttaagtac accgtgatca tcacggtcca tacaggagat caacaccagg ttggaaacga   1380
gacccaagga gtcactgccg aaatcacacc gcaggccagc acgacggagg ctattttgcc   1440
ggagtatggg acactgggac tggaatgctc ccctaggacg ggactagatt ttaatgagat   1500
gattctgctg acaatgaaga acaaggcttg gatggtgcat cgtcaatggt tctttgatct   1560
gccactgccg tgggccagcg cgccacgac agagaccca acctggaatc gaaaagagct   1620
gctggtcaca ttcaaaaacg cacacgccaa aaagcaagaa gtggtagtgc ttggctccca   1680
ggaaggtgcc atgcacactg cactcacagg ggctactgaa attcagaatt caggaggcac   1740
ttctattttc gccggccacc tcaaatgccg gttaaagatg gacaagctgg aactgaaagg   1800
tatgtcgtac gcaatgtgca ctaatacatt tgtgctaaag aaggaagtct ccgagactca   1860
gcacgggaca atactgatta aggtggaata caaaggtgag gatgctccct gtaagatccc   1920
cttctctact gaggatggtc agggcaaagc tcataatggt cggttgatca cagcgaatcc   1980
agtggttaca aagaaggagg agccagtgaa tatcgaagca gaacctccct tcggtgagtc   2040
aaacattgtc atcggtatcg gagataacgc tcttaagata aactggtaca aaaagggatc   2100
tagcggcggc ggcagccatc atcaccatca tcactgagct agcttgactg actgagatac   2160
agcgtacctt cagctcacag acatgataag atacattgat gagtttggac aaaccacaac   2220
tagaatgcag tgaaaaaaat gctttatttg tgaaatttgt gatgctattg ctttatttgt   2280
aaccattata agctgcaata aacaagttaa caacaacaat tgcattcatt ttatgtttca   2340
ggttcagggg gaggtgtggg aggttttta aagcaagtaa aacctctaca aatgtggtat   2400
tggcccatct ctatcggtat cgtagcataa ccccttgggg cctctaaacg ggtcttgagg   2460
ggttttttgt gcccctcggg ccggattgct atctaccggc attggcgcag aaaaaaatgc   2520
ctgatgcgac gctgcgcgtc ttatactccc acatatgcca gattcagcaa cggatacggc   2580 ttcccccaact tgcccacttc catacgtgtc ctccttacca gaaatttatc cttaaggtcg   2640
tcagctatcc tgcaggcgat ctctcgattt cgatcaagac attcctttaa tggtcttttc   2700
tggacaccac tagggggtcag aagtagttca tcaaactttc ttccctccct aatctcattg   2760
gttaccttgg gctatcgaaa cttaattaac cagtcaagtc agctacttgg cgagatcgac   2820
ttgtctgggt ttcgactacg ctcagaattg cgtcagtcaa gttcgatctg gtccttgcta   2880
ttgcacccgt tctccgatta cgagtttcat ttaaatcatg tgagcaaaag gccagcaaaa   2940
ggccaggaac cgtaaaaagg ccgcgttgct ggcgtttttc cataggctcc gccccctga   3000
```

```
cgagcatcac aaaaatcgac gctcaagtca gaggtggcga aacccgacag gactataaag    3060
ataccaggcg tttcccctg gaagctccct cgtgcgctct cctgttccga ccctgccgct     3120
taccggatac ctgtccgcct ttctcccttc gggaagcgtg gcgctttctc atagctcacg    3180
ctgtaggtat ctcagttcgg tgtaggtcgt tcgctccaag ctgggctgtg tgcacgaacc    3240
ccccgttcag cccgaccgct gcgccttatc cggtaactat cgtcttgagt ccaacccggt    3300
aagacacgac ttatcgccac tggcagcagc cactggtaac aggattagca gagcgaggta    3360
tgtaggcggt gctacagagt tcttgaagtg gtggcctaac tacggctaca ctagaagaac    3420
agtatttggt atctgcgctc tgctgaagcc agttaccttc ggaaaaagag ttggtagctc    3480
ttgatccggc aaacaaacca ccgctggtag cggtggtttt tttgtttgca agcagcagat    3540
tacgcgcaga aaaaaggat ctcaagaaga tcctttgatc ttttctacgg ggtctgacgc      3600
tcagtggaac gaaaactcac gttaagggat tttggtcatg agattatcaa aaaggatctt    3660
cacctagatc cttttaaatt aaaaatgaag ttttaaatca atctaaagta tatatgagta    3720
aacttggtct gacagttacc aatgcttaat cagtgaggca cctatctcag cgatctgtct    3780
atttcgttca tccatagttg catttaaatt tccgaactct ccaaggccct cgtcggaaaa    3840
tcttcaaacc tttcgtccga tccatcttgc aggctacctc tcgaacgaac tatcgcaagt    3900
ctcttggccg gccttgcgcc ttggctattg cttggcagcg cctatcgcca ggtattactc    3960
caatcccgaa tatccgagat cgggatcacc cgagagaagt tcaacctaca tcctcaatcc    4020
cgatctatcc gagatccgag gaatatcgaa atcggggcgc gcctggtgta ccgagaacga    4080
tcctctcagt gcgagtctcg acgatccata tcgttgcttg gcagtcagcc agtcggaatc    4140
cagcttggga cccaggaagt ccaatcgtca gatattgtac tcaagcctgg tcacggcagc    4200
gtaccgatct gtttaaacct agatattgat agtctgatcg gtcaacgtat aatcgagtcc    4260
tagcttttgc aaacatctat caagagacag gatcagcagg aggctttcgc atgagtattc    4320
aacatttccg tgtcgccctt attcccttt ttgcggcatt ttgccttcct gttttgctc      4380 acccagaaac gctggtgaaa gtaaaagatg ctgaagatca gttgggtgcg cgagtgggtt    4440
acatcgaact ggatctcaac agcggtaaga tccttgagag ttttcgcccc gaagaacgct    4500
ttccaatgat gagcactttt aaagttctgc tatgtggcgc ggtattatcc cgtattgacg    4560
ccgggcaaga gcaactcggt cgccgcatac actattctca gaatgacttg gttgagtatt    4620
caccagtcac agaaaagcat cttacggatg gcatgacagt aagagaatta tgcagtgctg    4680
ccataaccat gagtgataac actgcggcca acttacttct gacaacgatt ggaggaccga    4740
aggagctaac cgcttttttg cacaacatgg gggatcatgt aactcgcctt gatcgttggg    4800
aaccggagct gaatgaagcc ataccaaacg acgagcgtga caccacgatg cctgtagcaa    4860
tggcaacaac cttgcgtaaa ctattaactg gcgaactact tactctagct tcccggcaac    4920
agttgataga ctggatggag gcggataaag ttgcaggacc acttctgcgc tcggcccttc    4980
cggctggctg gtttattgct gataaatctg gagccggtga gcgtgggtct cgcggtatca    5040
ttgcagcact ggggccagat ggtaagccct cccgtatcgt agttatctac acgacgggga    5100
gtcaggcaac tatggatgaa cgaaatagac agatcgctga gataggtgcc tcactgatta    5160
agcattggta accgattcta ggtgcattgg cgcagaaaaa aatgcctgat gcgacgctgc    5220
gcgtcttata ctcccacata tgccagattc agcaacggat acggcttccc caacttgccc    5280
acttccatac gtgtcctcct taccagaaat ttatccttaa gatcccgaat cgtttaaact    5340
cgactctggc tctatcgaat ctccgtcgtt tcgagcttac gcgaacagcc gtggcgctca    5400
```

```
tttgctcgtc gggcatcgaa tctcgtcagc tatcgtcagc ttaccttttt ggca        5454
```

<210> SEQ ID NO 16
<211> LENGTH: 5460
<212> TYPE: DNA
<213> ORGANISM: Artificial Sequence
<220> FEATURE:
<223> OTHER INFORMATION: Plasmid expression vector pCRO24

<400> SEQUENCE: 16

```
gcgatcgcgg ctcccgacat cttggaccat tagctccaca ggtatcttct tccctctagt    60
ggtcataaca gcagcttcag ctacctctca attcaaaaaa ccctcaaga cccgtttaga    120
ggccccaagg ggttatgcta tcaatcgttg cgttacacac acaaaaaacc aacacacatc   180
catcttcgat ggatagcgat tttattatct aactgctgat cgagtgtagc cagatctagt   240
aatcaattac ggggtcatta gttcatagcc catatatgga gttccgcgtt acataactta   300
cggtaaatgg cccgcctggc tgaccgccca acgacccccg cccattgacg tcaataatga   360
cgtatgttcc catagtaacg ccaatagggga ctttccattg acgtcaatgg gtggagtatt   420
tacggtaaac tgcccacttg gcagtacatc aagtgtatca tatgccaagt acgcccccta   480
ttgacgtcaa tgacggtaaa tggcccgcct ggcattatgc ccagtacatg accttatggg   540
actttcctac ttggcagtac atctacgtat tagtcatcgc tattaccatg ctgatgcgt   600
tttggcagta catcaatggg cgtggatagc ggtttgactc acggggattt ccaagtctcc   660
accccattga cgtcaatggg agtttgtttt ggcaccaaaa tcaacgggac tttccaaaat   720
gtcgtaacaa ctccgcccca ttgacgcaaa tgggcggtag gcgtgtacgg tgggaggtct   780
atataagcag agctggttta gtgaaccgtc agatcagatc tttgtcgatc ctaccatcca   840
ctcgacacac ccgccagcgg ccgccaccat gaaggccaat ctactggtgt tgctgtgtgc   900
ccttgcggcg gcagatgcca tgcgatgcgt ggggtgggc aatagagatt tcgtggaagg   960
ggtgtctgga ggggcatggg tggatctggt gctggagcac ggcggatgtg tcacaactat  1020
ggcccagggg aagccaaccc tggatttcga gctaactaag accacagcta aggaggtagc  1080
cctgcttcgg acttactgta ttgaggcatc catctctaac atcaccaccg ccacgagatg  1140
cccgacacag ggcgaaccct acttgaagga agaacaggat cagcagtaca tttgccggcg  1200
cgatgttgtt gatagaggca atggctccgg tgtggcctc aacggctctg gtggggtggt  1260
cacctgtgcc aagttcagct gttctggcaa gatcacggga atctggtgc aaattgaaaa  1320
tttggaatat acgtcgttg tgactgtcca caatggcgat acacatgctg tgggcaacga  1380
taccagtaac cacggcgtca ccgcgatgat aactccccgg agcccatctg ttgaagttaa  1440
actgccgat tacggagagt tgacactcga ctgcgaaccg aggtctggaa tagatttcaa  1500
cgagatgata cttatgaaaa tgaagaaaaa gacctggctc gtacacaagc agtggttttt  1560
ggatttgccc ctcccttgga ccgcagggc cgataccagc gaggtgcatt ggaattacaa  1620
agagcgcatg gtgactttca agtgccccca cgcaaagcgg caagatgtga ctgtattagg  1680
atcacaggaa ggcgctatgc attccgcct ggctggtgcc acggaggtgg attcaggaga  1740
cggtaaccat atgtttgctg ccacctcaa atgtaaggtc cgcatggaaa acttcgcat   1800
taaaggaatg tcctacacga tgtgctcagg aaagttctct atcgacaagg aaatggccga  1860
gactcagcat ggaacgactg tagtcaaggt gaaatatgaa ggtgccgggg cgccttgcaa  1920
ggtgccaatc gaaatccgag acgttaacaa ggagaaggtg gttgggagga ttataagtag  1980
```

```
cactccgctc gcagagaaca ccaatagcgt gactaacata gaactggagc cccctttgg      2040 ggatagctac attgtgattg gagtagggaa tagtgcacta acattgcact ggttcagaaa      2100
agggtcttca ggcggcggca gccatcatca ccatcatcac tgagctagct tgactgactg      2160
agatacagcg taccttcagc tcacagacat gataagatac attgatgagt ttggacaaac      2220
cacaactaga atgcagtgaa aaaatgctt tatttgtgaa atttgtgatg ctattgcttt       2280
atttgtaacc attataagct gcaataaaca agttaacaac aacaattgca ttcattttat      2340
gtttcaggtt caggggagg tgtgggaggt tttttaaagc aagtaaaacc tctacaaatg       2400
tggtattggc ccatctctat cggtatcgta gcataacccc ttggggcctc taaacgggtc      2460
ttgaggggtt ttttgtgccc ctcgggccgg attgctatct accggcattg cgcagaaaa      2520 aaatgcctga tgcgacgctg cgcgtcttat actcccacat atgccagatt cagcaacgga     2580
tacggcttcc ccaacttgcc cacttccata cgtgtcctcc ttaccagaaa tttatcctta     2640
aggtcgtcag ctatcctgca ggcgatctct cgatttcgat caagacattc ctttaatggt    2700
cttttctgga caccactagg ggtcagaagt agttcatcaa actttcttcc ctccctaatc     2760
tcattggtta ccttgggcta tcgaaactta attaaccagt caagtcagct acttggcgag     2820
atcgacttgt ctgggtttcg actacgctca gaattgcgtc agtcaagttc gatctggtcc     2880
ttgctattgc acccgttctc cgattacgag tttcatttaa atcatgtgag caaaaggcca    2940 gcaaaggcc aggaaccgta aaaggccgc gttgctggcg ttttccata ggctccgccc        3000 ccctgacgag catcacaaaa atcgacgctc aagtcagagg tggcgaaacc cgacaggact    3060
ataaagatac caggcgtttc ccctggaag ctccctcgtg cgctctcctg ttccgaccct     3120
gccgcttacc ggatacctgt ccgcctttct cccttcggga agcgtggcgc tttctcatag    3180
ctcacgctgt aggtatctca gttcggtgta ggtcgttcgc tccaagctgg gctgtgtgca    3240
cgaacccccc gttcagcccg accgctgcgc cttatccggt aactatcgtc ttgagtccaa    3300
cccggtaaga cacgacttat cgccactggc agcagccact ggtaacagga ttagcagagc    3360
gaggtatgta ggcggtgcta cagagttctt gaagtggtgg cctaactacg gctacactag    3420
aagaacagta tttggtatct gcgctctgct gaagccagtt accttcggaa aaagagttgg    3480
tagctcttga tccggcaaac aaaccaccgc tggtagcggt ggtttttttg tttgcaagca    3540
gcagattacg cgcagaaaaa aaggatctca agaagatcct ttgatctttt ctacggggtc    3600
tgacgctcag tggaacgaaa actcacgtta agggattttg gtcatgagat tatcaaaaag    3660
gatcttcacc tagatccttt taaattaaaa atgaagtttt aaatcaatct aaagtatata    3720
tgagtaaact tggtctgaca gttaccaatg cttaatcagt gaggcaccta tctcagcgat    3780
ctgtctattt cgttcatcca tagttgcatt taaatttccg aactctccaa ggccctcgtc    3840
ggaaaatctt caaacctttc gtccgatcca tcttgcaggc tacctctcga acgaactatc    3900
gcaagtctct tggccggcct tgcgccttgg ctattgcttg gcagcgccta tcgccaggta    3960
ttactccaat cccgaatatc cgagatcggg atcacccgag agaagttcaa cctacatcct    4020
caatcccgat ctatccgaga tccgaggaat atcgaaatcg gggcgcgcct ggtgtaccga    4080
gaacgatcct ctcagtgcga gtctcgacga tccatatcgt tgcttggcag tcagccagtc    4140
ggaatccagc ttgggaccca ggaagtccaa tcgtcagata ttgtactcaa gcctggtcac    4200
ggcagcgtac cgatctgttt aaacctagat attgatagtc tgatcggtca acgtataatc    4260
gagtcctagc ttttgcaaac atctatcaag agacaggatc agcaggaggc tttcgcatga    4320
gtattcaaca tttccgtgtc gcccttattc cctttttgc ggcattttgc cttcctgttt    4380
```

```
ttgctcaccc agaaacgctg gtgaaagtaa aagatgctga agatcagttg ggtgcgcgag    4440
tgggttacat cgaactggat ctcaacagcg gtaagatcct tgagagtttt cgccccgaag    4500
aacgctttcc aatgatgagc acttttaaag ttctgctatg tggcgcggta ttatcccgta    4560
ttgacgccgg gcaagagcaa ctcggtcgcc gcatacacta ttctcagaat gacttggttg    4620
agtattcacc agtcacagaa aagcatctta cggatggcat gacagtaaga gaattatgca    4680
gtgctgccat aaccatgagt gataacactg cggccaactt acttctgaca acgattggag    4740
gaccgaagga gctaaccgct tttttgcaca acatggggga tcatgtaact cgccttgatc    4800
gttgggaacc ggagctgaat gaagccatac caaacgacga gcgtgacacc acgatgcctg    4860
tagcaatggc aacaaccttg cgtaaactat taactggcga actacttact ctagcttccc    4920
ggcaacagtt gatagactgg atggaggcgg ataaagttgc aggaccactt ctgcgctcgg    4980
cccttccggc tggctggttt attgctgata aatctggagc cggtgagcgt gggtctcgcg    5040
gtatcattgc agcactgggg ccagatggta agccctcccg tatcgtagtt atctacacga    5100
cggggagtca ggcaactatg gatgaacgaa atagacagat cgctgagata ggtgcctcac    5160
tgattaagca ttggtaaccg attctaggtg cattggcgca gaaaaaaatg cctgatgcga    5220
cgctgcgcgt cttatactcc cacatatgcc agattcagca acggatacgg cttccccaac    5280
ttgcccactt ccatacgtgt cctccttacc agaaatttat ccttaagatc ccgaatcgtt    5340
taaactcgac tctggctcta tcgaatctcc gtcgtttcga gcttacgcga acagccgtgg    5400
cgctcatttg ctcgtcgggc atcgaatctc gtcagctatc gtcagcttac cttttggca    5460
```

<210> SEQ ID NO 17
<211> LENGTH: 5502
<212> TYPE: DNA
<213> ORGANISM: Artificial Sequence
<220> FEATURE:
<223> OTHER INFORMATION: Plasmid expression vector pCRO28

<400> SEQUENCE: 17

```
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgacccccg cccattgacg tcaataatga     360
cgtatgttcc catagtaacg ccaatagga cttttccattg acgtcaatgg gtggagtatt    420
tacggtaaac tgcccacttg gcagtacatc aagtgtatca tatgccaagt acgcccccta    480
ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac cgccagcgg ccgccaccat gaaggccaat ctactggtgt tgctgtgtgc    900
ccttgcggcg gcagatgcca tcaggtgcat tggagtcagc aacagggact tcgtcgaagg    960
```

```
catgtccggc ggcacctggg tggatgtggt gctcgaacac ggcggatgcg tgaccgtcat    1020
ggcccaggac aagcctaccg tcgatattga gctggtgacc accacagtga gcaacatggc    1080
cgaagtgaga agctactgct atgaggcctc catcagcgat atggcttccg attccagatg    1140
ccccacacag ggagaggctt atctggacaa acagtccgac acccagtacg tctgcaaaag    1200
aaccctggtg gacagaaacc acaccaacgg atgcggcctg ttcggcaaag gcagcctcgt    1260
gacatgtgcc aagttcgcct gcagcaaaaa gatgaccggc aagtccatcc agcccgagaa    1320
cctggaatac aggatcatgc tgtccgtgca tggatcccag cactccggca tgatcgtcaa    1380
cgataccggc cacgagaccg acgagaacag ggctaaagtg gagatcaccc ccaacagccc    1440
tagagccgaa gctacactgg gcggcttcgg aagcctgggc ctggattgcg aacccaggac    1500
cggcctggat ttcagcgacc tgtattacct gaccatgaac aataagcact ggctggtgca    1560
caaggaatgg ttccacgaca tcccctgcc ttggcatgct ggcgccgata ccggcacacc    1620
tcactggaac aataaggaag ccctggtcga gtttaaggac gcccacgcca aaagacagac    1680
cgtggtggtg ctgggaagcc aggagggagc tgtccacaca gccctggccg gagctctgga    1740
agccgagatg gatggcgcca agggcaggct gagctccggc cacctgaaat gcaggctcaa    1800
gatggacaag ctgaggctga agggcgtgag ctacagcctg tgcaccgccg ctttcacctt    1860
taccaagatc cctgccgaga cactgcacgg caccgtcacc gtggaggtgc aatacgccgg    1920
aaccgatgga ccttgcaaag tgcctgccca gatggctgtg gatatgcaga ccctcacacc    1980
cgtcggcagg ctgatcaccg ccaatcccgt cattaccgag tccaccgaga acagcaagat    2040
gatgctcgag ctcgatcccc cctttggcga cagctacatt gtgatcggcg tgggcgagaa    2100
gaagatcacc caccattggc acagaagcgg ctccacaggg ggtagcggtg gtagcggagg    2160
tagccatcac caccatcacc actgagctag cttgactgac tgagatacag cgtaccttca    2220
gctcacagac atgataagat acattgatga gtttggacaa accacaacta gaatgcagtg    2280
aaaaaaatgc tttatttgtg aaatttgtga tgctattgct ttatttgtaa ccattataag    2340
ctgcaataaa caagttaaca acaacaattg cattcatttt atgtttcagg ttcaggggga    2400
ggtgtgggag gttttttaaa gcaagtaaaa cctctacaaa tgtggtattg gcccatctct    2460
atcggtatcg tagcataacc ccttggggcc tctaaacggg tcttgagggg ttttttgtgc    2520
ccctcgggcc ggattgctat ctaccggcat ggcgcagaa aaaaatgcct gatgcgacgc    2580
tgcgcgtctt atactcccac atatgccaga ttcagcaacg gatacggctt ccccaacttg    2640
cccacttcca tacgtgtcct ccttaccaga aatttatcct taaggtcgtc agctatcctg    2700
caggcgatct ctcgatttcg atcaagacat tcctttaatg gtcttttctg gacaccacta    2760
ggggtcagaa gtagttcatc aaactttctt ccctcccta tctcattggt taccttgggc    2820
tatcgaaact taattaacca gtcaagtcag ctacttggcg agatcgactt gtctgggttt    2880
cgactacgct cagaattgcg tcagtcaagt tcgatctggt ccttgctatt gcacccgttc    2940
tccgattacg agtttcattt aaatcatgtg agcaaaaggc cagcaaaagg ccaggaaccg    3000
taaaaaggcc gcgttgctgg cgttttccca taggctccgc cccctgacg agcatcacaa    3060 aaatcgacgc tcaagtcaga ggtggcgaaa cccgacagga ctataaagat accaggcgtt    3120
tccccctgga agctccctcg tgcgctctcc tgttccgacc ctgccgctta ccggatacct    3180
gtccgccttt ctcccttcgg gaagcgtggc gctttctcat agctcacgct gtaggtatct    3240
cagttccggt aggtcgttc gctccaagct gggctgtgtg cacgaacccc ccgttcagcc    3300
cgaccgctgc gccttatccg gtaactatcg tcttgagtcc aacccggtaa gacacgactt    3360
```

```
atcgccactg gcagcagcca ctggtaacag gattagcaga gcgaggtatg taggcggtgc    3420
tacagagttc ttgaagtggt ggcctaacta cggctacact agaagaacag tatttggtat    3480
ctgcgctctg ctgaagccag ttaccttcgg aaaagagtt ggtagctctt gatccggcaa     3540
acaaaccacc gctggtagcg gtggtttttt tgtttgcaag cagcagatta cgcgcagaaa    3600
aaaaggatct caagaagatc ctttgatctt ttctacgggg tctgacgctc agtggaacga    3660
aaactcacgt taagggattt tggtcatgag attatcaaaa aggatcttca cctagatcct    3720
tttaaattaa aaatgaagtt ttaaatcaat ctaaagtata tatgagtaaa cttggtctga    3780
cagttaccaa tgcttaatca gtgaggcacc tatctcagcg atctgtctat ttcgttcatc    3840
catagttgca tttaaatttc cgaactctcc aaggccctcg tcggaaaatc ttcaaacctt    3900
tcgtccgatc catcttgcag gctacctctc gaacgaacta tcgcaagtct cttggccggc    3960
cttgcgcctt ggctattgct tggcagcgcc tatcgccagg tattactcca atcccgaata    4020
tccgagatcg ggatcacccg agagaagttc aacctacatc ctcaatcccg atctatccga    4080
gatccgagga atatcgaaat cggggcgcgc ctggtgtacc gagaacgatc ctctcagtgc    4140
gagtctcgac gatccatatc gttgcttggc agtcagccag tcggaatcca gcttgggacc    4200
caggaagtcc aatcgtcaga tattgtactc aagcctggtc acggcagcgt accgatctgt    4260
ttaaacctag atattgatag tctgatcggt caacgtataa tcgagtccta gcttttgcaa    4320
acatctatca agagacagga tcagcaggag ctttcgcat gagtattcaa catttccgtg     4380
tcgcccttat tccctttttt gcggcatttt gccttcctgt ttttgctcac ccagaaacgc    4440
tggtgaaagt aaaagatgct gaagatcagt tgggtgcgcg agtgggttac atcgaactgg    4500
atctcaacag cggtaagatc cttgagagtt ttcgccccga agaacgcttt ccaatgatga    4560
gcacttttaa agttctgcta tgtggcgcgg tattatcccg tattgacgcc gggcaagagc    4620
aactcggtcg ccgcatacac tattctcaga atgacttggt tgagtattca ccagtcacag    4680
aaaagcatct tacggatggc atgacagtaa gagaattatg cagtgctgcc ataaccatga    4740
gtgataacac tgcggccaac ttacttctga caacgattgg aggaccgaag gagctaaccg    4800
cttttttgca caacatgggg gatcatgtaa ctcgccttga tcgttgggaa ccggagctga    4860
atgaagccat accaaacgac gagcgtgaca ccacgatgcc tgtagcaatg gcaacaacct    4920
tgcgtaaact attaactggc gaactactta ctctagcttc ccggcaacag ttgatagact    4980
ggatggaggc ggataaagtt gcaggaccac ttctgcgctc ggcccttccg gctggctggt    5040
ttattgctga taaatctgga gccggtgagc gtgggtctcg cggtatcatt gcagcactgg    5100
ggccagatgg taagccctcc cgtatcgtag ttatctacac gacggggagt caggcaacta    5160
tggatgaacg aaatagacag atcgctgaga taggtgcctc actgattaag cattggtaac    5220
cgattctagg tgcattggcg cagaaaaaaa tgcctgatgc gacgctgcgc gtcttatact    5280
cccacatatg ccagattcag caacggatac ggcttcccca acttgcccac ttccatacgt    5340
gtcctcctta ccagaaattt atccttaaga tcccgaatcg tttaaactcg actctggctc    5400
tatcgaatct ccgtcgtttc gagcttacgc gaacagccgt ggcgctcatt tgctcgtcgg    5460
gcatcgaatc tcgtcagcta tcgtcagctt acctttttgg ca                      5502
```

<210> SEQ ID NO 18
<211> LENGTH: 5502
<212> TYPE: DNA
<213> ORGANISM: Artificial Sequence
<220> FEATURE:

<223> OTHER INFORMATION: Plasmid expression vector pCRO25

<400> SEQUENCE: 18

```
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgaccccg cccattgacg tcaataatga     360
cgtatgttcc catagtaacg ccaataggga cttttcattg acgtcaatgg gtggagtatt     420
tacggtaaac tgcccacttg gcagtacatc aagtgtatca tatgccaagt acgcccccta     480
ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
accccattga cgtcaatggg agtttgtttt ggcaccaaaa tcaacgggac tttccaaaat     720
gtcgtaacaa ctccgcccca ttgacgcaaa tgggcggtag gcgtgtacgg tgggaggtct     780
atataagcag agctggttta gtgaaccgtc agatcagatc tttgtcgatc ctaccatcca     840
ctcgacacac cgccagcgg ccgccaccat gaaggccaat ctactggtgt tgctgtgtgc     900
ccttgcggcg gcagatgcca tcaggtgcat tggagtcagc aacagggact tcgtcgaagg     960
catgtccggc ggcacctggg tggatgtggt gctcgaacac ggcggatgcg tgaccgtcat    1020
ggcccaggac aagcctaccg tcgatattga gctggtgacc accacagtga gcaacatggc    1080
cgaagtgaga agctactgct atgaggcctc catcagcgat atggcttccg attccagatg    1140
ccccacacag ggagaggctt atctggacaa acagtccgac acccagtacg tctgcaaaag    1200
aaccctggtg gacagaggca atggatccgg atgcggcctg aacggctctg gcagcctcgt    1260
gacatgtgcc aagttcgcct gcagcaaaaa gatgaccggc aagtccatcc agcccgagaa    1320
cctggaatac aggatcatgc tgtccgtgca tggatcccag cactccggca tgatcgtcaa    1380
cgataccggc cacgagaccg acgagaacag ggctaaagtg gagatcaccc ccaacagccc    1440
tagagccgaa gctacactgg gcggcttcgg aagcctgggc ctggattgcg aacccaggac    1500
cggcctggat ttcagcgacc tgtattacct gaccatgaac aataagcact ggctggtgca    1560
caaggaatgg ttccacgaca tccccctgcc ttggcatgct ggcgccgata ccggcacacc    1620
tcactggaac aataaggaag ccctggtcga gtttaaggac gcccacgcca aagacagac    1680
cgtggtggtg ctgggaagcc aggagggagc tgtccacaca gccctggccg gagctctgga    1740
agccgagatg gatggcgcca agggcaggct gagctccggc acctgaaat gcaggctcaa    1800
gatggacaag ctgaggctga agggcgtgag ctacagcctg tgcaccgccg ctttcacctt    1860
taccaagatc cctgccgaga cactgcacgg caccgtcacc gtggaggtgc aatacgccgg    1920
aaccgatgga ccttgcaaag tgcctgccca gatggctgtg gatatgcaga ccctcacacc    1980
cgtcggcagg ctgatcaccg ccaatcccgt cattaccgag tccaccgaga acagcaagat    2040
gatgctcgag ctcgatcccc cctttggcga cagctacatt gtgatcggcg tgggcgagaa    2100
gaagatcacc caccattggc acagaagcgg ctccacaggg ggtagcggtg gtagcggagg    2160
tagccatcac caccatcacc actgagctag cttgactgac tgagatacag cgtaccttca    2220
gctcacagac atgataagat acattgatga gtttggacaa accacaacta gaatgcagtg    2280
```

```
aaaaaaatgc tttatttgtg aaatttgtga tgctattgct ttatttgtaa ccattataag    2340
ctgcaataaa caagttaaca acaacaattg cattcatttt atgtttcagg ttcaggggga    2400
ggtgtgggag gttttttaaa gcaagtaaaa cctctacaaa tgtggtattg gcccatctct    2460
atcggtatcg tagcataacc ccttgggggcc tctaaacggg tcttgagggg ttttttgtgc   2520
ccctcgggcc ggattgctat ctaccggcat tggcgcagaa aaaaatgcct gatgcgacgc    2580
tgcgcgtctt atactcccac atatgccaga ttcagcaacg gatacggctt ccccaacttg    2640
cccacttcca tacgtgtcct ccttaccaga aatttatcct taaggtcgtc agctatcctg    2700
caggcgatct ctcgatttcg atcaagacat tcctttaatg gtcttttctg gacaccacta    2760
ggggtcagaa gtagttcatc aaactttctt ccctccctaa tctcattggt taccttgggc    2820
tatcgaaact taattaacca gtcaagtcag ctacttggcg agatcgactt gtctgggttt    2880
cgactacgct cagaattgcg tcagtcaagt tcgatctggt ccttgctatt gcacccgttc    2940
tccgattacg agtttcattt aaatcatgtg agcaaaaggc cagcaaaagg ccaggaaccg    3000
taaaaaggcc gcgttgctgg cgttttttcca taggctccgc ccccctgacg agcatcacaa   3060
aaatcgacgc tcaagtcaga ggtggcgaaa cccgacagga ctataaagat accaggcgtt    3120 tcccccctgga agctccctcg tgcgctctcc tgttccgacc ctgccgctta ccggatacct    3180
gtccgccttt ctcccttcgg gaagcgtggc gctttctcat agctcacgct gtaggtatct    3240
cagttcggtg taggtcgttc gctccaagct gggctgtgtg cacgaacccc ccgttcagcc    3300
cgaccgctgc gccttatccg gtaactatcg tcttgagtcc aacccggtaa gacacgactt    3360
atcgccactg gcagcagcca ctggtaacag gattagcaga gcgaggtatg taggcggtgc    3420
tacagagttc ttgaagtggt ggcctaacta cggctacact agaagaacag tatttggtat    3480
ctgcgctctg ctgaagccag ttaccttcgg aaaaagagtt ggtagctctt gatccggcaa    3540
acaaaccacc gctggtagcg gtggtttttt tgtttgcaag cagcagatta cgcgcagaaa    3600
aaaaggatct caagaagatc ctttgatctt ttctacgggg tctgacgctc agtggaacga    3660
aaactcacgt taagggattt tggtcatgag attatcaaaa aggatcttca cctagatcct    3720
tttaaattaa aaatgaagtt ttaaatcaat ctaaagtata tatgagtaaa cttggtctga    3780
cagttaccaa tgcttaatca gtgaggcacc tatctcagcg atctgtctat ttcgttcatc    3840
catagttgca tttaaatttc cgaactctcc aaggccctcg tcggaaaatc ttcaaacctt    3900
tcgtccgatc catcttgcag gctacctctc gaacgaacta tcgcaagtct cttggccggc    3960
cttgcgcctt ggctattgct tggcagcgcc tatcgccagg tattactcca atcccgaata    4020
tccgagatcg ggatcacccg agagaagttc aacctacatc ctcaatcccg atctatccga    4080
gatccgagga atatcgaaat cggggcgcgc ctggtgtacc gagaacgatc ctctcagtgc    4140
gagtctcgac gatccatatc gttgcttggc agtcagccag tcggaatcca gcttgggacc    4200
caggaagtcc aatcgtcaga tattgtactc aagcctggtc acggcagcgt accgatctgt    4260
ttaaacctag atattgatag tctgatcggt caacgtataa tcgagtccta gcttttgcaa    4320
acatctatca agagacagga tcagcaggag gctttcgcat gagtattcaa catttccgtg    4380
tcgcccttat tccctttttt gcggcatttt gccttcctgt ttttgctcac ccagaaacgc    4440
tggtgaaagt aaaagatgct gaagatcagt tgggtgcgcg agtgggttac atcgaactgg    4500
atctcaacag cggtaagatc cttgagagtt ttcgccccga agaacgcttt ccaatgatga    4560
gcacttttaa agttctgcta tgtggcgcgg tattatcccg tattgacgcc gggcaagagc    4620
```

| | |
|---|---|
| aactcggtcg ccgcatacac tattctcaga atgacttggt tgagtattca ccagtcacag | 4680 |
| aaaagcatct tacggatggc atgacagtaa gagaattatg cagtgctgcc ataaccatga | 4740 |
| gtgataacac tgcggccaac ttacttctga caacgattgg aggaccgaag gagctaaccg | 4800 |
| cttttttgca caacatgggg gatcatgtaa ctcgccttga tcgttgggaa ccggagctga | 4860 |
| atgaagccat accaaacgac gagcgtgaca ccacgatgcc tgtagcaatg gcaacaacct | 4920 |
| tgcgtaaact attaactggc gaactactta ctctagcttc ccggcaacag ttgatagact | 4980 |
| ggatggaggc ggataaagtt gcaggaccac ttctgcgctc ggcccttccg gctggctggt | 5040 |
| ttattgctga taaatctgga gccggtgagc gtgggtctcg cggtatcatt gcagcactgg | 5100 |
| ggccagatgg taagccctcc cgtatcgtag ttatctacac gacggggagt caggcaacta | 5160 |
| tggatgaacg aaatagacag atcgctgaga taggtgcctc actgattaag cattggtaac | 5220 |
| cgattctagg tgcattggcg cagaaaaaaa tgcctgatgc gacgctgcgc gtcttatact | 5280 |
| cccacatatg ccagattcag caacggatac ggcttcccca acttgcccac ttccatacgt | 5340 |
| gtcctcctta ccagaaattt atccttaaga tcccgaatcg tttaaactcg actctggctc | 5400 |
| tatcgaatct ccgtcgtttc gagcttacgc gaacagccgt ggcgctcatt tgctcgtcgg | 5460 |
| gcatcgaatc tcgtcagcta tcgtcagctt acctttttgg ca | 5502 |

<210> SEQ ID NO 19
<211> LENGTH: 5460
<212> TYPE: DNA
<213> ORGANISM: Artificial Sequence
<220> FEATURE:
<223> OTHER INFORMATION: Plasmid expression vector pCRO26

<400> SEQUENCE: 19

| | |
|---|---|
| gcgatcgcgg ctcccgacat cttggaccat tagctccaca ggtatcttct tccctctagt | 60 |
| ggtcataaca gcagcttcag ctacctctca attcaaaaaa cccctcaaga cccgtttaga | 120 |
| ggccccaagg ggttatgcta tcaatcgttg cgttacacac acaaaaaacc aacacacatc | 180 |
| catcttcgat ggatagcgat tttattatct aactgctgat cgagtgtagc cagatctagt | 240 |
| aatcaattac ggggtcatta gttcatagcc catatatgga gttccgcgtt acataactta | 300 |
| cggtaaatgg cccgcctggc tgaccgccca acgaccccg cccattgacg tcaataatga | 360 |
| cgtatgttcc catagtaacg ccaataggga ctttccattg acgtcaatgg gtggagtatt | 420 |
| tacggtaaac tgcccacttg gcagtacatc aagtgtatca tatgccaagt acgcccccta | 480 |
| ttgacgtcaa tgacggtaaa tggcccgcct ggcattatgc ccagtacatg accttatggg | 540 |
| actttcctac ttggcagtac atctacgtat tagtcatcgc tattaccatg ctgatgcggt | 600 |
| tttggcagta catcaatggg cgtggatagc ggtttgactc acggggattt ccaagtctcc | 660 |
| accccattga cgtcaatggg agtttgtttt ggcaccaaaa tcaacgggac tttccaaaat | 720 |
| gtcgtaacaa ctccgcccca ttgacgcaaa tgggcggtag gcgtgtacgg tgggaggtct | 780 |
| atataagcag agctggttta gtgaaccgtc agatcagatc tttgtcgatc ctaccatcca | 840 |
| ctcgacacac ccgccagcgg ccgccaccat gaaggccaat ctactggtgt tgctgtgtgc | 900 |
| ccttgcggcg gcagatgcca tgcggtgcgt ggggatcggc aatcgcgatt ttgtagaagg | 960 |
| actatctggt gccacgtggg tcgatgtggt tcttgaacac gggtcatgcg tgaccacgat | 1020 |
| ggctaaggat aagccgacct tggacatcga actactgaaa accgaggtca caaaccctgc | 1080 |
| tgtgctccgc aagctgtgca tcgaggctaa gatttccaac acaactactg atagccgctg | 1140 |
| ccccacccaa ggcgaggcga ccctcgttga agagcaggac agcaacttcg tgtgtcgccg | 1200 |

```
gactttcgtg gaccgcggta atgggtccgg atgcggactt tttggaaagg gttccttact    1260
gacttgcgcc aaatttaagt gcgtgactaa gttagagggg aaaatcgttc agtatgagaa    1320
cttaaaatac tcggtgatag ttaccgtgca cacaggcgac cagcatcaag ttgggaacga    1380
aacgacagag cacgggacaa tagcgaccat tacccacag gctccaacga gcgaaattca     1440
gctgacagac tacggtgcac tcaccctgga ctgtagccca cggaccgggc tagactttaa    1500
cgagatggtg ctcctgacta tgaaggaaaa gtcatggttg gtgcacaagc agtggttcct    1560
tgatcttcca ttgccctgga cctctggcgc ttcgacctca caagagactt ggaacaggca    1620
ggacttgctc gtgacattca aaacggctca cgctaaaaag caagaggtcg tggttctggg    1680
gagtcaggaa ggcgctatgc ataccgcgtt aacagggct acagagatcc agaccagtgg     1740
aacaaccact attttcgccg ggcatcttaa gtgtaggctg aagatggata agttgaccct    1800
gaaaggtatg tcatatgtga tgtgcaccgg tagtttcaaa ctggagaaag aagtggccga    1860
aacccagcat ggaacagtac tggtgcaagt caaatatgag ggcaccgatg caccatgtaa    1920
aatacccttc agcgcacaag acgagaaggg agttacccag aacggtaggc tgataacagc    1980
caatccaatc gtcaccgata aggagaaacc agtaaacatc gaaaccgagc cacccttcgg    2040
cgaaagctac atcgtggtcg gcgctggcga gaaagcactt aagctgagct ggtttaagaa    2100
aggtagcacg ggcggcggca gccatcatca ccatcatcac tgagctagct tgactgactg    2160
agatacagcg taccttcagc tcacagacat gataagatac attgatgagt ttggacaaac    2220
cacaactaga atgcagtgaa aaaaatgctt tatttgtgaa atttgtgatg ctattgcttt    2280
atttgtaacc attataagct gcaataaaca agttaacaac acaattgca ttcattttat      2340 gtttcaggtt caggggggagg tgtgggaggt tttttaaagc aagtaaaacc tctacaaatg    2400
tggtattggc ccatctctat cggtatcgta gcataacccc ttggggcctc taaacgggtc    2460
ttgaggggtt ttttgtgccc ctcgggccgg attgctatct accggcattg gcgcagaaaa    2520
aaatgcctga tgcgacgctg cgcgtcttat actcccacat atgccagatt cagcaacgga    2580
tacggcttcc ccaacttgcc cacttccata cgtgtcctcc ttaccagaaa tttatcctta    2640
aggtcgtcag ctatcctgca ggcgatctct cgatttcgat caagacattc ctttaatggt    2700
cttttctgga caccactagg ggtcagaagt agttcatcaa actttcttcc ctccctaatc    2760
tcattggtta ccttgggcta tcgaaactta attaaccagt caagtcagct acttggcgag    2820
atcgacttgt ctgggtttcg actacgctca gaattgcgtc agtcaagttc gatctggtcc    2880
ttgctattgc acccgttctc cgattacgag tttcatttaa atcatgtgag caaaaggcca    2940
gcaaaaggcc aggaaccgta aaaaggccgc gttgctggcg ttttccata ggctccgccc     3000 ccctgacgag catcacaaaa atcgacgctc aagtcagagg tggcgaaacc cgacaggact    3060
ataaagatac caggcgtttc ccctggaag ctccctcgtg cgctctcctg ttccgaccct     3120
gccgcttacc ggatacctgt ccgcctttct cccttcggga agcgtggcgc tttctcatag    3180
ctcacgctgt aggtatctca gttcggtgta ggtcgttcgc tccaagctgg gctgtgtgca    3240 cgaaccccc gttcagcccg accgctgcgc cttatccggt aactatcgtc ttgagtccaa      3300
cccggtaaga cacgacttat cgccactggc agcagccact ggtaacagga ttagcagagc    3360
gaggtatgta ggcggtgcta cagagttctt gaagtggtgg cctaactacg gctacactag    3420
aagaacagta tttggtatct gcgctctgct gaagccagtt accttcggaa aaagagttgg    3480
tagctcttga tccggcaaac aaaccaccgc tggtagcggt ggtttttttg tttgcaagca    3540
```

```
gcagattacg cgcagaaaaa aaggatctca agaagatcct tgatcttttt ctacggggtc    3600
tgacgctcag tggaacgaaa actcacgtta agggattttg gtcatgagat tatcaaaaag    3660
gatcttcacc tagatccttt taaattaaaa atgaagtttt aaatcaatct aaagtatata    3720
tgagtaaact tggtctgaca gttaccaatg cttaatcagt gaggcaccta tctcagcgat    3780
ctgtctattt cgttcatcca tagttgcatt taaatttccg aactctccaa ggccctcgtc    3840
ggaaaatctt caaacctttc gtccgatcca tcttgcaggc tacctctcga acgaactatc    3900
gcaagtctct tggccggcct tgcgccttgg ctattgcttg gcagcgccta tcgccaggta    3960
ttactccaat cccgaatatc cgagatcggg atcacccgag agaagttcaa cctacatcct    4020
caatcccgat ctatccgaga tccgaggaat atcgaaatcg gggcgcgcct ggtgtaccga    4080
gaacgatcct ctcagtgcga gtctcgacga tccatatcgt tgcttggcag tcagccagtc    4140
ggaatccagc ttgggaccca ggaagtccaa tcgtcagata ttgtactcaa gcctggtcac    4200
ggcagcgtac cgatctgttt aaacctagat attgatagtc tgatcggtca acgtataatc    4260
gagtcctagc ttttgcaaac atctatcaag agacaggatc agcaggaggc tttcgcatga    4320
gtattcaaca tttccgtgtc gcccttattc cctttttttgc ggcatttttgc cttcctgttt    4380
ttgctcaccc agaaacgctg gtgaaagtaa aagatgctga agatcagttg ggtgcgcgag    4440
tgggttacat cgaactggat ctcaacagcg gtaagatcct tgagagtttt cgccccgaag    4500
aacgctttcc aatgatgagc acttttaaag ttctgctatg tggcgcggta ttatcccgta    4560
ttgacgccgg gcaagagcaa ctcggtcgcc gcatacacta ttctcagaat gacttggttg    4620
agtattcacc agtcacagaa aagcatctta cggatggcat gacagtaaga gaattatgca    4680
gtgctgccat aaccatgagt gataacactg cggccaactt acttctgaca acgattggag    4740
gaccgaagga gctaaccgct tttttgcaca acatggggga tcatgtaact cgccttgatc    4800
gttgggaacc ggagctgaat gaagccatac caaacgacga gcgtgacacc acgatgcctg    4860
tagcaatggc aacaaccttg cgtaaactat taactggcga actacttact ctagcttccc    4920
ggcaacagtt gatagactgg atggaggcgg ataaagttgc aggaccactt ctgcgctcgg    4980
cccttccggc tggctggttt attgctgata aatctggagc cggtgagcgt gggtctcgcg    5040
gtatcattgc agcactgggg ccagatggta agccctcccg tatcgtagtt atctacacga    5100
cggggagtca ggcaactatg gatgaacgaa atagacagat cgctgagata ggtgcctcac    5160
tgattaagca ttggtaaccg attctaggtg cattggcgca gaaaaaaatg cctgatgcga    5220
cgctgcgcgt cttatactcc cacatatgcc agattcagca acggatacgg cttccccaac    5280
ttgcccactt ccatacgtgt cctccttacc agaaatttat ccttaagatc ccgaatcgtt    5340
taaactcgac tctggctcta tcgaatctcc gtcgtttcga gcttacgcga acagccgtgg    5400
cgctcatttg ctcgtcgggc atcgaatctc gtcagctatc gtcagcttac cttttttggca    5460
```

<210> SEQ ID NO 20
<211> LENGTH: 5460
<212> TYPE: DNA
<213> ORGANISM: Artificial Sequence
<220> FEATURE:
<223> OTHER INFORMATION: Plasmid expression vector pCRO27

<400> SEQUENCE: 20

```
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
```

```
catcttcgat ggatagcgat tttattatct aactgctgat cgagtgtagc cagatctagt    240
aatcaattac ggggtcatta gttcatagcc catatatgga gttccgcgtt acataactta    300
cggtaaatgg cccgcctggc tgaccgccca acgaccccg cccattgacg tcaataatga     360
cgtatgttcc catagtaacg ccaataggga ctttccattg acgtcaatgg gtggagtatt    420
tacggtaaac tgcccacttg gcagtacatc aagtgtatca tatgccaagt acgcccccta    480
ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag cgtgtacgg tgggaggtct     780 atataagcag agctggttta gtgaaccgtc agatcagatc tttgtcgatc ctaccatcca    840
ctcgacacac cgccagcgg ccgccaccat gaaggccaat ctactggtgt tgctgtgtgc     900
ccttgcggcg gcagatgcca tgcggtgcgt ggggatcggc aatcgcgatt ttgtagaagg    960
actatctggt gccacgtggg tcgatgtggt tcttgaacac gggtcatgcg tgaccacgat   1020
ggctaaggat aagccgacct tggacatcga actactgaaa accgaggtca caaaccctgc   1080
tgtgctccgc aagctgtgca tcgaggctaa gatttccaac acaactactg atagccgctg   1140
ccccacccaa ggcgaggcga ccctcgttga agagcaggac agcaacttcg tgtgtcgccg   1200
gactttcgtg gaccgcggtt gggggaatgg atgcggactt aacggatctg gttccttact   1260
gacttgcgcc aaatttaagt gcgtgactaa gttagagggg aaaatcgttc agtatgagaa   1320
cttaaaatac tcggtgatag ttaccgtgca cacaggcgac cagcatcaag ttgggaacga   1380
aacgacagag cacgggacaa tagcgaccat taccccacag gctccaacga gcgaaattca   1440
gctgacagac tacggtgcac tcaccctgga ctgtagccca cggaccgggc tagactttaa   1500
cgagatggtg ctcctgacta tgaaggaaaa gtcatggttg gtgcacaagc agtggttcct   1560
tgatcttcca ttgccctgga cctctggcgc ttcgacctca caagagactt ggaacaggca   1620
ggacttgctc gtgacattca aaacggctca cgctaaaaag caagaggtcg tggttctggg   1680
gagtcaggaa ggcgctatgc ataccgcgtt aacagggct acagagatcc agaccagtgg    1740
aacaaccact attttcgccg ggcatcttaa gtgtaggctg aagatggata agttgacctt   1800
gaaaggtatg tcatatgtga tgtgcaccgg tagtttcaaa ctggagaaag agtggccga    1860 aacccagcat ggaacagtac tggtgcaagt caaatatgag ggcaccgatg caccatgtaa   1920 aataccttc agcgcacaag acgagaaggg agttacccag aacggtaggc tgataacagc    1980
caatccaatc gtcaccgata aggagaaacc agtaaacatc gaaaccgagc cacccttcgg   2040
cgaaagctac atcgtggtcg gcgctggcga gaaagcactt aagctgagct ggtttaagaa   2100
aggtagcacg ggcggcggca gccatcatca ccatcatcac tgagctagct tgactgactg   2160
agatacagcg taccttcagc tcacagacat gataagatac attgatgagt ttggacaaac   2220
cacaactaga atgcagtgaa aaaaatgctt tatttgtgaa atttgtgatg ctattgcttt   2280
atttgtaacc attataagct gcaataaaca agttaacaac acaattgca ttcatttttat   2340 gtttcaggtt caggggagg tgtgggaggt tttttaaagc aagtaaaacc tctacaaatg    2400
tggtattggc ccatctctat cggtatcgta gcataacccc ttggggcctc taaacgggtc   2460
ttgaggggtt ttttgtgccc ctcgggccgg attgctatct accggcattg gcgcagaaaa   2520
```

```
aaatgcctga tgcgacgctg cgcgtcttat actcccacat atgccagatt cagcaacgga      2580
tacggcttcc ccaacttgcc cacttccata cgtgtcctcc ttaccagaaa tttatcctta      2640
aggtcgtcag ctatcctgca ggcgatctct cgatttcgat caagacattc ctttaatggt      2700
cttttctgga caccactagg ggtcagaagt agttcatcaa actttcttcc ctccctaatc      2760
tcattggtta ccttgggcta tcgaaactta attaaccagt caagtcagct acttggcgag      2820
atcgacttgt ctgggtttcg actacgctca gaattgcgtc agtcaagttc gatctggtcc      2880
ttgctattgc acccgttctc cgattacgag tttcatttaa atcatgtgag caaaaggcca      2940
gcaaaaggcc aggaaccgta aaaaggccgc gttgctggcg ttttttccata ggctccgccc      3000 ccctgacgag catcacaaaa atcgacgctc aagtcagagg tggcgaaacc cgacaggact      3060
ataaagatac caggcgtttc ccctggaag ctccctcgtg cgctctcctg ttccgaccct       3120
gccgcttacc ggatacctgt ccgcctttct cccttcggga agcgtggcgc tttctcatag      3180
ctcacgctgt aggtatctca gttcggtgta ggtcgttcgc tccaagctgg gctgtgtgca      3240 cgaaccccc gttcagcccg accgctgcgc cttatccggt aactatcgtc ttgagtccaa       3300
cccggtaaga cacgacttat cgccactggc agcagccact ggtaacagga ttagcagagc      3360
gaggtatgta ggcggtgcta cagagttctt gaagtggtgg cctaactacg gctacactag      3420
aagaacagta tttggtatct gcgctctgct gaagccagtt accttcggaa aaagagttgg      3480
tagctcttga tccggcaaac aaaccaccgc tggtagcggt ggttttttg tttgcaagca      3540 gcagattacg cgcagaaaaa aaggatctca agaagatcct ttgatctttt ctacggggtc      3600
tgacgctcag tggaacgaaa actcacgtta agggattttg gtcatgagat tatcaaaaag      3660
gatcttcacc tagatccttt taaattaaaa atgaagtttt aaatcaatct aaagtatata      3720
tgagtaaact tggtctgaca gttaccaatg cttaatcagt gaggcaccta tctcagcgat      3780
ctgtctattt cgttcatcca gttgcatt taaatttccg aactctccaa ggccctcgtc       3840
ggaaaatctt caaacctttc gtccgatcca tcttgcaggc tacctctcga acgaactatc      3900
gcaagtctct tggccggcct tgcgccttgg ctattgcttg gcagcgccta tcgccaggta      3960
ttactccaat cccgaatatc cgagatcggg atcacccgag agaagttcaa cctacatcct      4020
caatcccgat ctatccgaga tccgaggaat atcgaaatcg gggcgcgcct ggtgtaccga      4080
gaacgatcct ctcagtgcga gtctcgacga tccatatcgt tgcttggcag tcagccagtc      4140
ggaatccagc ttgggaccca ggaagtccaa tcgtcagata ttgtactcaa gcctggtcac      4200
ggcagcgtac cgatctgttt aaacctagat attgatagtc tgatcggtca acgtataatc      4260
gagtcctagc ttttgcaaac atctatcaag agacaggatc agcaggaggc tttcgcatga      4320
gtattcaaca tttccgtgtc gcccttattc cctttttgc ggcatttgc cttcctgttt       4380 ttgctcaccc agaaacgctg gtgaaagtaa aagatgctga gatcagttg ggtgcgcgag       4440 tgggttacat cgaactggat ctcaacagcg gtaagatcct tgagagtttt cgccccgaag      4500 aacgcttttcc aatgatgagc acttttaaag ttctgctatg tggcgcggta ttatcccgta     4560
ttgacgccgg gcaagagcaa ctcggtcgcc gcatacacta ttctcagaat gacttggttg      4620
agtattcacc agtcacagaa aagcatctta cggatggcat gacagtaaga gaattatgca      4680
gtgctgccat aaccatgagt gataacactg cggccaactt acttctgaca acgattggag      4740
gaccgaagga gctaaccgct ttttgcaca acatggggga tcatgtaact cgccttgatc       4800
gttgggaacc ggagctgaat gaagccatac caaacgacga gcgtgacacc acgatgcctg      4860
tagcaatggc aacaaccttg cgtaaactat taactggcga actacttact ctagcttccc      4920
```

```
ggcaacagtt gatagactgg atggaggcgg ataaagttgc aggaccactt ctgcgctcgg    4980
cccttccggc tggctggttt attgctgata atctggagc cggtgagcgt gggtctcgcg    5040
gtatcattgc agcactgggg ccagatggta agccctccg tatcgtagtt atctacacga    5100
cggggagtca ggcaactatg gatgaacgaa atagacagat cgctgagata ggtgcctcac    5160
tgattaagca ttggtaaccg attctaggtg cattggcgca gaaaaaaatg cctgatgcga    5220
cgctgcgcgt cttatactcc cacatatgcc agattcagca acggatacgg cttccccaac    5280
ttgcccactt ccatacgtgt cctccttacc agaaatttat ccttaagatc cgaatcgtt     5340 taaactcgac tctggctcta tcgaatctcc gtcgtttcga gcttacgcga acagccgtgg    5400
cgctcatttg ctcgtcgggc atcgaatctc gtcagctatc gtcagcttac cttttttggca   5460
```

<210> SEQ ID NO 21
<211> LENGTH: 5502
<212> TYPE: DNA
<213> ORGANISM: Artificial Sequence
<220> FEATURE:
<223> OTHER INFORMATION: Plasmid expression vector pCRO29

<400> SEQUENCE: 21

```
gcgatcgcgg ctcccgacat cttggaccat tagctccaca ggtatcttct tccctctagt      60
ggtcataaca gcagcttcag ctacctctca attcaaaaaa ccccctcaaga cccgtttaga    120 ggccccaagg ggttatgcta tcaatcgttg cgttacacac acaaaaaacc aacacacatc     180
catcttcgat ggatagcgat tttattatct aactgctgat cgagtgtagc cagatctagt    240
aatcaattac ggggtcatta gttcatagcc catatatgga gttccgcgtt acataactta    300
cggtaaatgg cccgcctggc tgaccgccca acgaccccg cccattgacg tcaataatga     360
cgtatgttcc catagtaacg ccaataggga cttttccattg acgtcaatgg gtggagtatt   420
tacggtaaac tgcccacttg gcagtacatc aagtgtatca tatgccaagt acgcccccta    480
ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac ccgccagcgg ccgccaccat gaaggccaat ctactggtgt tgctgtgtgc    900
ccttgcggcg gcagatgcca tcaggtgcat tggagtcagc aacagggact tcgtcgaagg    960
catgtccggg gcacctgggt ggatgtggt gctcgaacac ggcggatgcg tgaccgtcat    1020
ggcccaggac aagcctaccg tcgatattga gctggtgacc accacagtga gcaacatggc    1080
cgaagtgaga agctactgct atgaggcctc catcagcgat atggcttccg attccagatg    1140
ccccacacag ggagaggctt atctggacaa acagtccgac acccagtacg tctgcaaaag    1200
aaccctggtg gacagaggct ggggaaacgg atgcggcaac cacaccaaag gcagcctcgt    1260
gacatgtgcc aagttcgcct gcagcaaaaa gatgaccggg aagtccatcc agccggaaaa    1320
cctggaatac aggatcatgc tgtccgtgca tggatcccag cactccggca tgatcgtcaa    1380
cgataccggc cacgagaccg acgagaacag ggctaaagtg gagatcaccc ccaacagccc    1440
tagagccgaa gctacactgg gcggcttcgg aagcctgggc ctggattgcg aacccaggac    1500
```

```
cggcctggat ttcagcgacc tgtattacct gaccatgaac aataagcact ggctggtgca    1560
caaggaatgg ttccacgaca tcccctgcc ttggcatgct ggcgccgata ccggcacacc    1620
tcactggaac aataaggaag ccctggtcga gtttaaggac gcccacgcca aagacagac    1680 cgtggtggtg ctgggaagcc aggagggagc tgtccacaca gccctggccg gagctctgga    1740
agccgagatg gatggcgcca agggcaggct gagctccggc cacctgaaat gcaggctcaa    1800
gatggacaag ctgaggctga agggcgtgag ctacagcctg tgcaccgccg ctttcacctt    1860
taccaagatc cctgccgaga cactgcacgg caccgtcacc gtggaggtgc aatacgccgg    1920
aaccgatgga ccttgcaaag tgcctgccca gatggctgtg gatatgcaga ccctcacacc    1980
cgtcggcagg ctgatcaccg ccaatcccgt cattaccgag tccaccgaga acagcaagat    2040
gatgctcgag ctcgatcccc cctttggcga cagctacatt gtgatcggcg tgggcgagaa    2100
gaagatcacc caccattggc acagaagcgg ctccacaggg ggtagcggtg gtagcggagg    2160
tagccatcac caccatcacc actgagctag cttgactgac tgagatacag cgtaccttca    2220
gctcacagac atgataagat acattgatga gtttggacaa accacaacta gaatgcagtg    2280
aaaaaaatgc tttatttgtg aaatttgtga tgctattgct ttatttgtaa ccattataag    2340
ctgcaataaa caagttaaca acaacaattg cattcatttt atgtttcagg ttcaggggga    2400
ggtgtgggag gttttttaaa gcaagtaaaa cctctacaaa tgtggtattg gcccatctct    2460
atcggtatcg tagcataacc ccttgggggcc tctaaacggg tcttgagggg tttttttgtgc    2520 ccctcgggcc ggattgctat ctaccggcat ggcgcagaa aaaaatgcct gatgcgacgc    2580
tgcgcgtctt atactcccac atatgccaga ttcagcaacg gatacggctt ccccaacttg    2640
cccacttcca tacgtgtcct ccttaccaga aatttatcct taaggtcgtc agctatcctg    2700
caggcgatct ctcgatttcg atcaagacat tcctttaatg gtcttttctg gacaccacta    2760
ggggtcagaa gtagttcatc aaactttctt ccctccctaa tctcattggt taccttgggc    2820
tatcgaaact taattaacca gtcaagtcag ctacttggcg agatcgactt gtctgggttt    2880
cgactacgct cagaattgcg tcagtcaagt tcgatctggt ccttgctatt gcaccgttc    2940 tccgattacg agtttcattt aaatcatgtg agcaaaaggc cagcaaaagg ccaggaaccg    3000
taaaaaggcc gcgttgctgg cgttttttcca taggctccgc ccccctgacg agcatcacaa    3060
aaatcgacgc tcaagtcaga ggtggcgaaa cccgacagga ctataaagat accaggcgtt    3120
tccccctgga agctccctcg tgcgctctcc tgttccgacc ctgccgctta ccggatacct    3180
gtccgccttt ctcccttcgg gaagcgtggc gctttctcat agctcacgct gtaggtatct    3240
cagttcggtg taggtcgttc gctccaagct gggctgtgtg cacgaacccc ccgttcagcc    3300
cgaccgctgc gccttatccg gtaactatcg tcttgagtcc aacccggtaa gacacgactt    3360
atcgccactg gcagcagcca ctggtaacag gattagcaga gcgaggtatg taggcggtgc    3420
tacagagttc ttgaagtggt ggcctaacta cggctacact agaagaacag tatttggtat    3480
ctgcgctctg ctgaagccag ttaccttcgg aaaaagagtt ggtagctctt gatccggcaa    3540
acaaaccacc gctggtagcg gtggtttttt tgtttgcaag cagcagatta cgcgcagaaa    3600
aaaaggatct caagaagatc ctttgatctt ttctacgggg tctgacgctc agtggaacga    3660
aaactcacgt taagggattt tggtcatgag attatcaaaa aggatcttca cctagatcct    3720
tttaaattaa aaatgaagtt ttaaatcaat ctaaagtata tatgagtaaa cttggtctga    3780
cagttaccaa tgcttaatca gtgaggcacc tatctcagcg atctgtctat ttcgttcatc    3840
catagttgca tttaaatttc cgaactctcc aaggccctcg tcggaaaatc ttcaaacctt    3900
```

| | |
|---|---:|
| tcgtccgatc catcttgcag gctacctctc gaacgaacta tcgcaagtct cttggccggc | 3960 |
| cttgcgccttt ggctattgct tggcagcgcc tatcgccagg tattactcca atcccgaata | 4020 |
| tccgagatcg ggatcacccg agagaagttc aacctacatc ctcaatcccg atctatccga | 4080 |
| gatccgagga atatcgaaat cggggcgcgc ctggtgtacc gagaacgatc ctctcagtgc | 4140 |
| gagtctcgac gatccatatc gttgcttggc agtcagccag tcggaatcca gcttgggacc | 4200 |
| caggaagtcc aatcgtcaga tattgtactc aagcctggtc acggcagcgt accgatctgt | 4260 |
| ttaaacctag atattgatag tctgatcggt caacgtataa tcgagtccta gcttttgcaa | 4320 |
| acatctatca agagacagga tcagcaggag gcttttcgcat gagtattcaa catttccgtg | 4380 |
| tcgcccttat tccctttttt gcggcatttt gccttcctgt ttttgctcac ccagaaacgc | 4440 |
| tggtgaaagt aaaagatgct gaagatcagt tgggtgcgcg agtgggttac atcgaactgg | 4500 |
| atctcaacag cggtaagatc cttgagagtt ttcgccccga agaacgcttt ccaatgatga | 4560 |
| gcacttttaa agttctgcta tgtggcgcgg tattatcccg tattgacgcc gggcaagagc | 4620 |
| aactcggtcg ccgcatacac tattctcaga atgacttggt tgagtattca ccagtcacag | 4680 |
| aaaagcatct tacgatggc atgacagtaa gagaattatg cagtgctgcc ataaccatga | 4740 |
| gtgataacac tgcggccaac ttacttctga caacgattgg aggaccgaag gagctaaccg | 4800 |
| cttttttgca caacatgggg gatcatgtaa ctcgccttga tcgttgggaa ccggagctga | 4860 |
| atgaagccat accaaacgac gagcgtgaca ccacgatgcc tgtagcaatg gcaacaacct | 4920 |
| tgcgtaaact attaactggc gaactactta ctctagcttc ccggcaacag ttgatagact | 4980 |
| ggatggaggc ggataaagtt gcaggaccac ttctgcgctc ggcccttccg gctggctggt | 5040 |
| ttattgctga taaatctgga gccggtgagc gtgggtctcg cggtatcatt gcagcactgg | 5100 |
| ggccagatgg taagccctcc cgtatcgtag ttatctacac gacggggagt caggcaacta | 5160 |
| tggatgaacg aaatagacag atcgctgaga taggtgcctc actgattaag cattggtaac | 5220 |
| cgattctagg tgcattggcg cagaaaaaaa tgcctgatgc gacgctgcgc gtcttatact | 5280 |
| cccacatatg ccagattcag caacggtac ggcttcccca acttgcccac ttccatacgt | 5340 |
| gtcctcctta ccagaaattt atccttaaga tcccgaatcg tttaaactcg actctggctc | 5400 |
| tatcgaatct ccgtcgtttc gagcttacgc gaacagccgt ggcgctcatt tgctcgtcgg | 5460 |
| gcatcgaatc tcgtcagcta tcgtcagctt accttttttgg ca | 5502 |

<210> SEQ ID NO 22
<211> LENGTH: 5502
<212> TYPE: DNA
<213> ORGANISM: Artificial Sequence
<220> FEATURE:
<223> OTHER INFORMATION: Plasmid expression vector pCRO30

<400> SEQUENCE: 22

| | |
|---|---:|
| gcgatcgcgg ctcccgacat cttggaccat tagctccaca ggtatcttct tccctctagt | 60 |
| ggtcataaca gcagcttcag ctacctctca attcaaaaaa cccctcaaga cccgtttaga | 120 |
| ggccccaagg ggttatgcta tcaatcgttg cgttacacac acaaaaaacc aacacacatc | 180 |
| catcttcgat ggatagcgat tttattatct aactgctgat cgagtgtagc cagatctagt | 240 |
| aatcaattac ggggtcatta gttcatagcc catatatgga gttccgcgtt acataactta | 300 |
| cggtaaatgg cccgcctggc tgaccgccca acgacccccg cccattgacg tcaataatga | 360 |
| cgtatgttcc catagtaacg ccaatagggga ctttccattg acgtcaatgg gtggagtatt | 420 |

```
tacggtaaac tgcccacttg gcagtacatc aagtgtatca tatgccaagt acgcccccta      480
ttgacgtcaa tgacggtaaa tggcccgcct ggcattatgc ccagtacatg accttatggg      540
actttcctac ttggcagtac atctacgtat tagtcatcgc tattaccatg ctgatgcggt      600
tttggcagta catcaatggg cgtggatagc ggtttgactc acggggattt ccaagtctcc      660
accccattga cgtcaatggg agtttgtttt ggcaccaaaa tcaacgggac tttccaaaat      720
gtcgtaacaa ctccgcccca ttgacgcaaa tgggcggtag gcgtgtacgg tgggaggtct      780
atataagcag agctggttta gtgaaccgtc agatcagatc tttgtcgatc ctaccatcca      840
ctcgacacac cgccagcgg ccgccaccat gaaggccaat ctactggtgt tgctgtgtgc       900
ccttgcggcg gcagatgcca tcaggtgcat ggagtcagc aacagggact cgtcgaagg       960 catgtccggc ggcacctggg tggatgtggt gctcgaacac ggcggatgcg tgaccgtcat     1020
ggcccaggac aagcctaccg tcgatattga gctggtgacc accacagtga gcaacatggc     1080
cgaagtgaga agctactgct atgaggcctc catcagcgat atggcttccg attccagatg     1140
ccccacacag ggagaggctt atctggacaa acagtccgac acccagtacg tctgcaaaag     1200
aaccctggtg gacagaggca acggatccgg atgcggcctg ttcggcaaag gcagcctcgt     1260
gacatgtgcc aagttcgcct gcagcaaaaa gatgaccggc aagtccatcc agcccgagaa     1320
cctggaatac aggatcatgc tgtccgtgca tggatcccag cactccggca tgatcgtcaa     1380
cgataccggc cacgagaccg acgagaacag ggctaaagtg gagatcaccc caacagccc     1440 tagagccgaa gctacactgg gcggcttcgg aagcctgggc ctggattgcg aacccaggac     1500
cggcctggat tcagcgacc tgtattacct gaccatgaac aataagcact ggctggtgca      1560
caaggaatgg ttccacgaca tcccctgcc ttggcatgct ggcgccgata ccggcacacc      1620 tcactgaac aataaggaag ccctggtcga gtttaaggac gcccacgcca aaagacagac      1680
cgtggtggtg ctgggaagcc aggagggagc tgtccacaca gccctggccg agctctgga      1740 agccgagatg gatggcgcca agggcaggct gagctccggc cacctgaaat gcaggctcaa     1800
gatggacaag ctgaggctga agggcgtgag ctacagcctg tgcaccgccg ctttcacctt      1860
taccaagatc cctgccgaga cactgcacgg caccgtcacc gtggaggtgc aatacgccgg     1920
aaccgatgga ccttgcaaag tgcctgccca gatggctgtg gatatgcaga ccctcacacc     1980
cgtcggcagg ctgatcaccg ccaatcccgt cattaccgag tccaccgaga acagcaagat     2040
gatgctcgag ctcgatcccc cctttggcga cagctacatt gtgatcggcg tgggcgagaa     2100
gaagatcacc caccattggc acagaagcgg ctccacaggg ggtagcggtg gtagcggagg     2160
tagccatcac caccatcacc actgagctag cttgactgac tgagatacag cgtaccttca     2220
gctcacagac atgataagat acattgatga gtttggacaa accacaacta gaatgcagtg     2280
aaaaaaatgc tttatttgtg aaatttgtga tgctattgct ttatttgtaa ccattataag     2340
ctgcaataaa caagttaaca acaacaattg cattcatttt atgtttcagg ttcaggggga     2400
ggtgtgggag gttttttaaa gcaagtaaaa cctctacaaa tgtggtattg gcccatctct     2460
atcggtatcg tagcataacc ccttggggcc tctaaacggg tcttgagggg ttttttgtgc     2520
ccctcgggcc ggattgctat ctaccggcat ggcgcagaa aaaatgcct gatgcgacgc       2580 tgcgcgtctt atactcccac atatgccaga ttcagcaacg gatacggctt ccccaacttg     2640
cccacttcca tacgtgtcct ccttaccaga aatttatcct taaggtcgtc agctatcctg     2700
caggcgatct ctcgatttcg atcaagacat tcctttaatg gtcttttctg gacaccacta     2760
ggggtcagaa gtagttcatc aaactttctt ccctccctaa tctcattggt taccttgggc     2820
```

```
tatcgaaact taattaacca gtcaagtcag ctacttggcg agatcgactt gtctgggttt    2880
cgactacgct cagaattgcg tcagtcaagt tcgatctggt ccttgctatt gcacccgttc    2940
tccgattacg agtttcattt aaatcatgtg agcaaaaggc cagcaaaagg ccaggaaccg    3000
taaaaaggcc gcgttgctgg cgttttccca taggctccgc cccctgacg agcatcacaa    3060 aaatcgacgc tcaagtcaga ggtggcgaaa cccgacagga ctataaagat accaggcgtt    3120
tccccctgga agctccctcg tgcgctctcc tgttccgacc ctgccgctta ccggatacct    3180
gtccgccttt ctcccttcgg gaagcgtggc gctttctcat agctcacgct gtaggtatct    3240
cagttcggtg taggtcgttc gctccaagct gggctgtgtg cacgaacccc ccgttcagcc    3300
cgaccgctgc gccttatccg gtaactatcg tcttgagtcc aacccggtaa gacacgactt    3360
atcgccactg gcagcagcca ctggtaacag gattagcaga gcgaggtatg taggcggtgc    3420
tacagagttc ttgaagtggt ggcctaacta cggctacact agaagaacag tatttggtat    3480
ctgcgctctg ctgaagccag ttaccttcgg aaaaagagtt ggtagctctt gatccggcaa    3540
acaaaccacc gctggtagcg gtggtttttt tgtttgcaag cagcagatta cgcgcagaaa    3600
aaaaggatct caagaagatc ctttgatctt ttctacgggg tctgacgctc agtggaacga    3660
aaactcacgt taagggattt tggtcatgag attatcaaaa aggatcttca cctagatcct    3720
tttaaattaa aaatgaagtt ttaaatcaat ctaaagtata tatgagtaaa cttggtctga    3780
cagttaccaa tgcttaatca gtgaggcacc tatctcagcg atctgtctat ttcgttcatc    3840
catagttgca tttaaatttc cgaactctcc aaggccctcg tcggaaaatc ttcaaacctt    3900
tcgtccgatc catcttgcag gctacctctc gaacgaacta tcgcaagtct cttggccggc    3960
cttgcgcctt ggctattgct tggcagcgcc tatcgccagg tattactcca atcccgaata    4020
tccgagatcg ggatcacccg agagaagttc aacctacatc ctcaatcccg atctatccga    4080
gatccgagga atatcgaaat cggggcgcgc ctggtgtacc gagaacgatc ctctcagtgc    4140
gagtctcgac gatccatatc gttgcttggc agtcagccag tcggaatcca gcttgggacc    4200
caggaagtcc aatcgtcaga tattgtactc aagcctggtc acggcagcgt accgatctgt    4260
ttaaacctag atattgatag tctgatcggt caacgtataa tcgagtccta gcttttgcaa    4320
acatctatca agagacagga tcagcaggag gctttcgcat gagtattcaa catttccgtg    4380
tcgcccttat tccctttttt gcggcatttt gccttcctgt ttttgctcac ccagaaacgc    4440
tggtgaaagt aaaagatgct gaagatcagt tgggtgcgcg agtgggttac atcgaactgg    4500
atctcaacag cggtaagatc cttgagagtt ttcgccccga agaacgcttt ccaatgatga    4560 gcactttaa agttctgcta tgtggcgcgg tattatcccg tattgacgcc gggcaagagc    4620
aactcggtcg ccgcatacac tattctcaga atgacttggt tgagtattca ccagtcacag    4680
aaaagcatct tacggatggc atgacagtaa gagaattatg cagtgctgcc ataaccatga    4740 gtgataaac tgcggccaac ttacttctga caacgattgg aggaccgaag gagctaaccg    4800
cttttttgca caacatgggg gatcatgtaa ctcgccttga tcgttgggaa ccggagctga    4860
atgaagccat accaaacgac gagcgtgaca ccacgatgcc tgtagcaatg gcaacaacct    4920
tgcgtaaact attaactggc gaactactta ctctagcttc ccggcaacag ttgatagact    4980
ggatggaggc ggataaagtt gcaggaccac ttctgcgctc ggcccttccg gctggctggt    5040
ttattgctga taaatctgga gccggtgagc gtgggtctcg cggtatcatt gcagcactgg    5100
ggccagatgg taagccctcc cgtatcgtag ttatctacac gacggggagt caggcaacta    5160
```

-continued

| | |
|---|---|
| tggatgaacg aaatagacag atcgctgaga taggtgcctc actgattaag cattggtaac | 5220 |
| cgattctagg tgcattggcg cagaaaaaaa tgcctgatgc gacgctgcgc gtcttatact | 5280 |
| cccacatatg ccagattcag caacggatac ggcttcccca acttgcccac ttccatacgt | 5340 |
| gtcctcctta ccagaaattt atccttaaga tcccgaatcg tttaaactcg actctggctc | 5400 |
| tatcgaatct ccgtcgtttc gagcttacgc gaacagccgt ggcgctcatt tgctcgtcgg | 5460 |
| gcatcgaatc tcgtcagcta tcgtcagctt accttttgg ca | 5502 |

<210> SEQ ID NO 23
<211> LENGTH: 5502
<212> TYPE: DNA
<213> ORGANISM: Artificial Sequence
<220> FEATURE:
<223> OTHER INFORMATION: Plasmid expression vector pCRO31

<400> SEQUENCE: 23

| | |
|---|---|
| gcgatcgcgg ctcccgacat cttggaccat tagctccaca ggtatcttct tccctctagt | 60 |
| ggtcataaca gcagcttcag ctacctctca attcaaaaaa cccctcaaga cccgtttaga | 120 |
| ggccccaagg ggttatgcta tcaatcgttg cgttacacac acaaaaaacc aacacacatc | 180 |
| catcttcgat ggatagcgat tttattatct aactgctgat cgagtgtagc cagatctagt | 240 |
| aatcaattac ggggtcatta gttcatagcc catatatgga gttccgcgtt acataactta | 300 |
| cggtaaatgg cccgcctggc tgaccgccca acgaccccg cccattgacg tcaataatga | 360 |
| cgtatgttcc catagtaacg ccaatagggga cttttccattg acgtcaatgg gtggagtatt | 420 |
| tacggtaaac tgcccacttg gcagtacatc aagtgtatca tatgccaagt acgcccccta | 480 |
| ttgacgtcaa tgacggtaaa tggcccgcct ggcattatgc ccagtacatg accttatggg | 540 |
| actttcctac ttggcagtac atctacgtat tagtcatcgc tattaccatg ctgatgcggt | 600 |
| tttggcagta catcaatggg cgtggatagc ggtttgactc acggggattt ccaagtctcc | 660 |
| accccattga cgtcaatggg agtttgtttt ggcaccaaaa tcaacgggac tttccaaaat | 720 |
| gtcgtaacaa ctccgcccca ttgacgcaaa tgggcggtag gcgtgtacgg tgggaggtct | 780 |
| atataagcag agctggttta gtgaaccgtc agatcagatc tttgtcgatc ctaccatcca | 840 |
| ctcgacacac ccgccagcgg ccgccaccat gaaggccaat ctactggtgt gctgtgtgc | 900 |
| ccttgcggcg gcagatgcca tcaggtgcat tggagtcagc aacagggact tcgtcgaagg | 960 |
| catgtccggc ggcacctggg tggatgtggt gctcgaacac ggcggatgcg tgaccgtcat | 1020 |
| ggcccaggac aagcctaccg tcgatattga gctggtgacc accacagtga gcaacatggc | 1080 |
| cgaagtgaga agctactgct atgaggcctc catcagcgat atggcttccg attccagatg | 1140 |
| ccccacacag ggagaggctt atctggacaa acagtccgac acccagtacg tctgcaaaag | 1200 |
| aaccctggtg gacagaggct ggggaaacgg atgcggcctg aacggatccg gcagcctcgt | 1260 |
| gacatgtgcc aagttcgcct gcagcaaaaa gatgaccggc aagtccatcc agcccgagaa | 1320 |
| cctggaatac aggatcatgc tgtccgtgca tggatcccag cactccggca tgatcgtcaa | 1380 |
| cgataccggc cacgagaccg acgagaacag ggctaaagtg gagatcaccc ccaacagccc | 1440 |
| tagagccgaa gctacactgg gcggcttcgg aagcctgggc ctggattgcg aacccaggac | 1500 |
| cggcctggat ttcagcgacc tgtattacct gaccatgaac aataagcact ggctggtgca | 1560 |
| caaggaatgg ttccacgaca tcccctgcc ttggcatgct ggcgccgata ccggcacacc | 1620 |
| tcactggaac aataaggaag ccctggtcga gtttaaggac gccacgcca aaagacagac | 1680 |
| cgtggtggtg ctgggaagcc aggagggagc tgtccacaca gccctggccg gagctctgga | 1740 |

```
agccgagatg gatggcgcca agggcaggct gagctccggc cacctgaaat gcaggctcaa    1800
gatggacaag ctgaggctga agggcgtgag ctacagcctg tgcaccgccg ctttcacctt    1860
taccaagatc cctgccgaga cactgcacgg caccgtcacc gtggaggtgc aatacgccgg    1920
aaccgatgga ccttgcaaag tgcctgccca gatggctgtg gatatgcaga ccctcacacc    1980
cgtcggcagg ctgatcaccg ccaatcccgt cattaccgag tccaccgaga acagcaagat    2040
gatgctcgag ctcgatcccc cctttggcga cagctacatt gtgatcggcg tgggcgagaa    2100
gaagatcacc caccattggc acagaagcgg ctccacaggg ggtagcggtg gtagcggagg    2160
tagccatcac caccatcacc actgagctag cttgactgac tgagatacag cgtaccttca    2220
gctcacagac atgataagat acattgatga gtttggacaa accacaacta gaatgcagtg    2280
aaaaaaatgc tttatttgtg aaatttgtga tgctattgct ttatttgtaa ccattataag    2340
ctgcaataaa caagttaaca acaacaattg cattcatttt atgtttcagg ttcaggggga    2400
ggtgtgggag gttttttaaa gcaagtaaaa cctctacaaa tgtggtattg gcccatctct    2460
atcggtatcg tagcataacc ccttggggcc tctaaacggg tcttgagggg ttttttgtgc    2520
ccctcgggcc ggattgctat ctaccggcat ggcgcagaaa aaaatgcct gatgcgacgc     2580 tgcgcgtctt atactcccac atatgccaga ttcagcaacg gatacggctt ccccaacttg    2640
cccacttcca tacgtgtcct ccttaccaga aatttatcct taaggtcgtc agctatcctg    2700
caggcgatct ctcgatttcg atcaagacat tcctttaatg gtcttttctg gacaccacta    2760
ggggtcagaa gtagttcatc aaactttctt ccctccctaa tctcattggt taccttgggc    2820
tatcgaaact taattaacca gtcaagtcag ctacttggcg agatcgactt gtctgggttt    2880
cgactacgct cagaattgcg tcagtcaagt tcgatctggt ccttgctatt gcacccgttc    2940
tccgattacg agtttcattt aaatcatgtg agcaaaaggc cagcaaaagg ccaggaaccg    3000
taaaaaggcc gcgttgctgg cgttttttcca taggctccgc cccctgacg agcatcacaa    3060 aaatcgacgc tcaagtcaga ggtggcgaaa cccgacagga ctataaagat accaggcgtt    3120
tccccctgga agctccctcg tgcgctctcc tgttccgacc ctgccgctta ccggatacct    3180
gtccgccttt ctcccttcgg gaagcgtggc gctttctcat agctcacgct gtaggtatct    3240
cagttcggtg taggtcgttc gctccaagct gggctgtgtg cacgaacccc ccgttcagcc    3300
cgaccgctgc gccttatccg gtaactatcg tcttgagtcc aacccggtaa gacacgactt    3360
atcgccactg gcagcagcca ctggtaacag gattagcaga gcgaggtatg taggcggtgc    3420
tacagagttc ttgaagtggt ggcctaacta cggctacact agaagaacag tatttggtat    3480
ctgcgctctg ctgaagccag ttaccttcgg aaaagagtt ggtagctctt gatccggcaa     3540
acaaaccacc gctggtagcg gtggttttt tgtttgcaag cagcagatta cgcgcagaaa     3600
aaaaggatct caagaagatc ctttgatctt ttctacgggg tctgacgctc agtggaacga    3660
aaactcacgt taagggattt tggtcatgag attatcaaaa aggatcttca cctagatcct    3720
tttaaattaa aaatgaagtt ttaaatcaat ctaaagtata tatgagtaaa cttggtctga    3780
cagttaccaa tgcttaatca gtgaggcacc tatctcagcg atctgtctat ttcgttcatc    3840
catagttgca tttaaatttc cgaactctcc aaggccctcg tcgaaaatc ttcaaacctt     3900 tcgtccgatc catcttgcag gctacctctc gaacgaacta tcgcaagtct cttggccggc    3960
cttgcgcctt ggctattgct tggcagcgcc tatcgcagg tattactcca atcccgaata     4020
tccgagatcg ggatcacccg agagaagttc aacctacatc tcaatcccg atctatccga     4080
```

```
gatccgagga atatcgaaat cggggcgcgc ctggtgtacc gagaacgatc ctctcagtgc    4140
gagtctcgac gatccatatc gttgcttggc agtcagccag tcggaatcca gcttgggacc    4200
caggaagtcc aatcgtcaga tattgtactc aagcctggtc acggcagcgt accgatctgt    4260
ttaaacctag atattgatag tctgatcggt caacgtataa tcgagtccta gcttttgcaa    4320
acatctatca agagacagga tcagcaggag ctttcgcat gagtattcaa catttccgtg     4380
tcgcccttat tccctttttt gcggcatttt gccttcctgt ttttgctcac ccagaaacgc    4440
tggtgaaagt aaaagatgct gaagatcagt tgggtgcgcg agtgggttac atcgaactgg    4500
atctcaacag cggtaagatc cttgagagtt ttcgccccga agaacgcttt ccaatgatga    4560 gcactttta agttctgcta tgtggcgcgg tattatcccg tattgacgcc gggcaagagc     4620
aactcggtcg ccgcatacac tattctcaga atgacttggt tgagtattca ccagtcacag    4680
aaaagcatct tacggatggc atgacagtaa gagaattatg cagtgctgcc ataaccatga    4740
gtgataacac tgcggccaac ttacttctga caacgattgg aggaccgaag gagctaaccg    4800
cttttttgca caacatgggg gatcatgtaa ctcgccttga tcgttgggaa ccggagctga    4860
atgaagccat accaaacgac gagcgtgaca ccacgatgcc tgtagcaatg gcaacaacct    4920
tgcgtaaact attaactggc gaactactta ctctagcttc ccggcaacag ttgatagact    4980
ggatggaggc ggataaagtt gcaggaccac ttctgcgctc ggcccttccg gctggctggt    5040
ttattgctga taaatctgga gccggtgagc gtgggtctcg cggtatcatt gcagcactgg    5100
ggccagatgg taagccctcc cgtatcgtag ttatctacac gacggggagt caggcaacta    5160
tggatgaacg aaatagacag atcgctgaga taggtgcctc actgattaag cattggtaac    5220
cgattctagg tgcattggcg cagaaaaaaa tgcctgatgc gacgctgcgc gtcttatact    5280
cccacatatg ccagattcag caacggatac ggcttcccca acttgcccac ttccatacgt    5340
gtcctcctta ccagaaattt atccttaaga tcccgaatcg tttaaactcg actctggctc    5400
tatcgaatct ccgtcgtttc gagcttacgc gaacagccgt ggcgctcatt tgctcgtcgg    5460
gcatcgaatc tcgtcagcta tcgtcagctt acctttttgg ca                      5502
```

<210> SEQ ID NO 24
<211> LENGTH: 407
<212> TYPE: PRT
<213> ORGANISM: Artificial Sequence
<220> FEATURE:
<223> OTHER INFORMATION: Hyperglycosylated exodomain D1 (from pCRO21)

<400> SEQUENCE: 24

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ser Asn Phe Val Cys Arg Arg Thr Phe
                85                  90                  95

Val Asp Arg Gly Asn Gly Ser Gly Cys Gly Leu Asn Gly Ser Gly Ser
            100                 105                 110
```

```
Leu Leu Thr Cys Ala Lys Phe Lys Cys Val Thr Lys Leu Glu Gly Lys
            115                 120                 125

Ile Val Gln Tyr Glu Asn Leu Lys Tyr Ser Val Ile Val Thr Val His
        130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ala Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Thr Glu Pro Pro Phe Gly Glu Ser Tyr Ile Val Val Gly Ala Gly Glu
    370                 375                 380

Lys Ala Leu Lys Leu Ser Trp Phe Lys Lys Gly Ser Thr Gly Gly Gly
385                 390                 395                 400

Ser His His His His His His
                405

<210> SEQ ID NO 25
<211> LENGTH: 407
<212> TYPE: PRT
<213> ORGANISM: Artificial Sequence
<220> FEATURE:
<223> OTHER INFORMATION: Hyperglycosylated exodomain D2 (from pCRO22)

<400> SEQUENCE: 25

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60
```

```
Leu Thr Asn Thr Thr Thr Glu Ser Arg Cys Pro Thr Gln Gly Glu Pro
 65                  70                  75                  80

Ser Leu Asn Glu Glu Gln Asp Lys Arg Phe Val Cys Lys His Ser Met
             85                  90                  95

Val Asp Arg Gly Asn Gly Ser Gly Cys Gly Leu Asn Gly Ser Gly Gly
            100                 105                 110

Ile Val Thr Cys Ala Met Phe Thr Cys Lys Lys Asn Met Glu Gly Lys
        115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Gly Val Glu Pro
    370                 375                 380

Gly Gln Leu Lys Leu Asn Trp Phe Lys Lys Gly Ser Ser Gly Gly
385                 390                 395                 400

Ser His His His His His His
                405

<210> SEQ ID NO 26
<211> LENGTH: 405
<212> TYPE: PRT
<213> ORGANISM: Artificial Sequence
<220> FEATURE:
<223> OTHER INFORMATION: Hyperglycosylated exodomain D3 (from pCRO23)

<400> SEQUENCE: 26

Met Arg Cys Val Gly Val Gly Asn Arg Asp Phe Val Glu Gly Leu Ser
1               5                   10                  15
```

```
Gly Ala Thr Trp Val Asp Val Val Leu Glu His Gly Gly Cys Val Thr
             20                  25                  30
Thr Met Ala Lys Asn Lys Pro Thr Leu Asp Ile Glu Leu Gln Lys Thr
         35                  40                  45
Glu Ala Thr Gln Leu Ala Thr Leu Arg Lys Leu Cys Ile Glu Gly Lys
     50                  55                  60
Ile Thr Asn Ile Thr Thr Asp Ser Arg Cys Pro Thr Gln Gly Glu Ala
 65                  70                  75                  80
Val Leu Pro Glu Glu Gln Asp Gln Asn Tyr Val Cys Lys His Thr Tyr
                 85                  90                  95
Val Asp Arg Gly Asn Gly Ser Gly Cys Gly Leu Asn Gly Ser Gly Ser
            100                 105                 110
Leu Val Thr Cys Ala Lys Phe Gln Cys Leu Glu Pro Ile Glu Gly Lys
        115                 120                 125
Val Val Gln Tyr Glu Asn Leu Lys Tyr Thr Val Ile Ile Thr Val His
    130                 135                 140
Thr Gly Asp Gln His Gln Val Gly Asn Glu Thr Gln Gly Val Thr Ala
145                 150                 155                 160
Glu Ile Thr Pro Gln Ala Ser Thr Thr Glu Ala Ile Leu Pro Glu Tyr
                165                 170                 175
Gly Thr Leu Gly Leu Glu Cys Ser Pro Arg Thr Gly Leu Asp Phe Asn
            180                 185                 190
Glu Met Ile Leu Leu Thr Met Lys Asn Lys Ala Trp Met Val His Arg
        195                 200                 205
Gln Trp Phe Phe Asp Leu Pro Leu Pro Trp Ala Ser Gly Ala Thr Thr
    210                 215                 220
Glu Thr Pro Thr Trp Asn Arg Lys Glu Leu Leu Val Thr Phe Lys Asn
225                 230                 235                 240
Ala His Ala Lys Lys Gln Glu Val Val Val Leu Gly Ser Gln Glu Gly
                245                 250                 255
Ala Met His Thr Ala Leu Thr Gly Ala Thr Glu Ile Gln Asn Ser Gly
            260                 265                 270
Gly Thr Ser Ile Phe Ala Gly His Leu Lys Cys Arg Leu Lys Met Asp
        275                 280                 285
Lys Leu Glu Leu Lys Gly Met Ser Tyr Ala Met Cys Thr Asn Thr Phe
    290                 295                 300
Val Leu Lys Lys Glu Val Ser Glu Thr Gln His Gly Thr Ile Leu Ile
305                 310                 315                 320
Lys Val Glu Tyr Lys Gly Glu Asp Ala Pro Cys Lys Ile Pro Phe Ser
                325                 330                 335
Thr Glu Asp Gly Gln Gly Lys Ala His Asn Gly Arg Leu Ile Thr Ala
            340                 345                 350
Asn Pro Val Val Thr Lys Lys Glu Glu Pro Val Asn Ile Glu Ala Glu
        355                 360                 365
Pro Pro Phe Gly Glu Ser Asn Ile Val Ile Gly Ile Gly Asp Asn Ala
    370                 375                 380
Leu Lys Ile Asn Trp Tyr Lys Lys Gly Ser Ser Gly Gly Ser His
385                 390                 395                 400
His His His His
            405

<210> SEQ ID NO 27
<211> LENGTH: 407
<212> TYPE: PRT
```

<213> ORGANISM: Artificial Sequence
<220> FEATURE:
<223> OTHER INFORMATION: Hyperglycosylated exodomain D4 (from pCRO24)

<400> SEQUENCE: 27

```
Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Asn Gly Ser Gly Cys Gly Leu Asn Gly Ser Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Thr Val His
130                 135                 140

Asn Gly Asp Thr His Ala Val Gly Asn Asp Thr Ser Asn His Gly Val
145                 150                 155                 160

Thr Ala Met Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Leu Ala Glu Asn Thr Asn Ser Val Thr Asn Ile Glu
        355                 360                 365

Leu Glu Pro Pro Phe Gly Asp Ser Tyr Ile Val Ile Gly Val Gly Asn
    370                 375                 380

Ser Ala Leu Thr Leu His Trp Phe Arg Lys Gly Ser Ser Gly Gly Gly
```

```
                385                 390                 395                 400
Ser His His His His His
                405

<210> SEQ ID NO 28
<211> LENGTH: 421
<212> TYPE: PRT
<213> ORGANISM: Artificial Sequence
<220> FEATURE:
<223> OTHER INFORMATION: Hyperglycosylated exodomain Zika (from pCRO25)

<400> SEQUENCE: 28

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Asn Gly Ser Gly Cys Gly Leu Asn Gly Ser Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
```

```
                     340                 345                 350
Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
        370                 375                 380

Ser Tyr Ile Val Ile Gly Val Gly Glu Lys Lys Ile Thr His His Trp
385                 390                 395                 400

His Arg Ser Gly Ser Thr Gly Ser Gly Ser Gly Gly Ser Gly Ser His
            405                 410                 415

His His His His His
        420

<210> SEQ ID NO 29
<211> LENGTH: 407
<212> TYPE: PRT
<213> ORGANISM: Artificial Sequence
<220> FEATURE:
<223> OTHER INFORMATION: DENV1_Eexo 2.1 (single sequon W101N;N103S)
      insert for pCRO26 plasmid

<400> SEQUENCE: 29

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ser Asn Phe Val Cys Arg Arg Thr Phe
                85                  90                  95

Val Asp Arg Gly Asn Gly Ser Gly Cys Gly Leu Phe Gly Lys Gly Ser
            100                 105                 110

Leu Leu Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270
```

```
Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ala Gln Asp Glu Lys Gly Val Thr Gln Asn Gly Arg Leu Ile
                340                 345                 350

Thr Ala Asn Pro Ile Val Thr Asp Lys Glu Lys Pro Val Asn Ile Glu
            355                 360                 365

Thr Glu Pro Pro Phe Gly Glu Ser Tyr Ile Val Val Gly Ala Gly Glu
370                 375                 380

Lys Ala Leu Lys Leu Ser Trp Phe Lys Lys Gly Ser Thr Gly Gly Gly
385                 390                 395                 400

Ser His His His His His His
            405

<210> SEQ ID NO 30
<211> LENGTH: 407
<212> TYPE: PRT
<213> ORGANISM: Artificial Sequence
<220> FEATURE:
<223> OTHER INFORMATION: DENV1_Eexo 2.2 (single sequon F108N;K110S)
      insert for pCRO27 plasmid

<400> SEQUENCE: 30

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys As

```
Ser Thr Ser Gln Glu Thr Trp Asn Arg Gln Asp Leu Leu Val Thr Phe
225                 230                 235                 240

Lys Thr Ala His Ala Lys Lys Gln Glu Val Val Leu Gly Ser Gln
            245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
            275                 280                 285

Met Asp Lys Leu Thr Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
            325                 330                 335

Phe Ser Ala Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
            355                 360                 365

Thr Glu Pro Pro Phe Gly Glu Ser Tyr Ile Val Val Gly Ala Gly Glu
            370                 375                 380

Lys Ala Leu Lys Leu Ser Trp Phe Lys Lys Gly Ser Thr Gly Gly
385                 390                 395                 400

Ser His His His His His
            405

<210> SEQ ID NO 31
<211> LENGTH: 421
<212> TYPE: PRT
<213> ORGANISM: Artificial Sequence
<220> FEATURE:
<223> OTHER INFORMATION: ZIKV_EEexo 2.1 (single sequon
      G100N;W101H;G102T) insert for pCRO28 plasmid

<400> SEQUENCE: 31

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
            85                  90                  95

Val Asp Arg Asn His Thr Asn Gly Cys Gly Leu Phe Gly Lys Gly Ser
            100                 105                 110

Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His
            130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
```

```
                165                 170                 175
Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
            210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
            275                 280                 285

Leu Lys Cys Arg Leu Lys Met Asp Lys Leu Arg Leu Lys Gly Val Ser
            290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
            370                 375                 380

Ser Tyr Ile Val Ile Gly Val Gly Glu Lys Lys Ile Thr His His Trp
385                 390                 395                 400

His Arg Ser Gly Ser Thr Gly Gly Ser Gly Gly Ser Gly Gly Ser His
                405                 410                 415

His His His His His
            420

<210> SEQ ID NO 32
<211> LENGTH: 421
<212> TYPE: PRT
<213> ORGANISM: Artificial Sequence
<220> FEATURE:
<223> OTHER INFORMATION: ZIKV_Eexo 2.2 (single sequon L107N;F108H;G109T)
      insert for pCRO29 plasmid

<400> SEQUENCE: 32

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95
```

Val Asp Arg Gly Trp Gly Asn Gly Cys Gly Asn His Thr Lys Gly Ser
            100                 105                 110

Leu Val Thr Cys Ala Lys Phe Ala Cys Ser Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Gly Gly Ser Gly Gly Ser Gly Gly Ser His
                405                 410                 415

His His His His His
        420

<210> SEQ ID NO 33
<211> LENGTH: 421
<212> TYPE: PRT
<213> ORGANISM: Artificial Sequence
<220> FEATURE:
<223> OTHER INFORMATION: ZIKV_Eexo 2.3 (single sequon W101N;N103S)
      insert for pCRO30 plasmid

<400> SEQUENCE: 33

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

```
Val Met Ala Gln Asp Lys Pro Thr Val Asp Ile Glu Leu Val Thr Thr
            35                  40                  45
Thr Val Ser Asn Met Ala Glu Val Arg Ser Tyr Cys Tyr Glu Ala Ser
 50                  55                  60
Ile Ser Asp Met Ala Ser Asp Ser Arg Cys Pro Thr Gln Gly Glu Ala
 65                  70                  75                  80
Tyr Leu Asp Lys Gln Ser Asp Thr Gln Tyr Val Cys Lys Arg Thr Leu
                85                  90                  95
Val Asp Arg Gly Asn Gly Ser Gly Cys Gly Leu Phe Gly Lys Gly Ser
               100                 105                 110
Leu Val Thr Cys Ala Lys Phe Ala Cys Ser Lys Lys Met Thr Gly Lys
               115                 120                 125
Ser Ile Gln Pro Glu Asn Leu Glu Tyr Arg Ile Met Leu Ser Val His
               130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
                180                 185                 190
Arg Thr Gly Leu Asp Phe Ser Asp Leu Tyr Tyr Leu Thr Met Asn Asn
                195                 200                 205
Lys His Trp Leu Val His Lys Glu Trp Phe His Asp Ile Pro Leu Pro
                210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
                260                 265                 270
Leu Glu Ala Glu Met Asp Gly Ala Lys Gly Arg Leu Ser Ser Gly His
                275                 280                 285
Leu Lys Cys Arg Leu Lys Met Asp Lys Leu Arg Leu Lys Gly Val Ser
                290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
                340                 345                 350
Thr Pro Val Gly Arg Leu Ile Thr Ala Asn Pro Val Ile Thr Glu Ser
                355                 360                 365
Thr Glu Asn Ser Lys Met Met Leu Glu Leu Asp Pro Pro Phe Gly Asp
                370                 375                 380
Ser Tyr Ile Val Ile Gly Val Gly Glu Lys Lys Ile Thr His His Trp
385                 390                 395                 400
His Arg Ser Gly Ser Thr Gly Gly Ser Gly Gly Ser Gly Gly Ser His
                405                 410                 415
His His His His
            420

<210> SEQ ID NO 34
<211> LENGTH: 421
```

<212> TYPE: PRT
<213> ORGANISM: Artificial Sequence
<220> FEATURE:
<223> OTHER INFORMATION: ZIKV_Eexo 2.4 (single sequon F108N;K110S)
    insert for pCRO31 plasmid

<400> SEQUENCE: 34

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Asn Gly Ser Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

```
Ser Tyr Ile Val Ile Gly Val Gly Glu Lys Lys Ile Thr His His Trp
385                 390                 395                 400

His Arg Ser Gly Ser Thr Gly Gly Ser Gly Gly Ser Gly Gly Ser His
                405                 410                 415

His His His His His
            420

<210> SEQ ID NO 35
<211> LENGTH: 23
<212> TYPE: PRT
<213> ORGANISM: Artificial Sequence
<220> FEATURE:
<223> OTHER INFORMATION: Hyperglycosylated dengue 2 exodomain tryptic
      peptide T15 (15th tryptic peptide containing substituted N
      residues at 101 and 108).

<400> SEQUENCE: 35

Gly Asn Gly Ser Gly Cys Gly Leu Asn Gly Ser Gly Gly Ile Val Thr
1               5                   10                  15

Cys Ala Met Phe Thr Cys Lys
            20

<210> SEQ ID NO 36
<211> LENGTH: 11
<212> TYPE: PRT
<213> ORGANISM: Artificial Sequence
<220> FEATURE:
<223> OTHER INFORMATION: Hyperglycosylated Zika exodomain peptide T10
      with single introduced glycosylation sequon NHT

<400> SEQUENCE: 36

Asn His Thr Asn Gly Cys Gly Leu Phe Gly Lys
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Dengue-2 (65-73) T10 peptide

<400> SEQUENCE: 37

Leu Thr Asn Thr Thr Thr Glu Ser Arg
1               5

<210> SEQ ID NO 38
<211> LENGTH: 9
<212> TYPE: PRT
<213> ORGANISM: Artificial Sequence
<220> FEATURE:
<223> OTHER INFORMATION: Dengue-2 (65-73) T10 peptide de-N glycosylated
      at position 67 (N67D)

<400> SEQUENCE: 38

Leu Thr Asp Thr Thr Thr Glu Ser Arg
1               5

<210> SEQ ID NO 39
<211> LENGTH: 23
<212> TYPE: PRT
<213> ORGANISM: Artificial Sequence
<220> FEATURE:
<223> OTHER INFORMATION: Dengue-2 (100-122)  T15 peptide

<400> SEQUENCE: 39
```

-continued

```
Gly Asn Gly Ser Gly Cys Gly Leu Asn Gly Ser Gly Gly Ile Val Thr
1               5                   10                  15

Cys Ala Met Phe Thr Cys Lys
            20

<210> SEQ ID NO 40
<211> LENGTH: 23
<212> TYPE: PRT
<213> ORGANISM: Artificial Sequence
<220> FEATURE:
<223> OTHER INFORMATION: Dengue-2 (100-122) T15 peptide with single de-N
      glycosylation at position 101 (N101D)

<400> SEQUENCE: 40

Gly Asp Gly Ser Gly Cys Gly Leu Asn Gly Ser Gly Gly Ile Val Thr
1               5                   10                  15

Cys Ala Met Phe Thr Cys Lys
            20

<210> SEQ ID NO 41
<211> LENGTH: 23
<212> TYPE: PRT
<213> ORGANISM: Artificial Sequence
<220> FEATURE:
<223> OTHER INFORMATION: Dengue-2 (100-122) T15 peptide with single de-N
      glycosylation at position 108 (N108D)

<400> SEQUENCE: 41

Gly Asn Gly Ser Gly Cys Gly Leu Asp Gly Ser Gly Gly Ile Val Thr
1               5                   10                  15

Cys Ala Met Phe Thr Cys Lys
            20

<210> SEQ ID NO 42
<211> LENGTH: 23
<212> TYPE: PRT
<213> ORGANISM: Artificial Sequence
<220> FEATURE:
<223> OTHER INFORMATION: Dengue-2 (100-122) T15 peptide with de-N
      glycosylation at positions 101 and 108 (N101D; N108D)

<400> SEQUENCE: 42

Gly Asp Gly Ser Gly Cys Gly Leu Asp Gly Ser Gly Gly Ile Val Thr
1               5                   10                  15

Cys Ala Met Phe Thr Cys Lys

```
<223> OTHER INFORMATION: Dengue-2 (129-157) T18 peptide with de-N
      glycosylation at position 153 (N153D)

<400> SEQUENCE: 44

Val Val Gln Pro Glu Asn Leu Glu Tyr Thr Ile Val Ile Thr Pro His
1               5                   10                  15

Ser Gly Glu Glu His Ala Val Gly Asp Asp Thr Gly Lys
            20                  25

<210> SEQ ID NO 45
<211> LENGTH: 17
<212> TYPE: PRT
<213> ORGANISM: Artificial Sequence
<220> FEATURE:
<223> OTHER INFORMATION: Zika (94-110) L4 peptide

<400> SEQUENCE: 45

Arg Thr Leu Val Asp Arg Asn His Thr Asn Gly Cys Gly Leu Phe Gly
1               5                   10                  15

Lys

<210> SEQ ID NO 46
<211> LENGTH: 17
<212> TYPE: PRT
<213> ORGANISM: Artificial Sequence
<220> FEATURE:
<223> OTHER INFORMATION: Zika (94-110) L4 peptide with de-N
      glycosylation at position 100 (N100D)

<400> SEQUENCE: 46

Arg Thr Leu Val Asp Arg Asp His Thr Asn Gly Cys Gly Leu Phe Gly
1               5                   10                  15

Lys

<210> SEQ ID NO 47
<211> LENGTH: 26
<212> TYPE: PRT
<213> ORGANISM: Artificial Sequence
<220> FEATURE:
<223> OTHER INFORMATION: Zika (139-164) T16 peptide

<400> SEQUENCE: 47

Ile Met Leu Ser Val His Gly Ser Gln His Ser Gly Met Ile Val Asn
1               5                   10                  15

Asp Thr Gly His Glu Thr Asp Glu Asn Arg
            20                  25

<210> SEQ ID NO 48
<211> LENGTH: 26
<212> TYPE: PRT
<213> ORGANISM: Artificial Sequence
<220> FEATURE:
<223> OTHER INFORMATION: Zika (139 - 164) peptide deglycosylated at
      position 154 (N154D)

<400> SEQUENCE: 48

Ile Met Leu Ser Val His Gly Ser Gln His Ser Gly Met Ile Val Asp
1               5                   10                  15

Asp Thr Gly His Glu Thr Asp Glu Asn Arg
            20                  25

<210> SEQ ID NO 49
<211> LENGTH: 407
<212> TYPE: PRT
```

<213> ORGANISM: Artificial
<220> FEATURE:
<223> OTHER INFORMATION: Dengue-2 serotype product of expression from pCRO22

<400> S

Gly Gln Leu Lys Leu Asn Trp Phe Lys Lys Gly Ser Ser Gly Gly Gly
    385                 390                 395                 400

Ser His His His His His
            405

<210> SEQ ID NO 50
<211> LENGTH: 7
<212> TYPE: PRT
<213> ORGANISM: Artificial Sequence
<220> FEATURE:
<223> OTHER INFORMATION: pCRO22 Dengue-2 T2 peptide

<400> SEQUENCE: 50

Cys Ile Gly Ile Ser Asn Arg
1               5

<210> SEQ ID NO 51
<211> LENGTH: 27
<212> TYPE: PRT
<213> ORGANISM: Artificial Sequence
<220> FEATURE:
<223> OTHER INFORMATION: pCRO22 Dengue-2 T3 peptide

<400> SEQUENCE: 51

Asp Phe Val Glu Gly Val Ser Gly Gly Ser Trp Val Asp Ile Val Leu
1               5                   10                  15

Glu His Gly Ser Cys Val Thr Thr Met Ala Lys
            20                  25

<210> SEQ ID NO 52
<211> LENGTH: 9
<212> TYPE: PRT
<213> ORGANISM: Artificial Sequence
<220> FEATURE:
<223> OTHER INFORMATION: pCRO22 Dengue-2 T5 peptide

<400> SEQUENCE: 52

Pro Thr Leu Asp Phe Glu Leu Ile Lys
1               5

<210> SEQ ID NO 53
<211> LENGTH: 4
<212> TYPE: PRT
<213> ORGANISM: Artificial Sequence
<220> FEATURE:
<223> OTHER INFORMATION: pCRO22 Dengue-2 T6 peptide

<400> SEQUENCE: 53

Thr Glu Ala Lys
1

<210> SEQ ID NO 54
<211> LENGTH: 6
<212> TYPE: PRT
<213> ORGANISM: Artificial Sequence
<220> FEATURE:
<223> OTHER INFORMATION: pCRO22 Dengue-2 T7 peptide

<400> SEQUENCE: 54

Gln Pro Ala Thr Leu Arg
1               5

<210> SEQ ID NO 55
<211> LENGTH: 6
<212> TYPE: PRT
<213> ORGANISM: Artificial Sequence

```
<220> FEATURE:
<223> OTHER INFORMATION: pCRO22 Dengue-2 T9 peptide

<400> SEQUENCE: 55

Tyr

```
<212> TYPE: PRT
<213> ORGANISM: Artificial Sequence
<220> FEATURE:
<223> OTHER INFORMATION: pCRO22 Dengue-2 T17 peptide

<400> SEQUENCE: 61

Asn Met Glu Gly Lys
1               5

<210> SEQ ID NO 62
<211> LENGTH: 29
<212> TYPE: PRT
<213> ORGANISM: Artificial Sequence
<220> FEATURE:
<223> OTHER INFORMATION: pCRO22 Dengue-2 T18 peptide

<400> SEQUENCE: 62

Val Val Gln Pro Glu Asn Leu Glu Tyr Thr Ile Val Ile Thr Pro His
1               5                   10                  15

Ser Gly Glu Glu His Ala Val Gly Asn Asp Thr Gly Lys
            20                  25

<210> SEQ ID NO 63
<211> LENGTH: 25
<212> TYPE: PRT
<213> ORGANISM: Artificial Sequence
<220> FEATURE:
<223> OTHER INFORMATION: pCRO22 Dengue-2 T21 peptide

<400> SEQUENCE: 63

Ile Thr Pro Gln Ser Ser Ile Thr Glu Ala Glu Leu Thr Gly Tyr Gly
1               5                   10                  15

Thr Val Thr Met Glu Cys Ser Pro Arg
            20                  25

<210> SEQ ID NO 64
<211> LENGTH: 16
<212> TYPE: PRT
<213> ORGANISM: Artificial Sequence
<220> FEATURE:
<223> OTHER INFORMATION: Dengue-2 T22 peptide

<400> SEQUENCE: 64

Thr Gly Leu Asp Phe Asn Glu Met Val Leu Leu Gln Met Glu Asn Lys
1               5                   10                  15

<210> SEQ ID NO 65
<211> LENGTH: 6
<212> TYPE: PRT
<213> ORGANISM: Artificial Sequence
<220> FEATURE:
<223> OTHER INFORMATION: pCRO22 Dengue-2 T23 peptide

<400> SEQUENCE: 65

Ala Trp Leu Val His Arg
1               5

<210> SEQ ID NO 66
<211> LENGTH: 24
<212> TYPE: PRT
<213> ORGANISM: Artificial Sequence
<220> FEATURE:
<223> OTHER INFORMATION: pCRO22 Dengue-2 T24 peptide

<400> SEQUENCE: 66

Gln Trp Phe Leu Asp Leu Pro Leu Pro Trp Leu Pro Gly Ala Asp Thr
```

```
<210> SEQ ID NO 67
<211> LENGTH: 7
<212> TYPE: PRT
<213> ORGANISM: Artificial Sequence
<220> FEATURE:
<223> OTHER INFORMATION: pCRO22 Dengue-2 T25 peptide

<400> SEQUENCE: 67

Glu Thr Leu Val Thr Phe Lys
1               5

<210> SEQ ID NO 68
<211> LENGTH: 5
<212> TYPE: PRT
<213> ORGANISM: Artificial Sequence
<220> FEATURE:
<223> OTHER INFORMATION: pCRO22 Dengue-2 T26 peptide

<400> SEQUENCE: 68

Asn Pro His Ala Lys
1               5

<210> SEQ ID NO 69
<211> LENGTH: 37
<212> TYPE: PRT
<213> ORGANISM: Artificial Sequence
<220> FEATURE:
<223> OTHER INFORMATION: pCRO22 Dengue-2 T28 peptide

<400> SEQUENCE: 69

Gln Asp Val Val Val Leu Gly Ser Gln Glu Gly Ala Met His Thr Ala
1               5                   10                  15

Leu Thr Gly Ala Thr Glu Ile Gln Met Ser Ser Gly Asn Leu Leu Phe
            20                  25                  30

Thr Gly His Leu Lys
        35

<210> SEQ ID NO 70
<211> LENGTH: 4
<212> TYPE: PRT
<213> ORGANISM: Artificial Sequence
<220> FEATURE:
<223> OTHER INFORMATION: pCRO22 Dengue-2 T32 peptide

<400> SEQUENCE: 70

Leu Gln Leu Lys
1

<210> SEQ ID NO 71
<211> LENGTH: 10
<212> TYPE: PRT
<213> ORGANISM: Artificial Sequence
<220> FEATURE:
<223> OTHER INFORMATION: pCRO22 Dengue-2 T33 peptide

<400> SEQUENCE: 71

Gly Met Ser Tyr Ser Met Cys Thr Gly Lys
1               5                   10

<210> SEQ ID NO 72
<211> LENGTH: 13
```

(continued from previous page)

```
1               5                   10                  15

Gln Gly Ser Asn Trp Ile Gln Lys
            20
```

```
<212> TYPE: PRT
<213> ORGANISM: Artificial Sequence
<220> FEATURE:
<223> OTHER INFORMATION: pCRO22 Dengue-2 T36 peptide

<400> SEQUENCE: 72

Glu Ile Ala Glu Thr Gln His Gly Thr Ile Val Ile Arg
1 5 10

<210> SEQ ID NO 73
<211> LENGTH: 11
<212> TYPE: PRT
<213> ORGANISM: Artificial Sequence
<220> FEATURE:
<223> OTHER INFORMATION: pCRO22 Dengue-2 T37 peptide

<400> SEQUENCE: 73

Val Gln Tyr Glu Gly Asp Gly Ser Pro Cys Lys
1 5 10

<210> SEQ ID NO 74
<211> LENGTH: 10
<212> TYPE: PRT
<213> ORGANISM: Artificial Sequence
<220> FEATURE:
<223> OTHER INFORMATION: pCRO22 Dengue-2 T38 peptide

<400> SEQUENCE: 74

Ile Pro Phe Glu Ile Met Asp Leu Glu Lys
1 5 10

<210> SEQ ID NO 75
<211> LENGTH: 5
<212> TYPE: PRT
<213> ORGANISM: Artificial Sequence
<220> FEATURE:
<223> OTHER INFORMATION: pCRO22 Dengue-2 T40 peptide

<400> SEQUENCE: 75

His Val Leu Gly Arg
1 5

<210> SEQ ID NO 76
<211> LENGTH: 11
<212> TYPE: PRT
<213> ORGANISM: Artificial Sequence
<220> FEATURE:
<223> OTHER INFORMATION: pCRO22 Dengue-2 T41 peptide

<400> SEQUENCE: 76

Leu Ile Thr Val Asn Pro Ile Val Thr Glu Lys
1 5 10

<210> SEQ ID NO 77
<211> LENGTH: 27
<212> TYPE: PRT
<213> ORGANISM: Artificial Sequence
<220> FEATURE:
<223> OTHER INFORMATION: pCRO22 Dengue-2 T42 peptide

<400> SEQUENCE: 77

Asp Ser Pro Val Asn Ile Glu Ala Glu Pro Pro Phe Gly Asp Ser Tyr
1 5 10 15

Ile Ile Ile Gly Val Glu Pro Gly Gln Leu Lys
20 25

```
<210> SEQ ID NO 78
<211> LENGTH: 5
<212> TYPE: PRT
<213> ORGANISM: Artificial Sequence
<220> FEATURE:
<223> OTHER INFORMATION: pCRO22 Dengue-2 T43 peptide

<400> SEQUENCE: 78

Leu Asn Trp Phe Lys
1               5

<210> SEQ ID NO 79
<211> LENGTH: 13
<212> TYPE: PRT
<213> ORGANISM: Artificial Sequence
<220> FEATURE:
<223> OTHER INFORMATION: pCRO22 Dengue-2 T45 peptide

<400> SEQUENCE: 79

Gly Ser Ser Gly Gly Gly Ser His His His His His His
1               5                   10

<210> SEQ ID NO 80
<211> LENGTH: 421
<212> TYPE: PRT
<213> ORGANISM: Artificial Sequence
<220> FEATURE:
<223> OTHER INFORMATION: Zika product of expression from pCRO28

<400> SEQUENCE: 80

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Asn His Thr Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240
```

```
Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
            275                 280                 285

Leu Lys Cys Arg Leu Lys Met Asp Lys Leu Arg Leu Lys Gly Val Ser
        290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Ser
                355                 360                 365

Thr Glu Asn Ser Lys Met Met Leu Glu Leu Asp Pro Pro Phe Gly Asp
            370                 375                 380

Ser Tyr Ile Val Ile Gly Val Gly Glu Lys Lys Ile Thr His His Trp
385                 390                 395                 400

His Arg Ser Gly Ser Thr Gly Ser Gly Ser Gly Ser Gly Gly Ser His
                405                 410                 415

His His His His His
            420

<210> SEQ ID NO 81
<211> LENGTH: 7
<212> TYPE: PRT
<213> ORGANISM: Artificial Sequence
<220> FEATURE:
<223> OTHER INFORMATION: pCRO28 Zika T2 peptide

<400> SEQUENCE: 81

Cys Ile Gly Val Ser Asn Arg
1               5

<210> SEQ ID NO 82
<211> LENGTH: 29
<212> TYPE: PRT
<213> ORGANISM: Artificial Sequence
<220> FEATURE:
<223> OTHER INFORMATION: pCRO28 Zika T3 peptide

<400> SEQUENCE: 82

Asp Phe Val Glu Gly Met Ser Gly Gly Thr Trp Val Asp Val Val Leu
1               5                   10                  15

Glu His Gly Gly Cys Val Thr Val Met Ala Gln Asp Lys
            20                  25

<210> SEQ ID NO 83
<211> LENGTH: 19
<212> TYPE: PRT
<213> ORGANISM: Artificial Sequence
<220> FEATURE:
<223> OTHER INFORMATION: pCRO28 Zika T4 peptide

<400> SEQUENCE: 83

Pro Thr Val Asp Ile Glu Leu Val Thr Thr Thr Val Ser Asn Met Ala
1               5                   10                  15
```

Glu Val Arg

<210> SEQ ID NO 84
<211> LENGTH: 16
<212> TYPE: PRT
<213> ORGANISM: Artificial Sequence
<220> FEATURE:
<223> OTHER INFORMATION: pCRO28 Zika T5 peptide

<400> SEQUENCE: 84

Ser Tyr Cys Tyr Glu Ala Ser Ile Ser Asp Met Ala Ser Asp Ser Arg
1               5                   10                  15

<210> SEQ ID NO 85
<211> LENGTH: 11
<212> TYPE: PRT
<213> ORGANISM: Artificial Sequence
<220> FEATURE:
<223> OTHER INFORMATION: pCRO28 Zika T6 peptide

<400> SEQUENCE: 85

Cys Pro Thr Gln Gly Glu Ala Tyr Leu Asp Lys
1               5                   10

<210> SEQ ID NO 86
<211> LENGTH: 9
<212> TYPE: PRT
<213> ORGANISM: Artificial Sequence
<220> FEATURE:
<223> OTHER INFORMATION: pCRO28 Zika T7 peptide

<400> SEQUENCE: 86

Gln Ser Asp Thr Gln Tyr Val Cys Lys
1               5

<210> SEQ ID NO 87
<211> LENGTH: 5
<212> TYPE: PRT
<213> ORGANISM: Artificial Sequence
<220> FEATURE:
<223> OTHER INFORMATION: pCRO28 Zika T9 peptide

<400> SEQUENCE: 87

Thr Leu Val Asp Arg
1               5

<210> SEQ ID NO 88
<211> LENGTH: 11
<212> TYPE: PRT
<213> ORGANISM: Artificial Sequence
<220> FEATURE:
<223> OTHER INFORMATION: pCRO28 Zika T10 peptide

<400> SEQUENCE: 88

Asn His Thr Asn Gly Cys Gly Leu Phe Gly Lys
1               5                   10

<210> SEQ ID NO 89
<211> LENGTH: 8
<212> TYPE: PRT
<213> ORGANISM: Artificial Sequence
<220> FEATURE:
<223> OTHER INFORMATION: pCRO28 Zika T11 peptide

<400> SEQUENCE: 89

Gly Ser Leu Val Thr Cys Ala Lys
1               5

<210> SEQ ID NO 90
<211> LENGTH: 5
<212> TYPE: PRT
<213> ORGANISM: Artificial Sequence
<220> FEATURE:
<223> OTHER INFORMATION: pCRO28 Zika T12 peptide

<400> SEQUENCE: 90

Phe Ala Cys Ser Lys
1               5

<210> SEQ ID NO 91
<211> LENGTH: 4
<212> TYPE: PRT
<213> ORGANISM: Artificial Sequence
<220> FEATURE:
<223> OTHER INFORMATION: pCRO28 Zika T14 peptide

<400> SEQUENCE: 91

Met Thr Gly Lys
1

<210> SEQ ID NO 92
<211> LENGTH: 10
<212> TYPE: PRT
<213> ORGANISM: Artificial Sequence
<220> FEATURE:
<223> OTHER INFORMATION: pCRO28 Zika T15 peptide

<400> SEQUENCE: 92

Ser Ile Gln Pro Glu Asn Leu Glu Tyr Arg
1               5                   10

<210> SEQ ID NO 93
<211> LENGTH: 26
<212> TYPE: PRT
<213> ORGANISM: Artificial Sequence
<220> FEATURE:
<223> OTHER INFORMATION: pCRO28 Zika T16 peptide

<400> SEQUENCE: 93

Ile Met Leu Ser Val His Gly Ser Gln His Ser Gly Met Ile Val Asn
1               5                   10                  15
Asp Thr Gly His Glu Thr Asp Glu Asn Arg
            20                  25

<210> SEQ ID NO 94
<211> LENGTH: 9
<212> TYPE: PRT
<213> ORGANISM: Artificial Sequence
<220> FEATURE:
<223> OTHER INFORMATION: pCRO28 Zika T18 peptide

<400> SEQUENCE: 94

Val Glu Ile Thr Pro Asn Ser Pro Arg
1               5

<210> SEQ ID NO 95
<211> LENGTH: 18
<212> TYPE: PRT
<213> ORGANISM: Artificial Sequence
<220> FEATURE:
<223> OTHER INFORMATION: pCRO28 Zika T19 peptide

<400> SEQUENCE: 95

```
Ala Glu Ala Thr Leu Gly Gly Phe Gly Ser Leu Gly Leu Asp Cys Glu
1               5                   10                  15

Pro Arg

<210> SEQ ID NO 96
<211> LENGTH: 16
<212> TYPE: PRT
<213> ORGANISM: Artificial Sequence
<220> FEATURE:
<223> OTHER INFORMATION: pCRO28 Zika T20 peptide

<400> SEQUENCE: 96

Thr Gly Leu Asp Phe Ser Asp Leu Tyr Tyr Leu Thr Met Asn Asn Lys
1               5                   10                  15

<210> SEQ ID NO 97
<211> LENGTH: 6
<212> TYPE: PRT
<213> ORGANISM: Artificial Sequence
<220> FEATURE:
<223> OTHER INFORMATION: pCRO28 Zika T21 peptide

<400> SEQUENCE: 97

His Trp Leu Val His Lys
1               5

<210> SEQ ID NO 98
<211> LENGTH: 24
<212> TYPE: PRT
<213> ORGANISM: Artificial Sequence
<220> FEATURE:
<223> OTHER INFORMATION: pCRO28 Zika T22 peptide

<400> SEQUENCE: 98

Glu Trp Phe His Asp Ile Pro Leu Pro Trp His Ala Gly Ala Asp Thr
1               5                   10                  15

Gly Thr Pro His Trp Asn Asn Lys
                20

<210> SEQ ID NO 99
<211> LENGTH: 7
<212> TYPE: PRT
<213> ORGANISM: Artificial Sequence
<220> FEATURE:
<223> OTHER INFORMATION: pCRO28 Zika T23 peptide

<400> SEQUENCE: 99

Glu Ala Leu Val Glu Phe Lys
1               5

<210> SEQ ID NO 100
<211> LENGTH: 5
<212> TYPE: PRT
<213> ORGANISM: Artificial Sequence
<220> FEATURE:
<223> OTHER INFORMATION: pCRO28 Zika T24 peptide

<400> SEQUENCE: 100

Asp Ala His Ala Lys
1               5

<210> SEQ ID NO 101
<211> LENGTH: 29
<212> TYPE: PRT
<213> ORGANISM: Artificial Sequence
<220> FEATURE:
```

<223> OTHER INFORMATION: pCRO28 Zika T26 peptide

<400> SEQUENCE: 101

```
Gln Thr Val Val Val Leu Gly Ser Gln Glu Gly Ala Val His Thr Ala
1               5                   10                  15
Leu Ala Gly Ala Leu Glu Ala Glu Met Asp Gly Ala Lys
            20                  25
```

<210> SEQ ID NO 102
<211> LENGTH: 7
<212> TYPE: PRT
<213> ORGANISM: Artificial Sequence
<220> FEATURE:
<223> OTHER INFORMATION: pCRO28 Zika T28 peptide

<400> SEQUENCE: 102

```
Leu Ser Ser Gly His Leu Lys
1               5
```

<210> SEQ ID NO 103
<211> LENGTH: 15
<212> TYPE: PRT
<213> ORGANISM: Artificial Sequence
<220> FEATURE:
<223> OTHER INFORMATION: pCRO28 Zika T34 peptide

<400> SEQUENCE: 103

```
Gly Val Ser Tyr Ser Leu Cys Thr Ala Ala Phe Thr Phe Thr Lys
1               5                   10                  15
```

<210> SEQ ID NO 104
<211> LENGTH: 24
<212> TYPE: PRT
<213> ORGANISM: Artificial Sequence
<220> FEATURE:
<223> OTHER INFORMATION: pCRO28 Zika T35 peptide

<400> SEQUENCE: 104

```
Ile Pro Ala Glu Thr Leu His Gly Thr Val Thr Val Glu Val Gln Tyr
1               5                   10                  15
Ala Gly Thr Asp Gly Pro Cys Lys
            20
```

<210> SEQ ID NO 105
<211> LENGTH: 17
<212> TYPE: PRT
<213> ORGANISM: Artificial Sequence
<220> FEATURE:
<223> OTHER INFORMATION: pCRO28 Zika T36 peptide

<400> SEQUENCE: 105

```
Val Pro Ala Gln Met Ala Val Asp Met Gln Thr Leu Thr Pro Val Gly
1               5                   10                  15
Arg
```

<210> SEQ ID NO 106
<211> LENGTH: 16
<212> TYPE: PRT
<213> ORGANISM: Artificial Sequence
<220> FEATURE:
<223> OTHER INFORMATION: pCRO28 Zika T37 peptide

<400> SEQUENCE: 106

```
Leu Ile Thr Ala Asn Pro Val Ile Thr Glu Ser Thr Glu Asn Ser Lys
1               5                   10                  15
```

<210> SEQ ID NO 107
<211> LENGTH: 21
<212> TYPE: PRT
<213> ORGANISM: Artificial Sequence
<220> FEATURE:
<223> OTHER INFORMATION: pCRO28 Zika T38 peptide

<400> SEQUENCE: 107

Met Met Leu Glu Leu Asp Pro Pro Phe Gly Asp Ser Tyr Ile Val Ile
1               5                   10                  15

Gly Val Gly Glu Lys
            20

<210> SEQ ID NO 108
<211> LENGTH: 7
<212> TYPE: PRT
<213> ORGANISM: Artificial Sequence
<220> FEATURE:
<223> OTHER INFORMATION: pCRO28 Zika T40 peptide

<400> SEQUENCE: 108

Ile Thr His His Trp His Arg
1               5

<210> SEQ ID NO 109
<211> LENGTH: 19
<212> TYPE: PRT
<213> ORGANISM: Artificial Sequence
<220> FEATURE:
<223> OTHER INFORMATION: pCRO28 Zika T41 peptide

<400> SEQUENCE: 109

Ser Gly Ser Thr Gly Gly Ser Gly Gly Ser Gly Gly Ser His His His
1               5                   10                  15

His His His

<210> SEQ ID NO 110
<211> LENGTH: 38
<212> TYPE: PRT
<213> ORGANISM: Artificial Sequence
<220> FEATURE:
<223> OTHER INFORMATION: pCRO28 Zika L1 peptide

<400> SEQUENCE: 110

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys
        35

<210> SEQ ID NO 111
<211> LENGTH: 46
<212> TYPE: PRT
<213> ORGANISM: Artificial Sequence
<220> FEATURE:
<223> OTHER INFORMATION: pCRO28 Zika L2 peptide

<400> SEQUENCE: 111

Pro Thr Val Asp Ile Glu Leu Val Thr Thr Thr Val Ser Asn Met Ala
1               5                   10                  15

Glu Val Arg Ser Tyr Cys Tyr Glu Ala Ser Ile Ser Asp Met Ala Ser
            20                  25                  30

```
Asp Ser Arg Cys Pro Thr Gln Gly Glu Ala Tyr Leu Asp Lys
        35                  40                  45

<210> SEQ ID NO 112
<211> LENGTH: 9
<212> TYPE: PRT
<213> ORGANISM: Artificial Sequence
<220> FEATURE:
<223> OTHER INFORMATION: pCRO28 Zika L3 peptide

<400> SEQUENCE: 112

Gln Ser Asp Thr Gln Tyr Val Cys Lys
1               5

<210> SEQ ID NO 113
<211> LENGTH: 17
<212> TYPE: PRT
<213> ORGANISM: Artificial Sequence
<220> FEATURE:
<223> OTHER INFORMATION: pCRO28 Zika L4 peptide

<400> SEQUENCE: 113

Arg Thr Leu Val Asp Arg Asn His Thr Asn Gly Cys Gly Leu Phe Gly
1               5                   10                  15

Lys

<210> SEQ ID NO 114
<211> LENGTH: 8
<212> TYPE: PRT
<213> ORGANISM: Artificial Sequence
<220> FEATURE:
<223> OTHER INFORMATION: pCRO28 Zika L5 peptide

<400> SEQUENCE: 114

Gly Ser Leu Val Thr Cys Ala Lys
1               5

<210> SEQ ID NO 115
<211> LENGTH: 5
<212> TYPE: PRT
<213> ORGANISM: Artificial Sequence
<220> FEATURE:
<223> OTHER INFORMATION: pCRO28 Zika L6 peptide

<400> SEQUENCE: 115

Phe Ala Cys Ser Lys
1               5

<210> SEQ ID NO 116
<211> LENGTH: 4
<212> TYPE: PRT
<213> ORGANISM: Artificial Sequence
<220> FEATURE:
<223> OTHER INFORMATION: pCRO28 Zika L8 peptide

<400> SEQUENCE: 116

Met Thr Gly Lys
1

<210> SEQ ID NO 117
<211> LENGTH: 38
<212> TYPE: PRT
<213> ORGANISM: Artificial Sequence
<220> FEATURE:
<223> OTHER INFORMATION: pCRO28 Zika L9 peptide
```

-continued

```
<400> SEQUENCE: 117

Ser Ile Gln Pro Glu Asn Leu Glu Tyr Arg Ile Met Leu Ser Val His
1               5                   10                  15

Gly Ser Gln His Ser Gly Met Ile Val Asn Asp Thr Gly His Glu Thr
            20                  25                  30

Asp Glu Asn Arg Ala Lys
        35

<210> SEQ ID NO 118
<211> LENGTH: 49
<212> TYPE: PRT
<213> ORGANISM: Artificial Sequence
<220> FEATURE:
<223> OTHER INFORMATION: pCRO28 Zika L10 peptide

<400> SEQUENCE: 118

Val Glu Ile Thr Pro Asn Ser Pro Arg Ala Glu Ala Thr Leu Gly Gly
1               5                   10                  15

Phe Gly Ser Leu Gly Leu Asp Cys Glu Pro Arg Thr Gly Leu Asp Phe
            20                  25                  30

Ser Asp Leu Tyr Tyr Leu Thr Met Asn Asn Lys His Trp Leu Val His
        35                  40                  45

Lys

<210> SEQ ID NO 119
<211> LENGTH: 24
<212> TYPE: PRT
<213> ORGANISM: Artificial Sequence
<220> FEATURE:
<223> OTHER INFORMATION: pCRO28 Zika L11 pepide

<400> SEQUENCE: 119

Glu Trp Phe His Asp Ile Pro Leu Pro Trp His Ala Gly Ala Asp Thr
1               5                   10                  15

Gly Thr Pro His Trp Asn Asn Lys
            20

<210> SEQ ID NO 120
<211> LENGTH: 7
<212> TYPE: PRT
<213> ORGANISM: Artificial Sequence
<220> FEATURE:
<223> OTHER INFORMATION: pCRO28 Zika L12 peptide

<400> SEQUENCE: 120

Glu Ala Leu Val Glu Phe Lys
1               5

<210> SEQ ID NO 121
<211> LENGTH: 5
<212> TYPE: PRT
<213> ORGANISM: Artificial Sequence
<220> FEATURE:
<223> OTHER INFORMATION: pCRO28 Zika L13 peptide

<400> SEQUENCE: 121

Asp Ala His Ala Lys
1               5

<210> SEQ ID NO 122
<211> LENGTH: 30
<212> TYPE: PRT
<213> ORGANISM: Artificial Sequence
```

<220> FEATURE:
<223> OTHER INFORMATION: pCRO28 Zika L14 peptide

<400> SEQUENCE: 122

Arg Gln Thr Val Val Val Leu Gly Ser Gln Glu Gly Ala Val His Thr
1 5 10 15

Ala Leu Ala Gly Ala Leu Glu Ala Glu Met Asp Gly Ala Lys
20 25 30

<210> SEQ ID NO 123
<211> LENGTH: 9
<212> TYPE: PRT
<213> ORGANISM: Artificial Sequence
<220> FEATURE:
<223> OTHER INFORMATION: pCRO28 Zika L15 peptide

<400> SEQUENCE: 123

Gly Arg Leu Ser Ser Gly His Leu Lys
1 5

<210> SEQ ID NO 124
<211> LENGTH: 4
<212> TYPE: PRT
<213> ORGANISM: Artificial Sequence
<220> FEATURE:
<223> OTHER INFORMATION: pCRO28 Zika L16 peptide

<400> SEQUENCE: 124

Cys Arg Leu Lys
1

<210> SEQ ID NO 125
<211> LENGTH: 4
<212> TYPE: PRT
<213> ORGANISM: Artificial Sequence
<220> FEATURE:
<223> OTHER INFORMATION: pCRO28 Zika L18 peptide

<400> SEQUENCE: 125

Leu Arg Leu Lys
1

<210> SEQ ID NO 126
<211> LENGTH: 15
<212> TYPE: PRT
<213> ORGANISM: Artificial Sequence
<220> FEATURE:
<223> OTHER INFORMATION: pCRO28 Zika L19 peptide

<400> SEQUENCE: 126

Gly Val Ser Tyr Ser Leu Cys Thr Ala Ala Phe Thr Phe Thr Lys
1 5 10 15

<210> SEQ ID NO 127
<211> LENGTH: 24
<212> TYPE: PRT
<213> ORGANISM: Artificial Sequence
<220> FEATURE:
<223> OTHER INFORMATION: pCRO28 Zika L20 peptide

<400> SEQUENCE: 127

Ile Pro Ala Glu Thr Leu His Gly Thr Val Thr Val Glu Val Gln Tyr
1 5 10 15

Ala Gly Thr Asp Gly Pro Cys Lys
20

```
<210> SEQ ID NO 128
<211> LENGTH: 33
<212> TYPE: PRT
<213> ORGANISM: Artificial Sequence
<220> FEATURE:
<223> OTHER INFORMATION: pCRO28 Zika L21 peptide

<400> SEQUENCE: 128

Val Pro Ala Gln Met Ala Val Asp Met Gln Thr Leu Thr Pro Val Gly
1               5                   10                  15

Arg Leu Ile Thr Ala Asn Pro Val Ile Thr Glu Ser Thr Glu Asn Ser
            20                  25                  30

Lys

<210> SEQ ID NO 129
<211> LENGTH: 21
<212> TYPE: PRT
<213> ORGANISM: Artificial Sequence
<220> FEATURE:
<223> OTHER INFORMATION: pCRO28 Zika L22 peptide

<400> SEQUENCE: 129

Met Met Leu Glu Leu Asp Pro Pro Phe Gly Asp Ser Tyr Ile Val Ile
1               5                   10                  15

Gly Val Gly Glu Lys
            20

<210> SEQ ID NO 130
<211> LENGTH: 26
<212> TYPE: PRT
<213> ORGANISM: Artificial Sequence
<220> FEATURE:
<223> OTHER INFORMATION: pCRO28 Zika L24 peptide

<400> SEQUENCE: 130

Ile Thr His His Trp His Arg Ser Gly Ser Thr Gly Gly Ser Gly Gly
1               5                   10                  15

Ser Gly Gly Ser His His His His His His
            20                  25
```